United States Patent
Xin et al.

(10) Patent No.: US 12,286,677 B2
(45) Date of Patent: *Apr. 29, 2025

(54) INHIBITION OF HSD17B13 IN THE TREATMENT OF LIVER DISEASE IN PATIENTS EXPRESSING THE PNPLA3 I148M VARIATION

(71) Applicant: Regeneron Pharmaceuticals, Inc., Tarrytown, NY (US)

(72) Inventors: Yurong Xin, Tarrytown, NY (US); Jesper Gromada, Tarrytown, NY (US); Xiping Cheng, Tarrytown, NY (US); Frederick Dewey, Tarrytown, NY (US); Tanya Teslovich Dostal, Tarrytown, NY (US); Claudia Schurmann, Tarrytown, NY (US); Aris Baras, Tarrytown, NY (US); Noura Abul-Husn, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/325,500

(22) Filed: May 30, 2023

(65) Prior Publication Data

US 2023/0383353 A1    Nov. 30, 2023

Related U.S. Application Data

(63) Continuation of application No. 17/178,420, filed on Feb. 18, 2021, now Pat. No. 11,702,700, which is a continuation of application No. 16/157,503, filed on Oct. 11, 2018, now Pat. No. 10,961,583.

(60) Provisional application No. 62/570,985, filed on Oct. 11, 2017.

(51) Int. Cl.
 *C12Q 1/6883* (2018.01)
 *C12Q 1/6886* (2018.01)

(52) U.S. Cl.
 CPC ......... *C12Q 1/6883* (2013.01); *C12Q 1/6886* (2013.01); *C12Q 2600/106* (2013.01); *C12Q 2600/156* (2013.01); *C12Q 2600/158* (2013.01)

(58) Field of Classification Search
 None
 See application file for complete search history.

(56) References Cited

U.S. PATENT DOCUMENTS

| | | | |
|---|---|---|---|
| 6,147,066 A | 11/2000 | Petit et al. | |
| 7,820,380 B2 | 10/2010 | Huang | |
| 7,951,382 B2 | 5/2011 | Gelber et al. | |
| 7,951,776 B2 | 5/2011 | Gelber | |
| 8,071,302 B2 | 12/2011 | Huang | |
| 8,945,847 B2 | 2/2015 | Benvenisty et al. | |
| 9,051,567 B2 | 6/2015 | Fitzgerald et al. | |
| 9,072,743 B2 | 7/2015 | Dilly et al. | |
| 9,328,346 B2 | 5/2016 | Lee et al. | |
| 9,375,433 B2 | 6/2016 | Dilly et al. | |
| 9,526,720 B2 | 12/2016 | Nagiec et al. | |
| 9,574,241 B2 | 2/2017 | Ferrando et al. | |
| 9,585,887 B2 | 3/2017 | Dilly et al. | |
| 9,585,890 B2 | 3/2017 | Dilly et al. | |
| 9,617,514 B2 | 4/2017 | Lunyak | |
| 9,629,804 B2 | 4/2017 | Heartlein et al. | |
| 9,632,090 B2 | 4/2017 | DePinho et al. | |
| 9,677,138 B2 | 6/2017 | Steiling et al. | |
| 9,796,762 B2 | 10/2017 | Kelly et al. | |
| 9,808,462 B2 | 11/2017 | Dilly et al. | |
| 9,816,094 B2 | 11/2017 | Lee et al. | |
| 10,052,284 B2 | 8/2018 | Heartlein et al. | |
| 10,577,630 B2 | 3/2020 | Zhang et al. | |
| 10,767,175 B2 | 9/2020 | Dellinger et al. | |
| 10,787,647 B2 | 9/2020 | Abul-Husn et al. | |
| 10,961,583 B2 | 3/2021 | Xin et al. | |
| 11,702,700 B2 * | 7/2023 | Xin ..................... | C12Q 1/6883 514/789 |
| 2003/0004102 A1 | 1/2003 | Ashkenazi | |
| 2005/0158376 A1 | 7/2005 | Sardi et al. | |
| 2007/0219169 A1 | 9/2007 | Becourt et al. | |
| 2008/0300170 A1 | 12/2008 | Gelber et al. | |
| 2009/0169585 A1 | 7/2009 | Sardi | |
| 2009/0203602 A1 | 8/2009 | Gelber et al. | |

(Continued)

FOREIGN PATENT DOCUMENTS

| | | |
|---|---|---|
| CN | 104698108 | 6/2015 |
| CN | 103520724 B | 5/2016 |

(Continued)

OTHER PUBLICATIONS

Official Action dated Jun. 12, 2019 issued in related U.S. Appl. No. 15/875,192 (189238.00801 (3015)).

(Continued)

*Primary Examiner* — Carla J Myers

(74) *Attorney, Agent, or Firm* — Armstrong Teasdale LLP

(57) ABSTRACT

The disclosure provides methods of identifying a human subject as a candidate for treating or inhibiting a liver disease by inhibiting HSD17B13. The disclosure also provides methods of treating a subject who is PNPLA3 Ile148Met+ by administering an inhibitor of HSD17B13. The disclosure also provides method of detecting a PNPLA3 Ile148Met variant and functional HSD17B13 in a subject. The disclosure also provides method of identifying a subject having a protective effect against liver disease. The disclosure also provides inhibitors of HSD17B13 for use in the treatment of a liver disease.

14 Claims, 48 Drawing Sheets

Specification includes a Sequence Listing.

(56) References Cited

U.S. PATENT DOCUMENTS

| | | |
|---|---|---|
| 2010/0028879 A1 | 2/2010 | Labrie et al. |
| 2010/0056384 A1 | 3/2010 | Hobbs et al. |
| 2010/0209427 A1 | 8/2010 | Li et al. |
| 2010/0266618 A1 | 10/2010 | Stojdl et al. |
| 2010/0267052 A1 | 10/2010 | Gelber et al. |
| 2011/0130442 A1 | 6/2011 | Kosaka et al. |
| 2011/0262462 A1 | 10/2011 | Platt et al. |
| 2011/0129831 A1 | 12/2011 | Cargill et al. |
| 2012/0015904 A1 | 1/2012 | Sharp et al. |
| 2012/0028816 A1 | 2/2012 | Warren et al. |
| 2012/0058088 A1 | 3/2012 | Sardi |
| 2012/0276528 A1 | 11/2012 | Cargill et al. |
| 2013/0005596 A1 | 1/2013 | Gong et al. |
| 2013/0029873 A1 | 1/2013 | de Perrot et al. |
| 2013/0079241 A1 | 3/2013 | Luo et al. |
| 2013/0237454 A1 | 9/2013 | Schutzer |
| 2013/0309769 A1 | 11/2013 | Benvenisty et al. |
| 2014/0004153 A1 | 1/2014 | Cowing et al. |
| 2014/0011889 A1 | 1/2014 | Sardi |
| 2014/0045915 A1 | 2/2014 | Skog et al. |
| 2014/0057800 A1 | 2/2014 | Brattbakk et al. |
| 2014/0072957 A1 | 3/2014 | Huang et al. |
| 2014/0088120 A1 | 3/2014 | Dilly et al. |
| 2014/0163118 A1 | 6/2014 | Giuliani et al. |
| 2014/0179536 A1 | 6/2014 | Hobbs et al. |
| 2014/0295425 A1 | 10/2014 | Nagy |
| 2014/0329704 A1 | 11/2014 | Melton et al. |
| 2014/0363502 A1 | 12/2014 | Sardi |
| 2014/0378425 A1 | 12/2014 | Wilde et al. |
| 2015/0050728 A1 | 2/2015 | Benvenisty et al. |
| 2015/0079061 A1 | 3/2015 | Casey et al. |
| 2015/0079062 A1 | 3/2015 | Casey et al. |
| 2015/0366997 A1 | 12/2015 | Guild et al. |
| 2016/0024498 A1 | 1/2016 | Fitzgerald et al. |
| 2016/0030585 A1 | 2/2016 | Barnes et al. |
| 2016/0032388 A1 | 2/2016 | Huang et al. |
| 2016/0032395 A1 | 2/2016 | Davicioni et al. |
| 2016/0184458 A1 | 6/2016 | Heartlein et al. |
| 2016/0237501 A1 | 8/2016 | Sharp et al. |
| 2016/0320395 A1 | 11/2016 | Ward et al. |
| 2016/0355806 A1 | 12/2016 | Lee et al. |
| 2016/0355813 A1 | 12/2016 | Lee et al. |
| 2016/0376598 A1 | 12/2016 | Lee et al. |
| 2017/0022504 A1 | 1/2017 | Lee et al. |
| 2017/0037396 A1 | 2/2017 | Lee et al. |
| 2017/0044550 A1 | 2/2017 | Lee et al. |
| 2017/0247758 A1 | 8/2017 | Spiller et al. |
| 2017/0247759 A1 | 8/2017 | Wilde et al. |
| 2017/0283770 A1 | 10/2017 | Lunyak |
| 2017/0335396 A1 | 11/2017 | Kennedy et al. |
| 2017/0340661 A1 | 11/2017 | Fitzgerald et al. |
| 2017/0349903 A1 | 12/2017 | Liu et al. |
| 2017/0356002 A1 | 12/2017 | Thompson et al. |
| 2018/0179553 A1 | 6/2018 | Watson et al. |
| 2018/0179593 A1 | 6/2018 | Melton et al. |
| 2018/0185516 A1 | 7/2018 | Ansell et al. |
| 2018/0201936 A1 | 7/2018 | Hinkle |
| 2018/0216084 A1 | 8/2018 | Abul-Husn et al. |
| 2018/0216104 A1 | 8/2018 | Abul-Husn et al. |
| 2018/0273955 A1 | 9/2018 | Fitzgerald et al. |
| 2019/0002869 A1 | 1/2019 | Yin et al. |
| 2019/0316121 A1 | 10/2019 | Smith et al. |
| 2019/0365924 A1 | 12/2019 | Conway et al. |
| 2019/0390195 A1 | 12/2019 | Tondera et al. |
| 2020/0354693 A1 | 11/2020 | Abul-Husn et al. |

FOREIGN PATENT DOCUMENTS

| | | |
|---|---|---|
| EP | 3011032 | 10/2019 |
| EP | 3620524 | 3/2020 |
| EP | 3011031 | 9/2020 |
| RU | 2545990 | 4/2015 |
| RU | 2562868 | 9/2015 |
| WO | 1995029255 | 11/1995 |
| WO | 9720942 | 6/1997 |
| WO | 1999046279 | 9/1999 |
| WO | 1999046281 | 9/1999 |
| WO | 2004110459 | 12/2004 |
| WO | 2005108415 | 11/2005 |
| WO | 2009039195 | 3/2009 |
| WO | 2010028110 | 3/2010 |
| WO | 2010040571 | 4/2010 |
| WO | 2010064702 | 6/2010 |
| WO | 2011006214 | 1/2011 |
| WO | 2011084747 | 7/2011 |
| WO | 2012052953 | 4/2012 |
| WO | 2012087983 | 6/2012 |
| WO | 2013126565 | 8/2013 |
| WO | 2013176772 | 11/2013 |
| WO | 2013177060 | 11/2013 |
| WO | 2013190075 | 12/2013 |
| WO | 2013166264 | 1/2014 |
| WO | 2014089313 | 6/2014 |
| WO | 2014196957 | 12/2014 |
| WO | 2015169971 | 11/2015 |
| WO | 2016004387 | 1/2016 |
| WO | 2016009246 | 1/2016 |
| WO | 2016130806 | 8/2016 |
| WO | 2017048620 | 3/2017 |
| WO | 2017106210 | 6/2017 |
| WO | 2017106283 | 6/2017 |
| WO | 2017106292 | 6/2017 |
| WO | 2017106364 | 6/2017 |
| WO | 2017106370 | 6/2017 |
| WO | 2017106375 | 6/2017 |
| WO | 2017106382 | 6/2017 |
| WO | 2017156310 | 9/2017 |
| WO | 2017191274 | 11/2017 |
| WO | 2017211947 | 12/2017 |
| WO | 2018107026 | 6/2018 |
| WO | 2018107028 | 6/2018 |
| WO | 2018136702 | 7/2018 |
| WO | 2018136758 | 7/2018 |
| WO | 2018220211 | 12/2018 |
| WO | 2019183164 | 9/2019 |
| WO | 2019183329 | 9/2019 |
| WO | 2019237069 | 12/2019 |
| WO | 2019246203 | 12/2019 |
| WO | 2021003295 | 1/2021 |

OTHER PUBLICATIONS

RefSNP cluster report rs72613567 (printed Jun. 6, 2019 from ncbi.nlm.nih.gov).
GenBank accession DR004209 (submitted Jan. 2011, printed Jun. 10, 2019, from ncbi.nim.nih.gov).
Hassan et al., "Nonalcoholic fatty liver disease: A comprehensive review of a growing epidemic", World J Gastroenterology, 2014, 20(34), pp. 12082-12101.
Nemudryi et al., "TALEN and CRISPR/Cas Genome Editing Systems: Tools of Discovery", Acta Nature, 2014, 6 (No.3 (22)), pp. 19-40.
Sun et al., "The CRSPR/Cas9 system for gene editing and its potential application in pain research", Transl Perioper Pain Med, 2016, 1(3), pp. 22-33.
Anstee et al., "Genetic Factors That Affect Risk of Alcoholic and Nonalcoholic Fatty Liver Disease", Gastroenterology, 2016, 150(8), pp. 1728-1744.
Brooks et al., "Basics of Enzymatic Assays for HTS", Assay Guidance Manual, 2012, pp. 1-12.
Doan et al., "Breast cancer prognosis predicted by nuclear receptor-coregulator networks", Molecular Oncology, 2014, 8, pp. 998-1013.
Ducharme et al., "Minireview: Lipid Droplets in Lipogenesis and Lipolysis", Endocrinology, 2008, 149(3), pp. 942-949.
Jequier et al., "Water as an essential nutrient: the physiological basis of hydration", European Journal of Clinical Nutrition, 2010, 64, pp. 115-123.
Karlson, "Introduction to Modern Biochemistry: Chapter V Enzymes and Biocatalysis", Fourth Edition, 1975, pp. 74-100.
Kuhl et al., "Pharmacology of estrogens and progestogens: influence of different routes of administration", Climacteric, 2005, 8, pp. 3-63.

(56) References Cited

OTHER PUBLICATIONS

Labrie, "Multiple intracrine hormonal targets in the prostate: opportunities and challenges", BJU Int, 2007, 100, pp. 48-51.
Mashek et al., "Hepatic Lipid Droplet Biology: Getting to the Root of Fatty Liver", Hepatology, 2015, 62, pp. 964-967.
Su et al., "Comparative proteomic study reveals 17beta-HSD13 as a pathogenic protein in nonalcoholic fatty liver disease", PNAS, 2014, 111(31), pp. 11437-11442.
Wolf et al., "To err is human: Patient misinterpretations of prescription drug label instructions", Patient Education and Counseling, 2007, 67, pp. 293-300.
Non-Final Office Action dated Sep. 8, 2021 in related U.S. Appl. No. 15/913,366 (189238.00101 (3023)(10350US01)).
Non-Final Office Action mailed Feb. 4, 2022 for U.S. Appl. No. 15/875,192 (189238.00801 (3015) (10263US01)).
Rao et al., "Genotyping single nucleotide polymorphisms directly from genomic DNA by invasive cleavage reaction on microspheres", Nucleic Acids Research, 2003, 31(11), pp. 1-8.
Stevens et al., "Analysis of single nucleotide polymorphisms with solid phase invasive cleavage reactions", Nucleic Acid Research, 2001, 29(16), pp. 1-8.
Final Office Action mailed May 5, 2022 for U.S. Appl. No. 15/913,366 (189238.00101 (3023) (10350US01)).
Third Party Submission filed Feb. 25, 2022 in U.S. Appl. No. 16,978,947.
Elphick et al., "Conserved valproic-acid-induced lipid droplet formation in Dictyostelium and human hepatocytes identifies structurally active compounds", Disease Models & Mechanisms, 2012, pp. 231-240.
Del Ben et al., "Non-alcoholic fatty liver disease, metabolic syndrome and patatin-like phospholipase domain-containing protein3 gene variants", European Journal of Internal Medicine, 2014, 25, pp. 566-570.
Advisory Action dated Jan. 27, 2023 in related U.S. Appl. No. 15/875,192.
Notice of Allowance dated Apr. 26, 2023 in related U.S. Appl. No. 17/709,965.
Notice of Allowance dated Jul. 18, 2023 in related U.S. Appl. No. 15/875,192.
Notice of Allowance dated Jul. 26, 2023 in related U.S. Appl. No. 15/875,192.
UniProtKB-Q7Z5P4-1, "17-beta-hydroxysteroid dehydrogenase 13", 2003, pp. 6.
UniProtKB-Q7Z5P4-2, "17-beta-hydroxysteroid dehydrogenase 13", 2003, pp. 6-7.
Van Der Meer, A. J., et al., "Association Between Sustained Virological Response and All-Cause Mortality Among Patients With Chronic Hepatitis C and Advanced Hepatic Fibrosis", JAMA, 2012. pp. 2584-2593, 308(24).
Victor, R. G., et al., "The Dallas Heart Study: A Population-Based Probability Sample for the Multidisciplinary Study of Ethnic Differences in Cardiovascular Health", Am J Cardiol, 2004, pp. 1473-1480, 93.
Willer, C. J., et al., "METAL: fast and efficient meta-analysis of genomewide association scans", Bioinformatics, 2010, pp. 2190-2191, 26(17).
Williams, C. D., et al., "Clinical Advances in Liver, Pancreas, and Biliary Tract", Gastroenterology, 2011, pp. 124-131, 140.
Wong, R. J., et al., "Nonalcoholic Steatohepatitis Is the Second Leading Etiology of Liver Disease Among Adults Awaiting Liver Transplantation in the United States", Gastroenterology, 2015, pp. 547-555, 148.
Yang, J., et al., "GCTA: A Tool for Genome-wide Complex Trait Analysis", The American Journal of Human Genetics, 2011, pp. 76-82, 88.
Younossi, Z. M., et al., "Changes in the Prevalence of the Most Common Causes of Chronic Liver Diseases in the United States From 1988 to 2008", Clinical Gastroenterology and Hepatology, 2011, pp. 524-530, 9.

Yuan, X., et al., "Population-Based Genome-wide Association Studies Reveal Six Loci Influencing Plasma Levels of Liver Enzymes", The American Journal of Human Genetics, 2008, pp. 520-528, 83.
Zhang, J., et al., "PowerBLAST: A New Network BLAST Application for Interactive of Automated Sequence Analysis and Annotation", Genome Research, 1997, pp. 649-656, 7.
Kitamoto et al., "Association of polymorphisms in GCKR and TRIB1 with nonalcoholic fatty liver disease and metabolic syndrome traits", Endocrine Journal, 2014, 61(7), pp. 683-689.
Edelman et al., "Genetic analysis of nonalcoholic fatty liver disease within a Caribbean-Hispanic population", Molecular Genetics & Genomic Medicine, 2015, 3(6), pp. 558-569.
Hotta et al., "R association of the rs738409 polymorphism in PNPLA3 with liver damage and the development of nonalcoholic fatty liver disease", BMC Medical Genetics, 2010, 11(172), pp. 1-10.
Kahali et al., "Insights from Genome-Wide Association Analyses of Nonalcoholic Fatty Liver Disease", Seminars in Liver Disease, 2015, 35(4), pp. 375-391.
Oniki et al., "Influence of the PNPLA3 rs738409 Polymorphism on Non-Alcoholic Fatty Liver Disease and Renal Function among Normal Weight Subjects", PLoS One, 2015, 10(7), pp. e0132640.
Shen et al., "The rs738409 (I148M) variant of the PNPLA3 gene and cirrhosis: a meta-analysis", Journal of Lipid Research, 2015, 56(1), pp. 167-175.
Office Action dated Feb. 4, 2020 in related U.S. Appl. No. 15/913,366 (189238.00101 (3023).
Leippe et al., "Bioluminescent Nicotinamide Adenine Dinucleotide Detection Assays Part 1: Technology and Features", 2014, hhttp://www.promega.com/resources/pubhub/bioluminescent-nicotinamide-adenine-dinucleotide-detection-assays/.
New England Biolabs Catalog, "Nucleic Acids, Linkers and Primers", 1998/199, pp. 121 and 284.
Schiavinato et al., "EMILIN-3, Peculiar Member of Elastin Microfibril Interface-located Protein (EMILIN) Family, Has Distinct Expression Pattern, Forms Oligomeric Assemblies, and Serves as Transforming Growth Factor B (TGF-B) Antagonist", Journal of Biological Chemistry, 2012, 187(14), pp. 11498-11515.
SNP(ss) Report in Submission Format for NCBI Assay Id (ss#): ss557289122, 2012, www.ncbi.nlm.gov/.
Non-Final Office Action dated Mar. 12, 2020 in related U.S. Appl. No. 15/875,192 (189238.00801 (3015)).
Ghanbari, et al., "Genetic Variations in MicroRNA-Binding Sites Affect MicroRNA-Mediated Regulation of Several Genes Associated With Cardio-metabolic Phenotypes," Circ. Cardiovasc. Genet., 2015, 8(3), pp. 473-486.
Gieger, et al., "New gene functions in megakaryopoiesis and platelet formation," Nature,2012, 480(7376), pp. 201-208 plus Supplementary Information.
Haapaniemi et al., "CRISPR-Cas9 genome editing induces a p53-mediated DNA damage response," Nat. Med. doi: 10.1038/s41591-018-0049-z, (Jun. 11, 2018, epub ahead of print).
Ihry et al., "p53 inhibits CRISPR-Cas9 engineering in human pluripotent stem cells," Nat. Med. doi: 10.1038/s41591-018-0050-6 (Jun. 11, 2018, epub ahead of print).
Jiang et al., "Structural Biology. A Cas9-guide RNA complex preorganized for target DNA recognition," Science, 2015, 348(6242), pp. 1477-1481.
Jinek et al., "RNA-programmed genome editing in human cells," eLife, 2013, 2:e00471.
Komor et al., "CRISPR-Based Technologies for the Manipulation of Eukaryotic Genomes," Cell, 2017, 168(1-2), pp. 20-36.
Kosicki et al., "Repair of double-strand breaks induced by CRISPR-Cas9 leads to large deletions and complex rearrangements," Nat. Biotechnol., 2018, 36(8), pp. 765-771.
Nishimasu et al., "Crystal Structure of Cas9 in Complex with Guide RNA and Target DNA," Cell, 2014, 156(5), pp. 935-949.
PubMed NCBI Search Results for ((CRISPR[Title] or Cas9[Title]) and ("Jan. 1, 2012"[PDate]: "Jan. 22, 2017")), https://www.ncbi.nlm.nih.gov/pubmed, retrieved on Sep. 22, 2019.
Quadri, et al., "Mutations in SLC30A10 Cause Parkinsonism and Dystonia with Hypermanganesemia, Polycthemia, and Chronic Liver

(56) References Cited

OTHER PUBLICATIONS

Disease," The American Journal of Human Genetics, 2012, 90, pp. 467-477 plus Supplemental Material.
Ratziu, et al., "Current efforts and trends in the treatment of NASH," Journal of Hepatology, 2015, 62, pp. S65-S75.
Santa Cruz Biotechnology, "17β-HSD13 Antibody (K-14): sc-161285" [Retrieved from the Internet Jun. 1, 2016: www.scbt.com/datasheet-161285-17betahsd13-k-14-antibody.html].
Santa Cruz Biotechnology, "17β-HSD13 siRNA (m), shRNA and Lentiviral Particle Gene Silencers" [Retrieved from the Internet Jun. 1, 2016: www.scbt.com/datasheet-108263-17beta-hsd13-sima-m. html].
Tang, et al., "A mouse knockout library for secreted and transmembrane proteins," Nature Biotechnology, 2010, 28(7), pp. 749-755 plus Online Methods and Supplementary Information.
Non-Final Office Action mailed Jul. 10, 2019 for U.S. Appl. No. 15/875,514.
Notice of Allowance mailed Jan. 22, 2020 in U.S. Appl. No. 15/875,514.
International Search Report and Written Opinion of the International Searching Authority mailed Jun. 6, 2018 for WIPO Application No. PCT/US2018/014454.
Notice of Allowance mailed May 1, 2020 in U.S. Appl. No. 15/875,514.
Moeller et al., "Multifunctionality of human 17β-hydroxysteriod dehydrogenases", Molecular and Cellular Endocrinology, 2006, 248, pp. 47-55.
Final Office Action mailed Sep. 22, 2020 for U.S. Appl. No. 15/913,366 (189238.00101 (3023) (10350US01)).
Final Office Action mailed Dec. 3, 2020 for U.S. Appl. No. 15/875,192 (189238.00801 (3015) (10263US01)).
Business Wire, "Arrowhead Pharmaceuticals Initiates Phase ½ Study of ARO-HSD in Normal Healthy Volunteers and Patients with NASH of Suspected NASH", Mar. 3, 2020, pp. 1-2. businesswire. com/news/home/20200303005396/en/Arrowhead-Pharmaceuticals-Initiates-Phase-12-Study-ARO-HSD.
Zhang et al., "Omic studies reveal the pathogenic lipid droplet proteins in non-alcoholic fatty liver disease", Protein Cell, 2017, 8(1), pp. 4-13.
International Search Report/Written Opinion dated Jun. 26, 2019 received in application No. PCT/US19/23079.
G. Sivan et al., "Identification of Restriction Factors by Human Genome-Wide RNA Interference Screening of Viral Host Range Mutants Exemplified by Discovery of SAMD9 and WDR6 as Inhibitors of the Vaccinia K1L-C7L-Mutant", mBIO, 2015, 6(4):e01122-15.
S.Q. Tsai and K. Young, "Defining and improving the genome-wide specificities of CRISPR-Cas9 nucleases", Nature Reviews Genetics, 2016, 17:300-312.
Zhang et al., "HSD17B13: A Potential Therapeutic Target for NAFLD", Frontiers in Molecular Biosciences, 2022, 8, pp. 1-8.
Ma et al., "Hsd17b13 Deficiency Does Not Protect Mice From Obesogenic Diet Injury", Hepatology, 2021, 73(5), pp. 1701-1716.
Thamm et al., "Discovery of a Novel Potent and Selective HSD17B13 Inhibitor, BI-3231, a Well-Characterized Chemical Probe Available for Open Science", Journal of Medicinal Chemistry, 2023, 66(4), pp. 2832-2850.
Mak et al., "A phase I/II study of ARO-HSD, an RNA interference therapeutic for the treatment of non-alcoholic steatohepatitis", Journal of Hepatology, 2022, 78(4), pp. 684-692.
Vilar-Gomez et al., "The Protection Conferred by HSD17B13 rs72613567 Polymorphism on Risk of Steatohepatitis and Fibrosis May Be Limited to Selected Subgroups of Patients With NAFLD", Clinical and Translational Gastroenterology, 2021, 12(9), pp. 1-13.
Abul-Husn et al., "A Protein-Truncating HSD17B13 Variant and Protection from Chronic Liver Disease", N Engl J Med, 2018, 378, pp. 1096-1106.
Adam, M., et al., "Hydroxysteroid (17b) dehydrogenase 13 deficiency triggers hepatic steatosis and inflammation in mice", The FASEB Journal, 2018, pp. 1-14.

Altschul, S. F., et al., "Basic Local Alignment Search Tool", J. Mol. Biol., 1990, pp. 403-410, 215.
Altschul, S. F., et al., "Gapped BLAST and PSI-BLAST: a new generation of protein database search programs", Nucleic Acids Research, 1997, pp. 3389-3402, 25 (17).
Brantly et al., "Crystal RG. Molecular basis of alpha-1-antitrypsin deficiency", Am J Med, 1988, pp. 13-31, 84.
Brasaemle, D. L., et al., "Isolation of Lipid Droplets from Cells by Density Gradient Centrifugation", Current Protocols in Cell Biology, 2005, 3.15.1-3.15.12.
Browning, J. D., et al., "Prevalence of Hepatic Steatosis in an Urban Population in the United States: Impact of Ethnicity", Hepatology, 2004, pp. 1387-1395, 40(6).
Chambers, J. C., et al., "Genome-wide association study identifies loci influencing concentrations of liver enzymes in plasma" Nat Genet, 2011, pp. 1131-1138, 43(11).
Cohen, J. C., et al., "Human Fatty Liver Disease: Old Questions and New Insights", Science, 2011, pp. 1519-1523, 332.
Denny, J. C., et al., "PheWAS: demonstrating the feasibility of a phenome-wide scan to discover gene-disease associations", Bioinformatics, 2010, pp. 1205-1210, 26(9).
Denny, J. C., et al., "Systematic comparison of phenome-wide association study of electronic medical record data and genome-wide association study data", Nat Biotechnol, 2013, pp. 1102-1110, 31(12).
Dewey, F. E., et al., "Distribution and clinical impact of functional variants in 50,726 whole-exome sequences from the DiscovEHR Study", Science, 2016, pp. aaf6814, 354(6319).
Ding, Y., et al., "Isolating lipid droplets from multiple species", Nature Protocols, 2013, pp. 43-51, 8(1).
Feitosa et al., "The ERLIN1-CHUK-CWF19L1 gene cluster influences liver fat deposition and hepatic inflammation in the NHLBI Family Heart Study", Atherosclerosis, 2013, pp. 175-180, 228.
Ford et al., "A New Assay for Picomole Levels of Androsterone and Testosterone Using Co-immobilized Luciferase, Oxidoreductase, and Steroid Dehydrogenase", Analytical Biochemistry, 1981, 110, pp. 43-48.
Huang et al., "Expression and Characterization of a PNPLA3 Protein Isoform (I148M) Associated with Nonalcoholic Fatty Liver Disease", J Biol Chem, 2011, pp. 37085-37093, 286.
International Search Report and Written Opinion for PCT Application PCT/US2018/014357 (189238.00802 (3016) (10263WO01)).
Kampf, C., et al., "The human liver-specific proteome defined by transcriptomics and antibody-based profiling", The FASEB Journal, 2014, pp. 2901-2914, 28(7).
Kitamoto et al., "Genome-wide scan revealed that polymorphisms in the PNPLA3, SAMM50, and PARVB genes are associated with development and progression of nonalcoholic fatty liver disease in Japan", Hum Genet, 2013, pp. 783-792, 132.
Kleiner, D. E., et al., "Design and Validation of a Histological Scoring System for Nonalcoholic Fatty Liver Disease", Hepatology, 2005, pp. 1313-1321, 41(6).
Kochanek, K. D., et al., "Deaths: Final Data for 2014", National Viral Statistics Reports, 2016, pp. 1-122, 65(4).
Kozlitina, J., et al., "Exome-wide association study identifies a TM6SF2 variant that confers susceptibility to nonalcoholic fatty liver disease", Nat Genet, 2014, pp. 352-356, 46(4).
Krazeisen et al., "Phytoestrogens inhibit human 17β-hydroxysteroid dehydrogenase type 5", Molecular and Cellular Endocrinology, 2001, 171, pp. 151-162.
Lazo, M., et al., "Prevalence of Nonalcoholic Fatty Liver Disease in the United States: The Third National Health and Nutrition Examination Survey, 1988-1994", Am J Epidemiol, 2013, pp. 38-45, 178(1).
Li, H., et al., "Fast and accurate short read alignment with Burrows-Wheeler transform", Bioinformatics, 2009, pp. 1754-1760, 25(14).
Li, P., et al., "LTB4 causes macrophage-mediated inflammation and directly induces insulin resistance in obesity", Nat Med, 2015, pp. 239-247, 21(3).
Liu, S., et al., "Molecular cloning and expression analysis of a new gene for shortchain dehydrogenase/reductase 9", Acta Biochimica Polonica, 2007, pp. 213-218, 54(1).

(56) References Cited

OTHER PUBLICATIONS

Liu, Y.-L., et al., "TM6SF2 rs58542926 influences hepatic fibrosis progression in patients with non-alcoholic fatty liver disease", Nature Communications, 2014, pp. 1-6, 5(4309).

Mahdessian et al., "TM6SF2 is a regulator of liver fat metabolism influencing triglyceride secretion and hepatic lipid droplet content", PNAS, 2014, pp. 8913-8918, 111.

McKenna, A., et al., "The Genome Analysis Toolkit: A MapReduce framework for analyzing next-generation DNA sequencing data", Genome Research, 2010, pp. 1297-1303, 20.

Moeller, G., et al., "Integrated view on 17betahydroxysteroid dehydrogenases", Molecular and Cellular Endocrinology, 2009, pp. 7-19, 301.

Morgan, R. L., et al., "Eradication of Hepatitis C Virus Infection and the Development of Hepatocellular Carcinoma", Annals of Internal Medicine, 2013, pp. 329-337 and W-158-W-160, 158(5)(Part 1).

NCBI Reference Sequence: NM_178135, "*Homo spiens* hydroxysteroid 17-beta dehydrogenase 13 (HSD17B13), transcript variant A, mRNA" 2017, pp. 1-5.

NCBI Reference Sequence: NM_001136230, "*Homo sapiens* hydroxysteroid 17-beta dehydrogenase 13 (HSD17B13), transcript variant B, mRNA" 2017, pp. 1-5.

NCBI Reference Sequence: NP_835236, "17-beta-hydroxysteroid dehydrogenase 13 isoform A precursor [*Homo sapiens*]", 2017 pp. 1-4.

NCBI Reference Sequence: NP_001129702, "17-beta-hydroxysteroid dehydrogenase 13 isoform B [*Homo sapiens*]", 2017, pp. 1-4.

Pirazzi et al., "Patatin-like phospholipase domain-containing 3 (PNPLA3) I148M (rs738409) affects hepatic VLDL secretion in humans and in vitro", J Hepatol, 2012, pp. 1276-1282, 57.

Promega "Technical Manual: NAD(P)H-Glo Detection System", 2017, TM398, pp. 1-15.

Pruim, R. J., et al., "LocusZoom: regional visualization of genome-wide association scan results", Bioinformatics, 2010, pp. 2336-2337, 26(18).

Reid, J. G., et al., "Launching genomics into the cloud: deployment of Mercury, a next generation sequence analysis pipeline", BMC Bioinformatics, 2014, pp. 1-11, 15(30).

Romeo, S., et al., "Genetic variation in PNPLA3 confers susceptibility to nonalcoholic fatty liver disease", Nat Genet, 2008, pp. 1461-1465, 40(12).

Rotman, Y., et al., "The Association of Genetic Variability in PNPLA3 with Histological Severity of Non-Alcoholic Fatty Liver Disease", Hepatology, 2010, pp. 894-903, 52(3).

Shen et al., "The rs738409 (I148M) variant of the PNPLA3 gene and cirrhosis: a meta-analysis", J Lipid Res, 2015, pp. 167-175, 56.

Smagris et al., "Inactivation of Tm6sf2, a Gene Defective in Fatty Liver Disease, Impairs Lipidation but Not Secretion of Very Low Density Lipoproteins", J Biol Chem, 2016, pp. 10659-10676, 291.

Smith, T. F., et al., "Comparsion of Biosequences", Advances in Applied Mathematics, 1981, pp. 482-489, 2.

Sookoian, S., et al., "A nonsynonymous gene variant in the adiponutrin gene is associated with nonalcoholic fatty liver disease severity", Journal of Lipid Research, 2009, pp. 2111-2116, 50.

Sookoian, S., et al., "Genetic Variation in Transmembrane 6 Superfamily Member 2 and the Risk of Nonalcoholic Fatty Liver Disease and Histological Disease Severity", Hepatology, 2015, pp. 515-525, 61(2).

Speliotes, E. K., et al., "Genome-Wide Association Analysis Identifies Variants Associated with Nonalcoholic Fatty Liver Disease That Have Distinct Effects on Metabolic Traits", PLoS Genetics, 2011, e1001324, 7(3).

Su, W., et al., "Comparative proteomic study reveals 17!-HSD13 as a pathogenic protein in nonalcoholic fatty liver disease", PNAS, 2014, pp. 11437-11442, 111(31).

Trepo, E., et al., "PNPLA3 gene in liver diseases", Journal of Hepatology, 2016, pp. 399-412, 65.

Final Office Action dated Oct. 15, 2024 in related U.S. Appl. No. 16/978,947.

GenBank accession BAZ46426, Human HSD12B13 transcript, Seq ID No. 41, 2014, pp. 1-2.

GenBank accession AED97982, Human membrane protein cDNA, Seq ID No. 697, 2008, pp. 1-2.

NCBI Reference Sequence: ss2030612272, 2016, pp. 1.

\* cited by examiner

| Characteristic | GHS Discovery Cohort (N = 46,544) | GHS Bariatric Surgery Cohort (N = 2,644) | Dallas Heart Study (N = 1,357) | Penn Medicine Biobank (N = 8,526) |
|---|---|---|---|---|
| Age (years) – median (IQR) | 63 (50 - 74) | 53 (44 - 61) | 46 (38 - 54) | 68 (60 - 76) |
| Female sex – number (%) | 26,875 (58) | 2,119 (80) | 724 (53) | 3,242 (38) |
| Body mass index – median (IQR) | 30 (25 - 45) | 47 (42 - 54) | 28 (25 - 32) | 30 (25 - 32) |
| Transaminase level (U/L) – median (IQR) | | | | |
| Alanine aminotransferase (ALT) | 22.0 (17.0 - 29.0) | 23.0 (17.5 - 29.5) | 20.0 (15.0 - 27.0) | 22.0 (17.0 - 30.0) |
| Aspartate aminotransferase (AST) | 23.0 (20.0 - 27.5) | 23.0 (20.0 - 27.0) | 21.0 (18.0 - 25.0) | 24.0 (20.0 - 30.5) |
| Presence of liver disease – N (%) | | | | |
| Alcoholic liver disease | 197 (0.4) | 7 (0.3) | - | - |
| Alcoholic cirrhosis | 130 (0.3) | 3 (0.1) | - | - |
| Nonalcoholic (non-viral) liver disease | 1,938 (4.2) | 1,543 (58.4) | - | - |
| Nonalcoholic cirrhosis | 382 (0.8) | 24 (0.9) | - | - |
| Hepatocellular carcinoma | 76 (0.2) | 1 (0.04) | - | - |
| No liver disease | 30,628 (65.8) | 1 (0.04) | - | - |

Figure 1

| Trait | Chr | BP | Ref | Alt | rsID | Gene | Annotation | AA Substitution | Beta (SE) | P | AAF | N |
|---|---|---|---|---|---|---|---|---|---|---|---|---|
| ALT | 1 | 220970028 | A | G | rs2642438 | MARC1 | missense | p.Thr165Ala | 0.008 (0.001) | 4.67E-08 | 0.7067 | 40,834 |
| | 4 | 88231392 | T | TA | rs72613567 | HSD17B13 | splice donor | | -0.009 (0.001) | 4.16E-12 | 0.2634 | 40,834 |
| | 8 | 144997604 | C | T | rs371119003 | PLEC | missense | p.Ala2302Thr | -0.160 (0.026) | 1.30E-09 | 0.0005 | 40,833 |
| | 8 | 145008502 | G | A | | PLEC | missense | p.Arg522Cys | -0.268 (0.032) | 3.26E-17 | 0.0003 | 40,834 |
| | 8 | 145692918 | G | A | rs35968570 | KIFC2 | missense | p.Glu174Lys | -0.033 (0.005) | 1.40E-11 | 0.0139 | 40,834 |
| | 8 | 145730072 | G | A | rs143408057 | GPT | missense | p.Arg83His | -0.314 (0.036) | 3.28E-18 | 0.0003 | 40,834 |
| | 8 | 145730161 | C | T | rs201815297 | GPT | missense | p.Ala87Val | -0.224 (0.014) | 6.28E-59 | 0.0018 | 40,834 |
| | 8 | 145730221 | G | A | rs112574791 | GPT | missense | p.Arg107Lys | -0.033 (0.005) | 4.25E-11 | 0.0136 | 40,834 |
| | 8 | 145731636 | T | G | rs145155876 | GPT | stop gained | p.Tyr326* | -0.235 (0.031) | 1.76E-14 | 0.0004 | 40,814 |
| | 8 | 145732114 | G | C | rs141505249 | GPT | missense | p.Glu430Gln | -0.224 (0.013) | 8.84E-64 | 0.0019 | 40,795 |
| | 8 | 145732151 | G | A | rs143462595 | GPT | missense | p.Arg442His | -0.077 (0.013) | 1.18E-09 | 0.0021 | 40,826 |
| | 8 | 145732180 | G | C | rs147998249 | GPT | missense | p.Val452Leu | -0.225 (0.013) | 8.19E-65 | 0.0019 | 40,833 |
| | 8 | 145732305 | G | GC | | GPT | frameshift | p.Glu475fs | -0.271 (0.031) | 1.00E-18 | 0.0004 | 40,834 |
| | 8 | 145748532 | A | G | rs567402720 | LRRC24 | missense | p.Leu290Ser | -0.185 (0.028) | 3.42E-11 | 0.0004 | 40,813 |
| | 9 | 117122202 | C | T | rs3748177 | AKNA | synonymous | p.Glu755Glu | -0.007 (0.001) | 9.51E-09 | 0.5232 | 40,834 |
| | 9 | 117124731 | G | A | rs3748176 | AKNA | missense | p.Pro624Leu | -0.007 (0.001) | 4.31E-09 | 0.5230 | 40,832 |
| | 10 | 101595996 | T | A | rs17222773 | ABCC2 | missense | p.Val1188Glu | -0.015 (0.003) | 2.97E-08 | 0.0608 | 40,834 |
| | 10 | 101606861 | G | T | rs1137968 | ABCC2 | synonymous | p.Val1430Val | -0.015 (0.003) | 2.71E-08 | 0.0608 | 40,834 |
| | 10 | 101610533 | C | T | rs8187707 | ABCC2 | synonymous | p.His1496His | -0.015 (0.003) | 2.77E-08 | 0.0608 | 40,834 |
| | 10 | 101611294 | G | A | rs8187710 | ABCC2 | missense | p.Cys1515Tyr | -0.015 (0.003) | 2.15E-08 | 0.0611 | 40,834 |
| | 10 | 101912064 | T | C | rs2862954 | ERLIN1 | missense | p.Ile291Val | 0.012 (0.001) | 2.43E-21 | 0.4755 | 40,834 |

Gray shading indicates variants having exome-wide-significant associations with both ALT and AST.
Abbreviations: AAF, alternate allele frequency; Alt, alternate allele; ALT, alanine aminotransferase; AST, aspartate aminotransferase; Ref, reference allele; SE, standard error;

Figure 2

| Trait | Chr | BP | Ref | Alt | rsID | Gene | Annotation | AA Substitution | N Ref/Ref | N Ref/Alt | N Alt/Alt | Mean ALT or AST level (U/L) Ref/Ref | Ref/Alt | Alt/Alt |
|---|---|---|---|---|---|---|---|---|---|---|---|---|---|---|
| ALT | 1 | 2.2E+08 | A | G | rs2642438 | MARC1 | missense | p.Thr165Ala | 3,515 | 17,262 | 20,637 | 23.88 | 24.52 | 24.92 |
|  | 4 | 8.8E+07 | T | TA | rs72613567 | HSD17B13 | splice donor |  | 22,441 | 16,130 | 2,843 | 25.02 | 24.26 | 24.1 |
|  | 8 | 1.4E+08 | C | T | rs371119203 | PLEC | missense | p.Ala2302Thr | 41,373 | 40 | 0 | 24.67 | 18.1 | NA |
|  | 8 | 1.5E+08 | G | A | | PLEC | missense | p.Arg522Cys | 41,387 | 27 | 0 | 24.67 | 13.8 | NA |
|  | 8 | 1.5E+08 | G | A | rs35968570 | KIF9 | missense | p.Glu174Lys | 40,271 | 1,133 | 10 | 24.67 | 12.07 | NA |
|  | 8 | 1.5E+08 | G | A | rs143408057 | GPT | missense | p.Arg83His | 41,393 | 21 | 0 | 24.67 | 12.07 | NA |
|  | 8 | 1.5E+08 | C | T | rs201815297 | GPT | missense | p.Ala87Val | 41,270 | 144 | 0 | 24.7 | 14.68 | NA |
|  | 8 | 1.5E+08 | G | A | rs112574791 | GPT | missense | p.Arg107Lys | 40,293 | 1,111 | 10 | 24.71 | 23.09 | 18.35 |
|  | 8 | 1.5E+08 | T | G | rs145155876 | GPT | stop gained | p.Tyr326* | 41,364 | 30 | 0 | 24.67 | 14.07 | NA |
|  | 8 | 1.5E+08 | G | C | rs141505249 | GPT | missense | p.Glu438Gln | 41,223 | 150 | 2 | 24.7 | 14.48 | 13.75 |
|  | 8 | 1.5E+08 | G | A | rs143462595 | GPT | missense | p.Arg442His | 41,232 | 174 | 0 | 24.68 | 20.87 | NA |
|  | 8 | 1.5E+08 | G | C | rs147998249 | GPT | missense | p.Val452Leu | 41,254 | 159 | 0 | 24.7 | 14.74 | NA |
|  | 8 | 1.5E+08 | G | GC | | GPT | frameshift | p.Glu475fs | 41,385 | 29 | 0 | 24.67 | 14.24 | NA |
|  | 8 | 1.5E+08 | A | G | rs567402720 | LRRC24 | missense | p.Leu290Ser | 41,358 | 35 | 0 | 24.67 | 17.71 | NA |
|  | 9 | 1.2E+08 | C | T | rs3748177 | AKNA | synonymous | p.Glu755Glu | 9,414 | 20,645 | 11,355 | 25.12 | 24.72 | 24.18 |
|  | 9 | 1.2E+08 | G | A | rs3748176 | AKNA | missense | p.Pro624Leu | 9,427 | 20,634 | 11,351 | 25.12 | 24.73 | 24.17 |
|  | 10 | 1E+08 | T | A | rs17222723 | ABCC2 | missense | p.Val1188Glu | 36,543 | 4,704 | 167 | 24.77 | 23.97 | 22.12 |
|  | 10 | 1E+08 | G | T | rs1137968 | ABCC2 | synonymous | p.Val1430Val | 36,543 | 4,704 | 167 | 24.77 | 23.97 | 22.04 |
|  | 10 | 1E+08 | C | T | rs8187707 | ABCC2 | synonymous | p.His1496His | 36,542 | 4,706 | 166 | 24.77 | 23.97 | 22.03 |
|  | 10 | 1E+08 | G | A | rs8187710 | ABCC2 | missense | p.Cys1515Tyr | 36,519 | 4,726 | 169 | 24.77 | 23.97 | 21.99 |
|  | 10 | 1E+08 | T | C | rs2862984 | ERLIN1 | missense | p.Ile291Val | 11,318 | 20,819 | 9,277 | 25.32 | 24.71 | 23.77 |

Gray shading indicates variants having exome-wide-significant associations with both ALT and AST.

Abbreviations: AAF, alternate allele frequency; Alt, alternate allele; ALT, alanine aminotransferase; AST, aspartate aminotransferase; Ref, reference allele; SE, standard error;

Figure 2 (cont.)

| Trait | Chr | BP | Ref | Alt | rsID | Gene | Annotation | AA Substitution | Beta (SE) | P | AAF | N |
|---|---|---|---|---|---|---|---|---|---|---|---|---|
| | 10 | 101977883 | C | T | rs2230804 | CHUK | missense | p.Val268Ile | -0.009 (0.001) | 1.93E-13 | 0.5072 | 40,834 |
| | 10 | 113917085 | T | A | rs2254537 | GPAM | synonymous | p.Pro681Pro | -0.008 (0.001) | 4.61E-10 | 0.7073 | 40,834 |
| | 10 | 113940329 | T | C | rs2792751 | GPAM | missense | p.Ile43Val | -0.008 (0.001) | 2.54E-10 | 0.7097 | 40,832 |
| | 14 | 94844947 | C | T | rs28929474 | SERPINA1 | missense | p.Glu366Lys | 0.042 (0.005) | 9.28E-21 | 0.0171 | 40,834 |
| | 19 | 19379549 | C | T | rs58542926 | TM6SF2 | missense | p.Glu167Lys | 0.014 (0.002) | 4.76E-09 | 0.0759 | 40,833 |
| | 22 | 44324727 | C | G | rs738409 | PNPLA3 | missense | p.Ile148Met | 0.023 (0.002) | 1.34E-50 | 0.2351 | 40,834 |
| | 22 | 44324730 | C | T | rs738408 | PNPLA3 | synonymous | p.Pro149Pro | 0.023 (0.002) | 1.11E-50 | 0.2349 | 40,834 |
| | 22 | 44342116 | A | G | rs2294918 | PNPLA3 | missense | p.Lys434Glu | 0.007 (0.001) | 8.26E-08 | 0.5986 | 40,832 |
| | 22 | 44368122 | A | G | rs3761472 | SAMM50 | missense | p.Asp110Gly | 0.019 (0.002) | 8.85E-30 | 0.1682 | 40,833 |
| | 22 | 44395451 | T | C | rs1007863 | PARVB | missense | p.Trp37Arg | 0.011 (0.001) | 7.98E-16 | 0.3963 | 40,834 |
| AST | 4 | 88231392 | T | TA | rs72613567 | HSD17B13 | splice donor | | -0.005 (0.001) | 6.24E-10 | 0.2638 | 40,193 |
| | 10 | 18242311 | A | G | rs10764176 | SLC39A12 | missense | p.Ser36Gly | -0.006 (0.001) | 1.09E-10 | 0.2881 | 40,193 |
| | 10 | 101157378 | CGTT | C | | GOT1 | inframe indel | p.Asn389del | -0.221 (0.024) | 1.96E-20 | 0.0002 | 40,193 |
| | 10 | 101165533 | G | C | rs374966349 | GOT1 | missense | p.Gln208Glu | 0.271 (0.027) | 2.43E-24 | 0.0002 | 40,193 |
| | 10 | 101912064 | T | C | rs2862954 | ERLIN1 | missense | p.Ile291Val | -0.005 (0.001) | 4.82E-09 | 0.4754 | 40,193 |
| | 11 | 22271870 | A | T | rs7481951 | ANO5 | missense | p.Leu322Phe | 0.004 (0.001) | 9.61E-08 | 0.5833 | 40,162 |
| | 14 | 94844947 | C | T | rs28929474 | SERPINA1 | missense | p.Glu366Lys | 0.027 (0.003) | 2.44E-20 | 0.0172 | 40,193 |
| | 19 | 19379549 | C | T | rs58542926 | TM6SF2 | missense | p.Glu167Lys | 0.008 (0.002) | 6.54E-08 | 0.0760 | 40,192 |
| | 22 | 44324727 | C | G | rs738409 | PNPLA3 | missense | p.Ile148Met | 0.014 (0.001) | 8.31E-46 | 0.2343 | 40,193 |
| | 22 | 44324730 | C | T | rs738408 | PNPLA3 | synonymous | p.Pro149Pro | 0.014 (0.001) | 8.93E-46 | 0.2341 | 40,193 |
| | 22 | 44368122 | A | G | rs3761472 | SAMM50 | missense | p.Asp110Gly | 0.011 (0.001) | 1.22E-22 | 0.1680 | 40,192 |
| | 22 | 44395451 | T | C | rs1007863 | PARVB | missense | p.Trp37Arg | 0.006 (0.001) | 1.31E-13 | 0.3961 | 40,193 |

Gray shading indicates variants having exome-wide-significant associations with both ALT and AST.

Abbreviations: AAF, alternate allele frequency; Alt, alternate allele; ALT, alanine aminotransferase; AST, aspartate aminotransferase; Ref, reference allele; SE, standard error.

Figure 2 (cont.)

| Trait | Chr | BP | Ref | Alt | rsID | Gene | Annotation | AA Substitution | N Ref/Ref | N Ref/Alt | N Alt/Alt | Mean ALT or AST level (U/L) Ref/Ref | Ref/Alt | Alt/Alt |
|---|---|---|---|---|---|---|---|---|---|---|---|---|---|---|
| | 10 | 101977883 | C | T | rs2230804 | CHUK | missense | p.Val268Ile | 10,048 | 20,733 | 10,633 | 25.18 | 24.75 | 24.01 |
| | 10 | 113917085 | T | A | rs2254537 | GPAM | synonymous | p.Pro681Pro | 3,627 | 16,984 | 20,803 | 25 | 24.97 | 24.36 |
| | 10 | 113940329 | T | C | rs2792751 | GPAM | missense | p.Ile43Val | 3,567 | 16,910 | 20,935 | 25 | 24.98 | 24.35 |
| | 14 | 94844947 | C | T | rs28929474 | SERPINA1 | missense | p.Glu366Lys | 40,006 | 1,399 | 9 | 24.58 | 16.91 | 43.89 |
| | 19 | 19379549 | C | T | rs58542926 | TM6SF2 | missense | p.Glu167Lys | 35,388 | 5,780 | 245 | 24.52 | 25.46 | 26.84 |
| | 22 | 44324727 | C | G | rs738409 | PNPLA3 | missense | p.Ile148Met | 24,257 | 14,837 | 2,320 | 24.06 | 24.99 | 28.91 |
| | 22 | 44324730 | C | T | rs738408 | PNPLA3 | synonymous | p.Pro149Pro | 24,273 | 14,824 | 2,317 | 24.06 | 24.98 | 28.92 |
| | 22 | 44342116 | A | G | rs2294918 | PNPLA3 | missense | p.Lys434Glu | 6,691 | 19,833 | 14,898 | 24.15 | 24.47 | 25.15 |
| | 22 | 44368122 | A | G | rs3761472 | SAMM50 | missense | p.Asp108Gly | 28,626 | 11,618 | 1,169 | 24.23 | 25.36 | 28.45 |
| | 22 | 44395451 | T | C | rs1007863 | PARVB | missense | p.Trp37Arg | 15,036 | 19,920 | 6,458 | 24.15 | 24.6 | 26.09 |
| AST | 4 | 88231392 | T | TA | rs72813567 | HSD17B13 | splice donor | | 22,068 | 15,870 | 2,815 | 24.47 | 24.1 | 23.96 |
| | 10 | 18242311 | A | G | rs10764176 | SLC39A12 | missense | p.Ser36Gly | 20,645 | 16,738 | 3,370 | 24.47 | 24.15 | 23.85 |
| | 10 | 101157378 | CGTT | C | rs3749663493 | GOT1 | inframe indel | p.Asn38del | 40,733 | 20 | 0 | 24.29 | 14.7 | NA |
| | 10 | 101165533 | G | C | | GOT1 | missense | p.Gln208Glu | 40,736 | 17 | 0 | 24.28 | 44.5 | NA |
| | 10 | 101912064 | T | C | rs2862954 | ERLIN1 | missense | p.Ile291Val | 11,139 | 20,486 | 9,129 | 24.59 | 24.26 | 23.99 |
| | 11 | 22271870 | A | T | rs7481951 | ANO5 | missense | p.Leu322Phe | 7,123 | 19,686 | 13,913 | 24.03 | 24.22 | 24.53 |
| | 14 | 94844947 | C | T | rs28929474 | SERPINA1 | missense | p.Glu366Lys | 39,361 | 1,384 | 8 | 24.24 | 25.76 | 34.5 |
| | 19 | 19379549 | C | T | rs58542926 | TM6SF2 | missense | p.Glu167Lys | 34,811 | 5,698 | 243 | 24.21 | 24.74 | 25.43 |
| | 22 | 44324727 | C | G | rs738409 | PNPLA3 | missense | p.Ile148Met | 23,889 | 14,622 | 2,242 | 23.96 | 24.48 | 26.62 |
| | 22 | 44324730 | C | T | rs738408 | PNPLA3 | synonymous | p.Pro149Pro | 23,905 | 14,609 | 2,239 | 23.96 | 24.47 | 26.63 |
| | 22 | 44368122 | A | G | rs3761472 | SAMM50 | missense | p.Asp108Gly | 28,170 | 11,450 | 1,132 | 24.07 | 24.64 | 26.24 |
| | 22 | 44395451 | T | C | rs1007863 | PARVB | missense | p.Trp37Arg | 14,761 | 19,678 | 6,314 | 24.02 | 24.23 | 25.1 |

Gray shading indicates variants having exome-wide-significant associations with both ALT and AST.

Abbreviations: AAF, alternate allele frequency; Alt, alternate allele; ALT, alanine aminotransferase; AST, aspartate aminotransferase; Ref, reference allele; SE, standard error.

Figure 2 (cont.)

| Trait | Chr | BP | Ref | Alt | RSID | Gene | Annotation | AA Substitution | GHS Discovery Cohort | | |
|---|---|---|---|---|---|---|---|---|---|---|---|
| | | | | | | | | | Beta (SE) | P discovery | N |
| ALT | 1 | 220970028 | A | G | rs2642438 | MARC1 | missense | p.Thr165Ala | 0.008 (0.001) | 4.67E-08 | 40834 |
| | 4 | 88231392 | T | TA | rs72613567 | HSD17B13 | splice donor | | -0.089 (0.001) | 4.16E-12 | 40834 |
| | 8 | 144997604 | C | T | rs371119003 | PLEC | missense | p.Ala2302Thr | -0.160 (0.026) | 1.30E-09 | 40833 |
| | 8 | 145608502 | G | A | | PLEC | missense | p.Arg522Cys | -0.268 (0.032) | 3.26E-17 | 40834 |
| | 8 | 145662918 | G | A | rs35968570 | KIFC2 | missense | p.Glu174Lys | -0.033 (0.005) | 1.40E-11 | 40834 |
| | 8 | 145730072 | G | A | rs1434408057 | GPT | missense | p.Arg83His | -0.314 (0.036) | 3.28E-18 | 40834 |
| | 8 | 145730161 | C | T | rs2018I5297 | GPT | missense | p.Ala87Val | -0.224 (0.014) | 6.28E-59 | 40834 |
| | 8 | 145730221 | G | A | rs112574791 | GPT | stop gained | p.Arg107Lys | -0.033 (0.005) | 4.25E-11 | 40814 |
| | 8 | 145731636 | T | G | rs145155876 | GPT | missense | p.Tyr326* | -0.235 (0.031) | 1.76E-14 | 40795 |
| | 8 | 145732114 | G | C | rs141505249 | GPT | missense | p.Glu430Gln | -0.224 (0.013) | 8.84E-64 | 40826 |
| | 8 | 145732151 | G | A | rs1434682595 | GPT | missense | p.Arg442His | -0.077 (0.013) | 1.18E-09 | 40833 |
| | 8 | 145732180 | G | C | rs147998249 | GPT | missense | p.Val452Leu | -0.225 (0.013) | 8.19E-65 | 40834 |
| | 8 | 145733305 | G | GC | | GPT | frameshift | p.Glu475fs | -0.271 (0.031) | 1.00E-18 | 40834 |
| | 8 | 145748532 | A | G | rs567402720 | LRRC24 | missense | p.Leu290Ser | -0.185 (0.028) | 3.42E-11 | 40813 |
| | 9 | 117122202 | C | T | rs3748177 | AKNA | synonymous | p.Glu755Glu | -0.007 (0.001) | 9.51E-09 | 40834 |
| | 9 | 117124731 | G | A | rs3748176 | AKNA | missense | p.Pro624Leu | -0.007 (0.001) | 4.31E-09 | 40832 |
| | 10 | 101595996 | T | A | rs17222723 | ABCC2 | missense | p.Val1188Glu | -0.015 (0.003) | 2.97E-08 | 40834 |

Gray shading indicates P-values meeting the Bonferroni significance threshold of P < 1.43x10-3

* Replication meta-analysis includes the three replication cohorts: GHS Bariatric Surgery Cohort, Dallas Heart Study, and Penn Medicine Biobank

* Joint meta-analysis includes the discovery cohort and the three replication cohorts: GHS Discovery Cohort, GHS Bariatric Surgery Cohort, Dallas Heart Study, and Penn Medicine Biobank Abbreviations: AAF, alternate allele frequency; Alt, alternate allele; ALT, alanine aminotransferase; AST, aspartate aminotransferase; Ref, reference allele; SE, standard error;

Figure 3

| Trait | Chr | BP | Ref | Alt | RSID | Gene | Annotation | AA Substitution | GHS Discovery Cohort Beta (SE) | GHS Discovery Cohort P discovery | GHS Discovery Cohort N |
|---|---|---|---|---|---|---|---|---|---|---|---|
| | 10 | 101606861 | G | T | rs113796 | ABCC2 | synonymous | p.Val1430Val | -0.015 (0.003) | 2.71E-08 | 40834 |
| | 10 | 101610533 | C | T | rs818770 | ABCC2 | synonymous | p.His1496His | -0.015 (0.003) | 2.77E-08 | 40834 |
| | 10 | 101611294 | G | A | rs818771 | ABCC2 | missense | p.Cys1515Tyr | -0.015 (0.003) | 2.15E-08 | 40834 |
| | 10 | 101912064 | T | C | rs286295 | ERLIN1 | missense | p.Ile291Val | -0.012 (0.001) | 2.43E-21 | 40834 |
| | 10 | 101977883 | C | T | rs223080 | CHUK | missense | p.Val268Ile | -0.009 (0.001) | 1.93E-13 | 40834 |
| | 10 | 113917085 | T | A | rs225453 | GPAM | synonymous | p.Pro681Pro | -0.008 (0.001) | 4.61E-10 | 40834 |
| | 10 | 113940329 | T | C | rs279275 | GPAM | missense | p.Ile43Val | -0.008 (0.001) | 2.54E-10 | 40832 |
| | 14 | 94844947 | C | T | rs289294 | SERPINA1 | missense | p.Glu366Lys | 0.042 (0.005) | 9.28E-21 | 40834 |
| | 19 | 19379549 | C | T | rs585429 | TM6SF2 | missense | p.Glu167Lys | 0.014 (0.002) | 4.76E-09 | 40833 |
| | 22 | 44324727 | C | G | rs738409 | PNPLA3 | missense | p.Ile148Met | 0.023 (0.002) | 1.34E-50 | 40834 |
| | 22 | 44324730 | C | T | rs738408 | PNPLA3 | synonymous | p.Pro149Pro | 0.023 (0.002) | 1.11E-50 | 40834 |
| | 22 | 44342116 | A | G | rs229491 | PNPLA3 | missense | p.Lys434Glu | 0.007 (0.001) | 8.26E-08 | 40832 |
| | 22 | 44368122 | A | G | rs376147 | SAMM50 | missense | p.Asp110Gly | 0.019 (0.002) | 8.85E-30 | 40833 |
| | 22 | 44395451 | T | C | rs100786 | PARVB | missense | p.Trp37Arg | 0.011 (0.001) | 7.98E-16 | 40834 |

Grey shading indicates P-values meeting the Bonferroni significance threshold of $P < 1.43 \times 10^{-3}$

* Replication meta-analysis includes the three replication cohorts: GHS Bariatric Surgery Cohort, Dallas Heart Study, and Penn Medicine Biobank

* Joint meta-analysis includes the discovery cohort and the three replication cohorts: GHS Discovery Cohort, GHS Bariatric Surgery Cohort, Dallas Heart Study, and Penn Medicine Biobank Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | BP | Ref | Alt | RSID | Gene | Annotation | AA Substitution | GHS Discovery Cohort | | |
|---|---|---|---|---|---|---|---|---|---|---|---|
| | | | | | | | | | Beta (SE) | P discovery | N |
| AST | 4 | 98231392 | T | TA | rs72613567 | HSD17B13 | splice donor | | -0.005 (0.001) | 6.24E-10 | 40193 |
| | 10 | 18242311 | A | G | rs10764176 | SLC39A12 | missense | p.Ser36Gly | -0.006 (0.001) | 1.09E-10 | 40193 |
| | 10 | 101157378 | CGTT | C | | GOT1 | inframe indel | p.Asn389del | -0.221 (0.024) | 1.96E-20 | 40193 |
| | 10 | 101165533 | G | C | rs374966349 | GOT1 | missense | p.Gln208Glu | 0.271 (0.027) | 2.43E-24 | 40193 |
| | 10 | 101912064 | T | C | rs2862954 | ERLIN1 | missense | p.Ile291Val | -0.005 (0.001) | 4.82E-09 | 40193 |
| | 11 | 22271870 | A | T | rs7481951 | ANO5 | missense | p.Leu322Phe | 0.004 (0.001) | 9.61E-08 | 40162 |
| | 14 | 94844947 | C | T | rs28929474 | SERPINA1 | missense | p.Glu366Lys | 0.027 (0.003) | 2.44E-20 | 40193 |
| | 19 | 19379549 | C | T | rs58542926 | TM6SF2 | missense | p.Glu167Lys | 0.008 (0.002) | 6.54E-08 | 40192 |
| | 22 | 44324727 | C | G | rs738409 | PNPLA3 | missense | p.Ile148Met | 0.014 (0.001) | 8.31E-46 | 40193 |
| | 22 | 44324730 | C | T | rs738408 | PNPLA3 | synonymous | p.Pro149Pro | 0.014 (0.001) | 8.93E-46 | 40193 |
| | 22 | 44368122 | A | G | rs3761472 | SAMM50 | missense | p.Asp110Gly | 0.011 (0.001) | 1.22E-22 | 40192 |
| | 22 | 44395451 | T | C | rs1807863 | PARVB | missense | p.Trp37Arg | 0.006 (0.001) | 1.31E-13 | 40193 |

Gray shading indicates P-values meeting the Bonferroni significance threshold of P < 1.43×10-3

* Replication meta-analysis includes the three replication cohorts: GHS Bariatric Sugery Cohort, Dallas Heart Study, and Penn Medicine Biobank

* Joint meta-analysis includes the discovery cohort and the three replication cohorts: GHS Discovery Cohort, GHS Bariatric Sugery Cohort, Dallas Heart Study, and Penn Medicine Biobank Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | GHS Bariatric Surgery Cohort | | | Replication Cohorts | | | | | |
|---|---|---|---|---|---|---|---|---|---|---|
| | | | | | Dallas Heart Study | | | Penn Medicine Biobank | | |
| | | Beta (SE) | P | N | Beta (SE) | P | N | Beta (SE) | P | N |
| ALT | 1 | 0.005 (0.005) | 3.10E-01 | 2475 | 0.009 (0.008) | 2.58E-01 | 1356 | 0.006 (0.004) | 1.81E-01 | 6158 |
| | 4 | -0.010 (0.005) | 5.57E-02 | 2475 | -0.014 (0.008) | 9.68E-02 | 1356 | -0.012 (0.004) | 4.85E-03 | 6158 |
| | 8 | -0.492 (0.165) | 2.84E-03 | 2475 | NA (NA) | NA | NA | -0.054 (0.071) | 4.46E-01 | 6158 |
| | 8 | -0.161 (0.165) | 3.29E-01 | 2475 | NA (NA) | NA | NA | -0.259 (0.143) | 6.90E-02 | 6158 |
| | 8 | -0.089 (0.02) | 6.48E-01 | 2475 | 0.027 (0.035) | 4.48E-01 | 1355 | -0.051 (0.019) | 7.52E-03 | 6158 |
| | 8 | -0.189 (0.165) | 2.50E-01 | 2475 | NA (NA) | NA | NA | -0.305 (0.101) | 2.54E-03 | 6158 |
| | 8 | -0.341 (0.074) | 3.64E-06 | 2475 | NA (NA) | NA | NA | -0.144 (0.054) | 7.67E-03 | 6158 |
| | 8 | -0.089 (0.02) | 6.45E-01 | 2475 | 0.024 (0.035) | 5.01E-01 | 1356 | -0.059 (0.018) | 1.13E-03 | 6158 |
| | 8 | -0.314 (0.165) | 5.71E-02 | 2475 | -0.334 (0.137) | 1.49E-02 | 1355 | -0.151 (0.143) | 2.90E-01 | 6157 |
| | 8 | -0.273 (0.048) | 9.83E-09 | 2474 | -0.244 (0.073) | 8.91E-04 | 1356 | -0.188 (0.041) | 5.52E-06 | 6157 |
| | 8 | -0.115 (0.058) | 4.82E-02 | 2475 | -0.092 (0.097) | 3.43E-01 | 1355 | -0.042 (0.043) | 3.36E-01 | 6157 |
| | 8 | -0.273 (0.050) | 4.26E-08 | 2475 | -0.198 (0.068) | 3.90E-03 | 1356 | -0.188 (0.041) | 5.52E-06 | 6158 |
| | 8 | -0.161 (0.165) | 3.29E-01 | 2475 | NA (NA) | NA | NA | -0.506 (0.202) | 1.22E-02 | 6158 |
| | 8 | -0.161 (0.165) | 3.29E-01 | 2475 | NA (NA) | NA | NA | -0.303 (0.143) | 3.37E-02 | NA |
| | 9 | -0.004 (0.005) | 4.09E-01 | 2475 | 0.003 (0.008) | 6.46E-01 | 1356 | -0.007 (0.004) | 6.38E-02 | 6158 |

Gray shading indicates P-values meeting the Bonferroni significance threshold of $P < 1.43 \times 10^{-3}$ \* Replication meta-analysis includes the three replication cohorts: GHS Bariatric Surgery Cohort, Dallas Heart Study, and Penn Medicine Biobank \* Joint meta-analysis includes the discovery cohort and the three replication cohorts: GHS Discovery Cohort, GHS Bariatric Surgery Cohort, Dallas Heart Study, and Penn Medicine Biobank Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | GHS Bariatric Surgery Cohort | | | Dallas Heart Study | | | Penn Medicine Biobank | | |
|---|---|---|---|---|---|---|---|---|---|---|
| | | Beta (SE) | P | N | Beta (SE) | P | N | Beta (SE) | P | N |
| | 9 | -0.004 (0.005) | 3.90E-01 | 2475 | 0.002 (0.008) | 7.69E-01 | 1355 | -0.007 (0.004) | 5.29E-02 | 6158 |
| | 10 | -0.002 (0.010) | 8.01E-01 | 2475 | -0.003 (0.017) | 8.37E-01 | 1356 | -0.015 (0.007) | 4.49E-02 | 6158 |
| | 10 | -0.003 (0.010) | 7.74E-01 | 2475 | -0.005 (0.017) | 7.49E-01 | 1356 | -0.014 (0.007) | 4.86E-02 | 6158 |
| | 10 | -0.003 (0.010) | 7.93E-01 | 2475 | -0.005 (0.017) | 7.49E-01 | 1356 | -0.014 (0.007) | 5.02E-02 | 6158 |
| | 10 | -0.001 (0.010) | 9.11E-01 | 2475 | -0.008 (0.016) | 6.41E-01 | 1356 | -0.013 (0.007) | 7.46E-02 | 6158 |
| | 10 | -0.01 (0.005) | 2.91E-02 | 2475 | -0.006 (0.007) | 4.02E-01 | 1356 | -0.009 (0.004) | 2.06E-02 | 6158 |
| | 10 | -0.006 (0.005) | 2.05E-01 | 2475 | -0.001 (0.007) | 9.07E-01 | 1356 | -0.011 (0.004) | 5.26E-03 | 6158 |
| | 10 | -0.003 (0.005) | 5.80E-01 | 2475 | -0.014 (0.008) | 8.25E-02 | 1356 | -0.007 (0.004) | 7.45E-02 | 6158 |
| | 10 | -0.003 (0.005) | 5.61E-01 | 2475 | -0.014 (0.008) | 9.08E-02 | 1356 | -0.008 (0.004) | 6.34E-02 | 6158 |
| | 14 | 0.035 (0.020) | 7.97E-02 | 2475 | 0.044 (0.032) | 1.63E-01 | 1356 | 0.056 (0.013) | 1.38E-05 | 6158 |
| | 19 | 0.040 (0.010) | 2.40E-05 | 2475 | 0.025 (0.014) | 7.24E-02 | 1356 | 0.013 (0.008) | 1.07E-01 | 6158 |
| | 22 | 0.019 (0.006) | 5.54E-04 | 2475 | 0.005 (0.009) | 5.75E-01 | 1356 | 0.018 (0.005) | 5.51E-05 | 6158 |
| | 22 | 0.019 (0.006) | 5.51E-04 | 2475 | 0.005 (0.009) | 5.75E-01 | 1356 | 0.018 (0.005) | 5.78E-05 | 6158 |
| | 22 | 0.001 (0.005) | 7.77E-01 | 2475 | 0.004 (0.008) | 6.26E-01 | 1356 | 0.005 (0.004) | 2.00E-01 | 6158 |
| | 22 | 0.009 (0.006) | 1.66E-01 | 2475 | -0.002 (0.01) | 8.80E-01 | 1356 | 0.021 (0.005) | 5.29E-05 | 6158 |
| | 22 | 0.003 (0.005) | 5.22E-01 | 2475 | 0.007 (0.008) | 3.31E-01 | 1356 | 0.008 (0.004) | 3.82E-02 | 6158 |

Gray shading indicates p-values meeting the Bonferroni significance threshold of $P < 1.43 \times 10^{-3}$.

\* Replication meta-analysis includes the three replication cohorts: GHS Bariatric Surgery Cohort, Dallas Heart Study, and Penn Medicine Biobank \* Joint meta-analysis includes the discovery cohort and the three replication cohorts: GHS Discovery Cohort, GHS Bariatric Surgery Cohort, Dallas Heart Study, and Penn Medicine Biobank Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | Replication Meta-analysis* (N=3) | | Joint Meta-analysis** (N=4) | |
|---|---|---|---|---|---|
| | | Beta (SE) | P replication | Beta (SE) | P joint |
| ALT | 1 | 0.006 (0.003) | 4.77E-02 | 0.007 (0.001) | 6.91E-09 |
| | 4 | -0.012 (0.003) | 1.67E-04 | -0.010 (0.001) | 3.85E-15 |
| | 8 | -0.124 (0.066) | 5.92E-02 | -0.155 (0.024) | 2.41E-10 |
| | 8 | -0.259 (0.143) | 6.90E-02 | -0.264 (0.03) | 4.65E-18 |
| | 8 | -0.024 (0.013) | 6.89E-02 | -0.032 (0.005) | 3.36E-12 |
| | 8 | -0.305 (0.101) | 2.54E-03 | -0.308 (0.033) | 2.21E-20 |
| | 8 | -0.213 (0.044) | 1.01E-06 | -0.223 (0.013) | 4.00E-64 |
| | 8 | -0.029 (0.013) | 2.09E-02 | -0.032 (0.005) | 2.89E-12 |
| | 8 | -0.264 (0.085) | 1.84E-03 | -0.238 (0.029) | 1.35E-16 |
| | 8 | -0.227 (0.029) | 2.39E-15 | -0.224 (0.012) | 1.94E-77 |
| | 8 | -0.070 (0.033) | 3.12E-02 | -0.076 (0.012) | 1.12E-10 |
| | 8 | -0.218 (0.029) | 3.94E-14 | -0.224 (0.012) | 2.92E-77 |
| | 8 | -0.506 (0.202) | 1.22E-02 | -0.272 (0.030) | 6.42E-20 |
| | 8 | -0.303 (0.143) | 3.37E-02 | -0.189 (0.027) | 2.99E-12 |
| | 9 | -0.005 (0.003) | 9.79E-02 | -0.007 (0.001) | 3.57E-09 |

Gray shading indicates P-values meeting the Bonferroni significance threshold of $P < 1.43 \times 10^{-3}$

* Replication meta-analysis includes the three replication cohorts: GHS Bariatric Sugery Cohort, Dallas Heart Study, and Penn Medicine Biobank

** Joint meta-analysis includes the discovery cohort and the three replication cohorts: GHS Discovery Cohort, GHS Bariatric Sugery Cohort, Dallas Heart Study, and Penn Medicine Biobank Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | Replication Meta-analysis* (N=3) | | Joint Meta-analysis** (N=4) | |
|---|---|---|---|---|---|
| | | Beta (SE) | P replication | Beta (SE) | P joint |
| | 9 | -0.005 (0.003) | 7.27E-02 | -0.007 (0.001) | 1.19E-09 |
| | 10 | -0.01 (0.006) | 8.55E-02 | -0.014 (0.002) | 9.49E-09 |
| | 10 | -0.01 (0.006) | 7.96E-02 | -0.014 (0.002) | 8.03E-09 |
| | 10 | -0.01 (0.006) | 8.38E-02 | -0.014 (0.002) | 8.70E-09 |
| | 10 | -0.009 (0.006) | 1.19E-01 | -0.014 (0.002) | 1.07E-08 |
| | 10 | -0.009 (0.003) | 1.14E-03 | -0.011 (0.001) | 1.76E-23 |
| | 10 | -0.008 (0.003) | 5.11E-03 | -0.009 (0.001) | 4.17E-15 |
| | 10 | -0.007 (0.003) | 2.44E-02 | -0.008 (0.001) | 3.82E-11 |
| | 10 | -0.007 (0.003) | 2.13E-02 | -0.008 (0.001) | 1.85E-11 |
| | 14 | 0.049 (0.010) | 1.51E-06 | 0.044 (0.004) | 9.55E-26 |
| | 19 | 0.024 (0.006) | 1.58E-05 | 0.016 (0.002) | 1.35E-12 |
| | 22 | 0.017 (0.003) | 2.60E-07 | 0.022 (0.001) | 7.75E-56 |
| | 22 | 0.017 (0.003) | 2.71E-07 | 0.022 (0.001) | 6.77E-56 |
| | 22 | 0.004 (0.003) | 2.03E-01 | 0.006 (0.001) | 6.49E-08 |
| | 22 | 0.014 (0.004) | 2.57E-04 | 0.018 (0.002) | 2.36E-32 |
| | 22 | 0.006 (0.003) | 2.63E-02 | 0.01 (0.001) | 1.83E-16 |

Gray shading indicates P-values meeting the Bonferroni significance threshold of $P < 1.43 \times 10^{-3}$
* Replication meta-analysis includes the three replication cohorts: GHS Bariatric Sugery Cohort, Dallas Heart Study, and Penn Medicine Biobank
** Joint meta-analysis includes the discovery cohort and the three replication cohorts: GHS Discovery Cohort, GHS Bariatric Sugery Cohort, Dallas Heart Study, and Penn Medicine Biobank
Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | GHS Bariatric Surgery Cohort | | | Dallas Heart Study | | | Penn Medicine Biobank | | |
|---|---|---|---|---|---|---|---|---|---|---|
| | | Beta (SE) | P | N | Beta (SE) | P | N | Beta (SE) | P | N |
| AST | 4 | -0.010 (0.003) | 3.12E-03 | 2469 | -0.012 (0.006) | 5.87E-02 | 1356 | -0.006 (0.004) | 1.02E-01 | 6166 |
| | 10 | -0.010 (0.003) | 2.91E-03 | 2469 | -0.003 (0.006) | 6.25E-01 | 1356 | -0.010 (0.004) | 6.75E-03 | 6166 |
| | 10 | -0.205 (0.062) | 8.57E-04 | 2469 | NA (NA) | NA | NA | -0.244 (0.089) | 5.90E-03 | 6165 |
| | 10 | NA (NA) | NA | 2469 | NA (NA) | NA | NA | 0.339 (0.079) | 1.85E-05 | 6166 |
| | 10 | -0.004 (0.003) | 1.54E-01 | 2469 | -0.007 (0.006) | 2.18E-01 | 1356 | -0.003 (0.003) | 3.13E-01 | 6166 |
| | 11 | -0.001 (0.003) | 7.85E-01 | 2466 | 0.006 (0.006) | 2.80E-01 | 1356 | -0.003 (0.003) | 3.54E-01 | 6165 |
| | 14 | 0.023 (0.013) | 7.79E-02 | 2469 | 0.046 (0.024) | 6.09E-02 | 1356 | 0.052 (0.011) | 4.75E-06 | 6166 |
| | 19 | 0.023 (0.006) | 1.99E-04 | 2469 | 0.010 (0.011) | 3.42E-01 | 1356 | 0.004 (0.007) | 5.94E-01 | 6166 |
| | 22 | 0.014 (0.004) | 1.27E-04 | 2469 | 0.004 (0.007) | 5.53E-01 | 1356 | 0.017 (0.004) | 1.16E-05 | 6166 |
| | 22 | 0.014 (0.004) | 1.32E-04 | 2469 | 0.004 (0.007) | 5.53E-01 | 1356 | 0.017 (0.004) | 1.17E-05 | 6166 |
| | 22 | 0.008 (0.004) | 6.03E-02 | 2469 | -0.001 (0.008) | 9.33E-01 | 1356 | 0.018 (0.005) | 6.47E-05 | 6166 |
| | 22 | 0.003 (0.003) | 4.12E-01 | 2469 | 0.006 (0.06) | 3.03E-01 | 1356 | 0.009 (0.003) | 1.37E-02 | 6166 |

Gray shading indicates P-values meeting the Bonferroni significance threshold of $P < 1.43 \times 10^{-3}$
* Replication meta-analysis includes the three replication cohorts: GHS Bariatric Sugery Cohort, Dallas Heart Study, and Penn Medicine Biobank
* Joint meta-analysis includes the discovery cohort and the three replication cohorts: GHS Discovery Cohort, GHS Bariatric Sugery Cohort, Dallas Heart Study, and Penn Medicine Biobank
Abbreviations: AAF, alternate allele frequency; Alt, alternate allele; ALT, alanine aminotransferase; AST, aspartate aminotransferase; Ref, reference allele; SE, standard error.

Figure 3 (cont.)

| Trait | Chr | Replication Meta-analysis* (N=3) | | Joint Meta-analysis** (N=4) | |
|---|---|---|---|---|---|
| | | Beta (SE) | P replication | Beta (SE) | P joint |
| AST | 4 | -0.009 (0.002) | 1.69E-04 | -0.006 (0.001) | 1.13E-12 |
| | 10 | -0.009 (0.002) | 8.86E-05 | -0.006 (0.001) | 9.66E-14 |
| | 10 | -0.205 (0.062) | 8.57E-04 | -0.220 (0.022) | 1.66E-24 |
| | 10 | 0.339 (0.079) | 1.85E-05 | 0.271 (0.027) | 2.43E-24 |
| | 10 | -0.004 (0.002) | 3.92E-02 | -0.005 (0.001) | 5.52E-10 |
| | 11 | -0.001 (0.002) | 7.03E-01 | 0.004 (0.001) | 1.48E-06 |
| | 14 | 0.040 (0.008) | 6.56E-07 | 0.029 (0.003) | 2.78E-25 |
| | 19 | 0.014 (0.004) | 1.20E-03 | 0.009 (0.002) | 5.92E-10 |
| | 22 | 0.014 (0.002) | 2.00E-08 | 0.014 (0.001) | 1.12E-52 |
| | 22 | 0.014 (0.002) | 2.10E-08 | 0.014 (0.001) | 1.26E-52 |
| | 22 | 0.011 (0.003) | 1.77E-04 | 0.011 (0.001) | 1.01E-25 |
| | 22 | 0.005 (0.002) | 1.34E-02 | 0.006 (0.001) | 6.61E-15 |

Gray shading indicates P-values meeting the Bonferroni significance threshold of $P < 1.43 \times 10^{-3}$
* Replication meta-analysis includes the three replication cohorts: GHS Bariatric Sugery Cohort, Dallas Heart Study, and Penn Medicine Biobank
** Joint meta-analysis includes the discovery cohort and the three replication cohorts: GHS Discovery Cohort, GHS Bariatric Sugery Cohort, Dallas Heart Study, and Penn Medicine Biobank
Abbreviations: AAF, alternate allele frequency; Alt, alternate allele; ALT, alanine aminotransferase; AST, aspartate aminotransferase; Ref, reference allele; SE, standard error;

Figure 3 (cont.)

| CHR:BP:Ref:Alt | Gene | rsID | Alcoholic liver disease OR (95% CI) | P | Alcoholic cirrhosis OR (95% CI) | P |
|---|---|---|---|---|---|---|
| 4:88231392:T:TA | HSD17B13 | rs72613567 | 0.62 (0.48-0.81) | 1.82E-04 | 0.56 (0.41-0.78) | 3.35E-04 |
| 8:145730161:C:T | GPT | rs201815297 | 3.83 (1.05-13.94) | 8.88E-02 | 6.33 (1.71-23.43) | 2.88E-02 |
| 8:145732114:G:C | GPT | rs141505249 | 0.77 (0.06-10.73) | 8.43E-01 | 1.13 (0.08-15.39) | 9.30E-01 |
| 8:145732180:G:C | GPT | rs147998249 | 0.73 (0.05-11.76) | 8.17E-01 | 1.07 (0.07-17.16) | 9.60E-01 |
| 10:18242311:A:G | SLC39A12 | rs10764176 | 0.85 (0.68-1.07) | 1.64E-01 | 0.92 (0.70-1.22) | 5.80E-01 |
| 10:101157378:CGTT:C | GOT1 | | 4.60 (0.25-86.41) | 3.93E-01 | 7.11 (0.38-133.19) | 3.00E-01 |
| 10:101165533:G:C | GOT1 | rs374966349 | 2.20 (0.13-37.68) | 6.24E-01 | 3.47 (0.20 - 59.04) | 4.70E-01 |
| 10:101912064:T:C | ERLIN1 | rs2862954 | 0.92 (0.75-1.12) | 4.05E-01 | 1.05 (0.82-1.34) | 7.13E-01 |
| 14:94844947:C:T | SERPINA1 | rs28929474 | 2.49 (1.49-4.17) | 2.30E-03 | 3.35 (1.93-5.83) | 3.01E-04 |
| 19:19379549:C:T | TM6SF2 | rs58542926 | 1.47 (1.06-2.04) | 2.76E-02 | 1.35 (0.89-2.04) | 1.80E-01 |
| 22:44324727:C:G | PNPLA3 | rs738409 | 1.76 (1.43-2.18) | 4.98E-07 | 2.07 (1.60-2.67) | 1.08E-07 |
| 22:44324730:C:T | PNPLA3 | rs738408 | 1.77 (1.43-2.18) | 4.70E-07 | 2.07 (1.61-2.67) | 1.03E-07 |
| 22:44368122:A:G | SAMM50 | rs3761472 | 1.90 (1.52-2.38) | 1.36E-07 | 2.28 (1.75-2.98) | 1.83E-08 |

Gray shading indicates P-values meeting the Bonferroni significance threshold of $P < 1.92 \times 10^{-3}$

Figure 4

| CHR:BP:Ref:Alt | Gene | rsID | Nonalcoholic liver disease OR (95% CI) | P | Nonalcoholic cirrhosis OR (95% CI) | P | Hepatocellular carcinoma OR (95% CI) | P |
|---|---|---|---|---|---|---|---|---|
| 4:8823139:T:TA | HSD17B13 | rs72613567 | 0.84 (0.78-0.91) | 1.31E-05 | 0.74 (0.62-0.88) | 4.48E-04 | 0.67 (0.45-1.00) | 4.66E-02 |
| 8:145730161:C:T | GPT | rs201815297 | 0.23 (0.04-1.14) | 1.86E-02 | 1.25 (0.24-6.38) | 7.98E-01 | 3.66 (0.70-19.01) | 2.01E-01 |
| 8:145732114:G:C | GPT | rs141505249 | 1.02 (0.49-2.11) | 9.70E-01 | 0.36 (0.02-5.37) | 3.82E-01 | 1.84 (0.15-23.25) | 6.88E-01 |
| 8:145732180:G:C | GPT | rs147998249 | 1.03 (0.49-2.17) | 9.30E-01 | 0.34 (0.02-5.59) | 3.67E-01 | 1.74 (0.11-27.05) | 7.21E-01 |
| 10:18242311:A:G | SLC39A12 | rs10764176 | 0.92 (0.86-0.99) | 3.43E-02 | 1.03 (0.88-1.21) | 7.15E-01 | 1.29 (0.93-1.79) | 1.37E-01 |
| 10:101157378:CGTT:C | GOT1 | | 2.37 (0.61-9.27) | 2.50E-01 | 8.27 (1.44-47.49) | 5.92E-02 | 9.81 (0.52-183.54) | 2.43E-01 |
| 10:101165533:G:C | GOT1 | rs374946349 | 1.63 (0.53-4.96) | 4.20E-01 | 1.17 (0.07-20.09) | 9.13E-01 | 5.37 (0.32-91.12) | 3.55E-01 |
| 10:101912064:T:C | ERLIN1 | rs2862954 | 0.98 (0.91-1.04) | 4.61E-01 | 1.13 (0.98-1.31) | 9.90E-02 | 0.94 (0.69-1.28) | 6.94E-01 |
| 14:94844947:C:T | SERPINA1 | rs28929474 | 1.50 (1.21-1.87) | 5.29E-04 | 2.99 (2.11-4.24) | 9.08E-08 | 1.86 (0.74-4.67) | 2.40E-01 |
| 19:19379549:C:T | TM6SF2 | rs58542926 | 1.36 (1.21-1.52) | 2.42E-07 | 1.64 (1.31-2.05) | 6.04E-05 | 1.93 (1.22-3.04) | 1.08E-02 |
| 22:44324727:C:G | PNPLA3 | rs738409 | 1.65 (1.54-1.78) | 1.31E-41 | 2.05 (1.76-2.38) | 1.70E-19 | 2.20 (1.60-3.02) | 5.59E-06 |
| 22:44324730:C:T | PNPLA3 | rs738408 | 1.65 (1.54-1.78) | 1.42E-41 | 2.05 (1.77-2.38) | 1.45E-19 | 2.20 (1.60-3.03) | 5.41E-06 |
| 22:44368122:A:G | SAMM50 | rs3761472 | 1.52 (1.41-1.65) | 7.33E-24 | 1.86 (1.58-2.19) | 1.81E-12 | 1.66 (1.16-2.39) | 1.05E-02 |

Gray shading indicates P-values meeting the Bonferroni significance threshold of $P < 1.92 \times 10^{-3}$

Figure 4 (cont.)

| Characteristic | Dallas Liver Study Cases (N = 517) | Dallas Liver Study Controls (N = 4,279) | Dallas Pediatric Liver Study Cases (N = 203) | Dallas Pediatric Liver Study Controls (N = 244) |
|---|---|---|---|---|
| Age (years) – median (IQR) | 55 (48 - 60) | 44 (36 - 53) | 12 (10 - 15) | 12 (11 - 14) |
| Female sex – number (%) | 277 (54) | 2,494 (58) | 65 (32) | 126 (52) |
| Body mass index – median (IQR) | 30 (27 - 35) | 30 (26 - 35) | 30 (27 - 34) | 31 (28 - 35) |
| Self-reported ethnicity | | | | |
| African American | 33 (6) | 2,291 (54) | - | - |
| European American | 158 (31) | 1,266 (30) | - | - |
| Hispanic American | 326 (63) | 722 (17) | 203 (100) | 244 (100) |
| Presence of liver disease – N (%) | | | | |
| Alcoholic liver disease | 223 (43) | - | - | - |
| Alcoholic cirrhosis | 215 (42) | - | - | - |
| Nonalcoholic (non-viral) liver disease | 212 (20) | - | - | - |
| Nonalcoholic cirrhosis | 100 (19) | - | - | - |
| Hepatocellular carcinoma | 44 (9) | - | - | - |
| No liver disease | - | 4,279 (100) | - | 244 (100) |

Figure 5

| Phenotype/Subset | N | | HSD17B13 rs72613567 [Interaction effect] | | HSD17B13 rs72613567 [Main effect] | | | PNPLA3 rs738409 [Main effect] | | |
|---|---|---|---|---|---|---|---|---|---|---|
| log₁₀ (ALT) | | | | | | | | | | |
| Subset | N | | Effect (95% CI) | p | Effect (95% CI) | AAF | p | Effect (95% CI) | AAF | p |
| All | 43,309 | | -0.007 (-0.011,-0.002) | 1.80E-03 | -0.006 (-0.009,-0.003) | 26.36% | 1.88E-04 | 0.026 (0.022,0.029) | 23.54% | 1.97E-50 |
| Obese | 23,051 | | -0.01 (-0.015,-0.004) | 1.01E-03 | -0.009 (-0.013,-0.005) | 26.48% | 6.53E-05 | 0.037 (0.032,0.042) | 23.57% | 3.13E-55 |
| Non-obese | 20,258 | | -0.004 (-0.01,0.002) | 1.49E-01 | -0.002 (-0.007,0.002) | 26.22% | 3.53E-01 | 0.013 (0.008,0.018) | 23.51% | 1.56E-07 |
| log₁₀ (AST) | | | | | | | | | | |
| Subset | N | | Effect (95% CI) | p | Effect (95% CI) | AAF | p | Effect (95% CI) | AAF | p |
| All | 42,862 | | -0.004 (-0.007,-0.001) | 4.53E-03 | -0.004 (-0.006,-0.002) | 26.40% | 4.78E-04 | 0.016 (0.014,0.018) | 23.47% | 9.69E-46 |
| Obese | 22,719 | | -0.006 (-0.01,-0.003) | 1.04E-03 | -0.006 (-0.009,-0.003) | 26.51% | 1.42E-04 | 0.023 (0.02,0.027) | 23.53% | 7.65E-49 |
| Non-obese | 19,943 | | -0.001 (-0.005,0.003) | 4.97E-01 | -0.001 (-0.004,0.002) | 26.26% | 3.42E-01 | 0.008 (0.005,0.011) | 23.41% | 1.56E-06 |
| Nonalcoholic liver disease | | | | | | | | | | |
| Subset | N Controls | N Cases | OR (95% CI) | p | OR (95% CI) | AAF | p | OR (95% CI) | AAF | p |
| All | 29,928 | 1,857 | 0.919 (0.812,1.039) | 1.78E-01 | 0.88 (0.787,0.983) | 26.43% | 2.40E-02 | 1.764 (1.606,1.938) | 23.51% | 1.76E-32 |
| Obese | 14,243 | 1,445 | 0.906 (0.786,1.044) | 1.74E-01 | 0.894 (0.788,1.012) | 26.36% | 7.81E-02 | 1.714 (1.537,1.911) | 23.65% | 2.06E-22 |
| Non-obese | 15,685 | 412 | 0.964 (0.75,1.235) | 7.71E-01 | 0.845 (0.662,1.069) | 26.50% | 1.67E-01 | 1.887 (1.566,2.269) | 23.38% | 1.96E-11 |
| Alcoholic liver disease | | | | | | | | | | |
| Subset | N Controls | N Cases | OR (95% CI) | p | OR (95% CI) | AAF | p | OR (95% CI) | AAF | p |
| All | 29,928 | 190 | 1.112 (0.749,1.637) | 5.94E-01 | 0.578 (0.391,0.834) | 26.57% | 4.56E-03 | 1.689 (1.298,2.185) | 22.99% | 7.80E-05 |
| Obese | 14,243 | 97 | 1.295 (0.741,2.224) | 3.56E-01 | 0.501 (0.283,0.839) | 26.53% | 1.22E-02 | 1.533 (1.052,2.201) | 22.83% | 2.30E-02 |
| Non-obese | 15,685 | 93 | 0.956 (0.544,1.65) | 8.72E-01 | 0.666 (0.382,1.105) | 26.55% | 1.33E-01 | 1.853 (1.275,2.664) | 23.13% | 1.00E-03 |

Figure 9

E.
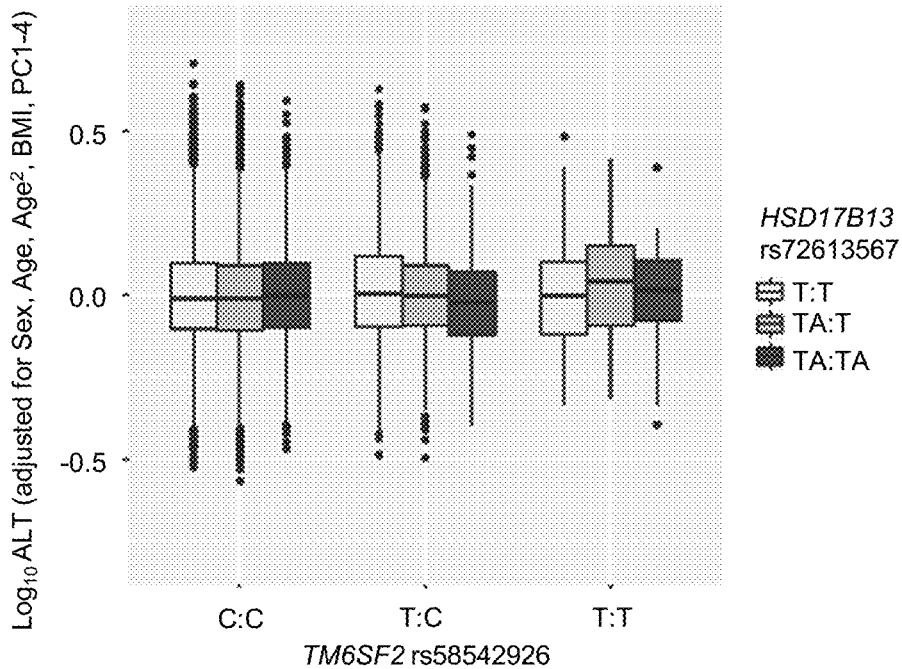
F.
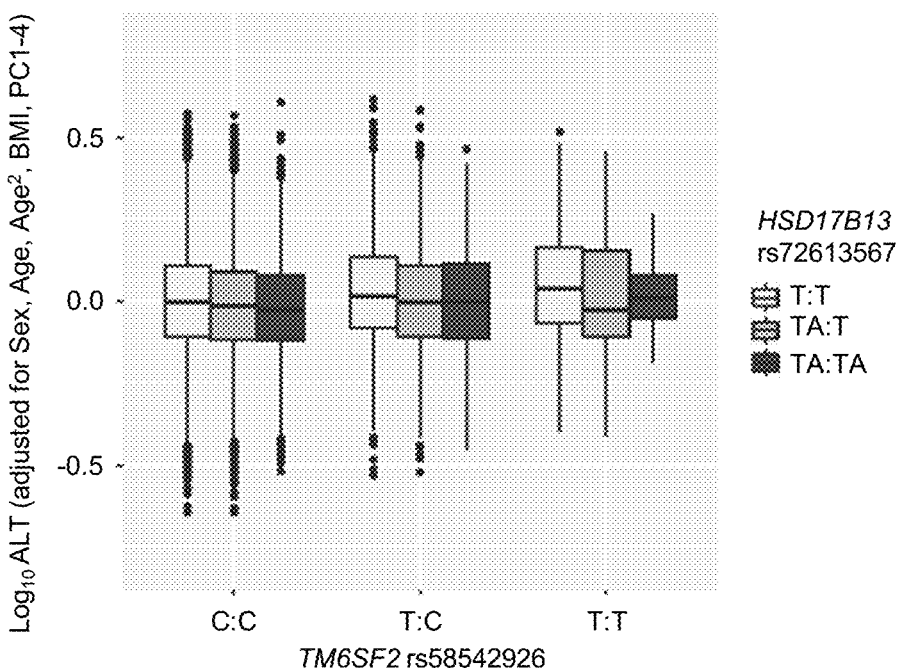
Figure 11 (cont.)

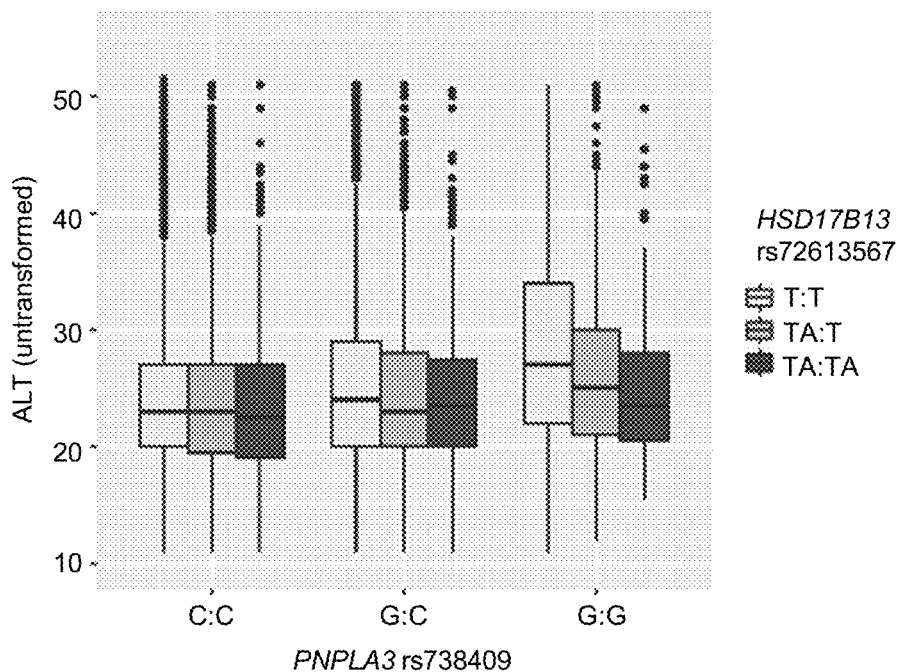
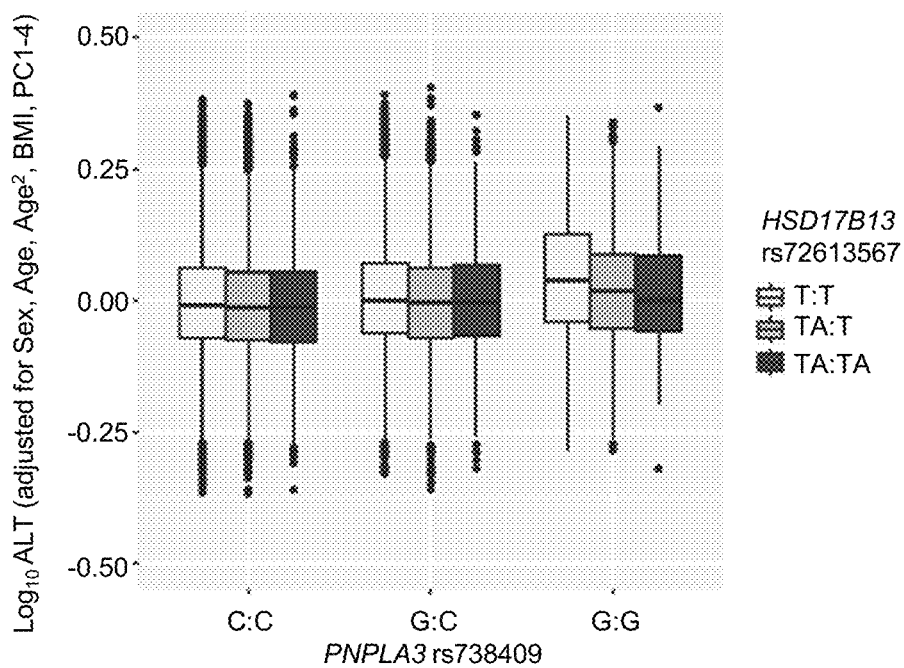
Figure 12 (cont.)

E.
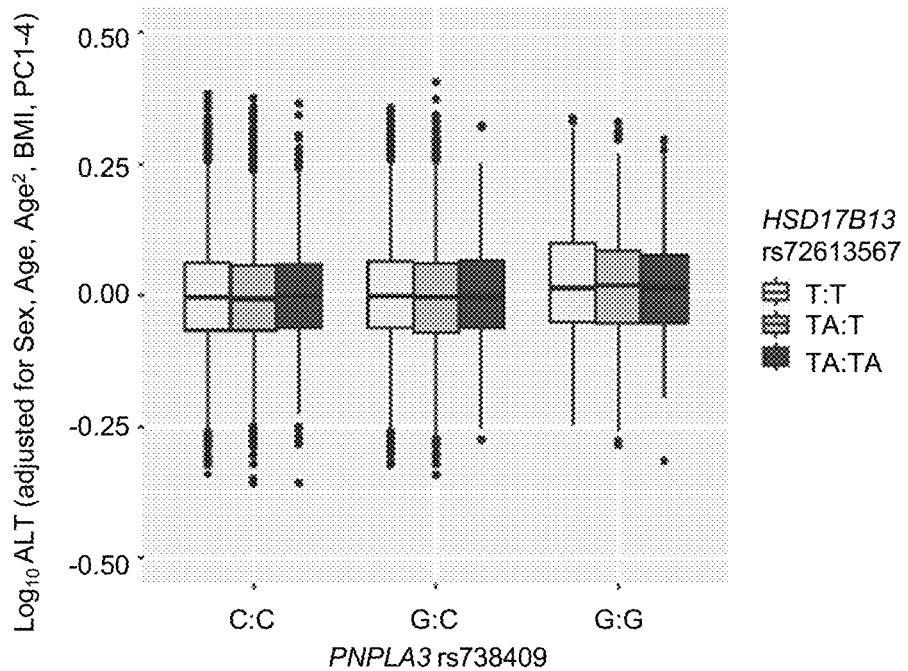
F.
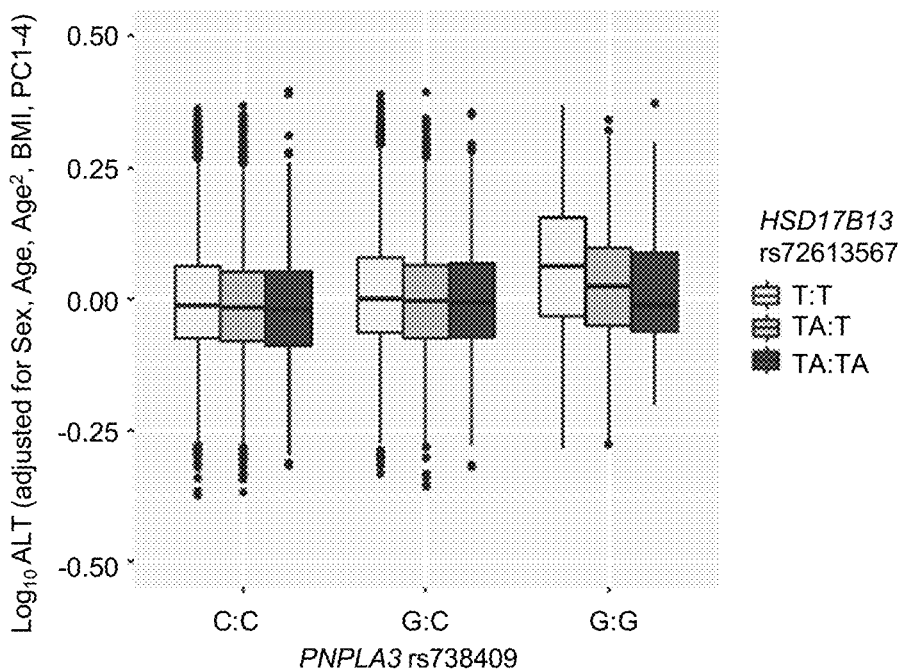
Figure 12 (cont.)

C.
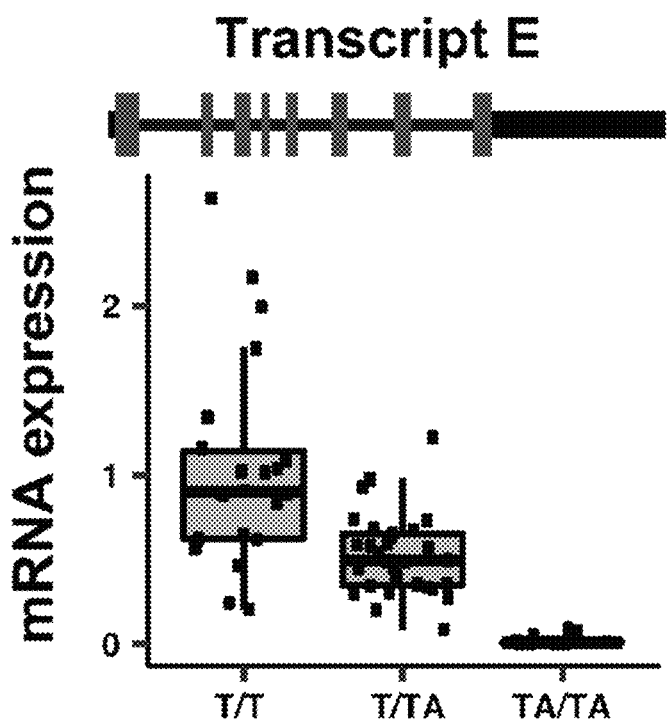
D.
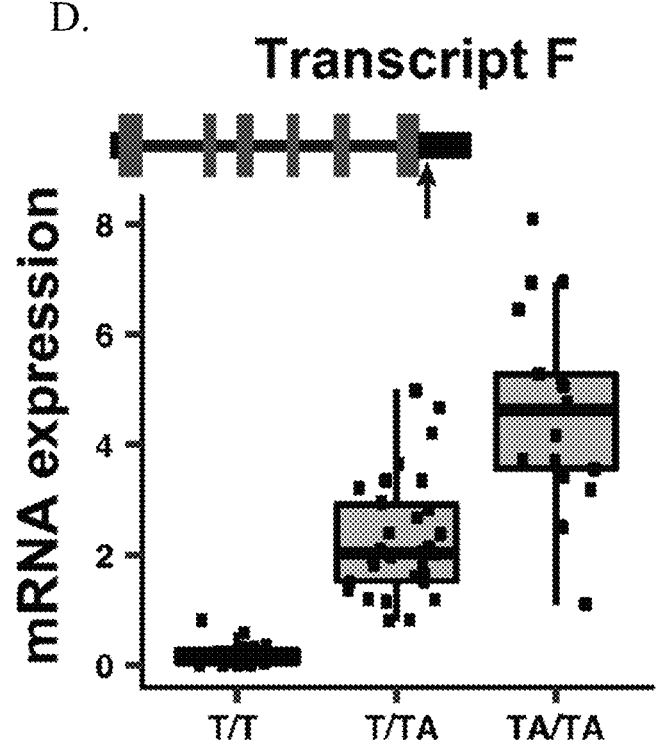
Figure 13 (cont.)

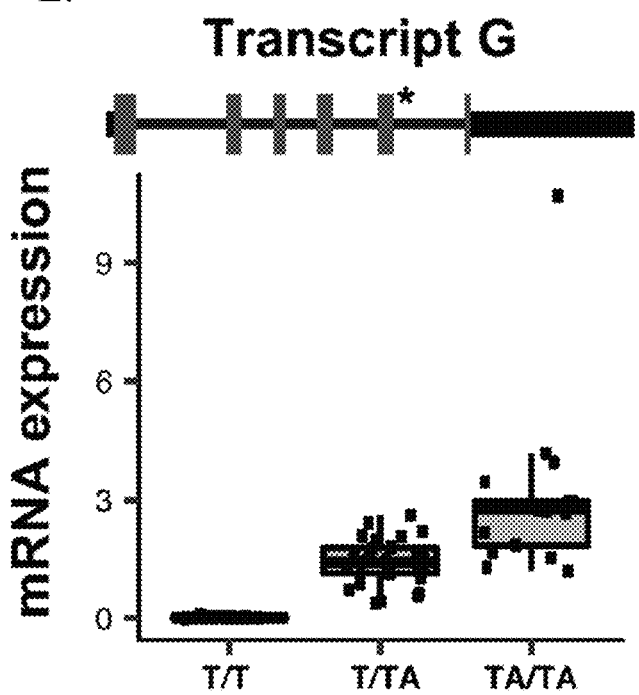
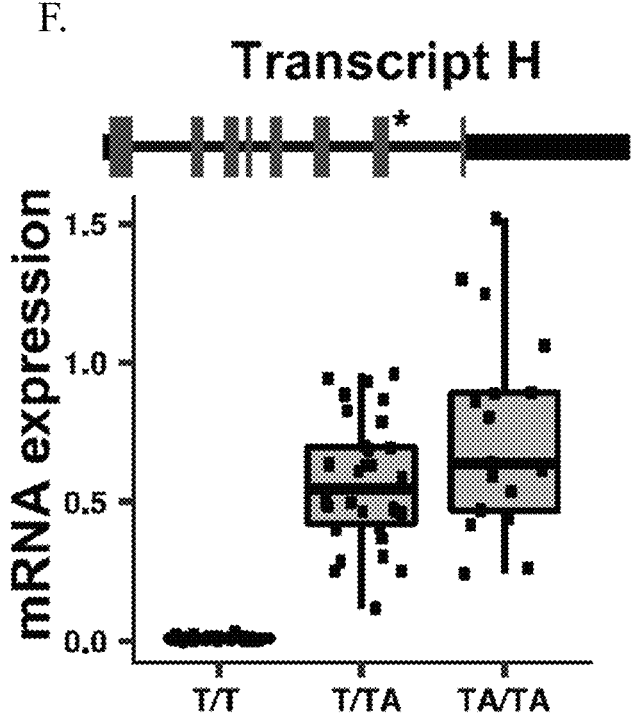
Figure 13 (cont.)

A.
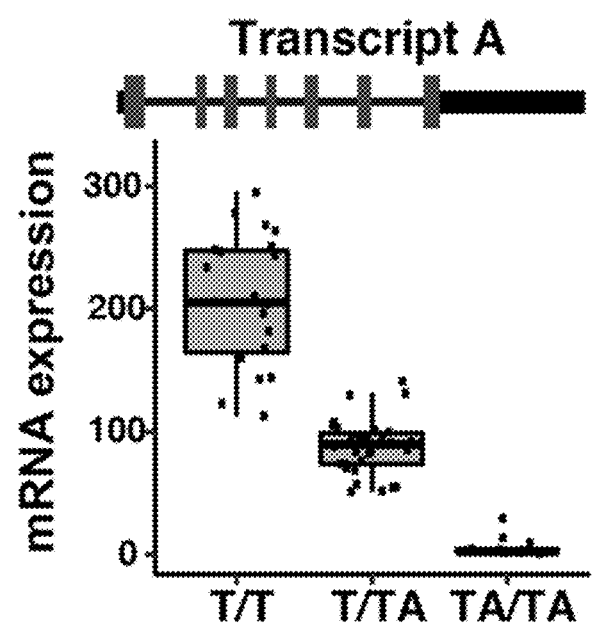
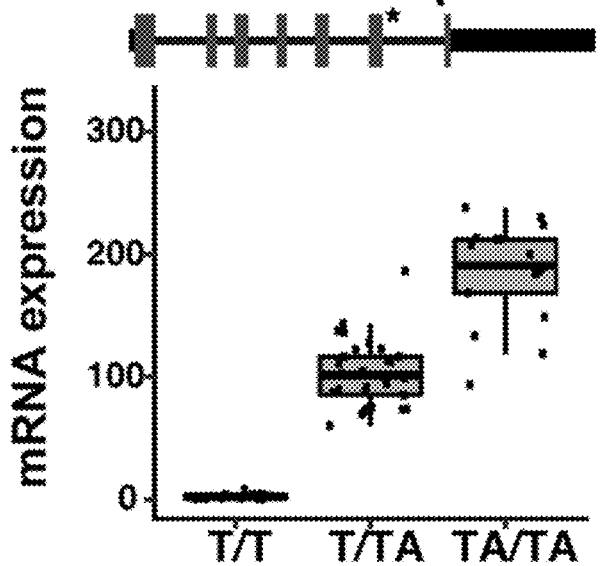
Figure 18

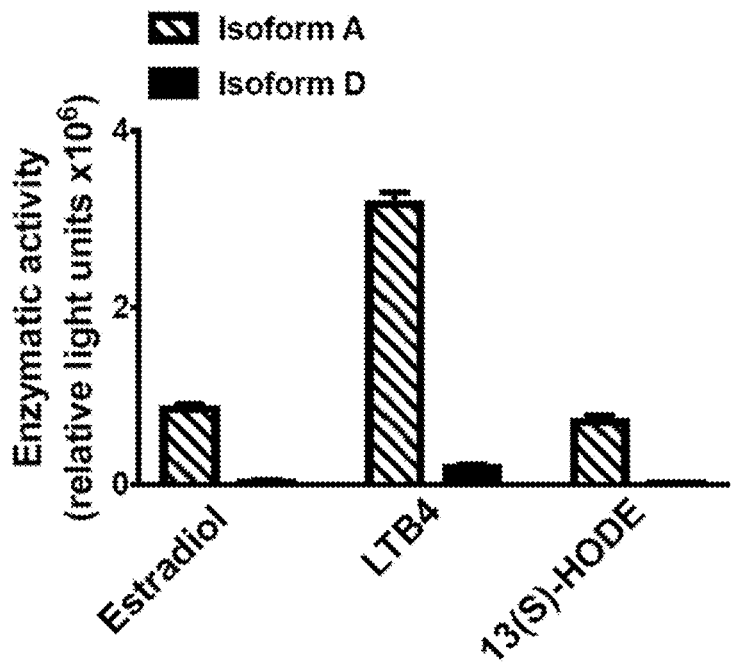
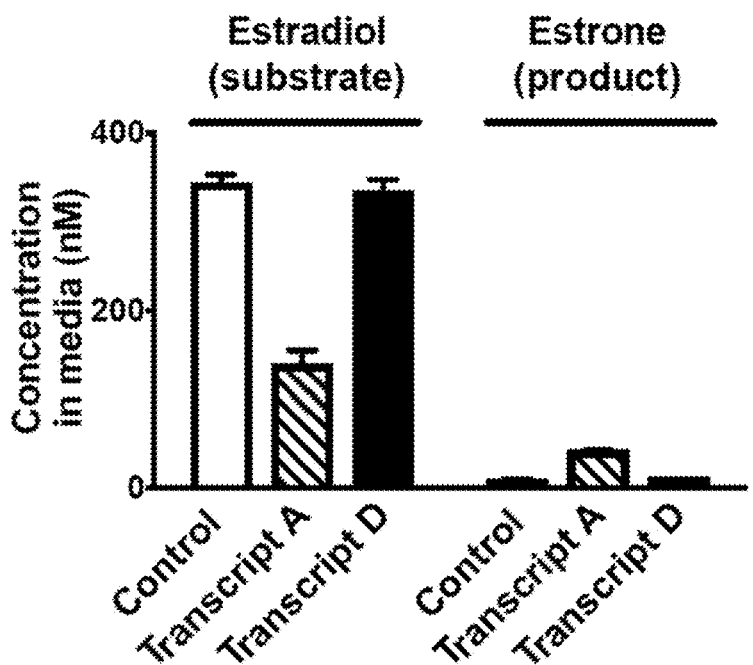
Figure 18 (cont.)

SEQUENCE LISTING

```
Sequence total quantity: 66
SEQ ID NO: 1           moltype = DNA   length = 19118
FEATURE                Location/Qualifiers
source                 1..19118
                       mol_type = genomic DNA
                       organism = Homo sapiens
SEQUENCE: 1
```

```
agacagtacc tcctccctag gactacacaa ggactgaacc agaaggaaga ggacagagca    60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catgaatag gcaggcagac tacttatgaa tttgcaaaac    240
gacagagcat attggttctg tgggatatta ataaggtaat gtatacatct tccaactttt   300
taaagtcaca gagtaagata tgtattttaa gaattatttg acttaccatc tacttatctt   360
tgtattttg tttttcaaag tttgataaat tccctggtcc cttagtctgt atatgtgtca   420
ggttagttag atgaagggaa tgtaattaag aactaagcag cgattttat gacatggtgt    480
gcaggttgat agaaagactc aggagccagt ctccttccaa gctgctaaat gaggcaagtc   540
acatattatc tctcagcctg ttttcttggc tctgaagtgg ggataataac ttaggggatg   600
ggcaagaacg ggatctgaaa attacagcta caaacaaaag tcaaacgaag aacttgcaac   660
agaaaccttt agtgcctccc ctcatgcaca agcaacacag ttctaaaata tttactgtct   720
gacccttac agaaaatgtt tgccagtccg tagtcaaaag gattaaataa gtaatatttt    780
cagcacttag catatgataa acgatacgtg gcacatgata aacaataact gtgttaaata   840
aaatatgtgc gcagtgagtc aggcttttcc ttggacatta gtattttcc tgtgttctta    900
cttgtaaaca ctacattaac aaccccaaat aaaactgaag gaactgaaat cttgtatcat   960
tttctctaaa cttgtaaatt ctggtaaggc catgaaaata tatgcagaga agtgtttaca  1020
ggattttagg attggaaaaa ttgtgaagta ctccttgaga atcacatttt ctgcaaatta  1080
cagtggtttt aattaccatt atattattac tttctcatgt tctttgctgt catgtttagt  1140
tgaaacctaa aatgtctctt acacttagag aactaattct tttctgtttt ttttctgaat  1200
agtgaagaat actatacaaa aaagctacta catttttatt taacagatat gagcatttat  1260
ataatagagg agttgatgta tataaaaatg atttgccatc ttttggtct ttgaagaaat   1320
tcgaatgaac tttctggaag atagcaagaa tttacaaata gagaaaattg ttgcctgctg  1380
ttctcaggca tttgtccaaa aatataaata agtataaatc tatgaaaagg gcttgatgaa  1440
atctaacctt caaatctctt tccagatgtg tattttggg gaaagggcta tatttattaa   1500
gtttttttta aatttaaaa tttccagaga caagagaaaa gtaaattgaa aggaagtgtt   1560
attaaaaatg acttaagggc gggtgcagtg gctcacacct gtaatcccag cactttggga  1620
gacggaggtg ggcagattgc tggagcccag gagttcaaga ccagcctggg cagcacagca  1680
aaaccccaa ctctacaaaa aatacaaaaa ttagctgggt gcggggtgc acaccctag     1740
tcccagctac tcgggaggct gaggtgggag gatcgtttca gttcaggaag ccaaggctg   1800
aatgagctat gatggcatca ttgcactcca agctgggcaa tagagccagg ctctgtctca  1860
aaaaaaataa aaaagactt aagaaaaata ggtaacccaa cctcaaaat tctctttgaa   1920
tcattaaatt tcatggttaa acatttaagc tactgaatga ttcactctaa ggctgtaatg  1980
taactcagat ctcctttagg cgaggaagat gctggctgag ttttcatcat aactggctcc  2040
ttttgccctg tgagatgaga gacacagtag cagtttggct cttatgcaat ctaaactgtt  2100
gcgttgggaa tacggttcaa aaaacacatt ggagtttaag ctaaagcaag tgttttgcta  2160
acaaaaagac aaggcatcac attttgcaat tgtctagctc agttataaaa cagaagaata  2220
ggccggacgc ggtggctcac gcctgtaatc ccagcacttt gggaggccga gacgggcgga  2280
tcacgaggtc aggagatcga gaccatcctg gataacacag tgaaaccccg tctctactaa  2340
aaatacaaaa aaattagcca ggcgtagtgg cgggcgcctg tagtcccagc tactcgggag  2400
gctgaggcag gagaatggtg tgaacccggg aggcggagct tgcagtgagc cgagatgacg  2460
ccactgcact ccagcctggg cgacagagcg agactccgtc tcaaaaaaaa aaaaaaaaa  2520
aaaactgaag aataattaat tcttcaatca aaacatctga tgaatgctct ggtaacttat  2580
gctctctact gacctagaaa caaatgagag agtatggtgt ggtttgtgca atctggcagt  2640
gagcaagcta ccaactaaat cagtgaaaga ctctcctatt ctttttttac tcttctgcaa  2700
tcccacaaaa ggctatttga ggggatactg actttgagac tgggtcctaa catccatgtt  2760
tggggagttc aggctgctgc tccagggttt agcctacagt agcgaaatac aaaggaccca  2820
gagaccactc attcaaggtt tgccctaaat agcagcaaca ccactgtcat ctcaatacac  2880
gaagaatagg gcttttcagg tatccttgcc tctttgtcac agagaagagt ttacagattg  2940
tgagacggaa aagtataatt tttaaaacct tataatattt tctataaaag tcacctgagg  3000
tgaaaacttg aaaagaatta taatttttcca gaatgtgaat caagaaacat tagagcaatt  3060
ttatcttagg aaagaggtct ttgaatttag gctgaaagta aattgctctg tctccatgtc  3120
ctatggttat gggcaagttt ggtacataaa tgagaaatcc atccagtggc cttgcccatc  3180
tcactcccaa acacctgaag aatgtaatgt tatatctcct agagtagcag catggtctcc  3240
ctatgaaagt cctttcttctt taaggagact tctttccctt ccctcctagg aggatgagtc  3300
agaatcatca agaaaaatat gatgggcaga ggcatacagt ttaccattac cactagttta  3360
gaattactac ttagcacttt actgccatt acatagttgg tgctcaacaa atgtatgata   3420
aattaatggt tgagttttc tttcttctcc atattcatct tccatgacac cacgaagagc  3480
aatgtttttc aagaatgttc ttcaaggttt gaaagtagcc tgctttagag aaactgccta  3540
ctgtacagcc tccaaccaag aggaaaagct gaaaaaagca tgaagggatt ttgttttgtt  3600
tgtttgttt tggttttaat atgagcattc cctggcagaa aagccagggg taatctcatt  3660
gcaactaggc aatcactctc aagaattttt ctaacaaata aggaggccaa ttttttatttt 3720
atttgagac gaagtccac tctgtcaccc aggttggagt gcaatggaat gatttcagct   3780
cactgcaacc tccgcctccc gggttcaagt gattctcctg tctaaacttc ccgagtagct  3840
gggattacag gctcccacca ccacgcccag ctaattttt tgtattttag tagagatggg  3900
gtttcaccat tttggccaga ctggtctcaa actcctgacc tcaagtgatc caccctcctc  3960
ggcctcctaa agtgctggga ttacaggcgt gagccaccac acctgaccca ggaggccaat  4020
ttttaaaagg ttaactaatc ttcatgtcca aaatgaatgt taattgttca ttttggacat  4080
gaatgttaat ttttttttt ttttttttg agacagagtc tcactctgtt gcccaggctg    4140
gagtccagtg gcactatctc cactcactgc aacttcctcc tcccaggttc aagcaattat  4200
cctgcctcag cctcccaagt agctgggatt acaggcccac accatcaggc ctggctaatt  4260
tttgtatttt tagtagagac ggggtttcac catgttggcc aggctggtct gaactcctg   4320
acctcgtgat ccgcccctcct cggccaacca agtgctggga ttacaggcg tgagccaccg   4380
cgcctggccg aatgttaatt gtctaaaaat tttcttcctc caatgtcttc tcctccactt  4440
ttttcggaat ttgtttcttc ctaattacag cgcggtgtgg aggaaactgc agctgagtgc  4500
cgaaaactag gcgtcactgc gcatgcgtat tggtagact gcagcaacag agaagagatc   4560
tatcgctctc taaatcaggt gagactgcag gttcacaaat tcttcagat tattttgttt   4620
cctaggacgc tgacgtggaa aatgagaaag gtctttatga ctgcctgatt taaattggat  4680
tttagctgct aactgaagta gttatgtcac caaggaagga tatatacttt ttttcttgta  4740
```

```
tgtaatccac tcagctctgc ccattattat tgttcatatt attaatcaat ttcattctga   4800
tcagaagtgt gagcagtggc acagagtgac tgacaaaaga tttatcatca gggaatatgg   4860
atcacttcct agttttgttt tagtcctatt aactttgcag taattccagc ttctctttaa   4920
ttatttccct tgtgagattt tattttggtg ttaatgtagt cttctgtaga aaatgtaata   4980
ttaataatta ttatcacaat tattttaaaa gagtaaatac caaataatca caatgaacta   5040
agcactctaa caaactttac attttttaat tcaatcccta caataactct gtaaacttca   5100
ttttacagat aagcaaatta tgactcagag aggttaagcc agaccaggt catgtagtta    5160
ttaggttatg aaaccaggat ttctcaacca gcactttaga ccaggtgcgg tggttcacac   5220
atgtaatccc agcactttgt gaggccaagg tggaaggatc acatgagacc aagagttcaa   5280
gaccagccca ggcaacatag tgagaccta tctctaaaaa aaaaaaaaaa aaaaaaaaaa    5340
aaagtttaaa gaaaaacaca ttttaaaaa atgaacactt taaaaatatt tggtcagaat    5400
ttatatagga atttatcaac ataaatgtta atttcactt actgataaac ttgcaaaaca    5460
tgatgtgctg ggtactgaaa tttagatgtt aaaagaacag tttatcccac ctttatgaca   5520
gtgttccctt ggcctccacg atttgagctc aacagtctgt cttgcctgaa ctctgagaga   5580
cctcatacaa tagaagaaag actctcatct ttggattata ttggtcccaa aactttgagt   5640
ttgaataata cacccagtga aagtgttctt tcaatttcaa aaggtgaaga aagaagtggg   5700
tgatgtaaca atcgtggtga ataatgctgg gacagtatat ccagccgatc ttctcagcac   5760
caaggatgaa gagattacca tgacatttga ggtcaacatc ctaggacatt tttgggtgag   5820
tgtgagtcag aaacatttct gatttgtgca ccttctctta agatacatga aacttataac   5880
ggagttcaca tacttctgga caggaaactg gccagatctt tgccttaatc aagaatcatt   5940
aaatttgttt gagtagaaga gccacagagt ctctgacaca aggacacaga attcaagtgg   6000
acacaacaca ccagaatgta agctacttgg tctgtcttgt ccaccagtat ctgacacaaa   6060
gcttggcatg taccaggagc tcaacaaatg tttgtggagg tttgttaagg gttgtcagtg   6120
tacatctttt caatgctgtc acttgtgact tcatttttt ccctccacac catgattttg    6180
taatgtgtcc tcattttgtg gaatttagaa atggaaagga catcagaagt aattacttgg   6240
atgtatatag gatcgaggac acttttggac gagactctga gcaagtgtt ctagatccat    6300
ggggtgctgg aactgagaaa tgcagctata cagacctcat ataattggtt agttttgtgg   6360
gagatggaaa tatcaacttc aactgccttt gtatagaaat ttttatgatt aatcttccag   6420
tgcctcaata ttagtgtaga atctagggca gatctggatt ctagaagaaa gaagaaaaaa   6480
aagagatgtg tcccccttac ctttaccagc tcttcacata tgtgaattgg ctcccatgcc   6540
caccaaacta cacggagacc tcatacatta gctacctata gctgcataac aaattataca   6600
aaacttagtg gttaaagca acaatgtatg ttcactatcc tctcacagtt tctatgggtt    6660
gggaatttgg aggtagcttg ggttgggagt tctagttcta tgaatttgca taggatttat   6720
taaattctta taaaattta ttgatgtttc tcacaaaaga gggttttgga aaaaaagaaa    6780
gacttgtttt ctgtaacatc aacatataat atacaatatt acaaataggg agatagtgaa   6840
ttcaatcatg attcattagt gtggtgtaga actctcagct tacactactc aactgtctta   6900
atacagttac acaagatttc actcttttaa ttagaatgat aaagcccaa accaaaaaat    6960
tatatgacac caaattatca taaggaataa ttttagttct gaaaactctg aattttttccc   7020
ttaatattgt ttagatgaca tatccaaaaa aggatctatt tgattcctc tgaagggaag    7080
gagggggagt actgagatta gtgttggcat ggggcttacc ataccaataa atttgtatct   7140
ttatttctat catttgtaaa gaattaatca tggaatgctt ggaagtattt tatttcattg   7200
tataagttcc ctcaaatgcc tttctgtctt aacaaaata aaactacctg atttggaaac    7260
ctaacgtcta tgtcattgtc tttcttcttt ctgcaatgat ccttaagatc acaaaagcaa   7320
ttcttccatc gatgatggag agaaatcatg gccacatcgt cacagtggct tcagtgtgcg   7380
gccacgaagg gattccttac ctcatcccat attggtaagt atcacatgcc agccatgtta   7440
tatatttta tactttgaag ggagcattac acttcaaatt gttaccactg gagagtcctg     7500
gttcttggca tcttgaacaa agaattggac aaaactcacc aacaaagcca ggaaagaatg   7560
aagcaacaaa agcagagatt tattgaaaat gaaagtacgc tttacagggt gggagtgggc   7620
ccaagcacag gggctcaaga gccaattaca gaattttctg gggtttaaat accccctaga   7680
ggtttccact ggttacttgg tgtacgcccct atgtaaatga agaggatgaa ttaaagttac   7740
agagtcgttt actcagtgta caccatatgt aaatggagag gatatttcct gtcatagctg   7800
gagtgttttcc atttgattta gttctaggaa gtcagcatga atcggcctta tgttccctgc   7860
ctccagaccc tgttctcctg cctcaagatt acaatgctga gagcagagtg atttggattt   7920
acagaattta aatttatagt agtttagaat gatttttaa atgactttt ctaaaacaat     7980
gaaaccaggt tgtaattata tttaagatat ttttagattt ctgcaaactc ctctgtagaa   8040
caatgagaga aaacagtaat gccaagcatg tttccattgt ttcctggaat aagaaacaga   8100
aaccccacag actgagaagc aaaacctaca gaagctaaaa tgaacacatg tctatgtcat   8160
ggccttggtg cccaagataa gacaatcaga gtggtccctg gatcaaaaca ttttacagtg   8220
tgcttgtgcc atgaaagtgt gtgtgtgtgt gtgtgtgtgt gtgtgagaga gagagagaga   8280
gagaaaacga ctctacctga ctaaaagttg cagataccac actccatgca ccaccaaaga   8340
cataaaggga aggaggtgag aggcgttaag gatgtactgc tgtatttgcc aaatatcctt   8400
tcctgtaaac tcttctccag atcctcataa taaaattaag aggccaaagt ggcaaccatt   8460
gtcaagagaa aaactatcaa ccattgtcaa gagataaact cagttattga gagagagagg   8520
agaaatgagc agagtcctac agaagtctgt caacacagat accagttttg tagaatttct   8580
aaatgtatt ttcctgattc atatttttca aaataaaagc agcaataaa actgattaga    8640
aaacagtttg aagattcaat ggaaaaacct tacatgtagg atggaaaact gaacattaag   8700
ccaatcaata gagttatttt tgttcttttg ttatcattgt tgtttaagaa atgagatacg   8760
ttcacaattc tgcttaatca tgtaagaaaa tgaaaatgaa ttgccattta tactctcaga   8820
aaaatcacaa gtggctgatt tttggcttcc acttgttctt aagccaaatg ataccgcctt   8880
ctcacagaaa gctgaggatt ggtttcactc tccccttagct aacaatgctt aataattctc   8940
ttacagttcc agcaaatttg ccgctgttgg ctttcacaga ggtctgacat cagaacttca   9000
ggccttggga aaaactggta tcaaaacctc atgtctctgc ccagttttgt gaatactgga   9060
gttcaccaaa aatccaagca caaggtaagg tcaaaatcaa gttagaatgg gtatgtggta   9120
tgataaattg atatgaaaac taatgagaaa tgtttaggca ggcaactaa tagaagaaaa    9180
tgaagaagga aaaataattt ttcttattat tattattatc ttgaaattaa aggaataaag   9240
ggggaaaaca cattagggac tagcaggaat gatcagccac cgatgaactg ggatatttat   9300
ttgtgtccgg gagaaagcac atacatttga tcaccgttac caccctgtct ttaaaatgca   9360
aatgttccaa ggaccagcaa ataaattgag tatctagctc cttagtcaag gtgaatttct   9420
gcaagaactc ttgtctctgg tgagacagga tttgagacca caagagaaga aaaattagtc   9480
```

```
ctgaaaggag aagaaaaaag caggaaggtg tggataagaa cccgaaaatt aagccatctg    9540
cttaacaaat ttttctaatc ctagtatata ttctgctgca ggttaacaaa atatactaag    9600
cttaatgatt cgaaaccaat tttttactgg aagggaatta atcctaaata tattcattca    9660
aaagaactaa acaattctct gttgagtgcc gcctcatttg aggatactga ctcttacagc    9720
ctgagttagc tatgtggtct ctgcagctgg aatcactccc tgccactgga gtccttcatg    9780
gtgttagacc ataggtactg ttgactaaag aaaaaaaaaa gttttttgttt ttatttttgt    9840
tttttttgag acagagtctc actctgtcac ccaggctgga gtacagtggc gcgatctcag    9900
ctcaccgcaa cctccgcctt tctgggttca agcaattctc cttcctcagc ctcctgagta    9960
tttggattac aggcgcccac caccacgcct ggctaatttt tgtattttta gtagagacgg   10020
ggtttcacca tgttggccag gctggtctca aactcctgac ctcaggtgtc ctacctgcct   10080
tggcctccta aaatgctggg attacaggag tgagccacca tgcccggcca aaaaaataag   10140
tttttaaaga attaaaggtc atcctggcta acacagtgaa accccgtctc tactaaaaaa   10200
cacaaaaaaa ttagccgggc gtggtggcgg gcgcctgtag tcccagctgc gcgggaggct   10260
gaggcaggag aatggcgtga acccgggagg cggagcttgc agtgagccga gatcgcgcca   10320
ctgcactcca gcctgggcga cagagcgaga ctccgtctca aaaaaaaaaa aaaaaaaaaa   10380
aaaaaaaaga attaaaggtg ttaattttat ttagaagcct tactgaagac tacagtcgga   10440
ggcctatagc ctgagagcag cccttttgag aggttcagtt gaactgttct gatagtgggg   10500
gccatgtgct ctatcctgta ttgtcttcaa agcatctttc cagagagctg cacattgtca   10560
cagagtcagg gactttgtga aattatgctg acaaccagaa gtgagtaaac gtggcttctt   10620
acatttgcta cgttgtctca cagtacttaa taagtatgca atatgtaagt aaatactata   10680
gtactattgc aactcctgat tgttttctta gacaaggaat tgggcccaat aaaaaccctc   10740
ttggtaggca ttcaggcttc gtgtaccatg agctttccta agggtatcct gccactcttg   10800
gggaaggcat gatagatgag gggagtaagg ataatggaac tctgggtaca gggttcctgg   10860
gggctaactt agaggtagac acaggcaatg ctaaatattt gggattgatt ttatagaggt   10920
tgctagattg tgaatttcct tagtaagggc taaggcattg atatgtaatg tcacacttgg   10980
ctccgaggct gggttgttgg atccatgtag atgaaatcag gggagaaaag ggcagaaggg   11040
agtaatttag aaatgtattg atttgtatta ctctctgttg gcttgctatt caaggcagtg   11100
gagaactcaa tcacataata atctgcagca aaccacagat catcccaggg aatgaagttt   11160
taacattcgc tggctcccta actcctcacc cagcctttac attcactggc tgttcagtcc   11220
atgcctggac atcttaattt gaatacaaca tttaaatcc atttttctgt catcatcttg   11280
cactaacaga caattctaca ctaagcctat gtttatgaat atttctcaag agtcacatga   11340
cacagccttc agtataagga aaactggaag tatgacatac ctccagttgt catactcctt   11400
gggccctct taaattctca ttaaactgca ggataggcaa gtcagaggtg aatctcaaat   11460
acgaaattct taccggaaag gggttccaat ccagacccca agagagggtt cttagattc    11520
tcgcaagaaa taattcgggg caaggccaca gtgcaaagca aaagcaagtt tattaggaaa   11580
gtaaaggagt agagaacagc tactccatgg agaagaatgg cttgagctgc tccaccaagg   11640
gtatttagag ttacttcttg attatatgct aaacaagggg tggattattc atgagtttc    11700
cgggaaaagg gtgagcaatt cccagaactg agatttcctc ccctttttag gccatatagg   11760
gtaacttcct gccattgcca tggtatttgt aaactgtcat aggctggtg gaagtgtctc    11820
ttagcttgct aatgtattat agttagctta taatgagcag tgaggacaac cagaggtcac   11880
tttcatcacc atcttggttt tggtgggttt tggccggctt ctttactgca ccctattta    11940
tcaacaaggt ctttatgacc tgaatcttgt gccaacctcc tatctcatcc tgtgacaaag   12000
aatgccttaa cttcctggga atgcagccca gtaggtgcta ggcctttt accccagacca   12060
tattcaagat ggagttgctc tgatttaaac gcctctgaca aaatgacgac ctcaaaacaa   12120
tccagcttta tggaatacct ccacaagaaa gaaagtatac ttagctatag aattttctcc   12180
ttgcatccaa caggctttga gatgtcagat gttttccttc ctgtccatga ttaatcctag   12240
ccattcctct ttcttgtctg gctccactac tccttaccat ctaatgcctc gccaccattt   12300
tgatattttg actaagtgag ctatgaaaca cacctactgg atatgaaagt ataagttct    12360
gataacaaaa catcaacatg ggatgtggag gaagtgggta gggtggcatt aatgcagcaa   12420
atcctggaat atttaatc ttcattctaa atttagtaaa aatataggat aattttcctg    12480
ccatcattta cttataaat taaaatttta gaaaataaaa atatattttt cctcttttta   12540
atcacagatt atggcctgta ttggagacag atgaagtcgt aagaagtctg atagatggaa   12600
tacttaccaa taagaaaatg atttttgttc catcgtatat caatatcttt ctgagactac   12660
agaagtaagt acagcacaga acacccaaat actaaaacac caatagagct tttttttttg   12720
cttttttttt tttagacag agtctcactc tgtcacccg gctggattgc ggtggttgca    12780
gtggcatgat cttggctcac tgcaacctcc gcctcctggg ttcaagcaat tctcatgcct   12840
cagacccccaa gtaactggg attataggtg tgtgctgcca cactacaccc agctaatttt   12900
tgtattttt gatagagaca ggtttcccca tgttggccag gctggactcg aactcctgac   12960
ctcaagttat cctcctgtct cggcctccca aagtgctggg attacagtca tgagccacca   13020
tgcctggccc aatagagcta ttattatgga gcatctttca gttgtgaaaa ttggcatgaa   13080
aactctccat ccctggggag aacagttatt tcctctgtta ttttcctacc cagtctataa   13140
aaagagagtg attcattttc tctaccaaat ctactgtctc tgcccaaact ttgctgaaga   13200
ctattctaac taaaggaaac acagttttaaa aagaatgcaa tatagtgaag tagttaataa   13260
taaagactcc atttttaaaa gtctgctgga agtttggttg ggattgcact gaatctatag   13320
agcaattggg gagtattgac atatcaacaa tattgagttt tctaatccaa gaacataata   13380
tctatttta aaatcttctt caaaatcttt aaatctttaa attgtatttt gtagttttg    13440
gtgtttaagt cttgcacata ttttgtcaga tttattccaa agtatttcac gggttcttt    13500
ttttttttt tttttttttt ttgagacaga gtttcaccct tgttgcccag gctggagtgc   13560
agtggcgtga tcttggctca ctgcagcttc tgcctcctgg cttcaagtga ttctcctgcc   13620
tcagcctccc aagtagctgg gattacaggc acctgccccc cgcccaact aacttttgt    13680
gtttgtagta gagacagggt ttcaccatgt tggccaggct ggtctcgaac tcctgacctc   13740
atgtgatcca cctgcctcag cctcccaaag tgctgggatt acaggcatga gccatcatgc   13800
ccagcctat ttgacggttt ttgacgctaa tgcaagtggc atttaaaaa attttatatt    13860
tccattgtt tgttgtcagt atatattgga ttttgtaat ttgatctcat attttgcagt    13920
cttgctaaat tgctaaacct ttttttgcta aactcgataa gctttttttt ttttggtaga   13980
ttcctgggcc tctaatttc ttttatgggaa agttttttaat tacaaattta atttcttaa    14040
tagctacatg gctattcaat ttacttatta attcttggta atgtgtgtct ttcaaggaat   14100
ttgtccatt catctaagtt gtagaatttc tttggcataa atttgtacat aacattccct    14160
tattatcctt ttaatgtctt tagaatgtct tatttattta tttatttatt tttattatat   14220
```

```
tttttttgaga cagagtctcg ctctgttgcc caggctggag tgcagtggca caatcttggc   14280
tcactgcaag ctccgccttc tgggttcatg ccattctcct gcctcagcct ccctagttgc   14340
tgggactaca ggcgcctgca accatgccca gcttatttt tttttttttt tttttttttt   14400
tttttttttt tttttttttt tagtagagac ggggtttcac cctgttagcc aggatggtct   14460
cgatctcctg acctggtgat ccgcccgcct cagcctccca aagtgctggg attacaggcg   14520
tgagccacca agcccagcct atttatttat ttagtagaga cagtctcact ttgctgccca   14580
ggcaacaaag gttttgaatg cctggcctca agcagtcctc ctgccttggc ctcccaaagt   14640
gctgggatta caggcatgag ccactgcacc tggccaaatg aatatgctga taatatcttc   14700
tttataagga tgacataaga ataaaataat gtaatacaaa caaagcccct gtcactgaaa   14760
atgtatagac ttcaaatgtt aaagtcttag agaacagaat ttatatgaaa tagcaacagc   14820
aacaatttcc cagaggaaat actctctcag cttttcttctg aggagcagtt tctaaattga   14880
aattgtatca gtgagaagat aactatacta acttcataag ccttgggcct ttttgaaaca   14940
aatccatata aactatgaac aaacttgaaa tagaacaatt tgagaacagg gtacaaactg   15000
cattggtgta tcaatttcag tatttggttt tagcttaaat agactgactt gagataacat   15060
aaggagaacc ttgaccccca agcaacatca tctcgcgagt tgactaggcc gggtgtggtg   15120
tctcacgcct gtaattccag cactttggga ggccacagca ggcagatcac ttgaggtcag   15180
gcattcgaga ccagcctggc caacatggtg aaaccctcagc tctactaaag atacgaaaat   15240
tagcaggcat agtggcctgc acctgtaata ccaggcactc gcaggagaat cccttgaacc   15300
cggaaggcgg agattgcagt aaaccatgat tgtgccactg cactccagcc tgggcaacag   15360
gagactctgt ctcggaaaaa taaattttt aaaaaaatga aaaaaaataa aagttgacta   15420
aattagtgtc ttggtactaa gcactgtagg aagtgagttt catggaaccc caactctctt   15480
ggggcccaaa gcaagtcata ttaatattga aaattacatg catatacatg catatgacca   15540
aggtgataaa aacaattatt ctgcctgagt tggagaataa tatcccagta aaataaacaa   15600
gagtctcaaa gtcttttgta tcctttgaag ctgtcatggt ggtttgtaac taggcaacag   15660
gtatatattg ttaatcttct ttgcatttaa ttccttttat agagagacac aattttacga   15720
gcagatgcaa ttactagcat gaaggtttct ttgtgagggt agttaaaagg cccacatgag   15780
ctctcttctt atccttgtcc ttctttcagc cagatcttcc ctgccccttt gctcattcca   15840
tctttcaccc acctaccccc aaaacaagga agtaaatctt gcattagtca acaataccaa   15900
agtgattttc aatatgactt tctctgcaga atgttattat ttctgcctct ttacattcac   15960
atactgtctt cctttttttt tttttttttt tagattgggt ctcactctgt   16020
tgcccaggct ggagtgcagt ggcttgatct cagctcactg taacctccac ctcctgagtt   16080
caagcaattc tcctgcctca gcctcctgag tagctgggat tacaggcatg tgccaccaca   16140
cctggctagt ttttttgtat tttagtaga cagggtttt caccatgttg gtcaagctgg   16200
tctcgaactc ctgacctcat gatctgacca cctgtgcctc tcaaagtgct gggattacag   16260
gcgtgagcca ccgggccagc cactctcttc ctttcagttg cctactcatc tcttatgcat   16320
tcctggacat cagttgtcct tttgaagctt tcctccacta tcccagccca tgtgaatcct   16380
ccttccagtt atagccctta attctagatg gctgatattt ttcaataatt gttttaagat   16440
gaccatttta gcctatcagc taaacaatat caaagacaat agctattttt caagtacttt   16500
agtttacctt attatagagt gcataataga tattcagtaa atagtaaagg agaggtgaag   16560
gcttgcatag aatggattct ggtggtgtct cttggtgagc ttttagcatc aagattaatc   16620
agcagtttca gcaatgagct cagaccttca gttttagatc tttactcata tcagataaga   16680
gagtgagaag agtggtatgt atcagtgctt tatttatatt tgcatccaat ttgaactatg   16740
aatattacaa aggtgcacac ataggttcag acagattgat ttaaaatgac caaagatgac   16800
ctgtcgtaag caacctgggt atcttaagat gcactccttg gagagggaat gttcctaaaa   16860
acattttcag agggacgaac tgtatgaaat tcagtaaaac ataaatcatg aggaaaactg   16920
attactctct ttttgacatg aaatgagagt tttaatgcat ggttacgatt attaacgtac   16980
tccgctgcaa gacgttaata aagttactgt tttgcaggct agaatgtctt gatgctgtaa   17040
tcagaacaca cttttttcccc tttcttccag cttcaaatgc agattcataa ttgggctgac   17100
ttctaataac tgcaatgttt tctgccttgg gcttgcagca gaagcctgac aaaatagtgt   17160
ttgtttaggc aataatttat ttatttattt attgagatgg agtttcattc ttgtcgccca   17220
ggctggagtg caatggcgtg atctcggctc actgcaacct ctgtgttcag gcaataattt   17280
agacttacc ttacttgtga ttactatagc aattactata gccacaaggc ataattttac   17340
tgtctcattt caattttatg aatttgaatg ttttttacact tttcctaatg aagtccacta   17400
tgaagttatg tcaaaaaaaa aaagaaaaa gaaagatgca cacgtaaaag agaggtggtt   17460
gcaagagaag aaaagaacgg aggaaagtta aacgcaaacc agataactct cagcgtattc   17520
taaatgacca aaaacagaac tctgttgtca aagatttaa atggaaaatt ttcaattttt   17580
tttttctttt ttgtacaggt ttcttcctga acgcgcctca gcgattttaa atcgtatgca   17640
gaatattcaa tttgaagcag tggttggcca caaaatcaaa atgaaatgaa taaataagct   17700
ccagccagag atgtatgcat gataatgata tgaatagttt cgaatcaatg ctgcaaagct   17760
ttatttcaca tttttttcagt cctgataata ttaaaaacat tggtttggca ctagcagcag   17820
tcaaacgaac aagattaatt acctgtcttc ctgtttctca agaatattta cgtagttttt   17880
cataggtctg ttttttcctt catgcctctt aaaaacttct gtgcttacat aaacatactt   17940
aaaaggtttt ctttaagata ttttattttt ccatttaaag gtggacaaaa gctacctccc   18000
taaaagtaaa tacaaagaga acttatttac acagggaagg tttaagctg ttcaagtagc   18060
attccaatct gtagccatgc cacagaatat caacaagaac acagaatgag tgcacagcta   18120
agagatcaag tttcagcagg cagctttatc tcaacctgga catatttaa gattcagcat   18180
ttgaaagatt tccctagcct cttccttttt cattagccca aaacggtgca actctattct   18240
ggactttatt acttgattct gtcttctgta taactcttgaa gtccaccaaa agtggaccct   18300
ctatatttcc tcccttttta tagtcttata agatacatta tgaaggtga ccgactctat   18360
tttaaatctc agaattttaa gttctagccc catgataacc ttttttctttg taatttatgc   18420
tttcatatat ccttggtccc agagatgttt agacaatttt aggctcaaaa attaaagcta   18480
acacaggaaa aggaactgta ctggctatta cataagaaac aatggaccca agagaagaaa   18540
aggaagaaag aaaggttttt tggttttgt tttgttttgt tttgtttttt gtttttttga   18600
gatggagtct cactcttcg cccaggctgg agtcagtgg gtgatctcag gctcactgca   18660
agctccacct cccgggttca cgccattctc ctgcctcagc ctcctgagta gctgggacta   18720
caggcgcccg ccaccacacc cggctaattt tttgtatttt ttgtagagac ggggtttcac   18780
catgttagcc aagatggtct cgatctcctg acctcgtgat ccacctgcct cggcctccca   18840
aagtgctggg attacgggtg tgagccaccg tgcccagcct ttttttttt aatagaaaaa   18900
ataatccgac tcccactaca tcaagactaa tcttgttttg tgtgttttc acatgtatta   18960
```

```
tagaatgctt ttgcatggac tatcctcttg tttttattaa aaacaaatga ttttttaaa    19020
agtcacaaaa acaattcact aaaaataaat atgtcattgt gctttaaaaa aataaccct    19080
tgtagttata aaataaaacg tttgacttct aaactctg                           19118

SEQ ID NO: 2           moltype = DNA   length = 19119
FEATURE                Location/Qualifiers
source                 1..19119
                       mol_type = genomic DNA
                       organism = Homo sapiens
SEQUENCE: 2
agacagtacc tcctccctag gactacacaa ggactgaacc agaaggaaga ggacagagca      60
aagccatgaa catcatccta gaaatccttc tgcttctgat caccatcatc tactcctact     120
tggagtcgtt ggtgaagttt ttcattcctc agaggagaaa atctgtggct ggggagattg     180
ttctcattac tggagctggg catggaatag gcaggcagc tacttatgaa tttgcaaaac      240
gacagagcat attggttctg tgggatatta ataaggtaat gtatacatct tccaactttt     300
taaagtcaca gagtaagata tgtattttaa gaattatttg acttaccatc tacttatctt     360
tgtattttg ttttcaaag tttgataaat tccctggtcc cttagtctgt atatgtgtca      420
ggttagttag atgaagggaa tgtaattaag aactaagcag cgattttat gacatggtgt      480
gcaggttgat agaaagactc aggagccagt ctccttccaa gctgctaaat gaggcaagtc     540
acatattatc tctcagcctg ttttcttggc tctgaagtgg ggataataac ttaggggatg     600
ggcaagaacg ggatctgaaa attacagcta caaacaaaag tcaaacgaag aacttgcaac     660
agaaacctt agtgcctccc ctcatgcaca agcaacacag ttctaaaata tttactgtct     720
gacccttttac agaaaatgtt tgccagtccg tagtcaaaag gattaaataa gtaatattt     780
cagcacttag catatgataa acgatacgtg gcacatgata aacaataact gtgttaaata     840
aaatatgtgc gcagtgagtc aggcttttcc ttggacatta gtatttttcc tgtgttctta     900
cttgtaaaca ctacattaac aaccccaaat aaaactgaag gaactgaaat cttgtatcat     960
tttctctaaa cttgtaaatt ctggtaaggc catgaaaata tatgcagaga agtgtttaca    1020
ggattttagg attggaaaaa ttgtgaagta ctccttgaga atcacatttt ctgcaaatta    1080
cagtggtttt aattaccatt atattattac tttctcatgt tctttgctgt catgtttagt    1140
tgaaacctaa aatgtctctt acacttagag aactaattct ttctgttt ttttctgaat     1200
agtgaagaat actatacaaa aaagctacta cattttatt taacagatat gagcatttat    1260
ataatagagg agttgatgta tataaaaatg atttgccatc tttttggtct ttgaagaaat    1320
tcgaatgaac tttctggaag atagcaagaa tttacaaata gagaaaattg ttgcctgctg    1380
ttctcaggca tttgtccaaa atatataata agtataaatc tatgaaaagg gcttgatgaa    1440
atctaacctt caaatctctt tccagatgtg tattttggg gaaagggcta tatttattaa    1500
gtttttttta aattttaaaa tttccagaga caagagaaaa gtaaattaga aggaagtcgt    1560
attaaaaatg acttaagggc gggtgcagtg gctcacacct gtaatcccag cactttggga    1620
gacggaggtg ggcagattgc tggagcccag gagttcaaga ccagcctggg cagcacagca    1680
aaaccccccaa ctctacaaaa aatacaaaaa ttagctgggt gcgggggtgc acacccgtag    1740
tcccagctac tcgggaggct gaggtgggag gatcgtttca gttcaggaag ccaaggctgc    1800
aatgagctat gatggcatca ttgcactcca agctgggcaa tagagccagg ctctgtctca    1860
aaaaaaataa aaaaagactt aagaaaaata ggtaacccaa cctcaaaaat tctctttgaa    1920
tcattaaatt tcatggttaa acatttaagc tactgaatga ttcactcata ggctgtaatg    1980
taactcagat ctcctttagg cgaggaagat gctggctgag ttttcatcat aactggctcc    2040
ttttgccctg tgagatgaga gacacagtag cagtttggct cttatgcaat ctaaactgtt    2100
gcgttgggaa tacggttcaa aaaacacatt ggagtttaag ctaaagcaag tgttttgcta    2160
acaaaaagac aaggcatcac atttttgcaat tgtctagctc agttataaaa cagaagaata    2220
ggccggacgc ggtggctcac gcctgtaatc ccagcacttt ggggaggccga gacgggcgga    2280
tcacgaggtc aggagatcga gaccatcctg gataacacag tgaaacccccg tctctactaa    2340
aaatacaaaa aaattagcca ggcgtagtgg cgggcgcctg tagtcccagc tactcgggag    2400
gctgaggcag gagaatggtg tgaacccggg aggcggagct tgcagtgagc cgagatgacg    2460
ccactgcact ccagcctggg cgacagagcg agactccgtc tcaaaaaaa aaaaaaaaa    2520
aaaactgaag aataattaat tcttcaatca aaacatctga tgaatgctct ggtaacttat    2580
gctctctact gacctagaaa caaatgagag agtatggtgt ggtttgtgca atctggcagt    2640
gagcaagcta ccaactaaat cagtgaaaga ctctcctatt cttttttac tcttctgcaa    2700
tcccacaaaa ggctatttga ggggatactg actttgagac tgggtcctaa catccatgtt    2760
tggggagttc aggctgctgc tccagggttt agcctacagt agcgaaatac aaaggaccca    2820
gagaccactc attcaaggtt tgccctaaat agcagcaaca ccactgtcat ctcaatacac    2880
gaagaatagg gctttttcagg tatccttgcc tctttgtcac agagaagagt ttacagattg    2940
tgagacggaa aagtataatt tttaaaacct tataatattt tctataaaag tcacctgagg    3000
tgaaacttg aaaagaatta taattttcca gaatgtgagt caagaaacat tagagcaatt    3060
ttatcttagg aaagaggtct ttgaatttag gctgaaagta aattgctctg tctccatgtc    3120
ctatggttat gggcaagttt ggtacataaa tgagaaatcc atccagtggc cttgcccatc    3180
tcactcccaa acacctgaag aatgtaatgt tatatctcct agagtacgag catggtctcc    3240
ctatgaaagt cctccttctt taaggagact tctttccctt ccctcctagg aggatgagtc    3300
agaatcatca agaaaaatat gatgggcaga ggcatacagt ttaccattac cactagttta    3360
gaattactac ttagcacttt actgccactat acatagttgg tgctcaacaa atgtatgata    3420
aattaatggt tgagttttc ttcttctcc atattcatct tccatgacac cacgaagagc    3480
aatgttttc aagaatgttc ttcaaggttt gaaagtagcc tgcttagag aaactgccta    3540
ctgtacagcc tccaaccaag aggaaaagct gaaaaagca tgaagggatt ttgttttgtt    3600
ttgtttgttt tggttttaat atgagcattc cctggcagaa aagccagggg taatctcatt    3660
gcaactaggc aatcactctc aagaaatttt ctaacaaata aggaggccaa ttttattttt    3720
attttgagac gaagtcccac tctgtcaccc aggttggagt gcaatggaat gatttcagct    3780
cactgcaacc tccgcctccc gggttcaagt gattctctg tctaaacttc ccgagtgact    3840
gggattacag gctcccacca ccacgcccag ctaatttttt gtatttttag tagagatggg    3900
gtttcaccat tttggccaga ctggtctcaa actcctgacc tcaagtgatc caccctcctc    3960
ggcctcctaa agtgctggga ttacaggcgt gagccaccac acctgaccca ggaggccaat    4020
ttttaaaagg ttaactaatc ttcatgtcca aaatgaatgt taattgttca ttttggacat    4080
gaatgttaat tttttttttt ttttttttg agacagagtc tcactctgtt gcccaggctg    4140
```

```
gagtccagtg gcactatctc cactcactgc aacttcctcc tcccaggttc aagcaattat  4200
cctgcctcag cctcccaagt agctgggatt acaggcccac accatcaggc ctggctaatt  4260
tttgtatttt tagtagagac ggggtttcac catgttggcc aggctggtct tgaactcctg  4320
acctcgtgat ccgccctcct cggccaacca aagtgctggg attacaggcg tgagccaccg  4380
cgcctagccg aatgttaatt gtctaaaaat ttttcttctc caatgtcttc tcctccactt  4440
ttttcggaat ttgtttcttc ctaattacag cgcggtgtgg aggaaactgc agctgagtgc  4500
cgaaaactag gcgtcactgc gcatgcgtat gtggtagact gcagcaacag agaagagatc  4560
tatcgctctc taaatcaggt gagactgcag gttcacaaat tcttcagat tattttgttt  4620
cctaggacgc tgacgtggaa aatgagaaag gtctttatga ctgcctgatt taaattggat  4680
tttagctgct aactgaagta gttatgtcac caaggaagga tatatacttt ttttcttgta  4740
tgtaatccac tcagctctgc ccattattat tgttcatatt attaatcaat ttcattctga  4800
tcagaagtgt gagcagtggc acagagtgac tgacaaaaga tttatcatca gggaatatgg  4860
atcacttcct agtttttgttt tagtcctatt aacttgcag taattccagc ttctctcttaa  4920
ttatttccct tgtgagattt tattttggtg ttaatgtagt cttctgtaga aaatgtaata  4980
ttaataatta ttatcacaat tatttttaaa gagtaaatac caaataatca caatgaacta  5040
agcactctaa caaactttac attttttaat tcaatcccta caataactct gtaaacttca  5100
ttttacagat aagcaaatta tgactcagag aggttaagcc agacccaggt catgtagtta  5160
ttaggttatg aaaccaggat ttctcaacca gcacttaga ccaggtgcgg tggttcacac  5220
atgtaatccc agcactttgt gaggccaagg tggaaggatc acatgagacc aagagttcaa  5280
gaccagccca ggcaacatag tgagaccca tctctaaaaa aaaaaaaaaa aaaaaaaaaa  5340
aaagtttaaa gaaaaacaca ttttaaaaa atgaacactt taaaaatatt tggtcagaat  5400
ttatatagga atttatcaac ataaatgtta attcacttt actgataaac ttgcaaaaca  5460
tgatgtgctg ggtactgaaa tttagatgtt aaaagaacag tttatcccac ctttatgaca  5520
gtgttccctt ggcctccacg atttgagctc aacagtctgt cttgcctgaa ctctgagaga  5580
cctcatacaa tagaagaaag actctcatct ttggattata ttggtcccaa aactttgagt  5640
ttgaataata cacccagtga aagtgttctt tcaatttca aaggtgaaga aagaagtggg  5700
tgatgtaaca atcgtggtga ataatgctgg gacagtatat ccagccgatc ttctcagcac  5760
caaggatgaa gagattacca agacatttga ggtcaacatc ctaggacatt tttgggtgag  5820
tgtgagtcag aaacatttct gatttgtgca ccttctctta agatacatga aacttataac  5880
ggagttcaca tacttctgga caggaaactg gccagatctt tgccttaatc aagaatcatt  5940
aaatttgttt gagtagaaga gccacagagt ctctgcacaca aggacacaga attcaagtgt  6000
acacaacaca ccagaatgta agctacttgg tctgtcttgt ccaccagtat ctgacacaaa  6060
gcttggcatg taccaggagc tcaacaaatg tttgtgagg tttgttaagg gttgtcagtg  6120
tacatctttt caatgctgtc acttgtgact tcatttttt cccctccacac catgattttg  6180
taatgtgtcc tcattttgtg aatttttaga atgtgaaagga catcagaagt aattacttgg  6240
atgtatatag gatcgaggac acttttggac gagactctga ggcaagtgtt ctagatccat  6300
ggggtgctgg aactgagaaa tgcagctata cagacctcat ataattggtt agttttgtgg  6360
gagatggaaa tatcaacttc aactgcctt gtatagaaat tttatgatt aatcttccag  6420
tgcctcaata ttagtgtaga atctagggca gatctgaatt ctagaagaaa gaagaaaaaa  6480
aagagatgtg tccccttac ctttaccagc tcttcacata tgtgaattgg ctcccatgcc  6540
caccaaacta cacggagacc tcatacatta gctacctata gctgcataac aaattataca  6600
aaacttagtg gtttaaagca acaatgtatg ttcactatcc tctcacagtt tctatggggtt  6660
gggaatttgg aggtagcttg ggttgggagt tctagttcta tgaattttgca taggatttat  6720
taaattctta taaaatttta ttgatgtttc tcacaaagag ggtttttgga aaaaaagaaa  6780
gacttgtttt ctgtaacatc aacatataat atacaatatt acaaataggg agatagtgaa  6840
ttcaatcatg attcattagt gtggtgtaga actctcagct tacactactc aactgtctta  6900
atacagttac acaagatttc actctttta ttagaatgat aaagccccaa accaaaaaat  6960
tatatgacac caaattatca taaggaataa ttttagttct gaaaactctg aattttcc  7020
ttaatattgt ttagatgaca tatccaaaaa aggatctatt tgattcctc tgaagggaag  7080
gaggggagt actgagatta gtgttggcat ggggcttacc ataccaataa atttgtatct  7140
ttatttctat catttgtaaa gaattaatca tggaatgctt gaagtatttt tatttcattg  7200
tataagttct ctcaaatgcc tttctgtctt aacaaaaata aaactacctg atttggaaac  7260
ctaacgtcta tgtcattgtc tttcttcttt ctgcaatgat ccttaagatc acaaaagcac  7320
ttcttccatc gatgatggag agaaatcatg gccacatcgt cacagtggct tcagtgtgcg  7380
gccacgaagg gattccttac ctcatcccat attggtaagt atcacatgcc agccatgtta  7440
tatattttta tactttgaag ggagcattac acttcaaatt gttaccactg gagagtcctg  7500
gttcttggca tcttgaacaa agaattggac aaaactcacc aacaaagcca ggaaagaatg  7560
aagcaacaaa agcagagatt tattgaaaat gaaagtacgc tttacagggt gggagtgggc  7620
ccaagcacag gggctcaaga gccaattaca gaatttctg gggtttaaat accccctaga  7680
ggtttccact ggttacttgg tgtacgccct atgtaaatga agaggatgaa ttaaagttac  7740
agagtcgttt actcagtgta caccatatgt aaatggagag gatatttcct gtcatagctg  7800
gagtgtttcc atttgattta gttctaggaa gtcagcatga atcggcctta tgttccctgc  7860
ctccagaccc tgttctcctg cctcaagatt acaatgctga gagcagagtg atttggattt  7920
acagaattta aattttatag tgtttagaat gttgactttt ctaaaacaat  7980
gaaaccaggt tgtaattata tttaagatat ttttagattt ctgcaaactc ctctgtagaa  8040
caatgagaga aaacagtaat gccaagcatg tttccattgt ttcctggaat aagaaacaga  8100
aacccacag actgagaagc aaaacctaca gaagctaaaa tgaacacatg tctatgtcat  8160
ggccttggtg cccaagataa gacaatcaga gtggtccctg atcaaaaca ttttacagtg  8220
tgcttgtgcc atgaaagtgt gtgtgtgtgt gtgtgtgtgt gtgtgagaga gagagagaga  8280
gagaaaacga ctctacctga ctaaaagttg cagataccac actccatgca ccaccaaaga  8340
cataaaggga aggaggtgag aggcgttaag gatgtactgc tgtatttgcc aaatatcctt  8400
tcctgtaaac tcttctccag atcctcataa taaaattaag aggccaaagt ggcaaccatt  8460
gtcaagagaa aaactatcaa ccattgtcaa gagataaact cagttattga gagagagagg  8520
agaaatgaca gagtcctac agaagtctgt caacacagat accagttttg tagaatttct  8580
aaatgtattt ttcctgattc atatttttca aaataaaagc agcaataaaa actgattaga  8640
aaacagtttg aagattcaat ggaaaaacct tacatgtagg atggaaaact gaacattaag  8700
ccaatcaata gagttatttt tgttcttttg ttatcattgt tgtttaagaa atgagatacg  8760
ttcacaattc tgcttaatca tgtaagaaaa tgaaaatgaa ttgccattta tactctcaga  8820
aaaatcacaa gtggctgatt tttggcttcc acttgttctt aagccaaatg ataccgcctt  8880
```

```
ctcacagaaa gctgaggatt ggtttcactc tcccttagct aacaatgctt aataattctc   8940
ttacagttcc agcaaatttg ccgctgttgg cttttcacaga ggtctgacat cagaacttca   9000
ggccttggga aaaactggta tcaaaacctc atgtctctgc ccagtttttg tgaatactgg   9060
gttcaccaaa aatccaagca caaggtaagg tcaaaatcaa gttagaatgg gtatgtggta   9120
tgataaattg atatgaaaac taatgagaaa tgtttaggca ggccaactaa tagaagaaaa   9180
tgaagaagga aaaataattt ttcttattat tattattatc ttgaaattaa aggaataaag   9240
ggggaaaaca cattagggac tagcaggaat gatcagccac cgatgaactg ggatatttat   9300
ttgtgtccgg gagaaagcac atacatttga tcaccgttac caccctgtct ttaaaatgca   9360
aatgttccaa ggaccagcaa ataaattgag tatctagctc cttagtcaag gtgaatttct   9420
gcaagaactc ttgtctctgg tgagacagga tttgagacca caagagaaga aaaattagtc   9480
ctgaaaggag aagaaaaaag caggaaggtg tggataagaa cccgaaaatt aagccatctg   9540
cttaacaaat ttttctaatc ctagtatata ttctgctgca ggttaacaaa atatactaag   9600
cttaatgatt cgaaaccaat ttttttactgg aagggaatta atcctaaata tattcattca   9660
aaagaactaa acaattctct gttgagtgcc gcctcatttg aggatactga ctcttacagc   9720
ctgagttagc tatgtggtct ctgcagctgg aatcactccc tgccactgga gtccttcatg   9780
gtgttagacc ataggtactg ttgactaaag aaaaaaaaaa gttttttgttt ttatttttgt   9840
ttttttttgag acagagtctc actctgtcac ccaggctgga gtacagtggc gcgatctcag   9900
ctcaccgcaa cctccgcctt tctgggttca agcaattctc cttcctcagc ctcctgagta   9960
tttggattac aggcgcccac caccacgcct ggctaatttt tgtattttta gtagagacgg  10020
ggtttcacca tgttggccag gctggtctca aactcctgac ctcaggtgtc ctacctgcct  10080
tggcctccta aaatgctggg attacaggag tgagccacca tgcccggcca aaaaaataag  10140
ttttttaaaga attaaaggtc atcctggcta acacagtgaa acccgtctc tactaaaaaa  10200
cacaaaaaaa ttagccgggc gtggtggcgg cgcgcctgtag tcccagctgc gcggaggct  10260
gaggcaggag aatggcgtga acccgggagg cggagcttgc agtgagccga gatcgcgcca  10320
ctgcactcca gcctgggcga cagagcgaga ctccgtctca aaaaaaaaaa aaaaaaaaa  10380
aaaaaaaaga attaaaggtg ttaattttat ttagaagcct tactgaagac tacagtcgga  10440
ggcctatagc ctgagagcag ccctttagag aggttcagtt gaactgttct gatagtgggg  10500
gccatgtgct ctatcctgta ttgtcttcaa agcatctttc cagagagctg cacattgtca  10560
cagagtcagg gactttgtga aattatgctg acaaccagaa gtgagtaaac gtggcttctt  10620
acatttgcta cgttgtctca cagtacttaa taagtatgca atatgtaagt aaatactata  10680
gtactattgc aactcctgat tgttttctta gacaaggaat tgggcccaat aaaaaccctc  10740
ttggtaggca ttcaggcttc gtgtaccatg agctttccta agggtatcct gccactcttg  10800
gggaaggcat gatagatgag gggagtaagg ataatgaac tctgggtaca gggttcctgg  10860
gggctaactt agaggtagac acaggcaatg ctaaatattt gggattgatt ttatagaggt  10920
tgctagattg tgaatttcct tagtaagggc taaggcattg atatgtaatg tcacacttgg  10980
ctccgaggct gggttgttgg atccatgtag atgaaatcag ggagagaaag ggcagaacgg  11040
agtaatttag aaatgtattg atttgtatta ctctctgttg gcttgctatt caaggcagtg  11100
gagaactcaa tcacataata atctgcagca aaccacagat catcccaggg aatgaagttt  11160
taacattcgc tggctcccta actcctcacc cagccttac attcactggc tgttcagtcc  11220
atgcctggac atcttaattt gaatacaaca ttttaaatcc attttctgt catcatcttg  11280
cactaacaga caattctaca ctaagcctat gtttatgaat atttctcaag agtacatgta  11340
cacagccttc agtataagga aaactggaag tatgacatac ctccagttgt catactcctt  11400
gggccctct taaattctca ttaaactgca ggataggcaa gtcagaggtg aatctcaaat  11460
acgaaattct taccggaaag gggttccaat ccagacccca agagagggtt cttagatttc  11520
tcgcaagaaa taattcgggg caaggccaca gtgcaaagca aaagcaagtt tattaggaaa  11580
gtaaaggagt agagaacagc tactccatgg agaagaatgg cttgagctgc tccaccaagg  11640
gtatttagag ttacttcttg attatatgct aaacaagggg tggattattc atgagttttc  11700
cgggaaaagg gtgagcaatt cccagaactg agatttcctc cccttttag gccatatagg  11760
gtaacttcct gccattgcca tggtatttgt aaactgtcat agtgctggtg gaagtgtctc  11820
ttagcttgct aatgtattat agttagctta taatgagcag tgaggacaac cagaggtcac  11880
tttcatcaac atcttggttt tggtgggttt tggccggctc ctttactgca ccctattta  11940
tcaacaaggc ctttatgacc tgaatcttgt gccaacctcc tatctcatcc tgtgacaaag  12000
aatgccttaa cttcctggga atgcagccca gtaggtgtca gccttatttt acccagaccc  12060
tattcaagat ggagttgctc tgatttaaac gcctctgaca aaatgacgac ctcaaaacaa  12120
tccagcttta tggaatacct ccacaagaaa gaaagtatac ttagctatag aattttctcc  12180
ttgcatccaa caggctttga gatgtcagat gtttccttcc tgtcccatga ttaatcctag  12240
ccattcctct ttcttgtctg gctccactac tccttaccat ctaatgcctc gccaccattt  12300
tgatattttt actaagtgag ctatgaaaca cacctactgg atatgaaagt ataagtttct  12360
gataacaaaa catcaacatg ggatggtggag gaagtgggta gggtggcatt aatgcagcaa  12420
atcctggaat atttttaaatc ttcattctaa atttagtaaa aatataggat aattttcctg  12480
ccatcatttta cttataaaat taaaatttta gaaaataaaa ataatatttt cctcttttta  12540
atcacagatt atggcctgta ttggagacag atgaagtcgt aagaagtctg atagatggaa  12600
tacttaccaa taagaaaatg attttttgttc catcgtatat caatatcttt ctgagactac  12660
agaagttaag tacagcacag aacacccaaa tactaaaaca ccaatagge ttttttttct  12720
gcttttttttt ttttttagaca gagtctcact ctgtcaccct ggctggattg cggtggttgc  12780
agtggcatga tcttggctca ctgcaacctc cgcctcctgg gttcaagcaa ttctcatgcc  12840
tcagaccccc aagtaactgg gattataggt gtgtgctgcc acactacacc cagctaattt  12900
ttgtattttt tgatagagac aggtttcccc atgttggcca ggctggactc gaactcctga  12960
cctcaagtta tcctcctgtc tcggcctccc aaagtgctgg gattacagtc atgagccac  13020
atgcctggcc caatagagct attattatgg agcatctttc agttgtgaaa attggcatgg  13080
aaactctcca tccctgggga gaacagttat ttcctctgtt attttcctac ccagtctata  13140
aaaagagagt gattcatttt ctctaccaaa tctactgtct ctgcccaaac tttgctgaag  13200
actattctaa ctaaaggaaa cacagtttaa aagaatgca atatagtgaa gtagttaata  13260
ataaagactc cattttttaa agtctgctgg aagtttgga gggattgcac tgaatctata  13320
gagcaattgg ggagtattga catatcaaca atattgagtt ttctaatcca agaacataat  13380
atctatttt aaaatcttct tcaaaatctt taaatcttta aattgtattt tgtagttttt  13440
ggtgtttaag tcttgcacat atttttgtcag atttattcca aagtatttca cgggttcttt  13500
tttttttttt tttttttttt tttgagacag agtttcaccc ttgttgccca ggctggagtg  13560
cagtggcgtg atcttggctc actgcagctt ctgcctcctg gcttcaagtg attctcctgc  13620
```

```
ctcagcctcc caagtagctg ggattacagg cacctgcccc ctcgcccaac taacttttttg   13680
tgtttgtagt agagacaggg tttcaccatg ttggccaggc tggtctcgaa ctcctgacct   13740
catgtgatcc acctgcctca gcctcccaaa gtgctgggat tacaggcatg agccatcatg   13800
cccagcccta tttgacggtt tttgacgcta atgcaagtgg cattttaaaa aattttatat   13860
ttcccattgt ttgttgtcag tatatattgg attttttgtaa tttgatctca tatttttgcag   13920
tcttgctaaa ttgctaaacc tcttttttgct aaactcgata agcttttttt ttttttggtag   13980
attcctgggc ctctaatttt ctttatggga aagttttttaa ttacaaattt aatttctttta   14040
atagctacat ggctattcaa tttacttatt aattcttggt aatgtgtgtc tttcaaggaa   14100
tttgtccatt tcatctaagt tgtagaattt ctttggcata aatttgtaca taacattccc   14160
ttattatcct tttaatgtct ttagaatgtc ttatttattt atttatttat ttttattata   14220
tttttttgag acagagtctc gctctgttgc ccaggctgga gtgcagtggc acaatcttgg   14280
ctcactgcaa gctccgcctt ctgggttcat gccattctcc tgcctcagcc tcccagttg    14340
ctgggactac aggcgcctgc aaccatgccc agcttatttt ttttttttttt tttttttttt   14400
tttttttttt tttttttttt ttagtagaga cggggtttca ccctgttagc caggatggtc    14460
tcgatctcct gacctggtga tccgcccgcc tcagcctccc aaagtgctgg gattacaggc   14520
gtgagccacc aagcccagcc tatttattta tttagtagag acagtctcac tttgctgccc   14580
aggcaacaaa ggttttgaat gcctggcctc aagcagtcct cctgccttgg cctcccaaag   14640
tgctgggatt acaggcatga gccactgcac ctggccaaat gaatatgctg ataatatctt   14700
ctttataagg atgacataag aataaaataa tgtaatacaa acaaagcccc tgtcactgaa   14760
aatgtataga cttcaaatgt taaagtctta gagaacagaa tttatatgaa atagcaacag   14820
caacaatttc ccagaggaaa tactctctca gctttcttct gaggagcagt ttctaaattg   14880
aaattgtatc agtgagaaga taactatact aacttcataa gccttgggcc ttttttgaaac   14940
aaatccatat aaactatgaa caaacttgaa ataaaacaat ttgagaacag ggtacaaact   15000
gcattggtgt atcaatttca gtatttggtt ttagcttaaa tagactgact tgagataaca   15060
taaggagaac cttgaccccc aagcaacatc atctcgcgag ttgactaggc cgggtgtggt   15120
gtctcacgcc tgtaattcca gcactttggg aggccacagc aggcagatca cttgaggtca   15180
ggcattcgag accagcctgg ccaacatggt gaaaccctcag ctctactaaa gatacgaaaa   15240
ttagcaggca tagtggcctg cacctgtaat accaggcact cgcaggagaa tcccttgaac   15300
ccggaaggcg gagattgcag taaaccatga ttgtgccact gcactccagc ctgggcaaca   15360
ggagactctg tctcggaaaa aaaaatttttt taaaaaaatg aaaaaaaata aaagttgact   15420
aaattagtgt cttggtacta agcactgtag gaagtgagtt tcatggaacc ccaactctct   15480
tggggcccaa agcaagtcat attaataattg aaaattacat gcatatacat gcatatgacc   15540
aaggtgataa aaacaattat tctgcctgag ttggagaata gtatcccagt aaaataaaca   15600
agagtctcaa agtcttttgt atcctttgaa gctgtcatgg tggtttgtaa ctaggcaaaa   15660
ggtatatatt gttaatcttc tttgcattta attccttttta tagagagaca caattttacg   15720
agcagatgca attactagca tgaaggtttc tttgtgaggg tagttaaaag gcccacatga   15780
gctctcttct tatccttgtc cttcttttcag ccagatcttc cctgcccctt tgctcattcc   15840
atctttcacc cacctacccc caaaacaagg aagtaaatct tgcattagtc aacaatacca   15900
aagtgatttc caatatgact ttctctgcag aatgttatta tttctgcctc tttacattca   15960
catactgtct tcctttttttt tttttttttttt tttttttttt ttagattggg tctcactctg   16020
ttgcccaggc tggagtgcag tggcttgatc tcagctcact gtaacctcca cctcctgagt   16080
tcaagcaatt ctcctgcctc agcctcctga gtagctggga ttacaggcat gtgccaccac   16140
acctggctag tttttttgta ttttagtag agacagggtt tcaccatgtt ggtcaagctg   16200
gtctcgaact cctgacctca tgatctgacc acctgtgcct ctcaaagtgc tgggattaca   16260
ggcgtgagcc accgggccag ccactctctt cctttcagtt gcctactcat ctcttatgca   16320
ttcctggaca tcagttgtcc ttttgaagct ttcctccact atcccagccc atgtgaatcc   16380
tccttccagt tatagccctt aattctagat ggctgatatt tttcaataat tgttttaaga   16440
tgaccatttt agcctatcag ctaaacaata tcaaagacaa tagctatttt tcaagtactt   16500
tagtttacct tattatagag tgcataatag atattcagta aatagtaaag gagaggtgaa   16560
ggcttgcata gaatggattc tggtggtgtc tcttggtgag cttttagcat caagattaat   16620
cagcagtttc agcaatgagc tcagaccttc agtttttagat ctttactcat atcagataag   16680
agagtgagaa gagtggtatg tatcagtgct ttatttatat ttgcatccaa tttgaactat   16740
gaatattaca aaggtgcaca cataggttca gacagattga tttaaaatga ccaaagatga   16800
cctgtcgtaa gcaacctggg tatcttaaga tgcactcctt ggagagggaa tgttcctaaa   16860
aacatttttca gagggacgaa ctgtatgaaa ttcagtaaaa cataaatcat gagggaaaact   16920
gattactctc ttttttgacat gaaatgagag ttttaatgca tggttacgat tattaacgta   16980
ctccgctgca agacgttaat aaagttactg ttttgcaggc tagaatgtct tgatgctgta   17040
atcagaaacac acttttttccc cttttcttcca gcttcaaatg cagattcata attgggctga   17100
cttctaataa ctgcaatgtt ttctgccttg ggcttgcagc agaagcctga caaaatagtg   17160
tttgttttagg caataatttta ttttatttatt tattgagatg gagtttcatt cttgtcgccc   17220
aggctggagt gcaatggcgt gatctcggct cactgcaacc tctgtgttca ggcaataatt   17280
tagactttac cttacttgtg attactatag caattactat agccacaagg cataatttta   17340
ctgtctcatt tcaatttttat gaatttgaat gttttttacac ttttcctaat gaagtccact   17400
atgaagttat gtcaaaaaaa aaaaagaaaa agaaagtgc acacgtaaagg aggtggt    17460
tgcaagagaa gaaaagaacg gaggaaagtt aaacgcaaac cagataactc tcagcgtatt   17520
ctaaatgacc aaaaacagaa ctctgttgtc aaagatttta aatggaaaat ttttcaattt   17580
tttttttcttt tttgtacagg tttcttcctg aacgcgcctc agcgatttta aatcgtatgc   17640
agaatattca atttgaagca gtggttggcc acaaaatcaa aatgaaatga ataaataagc   17700
tccagccaga gatgtatgca tgataatgat atgaatagtt tcgaatcaat gctgcaaagc   17760
tttatttcac attttttcag tcctgataat attaaaaaca ttggtttggc actagcagca   17820
gtcaaacgaa caagattaat tacctgtctt cctgtttctc aagaatatttt acgtagttttt   17880
tcataggtct gttttttcctt tcatgcctct taaaaacttc tgtgcttaca taaacatact   17940
taaaaggttt tctttaagat attttatttt tccatttaaa ggtggacaaa agctacctcc   18000
ctaaaagtaa atacaaagag aacttattta cacaggaagg ttttaagact gttcaagtag   18060
cattccaatc tgtagccatg ccacagaata tcaacaagaa cacagaatga gtgcacagct   18120
aagagatcaa gttcagcag gcagcttttat ctcaacctgg acatatttta agattcagca   18180
tttgaaagat ttccctagcc tcttccttttt tcattagccc aaaacggtgc aactctattc   18240
tggactttat tacttgattc tgtcttctgt ataactctga agtccaccaa aagtggaccc   18300
tctatatttc ctcccttttt atagtcttat aagatacatt atgaaaggtg accgactcta   18360
```

```
ttttaaatct cagaatttta agttctagcc ccatgataac cttttctctt gtaatttatg  18420
ctttcatata tccttggtcc cagagatgtt tagacaattt taggctcaaa aattaaagct  18480
aacacaggaa aaggaactgt actggctatt acataagaaa caatggaccc aagagaagaa  18540
aaggaagaaa gaaaggtttt ttggttttg ttttgttttg ttttgttttt tgttttttg    18600
agatggagtc tcactctttc gcccaggctg gagtgcagtg gtatgatctc agctcactgc  18660
aagctccacc tcccgggttc acgccattct cctgcctcag cctcctgagt agctgggact  18720
acaggcgccc gccaccacac ccggctaatt ttttgtattt tttgtagaga cggggtttca  18780
ccatgttagc caagatggtc tcgatctcct gacctcgtga tccacctgcc tcggcctccc  18840
aaagtgctgg gattacgggt gtgagccacc gtgcccagcc tttttttttt taatagaaaa  18900
aataatccga ctcccactac atcaagacta atcttgtttt gtgtgttttt cacatgtatt  18960
atagaatgct tttgcatgga ctatcctctt gtttttatta aaacaaatg attttttaa    19020
aagtcacaaa aacaattcac taaaaataaa tatgtcattg tgctttaaaa aaataaccctc 19080
ttgtagttat aaaataaaac gtttgacttc taaactctg                         19119

SEQ ID NO: 3              moltype = RNA    length = 900
FEATURE                   Location/Qualifiers
source                    1..900
                          mol_type = mRNA
                          organism = Homo sapiens
SEQUENCE: 3
atgaacatca tcctagaaat ccttctgctt ctgatcacca tcatctactc ctacttggag   60
tcgttggtga agtttttcat tcctcagagg agaaaatctg tggctgggga gattgttctc   120
attactggag ctgggcatgg aataggcagg cagactactt atgaatttgc aaaacgacag   180
agcatattgg ttctgtggga tattaataag cgcggtgtgg aggaaactgc agctgagtgc   240
cgaaaactag gcgtcactgc gcatgcgtat gtggtagact gcagcaacag agaagagatc   300
tatcgctctc taaatcaggt gaagaaagaa gtgggtaatcgt ggtgaataat             360
gctgggacag tatatccagc cgatcttctc agcaccaagg atgaagagat taccaagaca   420
tttgaggtca acatcctagg acattttgg atcacaaaag cacttcttcc atcgatgatg    480
gagagaaatc atgccacat cgtcacagtg gcttcagtgt gcggcacga agggattcct     540
tacctcatcc catattgttc cagcaaattt gccgctgttg gctttcacag aggtctgaca   600
tcagaacttc aggccttggg aaaaactggt atcaaaacct catgtctctg cccagtttt    660
gtgaatactg ggttcaccaa aaatccaagc acaagattat ggcctgtatt ggagacagat   720
gaagtcgtaa gaagtctgat agatggaata cttaccaata agaaaatgat ttttgttcca   780
tcgtatatca atatctttct gagactacag aagtttcttc ctgaacgcgc ctcagcgatt   840
ttaaatcgta tgcagaatat tcaatttgaa gcagtggttg gccacaaaat caaaatgaaa   900

SEQ ID NO: 4              moltype = RNA    length = 792
FEATURE                   Location/Qualifiers
source                    1..792
                          mol_type = mRNA
                          organism = Homo sapiens
SEQUENCE: 4
atgaacatca tcctagaaat ccttctgctt ctgatcacca tcatctactc ctacttggag   60
tcgttggtga agtttttcat tcctcagagg agaaaatctg tggctgggga gattgttctc   120
attactggag ctgggcatgg aataggcagg cagactactt atgaatttgc aaaacgacag   180
agcatattgg ttctgtggga tattaataag gtgaagaaag aagtgggtga tgtaacaatc   240
gtgtgaata atgctgggac agtatatcca gccgatcttc tcagcaccaa ggatgaagag   300
attaccaaga catttgaggt caacatccta ggacattttt ggatcacaaa agcacttctt  360
ccatcgatga tggagagaaa tcatggccac atcgtcacag tggcttcagt gtgcggccac  420
gaagggattc cttacctcat cccatattgt tccagcaaat ttgccgctgt tggctttcac  480
agaggtctga catcagaact tcaggccttg ggaaaaactg gtatcaaaac ctcatgtctc  540
tgcccagttt ttgtgaatac tgggttcacc aaaaatccaa gcacaagatt atggcctgta  600
ttggagacag atgaagtcgt aagaagtctg atagatggaa tacttaccaa taagaaaatg  660
attttgttc catcgtatat caatatcttt ctgagactac agaagtttct tcctgaacgc   720
gcctcagcga ttttaaatcg tatgcagaat attcaatttg aagcagtggt tggccacaaa  780
atcaaaatga aa                                                      792

SEQ ID NO: 5              moltype = RNA    length = 783
FEATURE                   Location/Qualifiers
source                    1..783
                          mol_type = mRNA
                          organism = Homo sapiens
SEQUENCE: 5
atgaacatca tcctagaaat ccttctgctt ctgatcacca tcatctactc ctacttggag   60
tcgttggtga agtttttcat tcctcagagg agaaaatctg tggctgggga gattgttctc   120
attactggag ctgggcatgg aataggcagg cagactactt atgaatttgc aaaacgacag   180
agcatattgg ttctgtggga tattaataag cgcggtgtgg aggaaactgc agctgagtgc   240
cgaaaactag gcgtcactgc gcatgcgtat gtggtagact gcagcaacag agaagagatc   300
tatcgctctc taaatcaggt gaagaaagaa gtgggtgatg taacaatcgt ggtgaataat   360
gctgggacag tatatccagc cgatcttctc agcaccaagg atgaagagat taccaagaca   420
tttgaggtca acatcctagg acattttgg atcacaaaag cacttcttcc atcgatgatg    480
gagagaaatc atgccacat cgtcacagtg gcttcagtgt gcggcacga agggattcct     540
tacctcatcc catattgttc cagcaaattt gccgctgttg gctttcacag aggtctgaca   600
tcagaacttc aggccttggg aaaaactggt atcaaaacct catgtctctg cccagttttt   660
gtgaatactg ggttcaccaa aaatccaagc acaaggtttc ttcctgaacg cgcctcagcg   720
attttaaatc gtatgcagaa tattcaattt gaagcagtgg ttggccacaa aatcaaaatg   780
aaa                                                                783

SEQ ID NO: 6              moltype = RNA    length = 822
```

| FEATURE | Location/Qualifiers |
|---|---|
| source | 1..822<br>mol_type = mRNA<br>organism = Homo sapiens |

SEQUENCE: 6

```
atgaacatca tcctagaaat ccttctgctt ctgatcacca tcatctactc ctacttggag   60
tcgttggtga agttttcat tcctcagagg agaaaatctg tggctgggga gattgttctc   120
attactggag ctgggcatgg aataggcagg cagactactt atgaatttgc aaaacgacag   180
agcatattgg ttctgtggga tattaataag cgcggtgtgg aggaaactgc agctgagtgc   240
cgaaaactag gcgtcactgc gcatgcgtat gtggtagact gcagcaacag agaagagatc   300
tatcgctctc taaatcaggt gaagaaagaa gtgggtgatg taacaatcgt ggtgaataat   360
gctgggacag tatatccagc cgatcttctc agcaccaagg atgaagagat taccaagaca   420
tttgaggtca acatcctagg acatttttgg atcacaaaag cacttcttcc atcgatgatg   480
gagagaaatc atggccacat cgtcacagtg gcttcagtgt gcggccacga agggattcct   540
tacctcatcc catattgttc cagcaaattt gccgctgttg gctttcacag aggtctgaca   600
tcagaacttc aggccttggg aaaaactggt atcaaaacct catgtctctg cccagttttt   660
gtgaatactg ggttcaccaa aaatccaagc acaagattat ggcctgtatt ggagacagat   720
gaagtcgtaa aagtctgat agatggaata cttaccaata gaaaatgat ttttgttcca   780
tcgtatatca atatctttct gagactacag aaggtttctc cc                      822
```

| SEQ ID NO: 7 | moltype = RNA length = 972 |
|---|---|
| FEATURE | Location/Qualifiers |
| source | 1..972<br>mol_type = mRNA<br>organism = Homo sapiens |

SEQUENCE: 7

```
atgaacatca tcctagaaat ccttctgctt ctgatcacca tcatctactc ctacttggag   60
tcgttggtga agttttcat tcctcagagg agaaaatctg tggctgggga gattgttctc   120
attactggag ctgggcatgg aataggcagg cagactactt atgaatttgc aaaacgacag   180
agcatattgg ttctgtggga tattaataag cgcggtgtgg aggaaactgc agctgagtgc   240
cgaaaactag gcgtcactgc gcatgcgtat gtggtagact gcagcaacag agaagagatc   300
tatcgctctc taaatcaggt gaagaaagaa gtgggtgatg taacaatcgt ggtgaataat   360
gctgggacag tatatccagc cgatcttctc agcaccaagg atgaagagat taccaagaca   420
tttgaggtca acatcctagg acatttttgg aatggaaagg aatcagaagt taattacttg   480
gatgtatata ggatcgagga cacttttgga cgagactctg agatcgaaaa agcacttctt   540
ccatcgatga tggagagaaa tcatggccac atcgtcacag tggcttcagt gtgcggccac   600
gaagggattc cttacctcat cccatattgt tccagcaaat ttgccgctgt tggctttcac   660
agaggtctga catcagaact tcaggccttg ggaaaaactg gtatcaaaac ctcatgtctc   720
tgcccagttt ttgtgaatac tgggttcacc aaaaatccaa gcacaagatt atggcctgta   780
ttggagacag atgaagtcgt aagaagtctg atagatggaa tacttaccaa taagaaaatg   840
atttttgttc catcgtatat caatatcttt ctgagactac agaagtttct tcctgaacgc   900
gcctcagcga ttttaaatcg tatgcagaat attcaatttg aagcagtggt tggccacaaa   960
atcaaaatga aa                                                        972
```

| SEQ ID NO: 8 | moltype = RNA length = 852 |
|---|---|
| FEATURE | Location/Qualifiers |
| source | 1..852<br>mol_type = mRNA<br>organism = Homo sapiens |

SEQUENCE: 8

```
atgaacatca tcctagaaat ccttctgctt ctgatcacca tcatctactc ctacttggag   60
tcgttggtga agttttcat tcctcagagg agaaaatctg tggctgggga gattgttctc   120
attactggag ctgggcatgg aataggcagg cagactactt atgaatttgc aaaacgacag   180
agcatattgg ttctgtggga tattaataag cgcggtgtgg aggaaactgc agctgagtgc   240
cgaaaactag gcgtcactgc gcatgcgtat gtggtagact gcagcaacag agaagagatc   300
tatcgctctc taaatcaggt gaagaaagaa gtgggtgatg taacaatcgt ggtgaataat   360
gctgggacag tatatccagc cgatcttctc agcaccaagg atgaagagat taccaagaca   420
tttgaggtca acatcctagg acatttttgg atcacaaaag cacttcttcc atcgatgatg   480
gagagaaatc atggccacat cgtcacagtg gcttcagtgt gcggccacga agggattcct   540
tacctcatcc catattgttc cagcaaattt gccgctgttg gctttcacag aggtctgaca   600
tcagaacttc aggccttggg aaaaactggt atcaaaacct catgtctctg cccagttttt   660
gtgaatactg ggttcaccaa aaatccaagc acaagattat ggcctgtatt ggagacagat   720
gaagtcgtaa aagtctgat agatggaata cttaccaata gaaaatgat ttttgttcca   780
tcgtatatca atatctttct gagactacag aagttaagta cagcacagaa cacccaaata   840
ctaaaacacc aa                                                        852
```

| SEQ ID NO: 9 | moltype = RNA length = 714 |
|---|---|
| FEATURE | Location/Qualifiers |
| source | 1..714<br>mol_type = mRNA<br>organism = Homo sapiens |

SEQUENCE: 9

```
atgaacatca tcctagaaat ccttctgctt ctgatcacca tcatctactc ctacttggag   60
tcgttggtga agttttcat tcctcagagg agaaaatctg tggctgggga gattgttctc   120
attactggag ctgggcatgg aataggcagg cagactactt atgaatttgc aaaacgacag   180
agcatattgg ttctgtggga tattaataag gtgaagaaag aagtgggtga tgtaacaatc   240
gtggtgaata atgctgggac agtatatcca gccgatcttc tcagcaccaa ggatgaagag   300
attaccaaga catttgaggt caacatccta ggacattttt ggatcacaaa agcacttctt   360
ccatcgatga tggagagaaa tcatggccac atcgtcacag tggcttcagt gtgcggccac   420
```

```
gaagggattc cttacctcat cccatattgt tccagcaaat tgccgctgt tggctttcac    480
agaggtctga catcagaact tcaggccttg ggaaaaactg gtatcaaaac ctcatgtctc   540
tgcccagttt ttgtgaatac tgggttcacc aaaaatccaa gcacaagatt atggcctgta   600
ttggagacag atgaagtcgt aagaagtctg atagatggaa tacttaccaa taagaaaatg   660
attttttgttc catcgtatat caatatcttt ctgagactac agaaggtttc ttcc        714

SEQ ID NO: 10          moltype = RNA   length = 894
FEATURE                Location/Qualifiers
source                 1..894
                       mol_type = mRNA
                       organism = Homo sapiens
SEQUENCE: 10
atgaacatca tcctagaaat ccttctgctt ctgatcacca tcatctactc ctacttggag    60
tcgttggtga agttttttcat tcctcagagg agaaaatctg tggctgggga gattgttctc   120
attactggag ctgggcatgg aataggcagg cagactactt atgaatttgc aaaacgacag   180
agcatattgg ttctgtggga tattaataag cgcggtgtgg aggaaactgc agctgagtgc   240
cgaaaactag gcgtcactgc gcatgcgtat gtggtagact gcagcaacag agaagagatc   300
tatcgctctc taaatcaggt gaagaaagaa gtgggtgatg taacaatcgt ggtgaataat   360
gctgggacag tatatccagc cgatcttctc agcaccaagg atgaagagat taccaagaca   420
tttgaggtca acatcctagg acatttttgg aatggaaagg acatcagaag taattacttg   480
gatgtatata ggatcgagga cacttttgga cgagactctg agatcacaaa agcacttctt   540
ccatcgatga tggagagaaa tcatggccac atcgtcacag tggcttcagt gtgcggccac   600
gaagggattc cttacctcat cccatattgt tccagcaaat tgccgctgt tggctttcac    660
agaggtctga catcagaact tcaggccttg ggaaaaactg gtatcaaaac ctcatgtctc   720
tgcccagttt ttgtgaatac tgggttcacc aaaaatccaa gcacaagatt atggcctgta   780
ttggagacag atgaagtcgt aagaagtctg atagatggaa tacttaccaa taagaaaatg   840
attttttgttc catcgtatat caatatcttt ctgagactac agaaggtttc ttcc        894

SEQ ID NO: 11          moltype = RNA   length = 813
FEATURE                Location/Qualifiers
source                 1..813
                       mol_type = mRNA
                       organism = Homo sapiens
SEQUENCE: 11
atgaacatca tcctagaaat ccttctgctt ctgatcacca tcatctactc ctacttggag    60
tcgttggtga agttttttcat tcctcagagg agaaaatctg tggctgggga gattgttctc   120
attactggag ctgggcatgg aataggcagg cagactactt atgaatttgc aaaacgacag   180
agcatattgg ttctgtggga tattaataag cgcggtgtgg aggaaactgc agctgagtgc   240
cgaaaactag gcgtcactgc gcatgcgtat gtggtagact gcagcaacag agaagagatc   300
tatcgctctc taaatcaggt gaagaaagaa gtgggtgatg taacaatcgt ggtgaataat   360
gctgggacag tatatccagc cgatcttctc agcaccaagg atgaagagat taccaagaca   420
tttgaggtca acatcctagg acatttttgg atcacaaaag cacttcttcc atcgatgatg   480
gagagaaatc atggccacat cgtcacagtg gcttcagtg gcggccacga agggattcct   540
tacctcatcc catattgttc cagcaaattt gccgctgttg ctttcacag aggtctgaca   600
tcagaacttc aggcctggg aaaaactggt atcaaaacct catgtctctg cccagttttt   660
gtgaatactg gttcaccaa aaatccaagc acaagattat ggcctgtatt ggagacagat   720
gaagtcgtaa gaagtctgat agatggaata cttaccaata agaaaatgat ttttgttcca   780
tcgtatatca atatcttttct gagactacag aag                               813

SEQ ID NO: 12          moltype = DNA   length = 900
FEATURE                Location/Qualifiers
source                 1..900
                       mol_type = other DNA
                       organism = Homo sapiens
SEQUENCE: 12
atgaacatca tcctagaaat ccttctgctt ctgatcacca tcatctactc ctacttggag    60
tcgttggtga agttttttcat tcctcagagg agaaaatctg tggctgggga gattgttctc   120
attactggag ctgggcatgg aataggcagg cagactactt atgaatttgc aaaacgacag   180
agcatattgg ttctgtggga tattaataag cgcggtgtgg aggaaactgc agctgagtgc   240
cgaaaactag gcgtcactgc gcatgcgtat gtggtagact gcagcaacag agaagagatc   300
tatcgctctc taaatcaggt gaagaaagaa gtgggtgatg taacaatcgt ggtgaataat   360
gctgggacag tatatccagc cgatcttctc agcaccaagg atgaagagat taccaagaca   420
tttgaggtca acatcctagg acatttttgg atcacaaaag cacttcttcc atcgatgatg   480
gagagaaatc atggccacat cgtcacagtg gcttcagtg gcggccacga agggattcct   540
tacctcatcc catattgttc cagcaaattt gccgctgttg ctttcacag aggtctgaca   600
tcagaacttc aggcctggg aaaaactggt atcaaaacct catgtctctg cccagttttt   660
gtgaatactg gttcaccaa aaatccaagc acaagattat ggcctgtatt ggagacagat   720
gaagtcgtaa gaagtctgat agatggaata cttaccaata agaaaatgat ttttgttcca   780
tcgtatatca atatcttttct gagactacag aagtttcttc ctgaacgcgc tcagcgatt   840
ttaaatcgta tgcagaatat tcaatttgaa gcagtggttg gccacaaaat caaatgaaa   900

SEQ ID NO: 13          moltype = DNA   length = 792
FEATURE                Location/Qualifiers
source                 1..792
                       mol_type = other DNA
                       organism = Homo sapiens
SEQUENCE: 13
atgaacatca tcctagaaat ccttctgctt ctgatcacca tcatctactc ctacttggag    60
tcgttggtga agttttttcat tcctcagagg agaaaatctg tggctgggga gattgttctc   120
```

```
attactggag ctgggcatgg aataggcagg cagactactt atgaatttgc aaaacgacag    180
agcatattgg ttctgtggga tattaataag gtgaagaaag aagtgggtga tgtaacaatc    240
gtggtgaata atgctgggac agtatatcca gccgatcttc tcagcaccaa ggatgaagag    300
attaccaaga catttgaggt caacatccta ggacattttt ggatcacaaa agcacttctt    360
ccatcgatga tggagagaaa tcatggccac atcgtcacag tggcttcagt gtgcggccac    420
gaagggattc cttacctcat cccatattgt tccagcaaat ttgccgctgt tggctttcac    480
agaggtctga catcagaact tcaggccttg ggaaaaactg gtatcaaaac ctcatgtctc    540
tgcccagttt ttgtgaatac tgggttcacc aaaaatccaa gcacaagatt atggcctgta    600
ttggagacag atgaagtcgt aagaagtctg atagatgaa tacttaccaa taagaaaatg    660
atttttgttc catcgtatat caatatcttt ctgagactac agaagtttct tcctgaacgc    720
gcctcagcga ttttaaatcg tatgcagaat attcaatttg aagcagtggt tggccacaaa    780
atcaaaatga aa                                                        792

SEQ ID NO: 14           moltype = DNA length = 783
FEATURE                 Location/Qualifiers
source                  1..783
                        mol_type = other DNA
                        organism = Homo sapiens
SEQUENCE: 14
atgaacatca tcctagaaat ccttctgctt ctgatcacca tcatctactc ctacttggag     60
tcgttggtga agttttcat tcctcagagg agaaaatctg tggctgggga gattgttctc    120
attactggag ctgggcatgg aataggcagg cagactactt atgaatttgc aaaacgacag    180
agcatattgg ttctgtggga tattaataag cgcggtgtgg aggaaactgc agctgagtgc    240
cgaaaactag gcgtcactgc gcatgcgtat gtggtagact gcagcaacag agaagagatc    300
tatcgctctc taaatcaggt gaagaaagaa gtgggtgatg taacaatcgt ggtgaataat    360
gctgggacag tatatccagc cgatcttctc agcaccaagg atgaagagat taccaagaca    420
tttgaggtca acatcctagg acattttgg atcacaaaag cacttcttcc atcgatgatg    480
gagagaaatc atgccacat cgtcacagtg gcttcagtgt gcggcacga agggattcct    540
tacctcatcc catattgttc cagcaaattt gccgctgttg gctttcacag aggtctgaca    600
tcagaacttc aggcctgggg aaaaactggt atcaaaacct catgtctctg cccagttttt    660
gtgaatactg ggttcaccaa aaatccaagc acaaggtttc ttcctgaacg cgcctcagcg    720
attttaaatc gtatgcagaa tattcaattt gaagcagtgg ttggccacaa aatcaaaatg    780
aaa                                                                  783

SEQ ID NO: 15           moltype = DNA length = 822
FEATURE                 Location/Qualifiers
source                  1..822
                        mol_type = other DNA
                        organism = Homo sapiens
SEQUENCE: 15
atgaacatca tcctagaaat ccttctgctt ctgatcacca tcatctactc ctacttggag     60
tcgttggtga agttttcat tcctcagagg agaaaatctg tggctgggga gattgttctc    120
attactggag ctgggcatgg aataggcagg cagactactt atgaatttgc aaaacgacag    180
agcatattgg ttctgtggga tattaataag cgcggtgtgg aggaaactgc agctgagtgc    240
cgaaaactag gcgtcactgc gcatgcgtat gtggtagact gcagcaacag agaagagatc    300
tatcgctctc taaatcaggt gaagaaagaa gtgggtgatg taacaatcgt ggtgaataat    360
gctgggacag tatatccagc cgatcttctc agcaccaagg atgaagagat taccaagaca    420
tttgaggtca acatcctagg acattttgg atcacaaaag cacttcttcc atcgatgatg    480
gagagaaatc atgccacat cgtcacagtg gcttcagtgt gcggcacga agggattcct    540
tacctcatcc catattgttc cagcaaattt gccgctgttg gctttcacag aggtctgaca    600
tcagaacttc aggcctgggg aaaaactggt atcaaaacct catgtctctg cccagttttt    660
gtgaatactg ggttcaccaa aaatccaagc acaagattat ggcctgtatt ggagacagat    720
gaagtcgtaa gaagtctgat agatggaata cttaccaata gaaaatgat ttttgttcca    780
tcgtatatca atatctttct gagactacag aaggtttctt cc                       822

SEQ ID NO: 16           moltype = DNA length = 972
FEATURE                 Location/Qualifiers
source                  1..972
                        mol_type = other DNA
                        organism = Homo sapiens
SEQUENCE: 16
atgaacatca tcctagaaat ccttctgctt ctgatcacca tcatctactc ctacttggag     60
tcgttggtga agttttcat tcctcagagg agaaaatctg tggctgggga gattgttctc    120
attactggag ctgggcatgg aataggcagg cagactactt atgaatttgc aaaacgacag    180
agcatattgg ttctgtggga tattaataag cgcggtgtgg aggaaactgc agctgagtgc    240
cgaaaactag gcgtcactgc gcatgcgtat gtggtagact gcagcaacag agaagagatc    300
tatcgctctc taaatcaggt gaagaaagaa gtgggtgatg taacaatcgt ggtgaataat    360
gctgggacag tatatccagc cgatcttctc agcaccaagg atgaagagat taccaagaca    420
tttgaggtca acatcctagg acattttgg aatgaaaagg acatcagaag taattacttg    480
gatgtatata ggatcgagga cacttttgga cgagactctg agatcacaaa agcacttctt    540
ccatcgatga tggagagaaa tcatggccac atcgtcacag tggcttcagt gtgcggccac    600
gaagggattc cttacctcat cccatattgt tccagcaaat ttgccgctgt tggctttcac    660
agaggtctga catcagaact tcaggccttg ggaaaaactg gtatcaaaac ctcatgtctc    720
tgcccagttt ttgtgaatac tgggttcacc aaaaatccaa gcacaagatt atggcctgta    780
ttggagacag atgaagtcgt aagaagtctg atagatgaa tacttaccaa taagaaaatg    840
atttttgttc catcgtatat caatatcttt ctgagactac agaagtttct tcctgaacgc    900
gcctcagcga ttttaaatcg tatgcagaat attcaatttg aagcagtggt tggccacaaa    960
atcaaaatga aa                                                        972
```

```
SEQ ID NO: 17           moltype = DNA  length = 852
FEATURE                 Location/Qualifiers
source                  1..852
                        mol_type = other DNA
                        organism = Homo sapiens
SEQUENCE: 17
atgaacatca tcctagaaat ccttctgctt ctgatcacca tcatctactc ctacttggag   60
tcgttggtga agttttcat tcctcagagg agaaaatctg tggctgggga gattgttctc   120
attactggag ctgggcatgg aataggcagg cagactactt atgaatttgc aaaacgacag   180
agcatattgg ttctgtggga tattaataag cgcggtgtgg aggaaactgc agctgagtgc   240
cgaaaactag gcgtcactgc gcatgcgtat gtggtagact gcagcaacag agaagagatc   300
tatcgctctc taaatcaggt gaagaaagaa gtgggtgatg taacaatcgt ggtgaataat   360
gctgggacag tatatccagc cgatcttctc agcaccaagg atgaagagat taccaagaca   420
tttgaggtca acatcctagg acattttgg atcacagatg cacttcttcc atcgatgatg   480
gagagaaatc atggccacat cgtcacagtg gcttcagtgt gcggccacga agggattcct   540
tacctcatcc catattgttc cagcaaattt gccgctgttg gctttcacag aggtctgaca   600
tcagaacttc aggccttggg aaaaactggt atcaaaacct catgtctctg cccagttttt   660
gtgaatactg ggttcaccaa aaatccaagc acaagattat ggcctgtatt ggagacagat   720
gaagtcgtaa aagtctgat agatggaata cttaccaata agaaaatgat tttgttcca   780
tcgtatatca atatctttct gagactacag aagttaagta cagcacagaa cacccaaata   840
ctaaaacacc aa                                                      852

SEQ ID NO: 18           moltype = DNA  length = 714
FEATURE                 Location/Qualifiers
source                  1..714
                        mol_type = other DNA
                        organism = Homo sapiens
SEQUENCE: 18
atgaacatca tcctagaaat ccttctgctt ctgatcacca tcatctactc ctacttggag   60
tcgttggtga agttttcat tcctcagagg agaaaatctg tggctgggga gattgttctc   120
attactggag ctgggcatgg aataggcagg cagactactt atgaatttgc aaaacgacag   180
agcatattgg ttctgtggga tattaataag gtgaagaaag aagtgggtga tgtaacaatc   240
gtggtgaata atgctgggac agtatatcca gccgatcttc tcagcaccaa ggatgaagag   300
attaccaaga catttgaggt caacatccta ggacattttg gacattttt ggatcacaaa   360
agcacttctt ccatcgatga tggagagaaa tcatggccac atcgtcacag tggcttcagt   420
gtgcggccac gaagggattc cttacctcat cccatattgt tccagcaaat ttgccgctgt   480
tggctttcac agaggtctga catcagaact tcaggccttg ggaaaaactg gtatcaaaac   540
ctcatgtctc tgcccagttt ttgtgaatac tgggttcacc aaaaatccaa gcacaagatt   600
atggcctgta ttggagacag atgaagtcgt aagaagtctg atagatggaa tacttaccaa   660
taagaaaatg atttttgttc catcgtatat caatatcttt ctgagactac agaaggtttc ttcc   714

SEQ ID NO: 19           moltype = DNA  length = 894
FEATURE                 Location/Qualifiers
source                  1..894
                        mol_type = other DNA
                        organism = Homo sapiens
SEQUENCE: 19
atgaacatca tcctagaaat ccttctgctt ctgatcacca tcatctactc ctacttggag   60
tcgttggtga agttttcat tcctcagagg agaaaatctg tggctgggga gattgttctc   120
attactggag ctgggcatgg aataggcagg cagactactt atgaatttgc aaaacgacag   180
agcatattgg ttctgtggga tattaataag cgcggtgtgg aggaaactgc agctgagtgc   240
cgaaaactag gcgtcactgc gcatgcgtat gtggtagact gcagcaacag agaagagatc   300
tatcgctctc taaatcaggt gaagaaagaa gtgggtgatg taacaatcgt ggtgaataat   360
gctgggacag tatatccagc cgatcttctc agcaccaagg atgaagagat taccaagaca   420
tttgaggtca acatcctagg acattttgg aatggaaagg acatcagaag taattacttg   480
gatgtatata ggatcgagga cacttttgga cgagactctg agatcacaaa agcacttctt   540
ccatcgatga tggagagaaa tcatggccac atcgtcacag tggcttcagt gtgcggccac   600
gaagggattc cttacctcat cccatattgt tccagcaaat ttgccgctgt tggctttcac   660
agaggtctga catcagaact tcaggccttg ggaaaaactg gtatcaaaac ctcatgtctc   720
tgcccagttt ttgtgaatac tgggttcacc aaaaatccaa gcacaagatt atggcctgta   780
ttggagacag atgaagtcgt aagaagtctg atagatggaa tacttaccaa taagaaaatg   840
atttttgttc catcgtatat caatatcttt ctgagactac agaaggtttc ttcc          894

SEQ ID NO: 20           moltype = DNA  length = 813
FEATURE                 Location/Qualifiers
source                  1..813
                        mol_type = other DNA
                        organism = Homo sapiens
SEQUENCE: 20
atgaacatca tcctagaaat ccttctgctt ctgatcacca tcatctactc ctacttggag   60
tcgttggtga agttttcat tcctcagagg agaaaatctg tggctgggga gattgttctc   120
attactggag ctgggcatgg aataggcagg cagactactt atgaatttgc aaaacgacag   180
agcatattgg ttctgtggga tattaataag cgcggtgtgg aggaaactgc agctgagtgc   240
cgaaaactag gcgtcactgc gcatgcgtat gtggtagact gcagcaacag agaagagatc   300
tatcgctctc taaatcaggt gaagaaagaa gtgggtgatg taacaatcgt ggtgaataat   360
gctgggacag tatatccagc cgatcttctc agcaccaagg atgaagagat taccaagaca   420
tttgaggtca acatcctagg acattttgg atcacaaaag cacttcttcc atcgatgatg   480
gagagaaatc atggccacat cgtcacagtg gcttcagtgt gcggccacga agggattcct   540
tacctcatcc catattgttc cagcaaattt gccgctgttg gctttcacag aggtctgaca   600
```

```
tcagaacttc aggccttggg aaaaactggt atcaaaacct catgtctctg cccagttttt     660
gtgaatactg ggttcaccaa aaatccaagc acaagattat ggcctgtatt ggagacagat     720
gaagtcgtaa aagtctgat  agatggaata cttaccaata agaaaatgat ttttgttcca     780
tcgtatatca atatctttct gagactacag aag                                  813
```

| | | |
|---|---|---|
| SEQ ID NO: 21 | moltype = AA length = 300 | |
| FEATURE | Location/Qualifiers | |
| source | 1..300 | |
| | mol_type = protein | |
| | organism = Homo sapiens | |

```
SEQUENCE: 21
MNIILEILLL LITIIYSYLE SLVKFFIPQR RKSVAGEIVL ITGAGHGIGR QTTYEFAKRQ     60
SILVLWDINK RGVEETAAEC RKLGVTAHAY VVDCSNREEI YRSLNQVKKE VGDVTIVVNN    120
AGTVYPADLL STKDEEITKT FEVNILGHFW ITKALLPSMM ERNHGHIVTV ASVCGHEGIP    180
YLIPYCSSKF AAVGFHRGLT SELQALGKTG IKTSCLCPVF VNTGFTKNPS TRLWPVLETD    240
EVVRSLIDGI LTNKKMIFVP SYINIFLRLQ KFLPERASAI LNRMQNIQFE AVVGHKIKMK    300
```

| | | |
|---|---|---|
| SEQ ID NO: 22 | moltype = AA length = 264 | |
| FEATURE | Location/Qualifiers | |
| source | 1..264 | |
| | mol_type = protein | |
| | organism = Homo sapiens | |

```
SEQUENCE: 22
MNIILEILLL LITIIYSYLE SLVKFFIPQR RKSVAGEIVL ITGAGHGIGR QTTYEFAKRQ     60
SILVLWDINK VKKEVGDVTI VVNNAGTVYP ADLLSTKDEE ITKTFEVNIL GHFWITKALL    120
PSMMERNHGH IVTVASVCGH EGIPYLIPYC SSKFAAVGFH RGLTSELQAL GKTGIKTSCL    180
CPVFVNTGFT KNPSTRLWPV LETDEVVRSL IDGILTNKKM IFVPSYINIF LRLQKFLPER    240
ASAILNRMQN IQFEAVVGHK IKMK                                           264
```

| | | |
|---|---|---|
| SEQ ID NO: 23 | moltype = AA length = 261 | |
| FEATURE | Location/Qualifiers | |
| source | 1..261 | |
| | mol_type = protein | |
| | organism = Homo sapiens | |

```
SEQUENCE: 23
MNIILEILLL LITIIYSYLE SLVKFFIPQR RKSVAGEIVL ITGAGHGIGR QTTYEFAKRQ     60
SILVLWDINK RGVEETAAEC RKLGVTAHAY VVDCSNREEI YRSLNQVKKE VGDVTIVVNN    120
AGTVYPADLL STKDEEITKT FEVNILGHFW ITKALLPSMM ERNHGHIVTV ASVCGHEGIP    180
YLIPYCSSKF AAVGFHRGLT SELQALGKTG IKTSCLCPVF VNTGFTKNPS TRFLPERASA    240
ILNRMQNIQF EAVVGHKIKM K                                              261
```

| | | |
|---|---|---|
| SEQ ID NO: 24 | moltype = AA length = 274 | |
| FEATURE | Location/Qualifiers | |
| source | 1..274 | |
| | mol_type = protein | |
| | organism = Homo sapiens | |

```
SEQUENCE: 24
MNIILEILLL LITIIYSYLE SLVKFFIPQR RKSVAGEIVL ITGAGHGIGR QTTYEFAKRQ     60
SILVLWDINK RGVEETAAEC RKLGVTAHAY VVDCSNREEI YRSLNQVKKE VGDVTIVVNN    120
AGTVYPADLL STKDEEITKT FEVNILGHFW ITKALLPSMM ERNHGHIVTV ASVCGHEGIP    180
YLIPYCSSKF AAVGFHRGLT SELQALGKTG IKTSCLCPVF VNTGFTKNPS TRLWPVLETD    240
EVVRSLIDGI LTNKKMIFVP SYINIFLRLQ KVSS                                274
```

| | | |
|---|---|---|
| SEQ ID NO: 25 | moltype = AA length = 324 | |
| FEATURE | Location/Qualifiers | |
| source | 1..324 | |
| | mol_type = protein | |
| | organism = Homo sapiens | |

```
SEQUENCE: 25
MNIILEILLL LITIIYSYLE SLVKFFIPQR RKSVAGEIVL ITGAGHGIGR QTTYEFAKRQ     60
SILVLWDINK RGVEETAAEC RKLGVTAHAY VVDCSNREEI YRSLNQVKKE VGDVTIVVNN    120
AGTVYPADLL STKDEEITKT FEVNILGHFW NGKDIRSNYL DVYRIEDTFG RDSEITKALL    180
PSMMERNHGH IVTVASVCGH EGIPYLIPYC SSKFAAVGFH RGLTSELQAL GKTGIKTSCL    240
CPVFVNTGFT KNPSTRLWPV LETDEVVRSL IDGILTNKKM IFVPSYINIF LRLQKFLPER    300
ASAILNRMQN IQFEAVVGHK IKMK                                           324
```

| | | |
|---|---|---|
| SEQ ID NO: 26 | moltype = AA length = 284 | |
| FEATURE | Location/Qualifiers | |
| source | 1..284 | |
| | mol_type = protein | |
| | organism = Homo sapiens | |

```
SEQUENCE: 26
MNIILEILLL LITIIYSYLE SLVKFFIPQR RKSVAGEIVL ITGAGHGIGR QTTYEFAKRQ     60
SILVLWDINK RGVEETAAEC RKLGVTAHAY VVDCSNREEI YRSLNQVKKE VGDVTIVVNN    120
AGTVYPADLL STKDEEITKT FEVNILGHFW ITKALLPSMM ERNHGHIVTV ASVCGHEGIP    180
YLIPYCSSKF AAVGFHRGLT SELQALGKTG IKTSCLCPVF VNTGFTKNPS TRLWPVLETD    240
EVVRSLIDGI LTNKKMIFVP SYINIFLRLQ KLSTAQNTQI LKHQ                     284
```

| | |
|---|---|
| SEQ ID NO: 27 | moltype = AA length = 238 |

```
FEATURE                 Location/Qualifiers
source                  1..238
                        mol_type = protein
                        organism = Homo sapiens
SEQUENCE: 27
MNIILEILLL LITIIYSYLE SLVKFFIPQR RKSVAGEIVL ITGAGHGIGR QTTYEFAKRQ    60
SILVLWDINK VKKEVGDVTI VVNNAGTVYP ADLLSTKDEE ITKTFEVNIL GHFWITKALL   120
PSMMERNHGH IVTVASVCGH EGIPYLIPYC SSKFAAVGFH RGLTSELQAL GKTGIKTSCL   180
CPVFVNTGFT KNPSTRLWPV LETDEVVRSL IDGILTNKKM IFVPSYINIF LRLQKVSS    238

SEQ ID NO: 28           moltype = AA  length = 298
FEATURE                 Location/Qualifiers
source                  1..298
                        mol_type = protein
                        organism = Homo sapiens
SEQUENCE: 28
MNIILEILLL LITIIYSYLE SLVKFFIPQR RKSVAGEIVL ITGAGHGIGR QTTYEFAKRQ    60
SILVLWDINK RGVEETAAEC RKLGVTAHAY VVDCSNREEI YRSLNQVKKE VGDTIVVNN   120
AGTVYPADLL STKDEEITKT FEVNILGHFW NGKDIRSNYL DVYRIEDTFG RDSEITKALL   180
PSMMERNHGH IVTVASVCGH EGIPYLIPYC SSKFAAVGFH RGLTSELQAL GKTGIKTSCL   240
CPVFVNTGFT KNPSTRLWPV LETDEVVRSL IDGILTNKKM IFVPSYINIF LRLQKVSS    298

SEQ ID NO: 29           moltype = AA  length = 271
FEATURE                 Location/Qualifiers
source                  1..271
                        mol_type = protein
                        organism = Homo sapiens
SEQUENCE: 29
MNIILEILLL LITIIYSYLE SLVKFFIPQR RKSVAGEIVL ITGAGHGIGR QTTYEFAKRQ    60
SILVLWDINK RGVEETAAEC RKLGVTAHAY VVDCSNREEI YRSLNQVKKE VGDTIVVNN   120
AGTVYPADLL STKDEEITKT FEVNILGHFW ITKALLPSMM ERNHGIVTV ASVCGHEGIP   180
YLIPYCSSKF AAVGPHRGLT SELQALGKTG IKTSCLCPVF VNTGFTKNPS TRLWPVLETD   240
EVVRSLIDGI LTNKKMIFVP SYINIFLRLQ K                                 271

SEQ ID NO: 30           moltype = DNA  length = 23830
FEATURE                 Location/Qualifiers
source                  1..23830
                        mol_type = genomic DNA
                        organism = Homo sapiens
SEQUENCE: 30
atggtccgag gggggcgggg ctgacgtcgc gctgggaatg ccctggccga gacactgagg    60
cagggtagag agcgcttgcg ggcgccgggc ggagctgctg cggatcagga cccgagccga   120
ttcccgatcc cgacccagat cctaacccgc gccccccgcc cgccgccgcc gccatgtacg   180
acgcagagcg cggctggagc ttgtccttcg cgggctgcgg cttcctgggc ttctaccacg   240
tcggggcgac ccgctgcctg agcgagcacg ccccgcacct cctccgcgac gcgcgcatgt   300
tgttcggcgc ttcggccggg gcgttgcact gcgtcggcgt cctctccggt atcccgctgg   360
gtgcgtcggg ggacgctgcc cggggctcca ctgcgggtg ggtgccccct aggccgggga   420
gcggggatc cccaggggtc gcggggcct ggaggagcgg gcatcggacg cggacacggg   480
ggggtgcatc ccgaggggccc cctccgagge agatgcttcc tgcgggggcg ctgttcctgg   540
gcccgggaag ggggcgttgg aaccccgagc ggtccgggcc gaagcctggg actctcgtgc   600
gtccccaccc ctaccccccat caggcgcccg tgcatgaagg gagaccctca cctccggact   660
gagagtcgga gcgtctcgga gcgacgggga gtagggagcg ggaccggggg cggagggtag   720
tgctggcccc tgcggactcc gggtcccctg tgtcctctcg ggaggggctg acgggctga   780
gctgccgagg ggccgatttg ccctgggccg gacaaagagt gggggctttgg ccggtccccc   840
acggtgggct ccttccctct ggggattgag ggactcaaga caccccgcgc ctgcgctttt   900
cttttcttt tttcttttt ttttttgag acggagtttc gctcagtcgc ccaggctgga   960
gtgcagtggc gtgatctcaa ctcactgcaa gctccacctc ccaggttcac gccattctcc   1020
tgcctcagcc tcccgagtag ctgggactac aggcgccagc caccaagccc ggctaatttt   1080
ttgtattttt tagtagagac ggggttttcac cgtgttagcc aggatggtct cgatctcctg   1140
acctcgtgat ctgcccacct cggcctccca gaatgctggg gttacaggcg tgagccactg   1200
ctccctgctg cctacgctct ctgggtcgca gcccagcctt ctgggggctg ggtagcctcc   1260
cagaagggca accctgggca tcctccaggg caggctaact ggagtctagt ggggaggggt   1320
accttgaaag aggaaagttg tttcctcctc ctcctcctcc tccagtgttt gggaccttc   1380
ctggggggtg gagtgcatcc ctggacaccc ccaatcccaa tcctcttctc tagttttcac   1440
tgacctaggc ccaccctccc ctctccggct cagtactcct ggaaatgaga ttccgtacat   1500
ttgaatcttg tcctaatgaa atatttgtcc atgtgggtac ctgtgtgtgt gtggtggggg   1560
tgcagacgga gggtttgttt ctcactagct ggaactactg gggtgtggta tgcttcctgg   1620
gaatttgtgt gccacagtcc tggaggcgag gagggggttg tgaccagta ggcaggggct   1680
ggggcaagta gcattgtgaa gctattgaca cccagaggcc cccaggcagg agattatgcc   1740
cccattagcc ccctttttatc tgggcttcct taacaatgga ctctttgccc tgcctgccag   1800
agccagcagg gagtgactgt tcagtggtga ggaagcgggc agaggaagcc ctgccattgg   1860
gtaggagcag tgggcagccc ctgggctgac tgggaggtgg ggattaggga ttagacagtc   1920
ctggctgtct gccttcccct aagccagggg gagaggagca aagggcacga aatgtggcct   1980
ccaggaggat tagaccgcca catgatcatt gcagcctgct ggggtttagc aacaataaaa   2040
gtcagcttt tgtatccca aggtggcctg tggacaccca catgacaaa tgtttacact   2100
gggacagaat tcaaatgcag aggtcccagg agcctaaagt acactcactc tggtatagaa   2160
aggattccta actgggcaga ggacaggtgc agcctgggc tttccaggc aggacacagg   2220
gaggctcagg aaccaccaag tccctggaag gtggatctgg aggcgttggc aggagccact   2280
ccctgggttc cagggctcca ggttcctgct ttaaccccct gtctcacaga gggctgtgca   2340
```

```
cttgggggct gctgagcatg tcccagaggc tgcatcctgg acacagcacc tcagtgcatc   2400
tgagctgagg ctaacttggc aggagggaca ggcagaacct gccagccacg tgcaattcca   2460
cccctctggc cactcaggga aggagagctg tgagtcaaga tcagatttgg gtcaggacag   2520
gctgggcct gcctgtccct gtgcatccca agatttatgg ctggccaggg gttgggctgg    2580
gagggtggt cttgcatgcc aggagagtgc agatcagcct gagaggccag gccagtaagt    2640
gaggtcagat ctcctgcacc tgatagcatt aaggccatct acaccaaagc tctaatgctg   2700
atatgttcct ggcctctatg tggggcatgg aggtggggca tggaggtgag gcctgctcgc   2760
ctgggcttct ggaagtggga gactcattcc tgtggctgag gcctacagca gtgctgtgtg   2820
gtaaggaatac actggaagcc atgatgtcat tgtgcatttt ctagaagcca cattgaataa   2880
agtaaaagac acaggtagaa ttaatttcat tgagcccaat atatccaaaa taatatcatt   2940
ttcacatcta ttcaatataa aaatttacta atgagatatt tcatactaag ccactgaaat   3000
ccagtttgta tcttacacat ctcagttttg acgagccaca tttcaagggc gtgatagcca   3060
catgtggctc ccatagtaga cagtactggt ctagagaaat gttggtggca tccttgctgt   3120
ctggttttctg gccttgccaa aagtattacc atcccagtgt ggtacattct ttcatgtatt   3180
tgtctcctgt ccccagagca gactctgcag gtcctctcag atcttgtgcg gaaggccagg   3240
agtcggaaca ttggcatctt ccatccatcc ttcaacttaa gcaagttcct ccgacagggt   3300
ctctgcaaat gcctcccggc caatgtccac cagctcatct ccggcaaaat aggcatctct   3360
cttaccagag tgtctgatgg ggaaaacgtt ctggtgtctg actttcggtc caaagacgaa   3420
gtcgtggatg taagcagttt gcttatctgg acgttgtcaa gttagaaaag ctgttttggg   3480
atgggtgtgg tggctcatgc ctgtcatccc ggcactttgg gaggccgaag cgggtgggtt   3540
gcttgagccc aggagctcga gaccaacatg atgaaaccca gtctctacaa aaattacaga   3600
aaaattagct aggcatggtg ttgtgggccc atagtcccag ctactaggga ggctgaggca   3660
ggagaattgc ttgagcctgg gaggtggagg ttgcagtaag tcatgatcat gccactgtac   3720
tccagcccgg gtgacagtga gatgctgtct ggaaaaaaaa aaaaaagaaa gactgttttg   3780
ttttggaagc aacacaggca gttgtaggcc ccctgtgcca gagtgacata aactctgtac   3840
acctccagtg atttggtcca tgtttgtaaa ccctgaatgt tccagggcag tttctttttct  3900
tcacttttta tctctttttt ttgggtgggg gggcggggta cagagtcttg ctctgtctcc   3960
caggctggag tgcagtggcg caatctcaac ctcccgagga gctgggacta caggcacagg   4020
ccatcacacc ttgctaatgt ttgtactttt tgtagaacg gggttttgcc ctgttgccca     4080
ggctggtccc aaactcctgc acccaagtaa tctgcccacc tctgcctggc agttacaatt   4140
tcaaataatt cctccctttc cttcaacact tggctcatga ccgtccagtc caaggaacct   4200
gtcctgcagg tgtgcctctc ccgagcttcc tctatgcatc ttccataatg aagatgcctt   4260
ctcactggaa accctacaag ggtgggaacg tgccttattt gcctgtatcc tcagggtcta   4320
gcagagagaa gataatttgt aataccaaaa caccattaaa ttcagctgat gctttcataa   4380
gcgctccttg gaggaaggac tccatttact tgacagatct gtgcaagaca gcagcctggc   4440
gcgtctaacc tgcagccagt tgcatcctct gtttaacctt gtttgcggaa gctttctcta   4500
aacagccagc acttgtctgt tcccacatgg gtccgttctc ccagtgaatc accgtggtgc   4560
ctgctgactg ctctgtagca cagtgcttcg caaagtgtga tcctgggacc agcagagcag   4620
cagctccttt gagcttattg gaatggcaga ccctcaggtc ccacctctga cctgctgcat   4680
gggaattctg ggagggacg cagaatctct ggttccacag gctctccggt gatgctaatg   4740
aataccggca tttgaacagc accgatctag ccccctttcag tccatgagcc aacaaccctt   4800
ggtcctgtct gtggtgaccc agtgtgactc tcatggggag caaggagagg aagttgaagt   4860
tcactgacag gggttgttaag gggattatgc aatagatgag accatgggc tgaagtccg    4920
agggtgtatg ttagttccc gttctttga cccatggatt aacctactct gtgcaaaggg     4980
catttttcaag tttgttgccc tgctcacttg gagaaagctt atgaaggatc aggaaaatta   5040
aaagggtgct ctcgcctata acttctctct cctttgcttt cacaggcctt ggtatgttcc   5100
tgcttcatcc cctctacag tggcctttatc cctccttcct ctcagaggct ggtaagtcgg   5160
cttctctgc tagcgctgag tcctgggggc ctctgaagtg tgctcacaca tctcctgcct   5220
gcagggcact ggtgtcgggc acctcaggt ctgtcccatg gtggagcccc atgcctcact   5280
gcctttcaga cagagtagcc acagctggcc ctatttccag gctacccggg cagcaaaact   5340
tactgcatgt gtaattaatt atttggctat ctgtaaggta aactggctgc ttcacttaat   5400
ctgcaccta agcatcagat agcttctcag tgatctagtt aaactatatg atgttggcca    5460
ggcgcggtgg ctcatgtctg taatcccagc actttgggag cctgaagcag gcagatcact   5520
tgaggtcagg agttcgagac cagcctggcc aacagtgtga aactctgtct ctcctaaaaa   5580
tacaaaaatt agctgggcat ggtggtgtgc acctgtaatc ccagctgctc gggaggctga   5640
ggcaggagaa ttgcttgaac ttgggaggcg gaagttgcag tgagccaaga tcgcaccact   5700
gcactccatc ctgggtgaca gagcgagact ctatctcaaa agaaaaaaa aaaaaaggt     5760
aaataaagta tatgacactg aagaatctgt taccctgga aggtggagct ttactcttag    5820
ggggaactat aacagtcata tatatatatt tttttctttt cttttttttt ttttttgaga   5880
tggagtctgg ctctgtcgcc caggctggag tgcagtggtg caatctcggc tcactgcaac   5940
ctccacctca caggttcagg caattctcct gcctcaacct cccgagtagc tgggattaca   6000
ggtgcctgcc gtcacgccaa gctaattttt gtatttttag tagagacagg gtttcatcat   6060
attggccagg ctggtctcca actcctgacc tcaggtgatc cgcccgcctt ggcctcccaa   6120
agtgctgaga ttacaggcgt gagccatggt gcccggccag caccacatg tgttgtaaac    6180
aacaacaaaa atctgtcagc ctggtctaac ctagatttgt gctttgtttt gttttgccac   6240
tttgtgatgc acaggaggaa gtttaggctg taaaatacta gccttttagg gtaatttttg   6300
aactcacaag agcagcagcg gaaccttga tgcaatcctg tatgtagcac cagcagagcc    6360
acgtggcaga gggactcgca ttaggagcct cccattacag actacgtgct cctgtgcgtt   6420
atcttatagg gtccccacaa ccaaggggag atgtgattat tcatcctgtg tggctgtggg   6480
gaacttgaga gtcatacttg cccaaagagc acgccagcg agcttgcacc caggtcactc    6540
tctgctcctc tgtcagaaca gggcatgtct tggttcactg cagggcggct cttctcattc   6600
tctgtagttt ggggtccagg atagtggtcc acggagccac tggagtgccc agctactgag   6660
tgaccaaagc atattttgga tttccgacat tgccacagca tggttgggca tcagcaggac   6720
cccaaccct tgttatgctg gtggcttttat tggttatttt gatcttcccc agaactcgag   6780
aggagtgcac ccagcagcac cgtagtgatg ctctctggct cccagtgca ccggttctggc    6840
tttccttcct ggtcgagagt ttcaagccct ctggtcccta tctgtccttt tcagcccat     6900
agctttgttc aaaagctgct ggcagtgttc agatttggct gagttcagtg aatatgtgca   6960
ttggctgatt tctgagccat gccaggggga tggagaagcc gaagcaggag tgtttgttct   7020
gcaggctctg gagtaggcat tgggtctgtg ccggctcact tgctagtctt gcatccttcc   7080
```

```
ccaacccct  ctggggatgt  ctggccacat  cagaagacag  tttgggttgt  cagaactggg   7140
ggagtaccag  gccgaggtgg  gtggatcatg  aggtcaggag  atcgagacca  tcctggctaa   7200
cacagtgaaa  cctcatctct  actaaacata  cgaaaaaaat  tagctgggcg  tggtggcggg   7260
cgcctgtagt  cccagctact  cgggaggctg  aggcaggaga  atggtgtgaa  cccgggggc    7320
ggagcttgca  gtgagctgag  atcctgccac  tgcactccag  cctgggcaac  aaagcgagac   7380
tccgtctcac  aaacaaaaca  aaacaaaaca  aaacaaaatc  tggggggagtg  ccactggcat  7440
ctgatgtata  gaggcccgag  atgctgtgtc  atcacccgtt  gagtgcgctc  ataggcatct   7500
tcctgacaat  tagaacccat  tattcttcaa  attcaatgca  agcaaattca  aagcattact   7560
gtgtacatac  cgcatgctaa  tcaattgcac  cactggagct  cctaaattca  aaacattact   7620
ataaaaaagt  tcaaaatgca  tggaaaagtt  gtacatggca  ggagaatatt  tgggcttctg   7680
actacccctt  gaatgaagat  gatccaccag  ccgccttcct  ccttggtctt  cactccagat   7740
tcctagcatt  tcattctgtg  tctctttatg  cagtgaggtt  tttgtttgtt  ttttgagaca   7800
gagtctcact  gtatcaccta  ggcctggagt  gcagtggcgc  gatctcagct  cactgcaacc   7860
ctcggctcct  gggtttaagc  gattctcctg  cctcagcctc  ccgagcagct  gagattacaa   7920
gcacacatcc  ccatgcccag  ctaatttttg  tattttttagc  agagacaggg  tttcaccatg  7980
ttgcccaggc  tggtctcgaa  ctcctggcct  caagtgatcc  atgtgcctca  gccttccaaa   8040
gtgctgggat  tacaggcgtg  agccaccatg  cccagctcct  agtgaggttt  ttgatgcctt   8100
gctacatctg  ccctagaaat  tgtgtgacta  cgattttgaa  aatgttgctg  tgtaaacttg   8160
tgatcatttc  tggactccag  gcaagaatct  tgatggctaa  ggtgtggctg  aacatgtctg   8220
attctctcct  ggaccctgttt  taggccaaac  tctgctctga  aattcctccg  tgtgtgaaggg 8280
cgggctgggg  agagcctccc  agctggaatc  ttttggatgc  ctttctctgt  gggtatctga   8340
tggctggctc  tgatggctgg  ctgtgatggc  tgtggctgaa  aatcattgtt  gacatgagtt   8400
tcacagatgc  aggctctgtc  caaattgtag  caaaagctgc  ctgccccagc  cgagctatgg   8460
gcaataaggt  ggtttaagga  tatagatgaa  ggaaaactca  cccttagaat  aatttatcca   8520
aaatgctgct  gtgttgtggg  ttagaggaca  ttttctgagg  tcccaggttc  attgtttcat   8580
ttaagtctca  aaagtccctc  caggtgttgg  ttctaattgt  caaagcatgg  ggggagatgg   8640
gctcatgggt  taaggtctct  atcccagatt  tctgtatcct  ccttgcaagc  agcaaagggg   8700
tctgatttg   aatccatgac  catgtttctc  ctttgggttt  ccatcacact  ctgtcccgt    8760
gcactgagca  ccctttagtt  catatgaccc  ccttaggcat  gttacatggg  cactcctata   8820
ggtgccatc   tggccctagg  acttggccaa  cacaacatgg  actccagttt  ccatctgcct   8880
ctttgccagg  cacttttgtg  cagtgcacac  actgtacaag  agtagacggc  aaccctgaga   8940
gccagagtag  agcctgtcct  agcaccggaa  tgctcggtaa  ggatttgtcg  caggagtgat   9000
tccaaagcca  atgtcctccc  tccatatcag  cctgtttgtg  gctctgagaa  gctctgccca   9060
catgtgaaag  cttgttaagc  acttaagcac  taacccagag  cttcagacag  tgccagtcct   9120
ttttccccctt ctttaaaagc  gatatgtgga  tggaggagtg  agtgacaacg  tacccttcat   9180
tgatgccaaa  acaaccatca  ccgtgtcccc  cttcatgggg  gagtacgaca  tctgccctaa   9240
agtcaagtcc  acgaactttc  ttcatgtgga  catcaccaag  ctcagtctac  gcctctgcac   9300
agggaacctc  taccttctct  cgagagcttt  tgtccccccg  gatctcaagg  tgagttggtg   9360
gtgaggggc   aggtgttctg  gggtgcagct  cttcctttgcc  tccctgattg  ccaggagcta   9420
ccagttactg  tctgcacaat  caaacagaaa  tagacctgtc  cttgatggtt  aacgaaaata   9480
aaaggcgctt  gtcccagaag  ctcaggtgag  gcaccaccct  gattatggga  atcacctggg   9540
aacatatacc  cagacctaaa  actcagatcc  acttcccagg  ctgtggttat  atagtcaggg   9600
gggtgcagta  tgggtattag  gattttttat  ttttagtta   taaagattt   tttttggttt   9660
gtttttgaga  cagggtcttg  ctctgccgct  taggctggag  tgcagtggtg  caatcatagc   9720
tcactgaagc  ctcagactcc  tgggttcaag  cagtcctccc  acctcagcct  cctaaggagc   9780
tgggaccac   aggcatgcag  caccacacct  ggctaatttt  taaaaatttt  gtggagtgtt   9840
gcccaggctg  gtctcacact  cctggcctca  agcgatcctc  ccaccccagc  ctcccaatgt   9900
gttgggatta  caggcatgag  ccattgtacc  cagccactaa  gatgattctt  atttggaaac   9960
acggtcaaga  acaactgcgt  tcggtagttt  aaccttttt   gattgtgtg   gttttagtat  10020
gccttaccac  tctaccatag  taagaaattt  gcagaccatg  tacaccaacc  tttggtgctc  10080
ctggggagaa  agaaagaagg  ctatgcaatg  caatgcatgc  tcacagtcca  agggagaggg  10140
aaagctgtct  aacaggattg  gttttcccgt  gtgctttata  agcagatgag  tagaggagac  10200
agctcttatt  gtcctagtgg  caattgggat  aggctgcaaa  gtttgttagg  gtggaggctt  10260
attccgggac  caagggagcc  caaagaaaca  agctcctgcc  aggcgcggtg  gctcacgcct  10320
gtaatccag   cacttttggga ggctgaggca  ggtggatcac  ctgaggtcag  gagttttgaga 10380
ccagcctggc  caacatggtg  aaaccccgtc  tccatgaaaa  atacaaaaat  tacccgggca  10440
tggtggcggg  cacctgtaat  cccagctact  agggaggctg  aggcaggaaa  atggcttgaa  10500
cctcggaagt  ggaggtggcc  gttagccgag  atcacgccac  tgcactccag  cctgggcaac  10560
agagcaagac  tctgccttaa  aaaaaaaaaa  aaaaaaaaga  aaagtaaaag  gaaaaaaaag  10620
aggctctggc  ctgctggggt  gcctgcaaag  tctccggtga  agggtgacat  tcaagccgag  10680
acctccaggg  aactgtctcc  tgggagcaca  gagccctttg  ctcagccccc  aggtggctca  10740
gtgcccccag  ccagcagact  cagagcttgc  atgattcttt  ggtgctctct  gcggtcttcc  10800
aatgatgctg  aaataaatgg  tgcttggtgt  ctccctgctg  tagtcccctt  gcttgctttg  10860
ctcacaggtg  ctgggagaga  tatgccttcg  aggatatttg  gtgcattca   ggttcttgga  10920
agagaagggt  atgtatggc   tggaggatc   agccatgccc  ttttgacaag  catttactag  10980
cggtcttggt  aaagacttga  gatttgcctt  agttctaaca  cttagtgccc  aacgccttcc  11040
ttgtgttgct  caacctactc  atgagcccag  gagataggaa  atctccgtcc  cattgtacag  11100
atggggaaac  agaattttgg  aaaggagagc  caagcagcac  acaccctcc   ctgaggggca  11160
gagccgagat  ttgaactggg  atgtcatgac  tccaggggcc  tctccctccc  caggggtcccc 11220
ttatctgaag  gcggttttc   tttccagctc  gacctcttgt  gacccttagt  ttaacaaggg  11280
ccgaagttaa  agagttttctg cgcctggacc  ccaaatgaag  caatcagatt  tctcatctcc  11340
agtcaggtgt  gggtccaagc  ccactagaca  agttgctct   tcccagagca  catttctgcc  11400
ttcaagtcat  cctggcttgt  cagggctggg  ggagttctgc  tgtagaaata  ttagagtgga  11460
aggaaaaaga  tgtgttggga  gctatttttc  tttaatacta  aaagttggtt  gatgaatttg  11520
tcgttggcca  agaccaagga  gactgcatt   ttaaggacat  atgtgtattt  atctgctcag  11580
aaaatgttca  ttgctgtgtg  ctagggatac  tgcagtgaac  acagaggtgt  gacccttgcc  11640
agccttgtga  gagaagtgag  cagataagta  agcagaaggg  tgatgctgtg  tcgatgggaa  11700
agtacaggtc  ccaatgagaa  ggcacaggtg  tcaaggagaa  gacacaggat  gctggaggct  11760
catgcaggat  ggatctccaa  ggcccagggg  aagaagggcc  tctcggagga  cgtgaatcca  11820
```

```
cattaagact ttggggataa gtaggagcgc cttaggcatg gggacccatg gatgcgaggc  11880
ctgtaggaca cagacaggat ggcatgaagg cctgtgcaac tggaggggtg gggatgggga  11940
cactaagaga tggctggaag tgtggggtg gggacactaa gagatgactg gagaagaggg   12000
ggtcaggagt ggtgaaaaat gggagaggag ggcaggctgg gccttttgga tacagggga   12060
ttgcatcctg cagtggtagg gagccactga gggctgccac agtaggagtg aggggatcag  12120
aggagagctt tggaagcccc ctggatgcgc gacaggaagc gagataccag tgtctaggag  12180
gccagtgagg cagccacagg ctccaccagg atcagggctg cgagggtcat gaggaggaaa  12240
ccaatttgaa ggagtccagg ggaataggac ttggaaatga ccgatgggac atttgggaag  12300
aggaagacag aagagccag tccccggcttc tggctttagc agttgggcaa ggggagatgg  12360
ggagatgtgc ccatggggttg aggggttgagg acattaggag ggagccggta tggcaggaag  12420
agctggtgtg ccagagatgc tggaagcagc atctgcctga aacagatac ctggcaatat    12480
tcctaaggga aagtgacatc tcggagggtg aggaggcat ctgatagggc ctggaaagag   12540
ccggggcaag catgaatgtg aggttatctt ggggggcaag gctcaggcgt tgaggagcag  12600
cccctggtct cttcagcctg aagttggaag ccagagttgg gccagtgca gctgtggttg   12660
tctgaagtcc ccctccccca gcccagtgtg ccaatgctgc aagagcaagg gccgctcact  12720
ggtgctggtg gctgagtccc agcacccagg acagggcctg gcacatactg gtgcccaatc  12780
ctcccttctg ggtgcttctt ccaaggcctt gtgatggaag tgagtaccct cttcgacatc  12840
agacccagct tcaaatcctg gctctgctat gtattggctg cgtggcttta gacaagtctt  12900
ttaaccttgc tgtgcttctg atttctcagc tgaaaaatgg agatgatgat agtggtttct  12960
gtaaggcctt atggtgaagc acctagctca gggcctggaa ggcaggtgta accagtggtt  13020
cagttgttat aaaccaacac taaccctcgc cttttgcacct catgaaacca gatatgtaga  13080
tggagcccac aaagctagca ggagccaagc tcacgtgtgt cctgctttaa agccccatac  13140
cccttctcc gggtgacaaa cacctgtgct cgttctcttc ccttcccctc ttccccttgc   13200
atttggctaa taacaggcca gctgcctgcc tccctgcagt ttggtagatg ggtgggtaac  13260
gaccaccact cccacgttcg cctgatgggc ttgttttccg tgcccttcac aggcatctgc  13320
aacaggcccc agccaggcct gaagtcatcc tcagaaggga tggatcctga ggtcgccagg  13380
cccagctggg caaacatgag tctgattcct tccccggagt cggctgcctt ggctgtgagg  13440
ctggagggag atgagctgct agaccacctg cgtctcagca tcctgccctg ggatgagagc  13500
atcctggaca ccctctcgcc caggctcgct acaggtaccc actcctcggg gtgagcacgg  13560
gcagcacctt gttttctttc ttgtgcatta tggaggaaga tggtactgcc acatgggagc  13620
gatagggtga ggcaaccatg acaggtggtt gggaacatct ccttccatgt gtacagcctg  13680
ggctgctgcc atcactccca gcacagcccc caacccccc aatcctggaa ccttgccaag    13740
tctcccttcc catggggtca tgaccaggag gaaaacaaac tccagctgag ccccttgggg  13800
ttccccatat aggctcctgc ctgtggcagc tgggcctct gtaccccttt ccaactctgt    13860
ctccctaaca tggcacctga gctcctgcca tcctggattt catgaccccc aaggatgggg  13920
gtcctgcatc tgggacttgg cctattactc ggagctcctt ttcagccgcc tcctccacc   13980
tgtccaccca cctcaaggct cctttcttga gacctctcct aatttctccc ttcccctaaa  14040
cccacaattt tgaacctcca tcgaatggtg ctgtattta taatgtcatc aaatatcaaa   14100
tggagacagt gctatggtcc aaatgattgt gtaccccca gaatttgtct tttgaaatcc    14160
taacccccaa catgatggtc ttaggaggtg gggcctttgg gaggagatta ggtcatgagg  14220
aaagggctgt catgaatggg attggtgccc ttattaaaca gacccaagag aggtccccttg 14280
tcccttctac tgtgtgagga ctcagaaggt ggtgtctatg aagaagcagg ccctcaccag  14340
acaccaacat gtctgctgcc ccttgatctg ggaccttgca cctctgaaaaa             14400
tcgatgtttg ttgttttata agccactcag ttggtggcat tttgttagag tagcctgaac  14460
acggactaag tcaaacagaa gaacccacaa accagctaca gagttgggca tttggagaaa  14520
ttcaaaaatg agtcagacat aactcctta tcttgaggtg cccctaagaga tgggacacag   14580
cagctgccca ggtgcattag tttgtttctca cattgctata aagaaatacc tgagactggg  14640
taactcataa agaaagaggt tgaattggct cacagttgca caggctggac aggaagcatg   14700
gtgctggcat ctgctcagct tctggggagg cctcaggaaa cttacaatca tggcagaagg  14760
tgaacggaa gcatgcacat cccatgactg gagcaggagt gagagagaga gggaaataga   14820
gggaaggtgc catacacttt taaacaacca gatctcatga gaacacattc actatcaaga   14880
gaacagcacc agtggggaaa tccgccccca tgatccaatc acctcccatc aggctccgcc  14940
tccaacactg ggaattacaa tttgacatga gatgtgggca gggacacaga tccaaaccat   15000
atgaccagat taatacgatt tgaggcatca cgaggtcatt aaagagaggg aataaaaagac 15060
tggggctcca ggaagaaggc tctggaatcc agcagagggt caaggaccag cttgtaaagc  15120
tggtggtgcc tgagaagtac ctaggagaac atagatgctg tgacgtttga tgtagctgtt  15180
ttttgttttg tgtttggtt tttgagacag agtctcactc tgttgcccag gctggagtgt   15240
gcagtggcgt gatcttggct cactggagcc tccatctccc aggttcaaat gatcctcatg  15300
cctcagcctc ctgagttgct gggattacag gtgcacacca ccacgcctgg ctaattttg   15360
tgttttcagt agagacaggg tttcaccatg ttggccagge tggtcttgaa ctcctgacct  15420
caagtgatcc aacaacttca gcctcccaaa gtgctgggat gacaggcatg agccaccatg  15480
cccagcctga tgtagctgtt tctgtgcaca ttatttgctg tggggtatat tcagatttct  15540
taatacaaga tgattcttg cctcatgact tacacaccat tttctattta atttcagcta    15600
tgatattgga aatggacatg tcttttcaag gaaaataaaa gcaggctttc tggaatggcg  15660
acttccaaac atatttgtca atttaaagga gctgggagtg gggaccctat gctccgtaag  15720
cactctctta gctgttcttg gctgtgctcc ccgcttcagc ttcacactgc ccttgctgtg  15780
aagggagcag cctgggccgg gcgcggtggc ttacacctgt aatcctagca ctttgggagg  15840
ccgaggtggg tggatcacct gaggtcagga gttcaagacc agcctggcca acatggtgaa  15900
actccatctc tactaaaaat acaaaaaatt agctgggcagg gcctgtaatc                15960
ccagctactt gggaggctga ggcagaagaa tcgcttgaac ccaggaggcg gaggttgcag   16020
tgagccgaga ttgcgccatt gcactccagc ctggggcaa caagagcaaa actctgtctg    16080
gaaaaaaaag aaaggagcag cttggcaaac cccaccttgt cgcttttgtg agtgcctctg   16140
acccttttggc tgccaggacg ggcgtatttt atggaaatgc taagcaccaa cagagtaaag  16200
tggttttgtt tttcacagtg gtgggagata atagctccaa attgtcttt tcagcactga    16260
gtgaagaaat gaaagacaaa ggtggataca tgagcaagat ttgcaacttg ctacccatta    16320
ggataatgtc ttatgtaatg ctgccctgta ccctgcctgt ggaatctgcc attgcgattg    16380
tccagaggtg agcattttag gtggctccgt gtcttcctca cagggttgat atgaggatga   16440
aacaagatga tagatcatgg tggcatgtag tctgggacct ggattgtcgt gccacagatc   16500
acagctcaca gtctatgtgc aatgcccctg aatgttgccc acctgtcctc aagccacaca   16560
```

```
tgcacctgta actcagtgca agcccagaaa ctccccgtgg ggactcctag agctgtcagt  16620
ggcctcacat agcagctggt ccagtctctt gtgattgccc aaggaaactg aggcctggag  16680
agcttggggt cactgctctg aggccataga gatgcctagt agaagggcca ggcctagaag  16740
caggatcctt gctgcccctc tgagctgttt ccatttaaaa tcacatgaag gccggcgccg  16800
tggctcacgg ctgtaatccc agcatttttgg gaggccaagg tgggtggatc atgtgaggtc  16860
aggagtttga gaccagcttg gccaacatgg tgaaatgcca tctgtactaa aaatacaaaa  16920
attagtggag catggtggca cgtgcctgta ctcccagcta cttggaaggc tggggcagaa  16980
gaatcgcttg agcctgggag gcagaggttg tagtgagcca agattgtacc actgcactcc  17040
agcctgggtg acaggagaga aaccctatct caaaataaaa tgaaaggtaa tgaaatgaat  17100
aaaataataa atcaagtcac ggccgggcac ggtggctcac acctgtaatc ccagcgcttt  17160
gggaggccga ggtgggtgga taatgaggtc aggagttcaa gaccagcctg gccaacatgg  17220
tgaaaccatg tctctactaa aaatacaaaa attagctggg catggtggtg catgcctgta  17280
atcccagcta ctccggaggc taaggcagga gaattgcttg aagcaggacc taggaggcgg  17340
aggttggttg cagtgagccg agatcatgcc actgcactct agcctgggct acagagcgaa  17400
actccgactc aaaaaaaaaa aaaaaaaaaa atcaaatcac atgaaagtag aacatagga  17460
attccatctt tcgttctagg catagtttgt taatatgatt cagagccagc agttaggaga  17520
acacagtgtg actctcctag aacttcttga ttgggcttcc tctgattggg tttcctctga  17580
ttgggcttcc tctgaaagtg gggggatgg ggggtgggga gcaaatggt cagagcttgg  17640
ctcagcagtc agactgctct tcttcaaatc ctggctgcat tgcttactac agctgtgtga  17700
ctccagatga ctgaatccac ctctctgtgc tgcagcttcc cgtctagaga gatcacctgg  17760
agcagagggt ggtcaggaga ctcaatctgg ttactgactc acagtgcagg agtactcatc  17820
ccatagtaag catccagcta gagatgttga tttctatttt caggtaataa tgatgatcgt  17880
aaaattagag acagataaaa ggtatgggca ttaggccagg gcactgcaat ttctaagctg  17940
tgtgacctca ggcaagttac tcgacttctc tgagcctcag cggtttcatc cgcaatatat  18000
ggataggaaa accgacctca gtgggttgtc tgacagtgga gggcacttga ttaaaaaaaa  18060
aaaaattacc ctggtctgaa tattaccctg gactgaaaaa aaaatattga gctaatacag  18120
gcatcaggaa tggggctgca gggagtccag ggaagggaga acgaagagcc tgaaggtgtg  18180
aggaggtgcg agtgctgatc tgtctgctac aaagaggctg ctgagcctcc tgtggatgtg  18240
gccctggact tggcagttta atacctgagc tgttaaaata acctcagatg ctgtgttctt  18300
taaggggtag gattcagatt cctgctgaaa tgcttctgaa agggagggaa tgagccagcc  18360
catccccagt tgcttttttaa gatcattggg aagttctggt cttgccattt gtccctggac  18420
cactcttagg tcctcctgcc ccacttccat ctgggtgtgt gccctgggct gtccaccaca  18480
cagctacatc ctgccatctt ccctcctgga gccactgtgc catgcatgga tctgtagctt  18540
cattttttctt ggcttttccc tggttttttct ggagcagagt ctctagtaaa ctcccaagga  18600
agaaaacgtt tgactttatg tgtgttggga aacgtgcttt tttttctatta catctcagtg  18660
ataggttggc catgtctaga attgcaggtt gaaaatcatt tcctctcagt atattggtta  18720
gtgagaagcc tgggactgag acagtcacat tctcacttct ttgcaggtga gtgctcttag  18780
gactgtcttt ttatccctta tactctgaaa tgtcatatgt cttggtgtaa gtccttattt  18840
cagttattga gctggacaag tactggagac cccttcagtc aaagccttct gtcattctcc  18900
agctctagga aattatcttc tattgttatt tctgttattc cttcccttcc attttctttt  18960
ttcttttttt tttttttttt ttgagacagg gtcttactct ggtgcccagg ctggaatgca  19020
gtgacctgat catggtacac tgcagcctga acctcccaga ctcaagtgat cctcccacct  19080
caacctccta agtagctggg actgcaagca cacatccaca cacccaacaa atatttttta  19140
aaaatttttgt aagatgggat cttactatgt tgcccagact ttttcttcct cttcctgggg  19200
ctcttattag gaagatgttt gacttcctgg gttggattcc tgtctccgtg tctgactttc  19260
tctctttgtc atatttttca tcactcgttg tcttttttgcg tctgctctga cagatttcct  19320
caaattttgt cttctagtcc tatcctacag tttttacttt cagcaaatat aatttaatct  19380
ccaagagtac tctcttgttc ttttttcttta gcattctgtt cttgtttttat ggatgtaaca  19440
ttctcttgga atatttgctg tcctctagat catcccttct ccatttcttc ttgggctagt  19500
ttttctgttt cttcatcttt ctcttttatg ctacttattc tgggcgtgtt cttggtgggt  19560
tttttcccat atagcaacag aggacttgga gctcagggag aaaagggtag gtgcatcacc  19620
tggcagagct cccagacagt gacaggcagg ctgcgggaag gatgtctact tggcggtgct  19680
accgctttcc tagaaaccct ttccctggag ctggttgaac tgttgggttt gccctggtg   19740
gtgaacgctg gctcccgtg ctctgcctgt ttcatcacca gcccctccc cttctgcctg    19800
gggtccagta atctgttgaa atatatatct tgctcattgg tgagctcctg ctccttcctc  19860
gttgctcttg cagatttatc acttctcgta aggctgcgct tgtacttcgg gattttctct  19920
gtgccacact gggaaacata gggtggttgc atgctgcagt cctgagcact tatttcactc  19980
acatctttac acgaagattt ggtgggtgtt tactttgttt ttagtaagtt agtctgtcat  20040
gtcctttgat cctttttttt tgtttttttga gatggagtct ctctgtgtcc tccaggctgg  20100
agtgcaatgt cgcgatctca gctcactgca acctccacct cctgggctca agagattctc  20160
ctgcttcagt ctcctgagta gctgggatta caggcatgtg ccaccacacc tggctaattt  20220
ttgtattttt agtagaggtg gggtttgca tgttggccag cctggtctca aactcctgac  20280
ctcctgacct gcctgcttg gcctcccaaa gtgctggat tacaggtgtg agccaccaca   20340
cctgcccgta attaatctttt taatgcccag tctctccttc aaaagccggc tccttctctc  20400
ccctcgcctt cctagattcc ttctccactc cccaggatca gcctcctcct ccccacccca  20460
ccactgccgg ggggatgtct gtggtcaggc atttatcaga gacctgagg tggggtcct    20520
ttatgtgtct gggggatgga gagtctagag gaggtagcgt tcagacctct ccatggtgcc  20580
tctgctgggc tcacatgtga ccaagcacag caaaccatga ggcagggga ggtcttgacc   20640
atgagagccc ttgcagcagc tgcatgggc ctcagctctg ctccaagctg ggaagagccc   20700
tgaaaagcca aggtgttttt ttttccctct ttatttcagt gtaagtccct tgagcttct   20760
tgaaccagaa gtgggctcat tttgcttag agatttcagg tgggcttgtc cttgtcctag   20820
catcccagat ccaccttctg ggaagtcatc agattggagg tgatgttggc agcttttgta  20880
aacaaagggt agtgttgtaa gctgttgtgt tgcctatgt gtgtgtttgt gtacttggtc   20940
tcatctctga agactggtga catggcttcc agatatgcc gacgatgtgc tgtggttgca   21000
gtgggtgacc tcacaggtgt tcactcgagt gctgatgtgt ctgctcccg cctccaggta   21060
aatactttgg ctgtgggtgt gtgggccgga cgggcacctc tctcatctga tgaggcctca  21120
cacgacattc tagaaacagc tggctgaaca ccaagcaagg agcttgccct tgggtgtggg  21180
gaccctgtct catgggaggc agctgagtca gtcagaggtc ctggcacacc tgctgagagc  21240
tgccacccag gccaacctga accggagcct gggaagactt cccgtcggat gagtctcttt  21300
```

```
gagtgcagca ttgatggtgg aagagcagag aggccccaga taagcaggga aaggtgcttc   21360
agacagagtg gctgggatga ggactgggga gtgtcagata gcgctggcgt gtctgagcga   21420
aggagctctg gcaccatgg cacaggaagg aggtgggacc ctggagggc agggctagca    21480
gagctcctcg gagcgtgtgg ctaggtgcct ggtaatgcaa gcccctgtc ctccaccctc    21540
tgttgtactg agtcacagtc tccggggtga agcctgacag tctgcgttga caggccccag   21600
gggatgccgc tacttcctga attctgaatt ctgaaactg agccggagtt cagggcctga    21660
ctcccattac cagggttggg cgttatcctg aaaatcatag gccttggttt cctcacttgg   21720
ctaacagggg tgatccccat cccctcaatg ggtttccgtg agctcctgag agcccgtagc   21780
atggtacttg gcacatgctg ggcatcagga ggtatggcct ctcttgctat tgttgttatt   21840
ggtagacaca gaaggattta aaagtagggg aatgcaaaga tccgatttgc tagggaagag   21900
ggcagtagtg gccaagtaga gggtggatcc tgggccctgg ctgcagcag gcagcaaggg    21960
gggctgccag ggcccaggca gggacgatcc gtagaccgag aggcttccta aggctcttgg   22020
acaggaggag gtgtcggttc caagcctaag gagtgggca gccctggtga ctggtggtcaa   22080
gtggtgccag gcggtggtg gtaggacacc ctggcaggca agtaggtttg tgtgggggaa    22140
actgataggc ccctccaggg attcgttggt ggacaacacc tgtgatgtcc agtgggaggt   22200
gtccaggtag ctgggagggc acaggcttg gaagacctag gtggtgacat cagcccagca    22260
ctgagggcta gaagaagctg tgtctctggc tgtgacggca cccagagtg tgtgtggtgc    22320
cctctactgg ccggcaatgt gggtccaccg tagctcagac tgcacactgc agcagcgggaa  22380
acggcctcta agccaacttc ctccatgtgt ttcaggtccc aaatgccagt gagcagccaa   22440
caggcctccc catgcacacc tgagcaggac tggccctgct ggactcctg ctcccccaag    22500
ggctgtccag cagagaccaa agcagaggcc accccgcgt ccatcctcag gtccagcctg    22560
aacttcttct tgggcaataa agtacctgct ggtgctgagg ctctccac cttctcccagt    22620
ttttcactag agaagagtct gtgagtcact tgaggaggcg agtctagcag attctttcag   22680
aggtgctaaa gtttcccatc tttgtgcagc tacctccgca ttgctgtgta gtgaccctg   22740
cctgtgacgt ggaggatccc agcctctgag ctgagttggt tttatgaaaa gctaggaagc   22800
aaccttttcgc ctgtgcagcg gtccagcact taactctaat acatcagcat gcgttaattc   22860
agctggttgg gaaatgacac caggaagccc agtgcagagg gtcccttact gactgtttcg   22920
tggcccctatt aatggtcaga ctgttccagc atgaggttct tagaatgaca ggtgtttgga   22980
tgggtggggg ccttgtgatg gggggtaggc tggcccatgt gtgatcttgt ggggtggagg   23040
gaagagaata gcatgatccc acttccccat gctgtgggaa ggggtgcagt tcgtccccaa    23100
gaacgacact gcctgtcagg tggtctgcaa agatgataac cttgactcagt aaaaacgtct  23160
ccatggcggg ggtaacaaga tgataatcta cttaattta gaacacctt ttccctaac     23220
taaaataatg tttaaagagt tttgtataaa aatgtaagga agcgttgtta cctgttgaat  23280
tttgtattat gtgaatcagt gagatgttag tagaataagc cttaaaaaaa aaaaatgga   23340
ttgggtgcag tggcacacag ctgtaatccc agcactttgg gaggccaagg ttggcagatc   23400
acctgaggtc aggagttcaa gaccagtctg gccaacatag caaaaccctg tctctactaa   23460
aaatacaaaa attatctggg catggtggt catgcctgta atcccagcta ttcggaaggc    23520
tgaggcagga gaatcacttg aacccaggag gcggaggttg cggtgagctg agattgcacc  23580
atttcattcc agcctgggca acatgagtga aagtctgact caaaaaaaaa aaatttaaaa   23640
aacaaaataa tctagtgtgc agggcattca cctcagcccc ccaggcagga gccaagcaca    23700
gcaggagctt ccgcctcctc tccactggag cacacaactt gaacctggct tattttctgc   23760
agggaccagc cccacatggt cagtgagttt ctccccatgt gtggcgatga gagagtgtag   23820
aaataaagac                                                          23830

SEQ ID NO: 31          moltype = DNA   length = 23830
FEATURE                Location/Qualifiers
source                 1..23830
                       mol_type = genomic DNA
                       organism = Homo sapiens
SEQUENCE: 31
atggtccgag ggggcgggg ctgacgtcgc gctgggaatg ccctggccga gacactgagg    60
cagggtagag agcgcttgcg ggcgccgggc ggagctgctg cggatcagga cccgagccga   120
ttcccgatcc cgacccagat cctaaacccgc gccccgccc cgccgccgcc gccatgtacg   180
acgcagagcc cggctggagc ttgtccttcg cgggctgcgg cttcctggcc ttctaccacg   240
tcggggcgac ccgctgcctg agcgagcacg ccccgcacct cctccgcgca gcgcgcatgt   300
tgttcggcgc ttcggccggg gcgttgcact gcgtcggcgt cctctccggt atcccgctgg   360
gtgcgtctgg gacgctgcc cgggctccac gtgcggagtg ggtgccccct aggccggggga  420
gcgggggatc cccaggggtc gcggggcct ggaggagcgg gcatcggacg cggacacggc    480
gggtgcatc ccgagggccc cctccggagc agatgcttcc tgcgggggcg ctgttcctgg    540
gcccgggaag gggcgttgg aaccccgagc ggtccgggcc gaagcctggg actctcgtcg    600
gtccccaccc ctaccccat caggcgcccg tgcatgaagg gagaccctca cctccggact    660
gagagtcgga gcgtctcgga gcgacgggga gtagggagcg ggaccccggggg cggagggtag 720
tgctggcccc tgcggactcc gggtcccctg tgtcctctcg ggaggggctg gacgggctga   780
gctgccgagg ggcgatttg ccctgggccg gacaaagagt ggggcttgg ccggtccccc    840
acggtgggct ccttccctct ggggattgag ggactcaaga caccccgcgc ctgcgctttt   900
cttttctttt ttctttttt ttttttgag acggagttc gctcagtcgc ccaggctgga    960
gtgcagtggc gtgatctcaa ctcactgcaa gctccacctc caggttcac gccattctcc   1020
tgcctcagcc tccgagtag ctgggactac aggcgtgcage caccaagccc ggctaatttt   1080
ttgtattttt tagtagagac ggggtttcac cgtgttagcc aggatggtct cgatctcctg   1140
acctcgtgat ctgcccacct cggcctccca gaatgctggg gttacaggcg tgagccactg   1200
ctccctgctg cctacgctct ctgggtcgca gcccagcctt ctgggggctg ggtagcctcc   1260
cagaagggca accctgggca tcctccaggg caggctaact ggagtctagt ggggaggggt   1320
accttgaaag aggaaagttg tttcctcctc ctcctcctcc tccagtgttt gggacccttc   1380
ctgggggctg gagtgcatcc ctgacaccc ccaatccca tcctcttctc tagtttcac     1440
tgacctaggc ccaccctccc ctctccggct cagtactcct ggaaatgaga ttccgtacat   1500
ttgaatcttg tcctaatgaa atatttgtcc atgtgggtac ctgtgtgtgt gtggtggggg  1560
tgcagacgga gggtttgttt ctcactagct ggaactactg gggtgtggta tgcttcctgg   1620
gaatttgtgt gccacagtcc tggaggcgag gaggggttg tgagccagta ggcagggct    1680
ggggcaagta gcattgtgaa gctattgaca cccagacgtc cccaggcagg agattatgcc   1740
```

```
cccattagcc ccctttatc tgggcttcct taacaatgga ctctttgccc tgcctgccag   1800
agccagcagg gagtgactgt tcagtggtga ggaagcgggc agaggaagcc ctgccattgg   1860
gtaggagcag tgggcagccc ctgggctgac tgggaggtgg ggattaggga ttagacagtc   1920
ctggctgtct gccttcccct aagccagggg gagaggagca aagggcacga aatgtggcct   1980
ccaggaggat tagaccgcca catgatcatt tgcacaccct ggggtttagc aacaataaaa   2040
gtcagctttt ttgtatccca aggtggcctg tggacaccca catggacaaa tgtttacact   2100
gggacagaat tcaaatgcag aggtcccagg agcctaaagt acactcactc tggtatagaa   2160
aggattcctc actgggcaga ggacaggtgc agcctgggc tttcccaggc aggacacagg   2220
gaggctcagg aaccaccaag tccctggaag gtggatctgg aggcgttggc aggagccact   2280
ccctgggttc cagggctcca ggttcctgct ttaaccccct gtctcacaga gggctgtgca   2340
cttgggggct gctgagcatg tcccagaggc tgcatcctgg acacagcacc tcagtgcatc   2400
tgagctgagg ctaacttggc aggagggaca ggcagaacct gccagccacg tgcaattcca   2460
cccctctggc cactcaggga aggagagctg tgagtcaaga tcagatttgg gtcaggacag   2520
gctggggcct gcctgtccct gtgcatccca agatttatgg ctggccaggg gttgggctgg   2580
gaggggtggt cttgcatgcc aggagagtgc agatcagcct gagaggccag gccagtaagt   2640
gaggtcagat ctcctgcacc tgatagcatt aaggccatct acaccaaagc tctaatgctg   2700
atatgttcct ggcctctatg tggggcatgg aggtggggca tggaggtgag gcctgctcgc   2760
ctgggcttct ggaagtggga gactcattcc tgtggctgag gcctacagca gtgctgtgtg   2820
gtaggaatac actggaagcc atgatgtcat tgtgcatttt ctagaagcca cattgaataa   2880
agtaaaagac acaggtagaa ttaatttcat tgagcccaat atatccaaaa taatatcatt   2940
ttcacatcta ttcaatataa aaatttacta atgagatatt tcatactaag ccactgaaat   3000
ccagttttgt tcttacacat ctcagttttg acgagccaca tttcaaggc gtgatagcca   3060
catgtggctc ccatagtaga cagtactggt ctagagaaat gttggtggca tccttgctgt   3120
ctggtttctg gccttgccaa aagtattacc atcccagtgt ggtacattct ttcatgtatt   3180
tgtctcctgt ccccagagca gactctgcag gtcctctcag atcttgtgcg gaaggccagg   3240
agtcggaaca ttggcatctt ccatccatcc ttcaacttaa gcaagttcct ccgacagggt   3300
ctctgcaaat gcctcccggc caatgtccac cagctcatct ccggcaaaat aggcatctct   3360
cttaccagag tgtctgatgg ggaaaacgtt ctggtgtctg actttcggtc caaagacgaa   3420
gtcgtggatg taagcagttt gcttatctgg acgttgtcaa gttagaaaag ctgttttggg   3480
atgggtgtgg tggctcatgc ctgtcatccc ggcactttgg gaggccgaag cgggtgggtt   3540
gcttgagccc aggagctcga gaccaacatg atgaaaccca gtctctacaa aaattacaga   3600
aaaattagct aggcatggtg ttgtgggccc atagtcccag ctactaggga ggctgaggca   3660
ggagaattgc ttgagcctgg gaggtggagg ttgcagtaag tcatgatcat gccactgtac   3720
tccagcccgg gtgacagtga gatgctgtct ggaaaaaaaa aaaaaagaaa gactgttttg   3780
ttttggaagc aacacaggca gttgtaggcc ccctgtgcca gagtgcacata aactctgtac   3840
acctccagtg atttggtcca tgtttgtaaa ccctgaatgt tccagggcag tttcttttct   3900
tcactttta tctctttttt ttgggtgggg ggcggggta cagagtcttg ctctgtctcc   3960
caggctggag tgcagtggcg caatctcaac ctcccgagga gctgggacta caggcacagg   4020
ccatcacacc ttgctaatgt ttgtactttt tgtagagacg gggttttgcc ctgttgccca   4080
ggctggtccc aaactcctgc acccaagtaa tctgcccacc tctgcctggc agttacaatt   4140
tcaaataatt cctcccttc cttcaacact tggctcatga ccgtccagtc caaggaacct   4200
gtcctgcagg tgtgcctctc ccgagcttcc tctatgcatc ttccataatg aagatgcctt   4260
ctcactggaa accctacaag ggtgggaacg tgccttattt gccttatcc tcagggctca   4320
gcagagagaa gataatttgt aataccaaaa caccattaaa ttcagctgat gctttcataa   4380
gcgctccttg gaggaaggac tccatttact tgacagatct gtgcaagaca gcagcctggc   4440
gcgtctaacc tgcagccagt tgcatcctct gtttaacctt gtttgcggaa gctttctcta   4500
aacagccagc acttgtctgt tcccacatgg gtccgttctc ccagtgaatc accgtggtgc   4560
ctgctgactg ctctgtagca cagtgcttcg caaagtgtga tcctgggacc agcagagcag   4620
cagctccttt gagcttattg gaatggcaga ccctcaggtc ccacctctga cctgctgcat   4680
gggaattctg gggagggacg cagaatctct ggttccacag gctctccggt gatgctaatg   4740
aataccggca tttgaacagc accgatctag ccccttttca tccatgagcc acaaaccctt   4800
ggtcctgtct gtggtgaccc agtgtgactc tcatggggga caaggagagg aagttgaagt   4860
tcactgacag ggttgttaag gggattatgc aatagatgag acccatgggc ctgaagtccg   4920
agggtgtatg ttagttcccc gttctttga cccatggatt aacctactct gtgcaaaggg   4980
catttcaag tttgttgccc tgctcacttg gagaaagctt atgaaggatc aggaaaatta   5040
aaagggtgct ctcgcctata acttctctct ccttttgcttt cacaggcctt ggtatgttcc   5100
tgcttcatgc ccttctacag tggccttatc cctccttcct tcagaggcgt ggtaagtcgg   5160
cttttctctgc tagcgctgag tcctgggggc ctctgaagtg tgctcacaca tctcctgcct   5220
gcagggcact ggtgtcgggc acctcagggt ctgtcccatg gtggagcccc atgcctcact   5280
gccttcaga cagagtagcc ctggccc ctatttccag gctaccccggg cagcaaaact   5340
tactcatgt gtaattaatt atttggctat ctgtaaggta aactggctgg ttcacttaat   5400
ctgcacctta agcatcagat agcttctcag tgatctagtt aaactatatg atgttggcca   5460
ggcgcggtgg ctcatgtctg taatcccagc actttggag cctgaagcag gcagatcact   5520
tgaggtcagg agttcgagac cagcctgcc aacagtgtga aactctgtct ctcctaaaaa   5580
tacaaaaatt agctgggcat ggtggtgtgc acctgtaatc ccagctgctc gggaggctga   5640
ggcaggagaa ttgcttgaac ttgggaggcg gaagttgcag tgagccaaga tcgcaccact   5700
gcactccatc ctgggtgaca gagcgagact ctatctcaaa agaaaaaaa aaaaaaggt   5760
aaataaagta tatgacactg aagaatctgt taccccctgga aggtggagct ttactcttag   5820
ggggaactat aacagtcata tatatatatt ttttcttt ttttttttt   5880
tggagtctgg ctctgtcgcc caggctggag tgcagtggtg caatctcggc tcactgcaac   5940
ctccacctca caggttcagg caattctcct gcctcaacct cccgagtagc tgggattaca   6000
ggtgcctgcc gtcacgccaa gctaatttt gtatttag tagagacagg gtttcatcat   6060
attggccagg ctggtctcca actcctgacc tcaggtgatc cgcccgcctt ggcctcccaa   6120
gtgctgaga ttacaggcgt gagccatggt gcccggccaa caatcacatg tgttgtaaac   6180
aacaacaaaa atctgtcagc ctggtctaac ctagatttgt gctttgtttt gttttgccac   6240
tttgtgatgc acaggaggaa gtttaggctg taaaatacta gccttttagg gtaattttg   6300
aactcacaag agcagcagcg gaaccttga tgcaatcctg tatgtagcac cagcagagcc   6360
acgtggcaga gggactcgca ttaggagcct cccattacag actacgtgct cctgtgcgtt   6420
atcttatagg gtccccacaa ccaaggggag atgtgattat tcatcctgtg tggctgtggg   6480
```

```
gaacttgaga gtcatacttg cccaaagagc acggccagcg agcttgcacc caggtcactc  6540
tctgctcctc tgtcagaaca gggcatgtct tggttcactg cagggcggct cttctcattc  6600
tctgtagttt ggggtccagg atagtggtcc acggagccac tggagtgccc agctactgag  6660
tgaccaaagc atattttgga tttccgacat tgccacagca tggttgggca tcagcaggac  6720
cccaacccct tgttatgctg gtggctttat gtggttattt gatcttcccc agaactcagc  6780
aggagtgcac ccagcagcac cgtagtgatg ctctctggct ccccagtgca cggttctggc  6840
tttccttcct ggtcgagagt ttcaagccct ctgggtccta ctctgtcctt ttcagcccat  6900
agctttgttc aaaagctgct ggcagtgttc agatttggct gagttcagtg aatatgtgca  6960
ttggctgatt tctgagccat gccaggggga tggagaagcc gaagcaggag tgtttgttct  7020
gcaggctctg gagtaggcat tgggtctgtg ccggctcact tgctagtctt gcatccttcc  7080
ccaaccccct ctgggdatgt ctggccacat cagaagacag tttggggttgt cagaactggg  7140
ggagtaccag gccgaggtgg gtggatcatg aggtcaggag atcgagacca tcctggctaa  7200
cacagtgaaa cctcatctct actaaacata cgaaaaaaat tagctgggcg tggtggcggg  7260
cgcctgtagt cccagctact cgggaggctg aggcaggaga atggtgtgaa cccgggggc  7320
ggagcttgca gtgagctgag atcctgccac tgcactccag cctgggcaac aaagcgagac  7380
tccgtctcac aaacaaaaca aaacaaaaca aacaaaatc tggggagtg ccactggcat  7440
ctgatgtata gaggcccgag atgctgtgtc atcacccgtt gagtgcgctc ataggcatct  7500
tcctgacaat tagaacccat tattcttcaa attcaatgca agcaaattca aagcattact  7560
gtgtacatac cgcatgctaa tcaattgcac cactggagct cctaaattca aaacattact  7620
ataaaaagt tcaaaatgca tggaaaagtt gtacatggca ggagaatatt tgggcttctg  7680
actaccccct gaatgaagat gatccaccag ccgccttcct ccttggtctt cactccagat  7740
tcctagcatt tcattctgtg tctctttatg cagtgaggtt tttgttttgtt ttttgagaca  7800
gagtctcact gtatcaccta ggcctggagt gcagtggcgc gatctcagct cactgcaacc  7860
ctcggctcct gggtttaagc gattctcctg cctcagcctc ccgagcagct gagattacaa  7920
gcacacatcc ccatgcccag ctaattttttg tattttttagc agagacaggg tttcaccatg  7980
ttgcccaggc tggtctcgaa tcctggcct caagtgatcc atgtgcctca gccttccaaa  8040
gtgctgggat tacaggcgtg agccaccatg cccagctcct agtgaggtttt ttgatgcctt  8100
gctacatctg ccctagaaat tgtgtgacta cgattttgga aatgttgctg tgtaaacttg  8160
tgatcatttc tggactccag gcaagaatct tgatggctaa ggtgtggctg aacatgtctg  8220
attctctcct ggacctgttt taggccaaac tctgctctga aattcctccg tgtggaaggg  8280
cgggctgggg agagcctccc agctggaatc ttttgatgc cttttctctgt gggtatctga  8340
tggctggctc tgatgctgg ctgtgatggc tgtggctgga aatcattgtt gacatgagtt  8400
tcacagatgc aggctctgtc caaattgtag caaaagctgc ctgccccagc cgagctatgg  8460
gcaataaggt ggtttaagga tatagatgaa ggaaaactca cccttagaat aatttatcca  8520
aaatgctgct gtgttgtggg ttagaggaca ttttctgagg tcccaggttc attgtttcat  8580
ttaagtctca aaagtccctc caggtgttgg ttctaattgt caaagcatgg ggggagatgg  8640
gctcatgggt taaggtctt atcccagatt tctgtatcct ccttgcaagc agcaaagggg  8700
tctggatttg aatccatgac catgtttctc ctttgggtttt ccatcacact ctgtcccgt  8760
gcactgagca ccctttagtt catatgaccc ccttaggcat gttacatggg cactcctata  8820
ggtgcccatc tggcccctagg acttggccaa cacaacatgg actccagttt ccatctgcct  8880
cttttgccagg cacttttgtg cagtgcacac actgtacaac agtagacggc aaccctgaga  8940
gccagagtag agcctgtcct agcaccgaaa tgctcggtaa ggattttgtcg caggagtgat  9000
tccaaagcca atgtcctccc tccatatcag cctgtttgtg gctctgagaa gctctgccca  9060
catgtgaaag cttgttaagc acttaagcac taacccagag cttcagacag tgccagtcct  9120
ttttcccctt ctttaaaagc gatatgtgga tggaggagtg agtgacaacg tacccttcat  9180
tgatgccaaa acaaccatca ccgtgtcccc cttctatggg gagtacgaca tctgccctaa  9240
agtcaagtcc acgaactttc ttcatgtgga catcaccaag ctcagtctac gcctctgcac  9300
agggaacctc taccttctct cgagagcttt tgtcccccg gatctcaagg tgagttggtg  9360
gtgaggggc aggtgttctg gggtgcagct ctttcttgcc tccctgattg ccaggagcta  9420
ccagttactg tctgcacaat caaacagaaa tagacctgtc cttgatggtt aacgaaata  9480
aaaggcgctt gtcccagaag ctcaggtgag gcaccaccct gattatggga atcacctggg  9540
aacatatacc cagacctaaa actcagatcc acttcccagg ctgtggttat atagtcaggg  9600
gggtgcagta tgggtattag gatttttat tttttagtta taaagatttt tttttggttt  9660
gttttgaga cagggtcttg ctctgccgct taggctggag tgcagtggtg caatcatagc  9720
tcactgaagc ctcagactcc tgggttcaag cagtcctccc acctcagcct cctaaggagc  9780
tgggacccac aggcatgcag caccacacct ggctaatttt taaaattttt gtggagtgtt  9840
gcccaggctg gtctcacact cctggcctca agcgatcctc ccaccccagc ctcccaatgt  9900
gttgggatta caggcatgag ccattgtacc cagccactaa gatgattctt atttggaaac  9960
acggtcaaga acaactgcgt tcggtagttt aaccttttttt gattgtggtg gttttagtat  10020
gccttaccac tctaccatag taagaaattt gcagaccatg tacaccaacc tttggtgctc  10080
ctggggagaa agaaagaagg ctatgcaatg caatgcatgc tcacagtcca agggagaggg  10140
aaaagctgtct aacaggattg gttttcccgt gtgctttata agcagatgag tagaggagac  10200
agctcttatt gtcctagtgg caattgggat aggctgcaaa gtttgttagg gtggaggctt  10260
attccgggac caagggagcc caaagaaaca agctcctgcc agccgcggtg gctcacgcct  10320
gtaatcccag cactttggga ggctgaggca ggtggatcac ctgaggtcag gagtttgaga  10380
ccagcctggc caacatggtg aaaccccgtc tccatgaaaa atacaaaaat tacccgggca  10440
tggtggcggg cacctgtaat cccagctact agggaggctg aggcaggaaa atggcttgaa  10500
cctcggaagt ggaggtggcc gttagccgag atcacgccac tgcactccag cctgggcaac  10560
agagcaagac tctgccttaa aaaaaaaaaa aaaaaaaga aagtaaaag gaaaaaaaag  10620
aggctctggc ctgctgggt gcctgcaaag tctccgtgga agggtgacat tcaagccgag  10680
acctccaggg aactgtctcc tgggagcaca gagcccttttg ctcagccccc aggtggctca  10740
gtgccccag ccagcagact cagagcttgc atgattcttt ggtgctctct gcggtcttcc  10800
aatgatgctg aaataaatgg tgcttggtgt ctccctgctg tagtccccct gcttgctttg  10860
ctcacagctg ctgggagaga tatgccttcg aggattcatt gatgcattca ggttcttgga  10920
agagaagggt atgtatggc tgggaggatc agccatgccc ttttgacaag catttactag  10980
cggtcttggt aaagacttga gatttgcctt agttctaaca cttagtgccc aacgccttcc  11040
ttgtgttgct caacctactc atgagcccag gagataggaa atctccgtcc cattgtacag  11100
atggggaaac agaattttgg aaaggagagc caagcagcac acacccctcc ctgagggggca  11160
gagccgagat ttgaactggg atgtcatgac tccagggccc tctccctccc cagggtcccc  11220
```

```
ttatctgaag gcggttttc tttccagctc gacctcttgt gacccttagt ttaacaaggg  11280
ccgaagttaa agagtttctg cgcctggacc ccaaatgaag caatcagatt tctcatctcc  11340
agtcaggtgt gggtccaagc ccactagaca agtttgctct tcccagagca catttctgcc  11400
ttcaagtcat cctggcttgt cagggctggg ggagttctgc tgtagaaata ttagagtgga  11460
aggaaaaaga tgtgttggga gctatttttc tttaatacta aaagttggtt gatgaatttg  11520
tcgttggcca agaccaagga gactgcattt taaggacat atgtgtattt atctgctcag  11580
aaaatgttca ttgctgtgtg ctagggatac tgcagtgaac acagaggtgt gacccttgcc  11640
agccttgtga gagaagtgag cagataagta agcagaaggg tgatgctgtg tcgatgggaa  11700
agtacaggtg ccaatgagaa ggcacaggtg tcaaggagaa gacacaggat gctggaggct  11760
catgcaggat ggatctccaa ggcccagggg aagaagggcc tctcggagga cgtgaatcca  11820
cattaagact ttggggataa gtaggagcgc cttaggcatg gggacccatg gatgcgaggc  11880
ctgtaggaca cagacaggat ggcatgaagg cctgtgcaac tggagggggtg gggatgggga  11940
cactaagaga tggctggaag tgtggggggtg gggacactaa gagatgactg gagaagaggg  12000
ggtcaggagt ggtgaaaaat gggagaggag ggcaggcctg gccttttgga tacaggggga  12060
ttgcatcctg cagtggtagg gagccactga gggctgctgc agtaggagtg aggggatcag  12120
aggagagctt tggaagcccc ctggatgcgg gacaggaagc gagataccag tgtctaggag  12180
gccagtgagg cagccacagg ctccaccagg atcagggctg cgagggtcat gaggaggaaa  12240
ccaatttgaa ggagtccagg ggaataggac ttggaaatga ccgatgggac atttgggaag  12300
aggaagacag aagagcgcag tcccggcttc tggctttagc agttgggcaa ggggagatgg  12360
ggagatgtgc ccatgggttg aggggttgagg acattaggag ggagccggta tggcaggaag  12420
agctggtgtg ccagagatgc tggaagcagc atctgcctga gaacagatac ctggcaatat  12480
tcctaaggga aagtgacatc tcggagggtg aggagggcat ctgataggga ctggaaagag  12540
ccggggcaag catgaatgtg aggttatctt gggggggcaag gctcaggcgt tgaggagcag  12600
cccctggtct cttcagcctg aagttggaag ccagagttgg gccaggtgca gctgtggttg  12660
tctgaagtcc ccctcccccca gcccagtgtg ccaatgctgt aagagcaagg gccgctcact  12720
ggtgctggtg gctgagtccc acacccagg acagggccgg gcacatactg gtgcccaatc  12780
ctcccttctg ggtgcttctt ccaaggcctt gtgatgaag tgagtaccct cttcgacatc  12840
agacccagct tcaaatcctg gctctgctat gtattgctg cgtggcttta gacaagtctt  12900
ttaaccttgc tgtgcttctg atttctcagc tgaaaaatgg agatgatgat agtggtttct  12960
gtaaggcctt atggtgaagc acctagctca gggcctggaa ggcaggtgta accagtggtt  13020
cagttgttat aaaccaacac taaccctcgc ctttgcacct catgaaacca gatatgtaga  13080
tggagcccac aaagctagca ggagccaagc tcacgtgtgt cctgctttaa agccccatac  13140
cccttttctcc gggtgacaaa cacctgtgct cgttctcttc ccttcccctc ttccccttgc  13200
atttggctaa taacaggcca gctgcctgcc tccctgcagt ttggtagatg ggtgggtaac  13260
gaccaccact cccacgttcg cctgatgggc ttgttttccg tgcccttcac aggcatctgt  13320
aacaggcccc agccaggcct gaagtcatcc tcagaaggga tggatcctga ggtcgccatg  13380
cccagctggg caaacatgag tctgattct tccccggagt cggctgcctt ggctgtgagg  13440
ctggagggag atgagctgct agaccacctg cgtctcagca tcctgccctg ggatgagagc  13500
atcctggaca ccctctcgcc caggctcgct acaggtaccc actcctcggg gtgagcacgg  13560
gcagcacctt gtttcttctc ttgtgcatta tggaggaaga tggtactgcc acatgggagc  13620
gataggggtga ggcaaccatg acaggtggtt gggaacatct ccttccatgt gtacagcctg  13680
ggctgctgcc atcactccca gcacagcccc caacccccc aatcctggaa ccttgccaag  13740
tctccttcc catgggggtca tgaccaggag gaaaacaaac tccagctgag ccccttgggg  13800
ttccccatat aggctcctgc ctgtggcagc tgggccctct gtaccccttt ccaactctgt  13860
ctccctaaca tggcacctga gctcctgcca tcctggattt catggacccc aaggatgggg  13920
gtcctgcatc tgggacttgg cctattactc ggagctcctt ttcagccgcc tccctccacc  13980
tgtccaccca cctcaaggct cctttcttga gacctctcct aatttctccc ttcccctaaa  14040
cccacaattt tgaacctcca tcgaatggtc ctgtatttta taatgtcatc aaatatcaaa  14100
tggagacagt gctatggtcc aaatgattgt gtaccccccca gaatttgtct tttgaaatcc  14160
taacccccaa catgatggtc ttaggaggtg gggcctttgg gaggagatta ggtcatgagg  14220
aaaaggctgt cagacactgt ttattaaaca gacccaagag aggtccctg  14280
tccctctac tgtgtgagga ctcagaaggt ggtgtctatg aagaagcagg ccctcaccag  14340
acaccaacat gtctgctgcc ccttgatctg ggacttgca gcctctagaa ctctgaaaaa  14400
tcgatgtttt tgtttttata agccactcag ttggtggcat tttgttagag tagcctgaac  14460
acggactaag tcaaacagaa gaacccacaa accagctaca gagttgggca tttggagaaa  14520
ttcaaaaatg agtcagacat aactcctat tcttgaggtg ccctaagaga tgggacacag  14580
cagctgccca ggtgcattag tttgttctca cattgctata aagaaatacc tgagactggg  14640
taactcataa agaagaggt tgaattggct cacagttgca caggctggac aggaagcatg  14700
gtgctggcat ctgctcagct tctggggagg cctcaggaaa cttacaatca tggcagaagg  14760
tgaacgggaa gcatgcacat cccatgactg gagcaggagt gagagagaga gggaaataga  14820
gggaaggtgc catacacttt taaacaacca gatcatcatga aacacattc actatcaaga  14880
gaacagcacc agtggggaaa tccgccccca tgatccaatc acctccatc aggctccgcc  14940
tccaacactg ggaattacaa tttgacatga gatgtgggca gggacacaga tccaaaccat  15000
atgaccagat taatacgatt tgaggcatca cgaggtcatt aagagaggga aataaaagac  15060
tggggctcca ggaagaaggc tctggaatcc agcagagggt caaggaccag cttgtaaagc  15120
tggtggtgcc tgagaagtac ctaggagaac atagatgctg tgacgtttga tgtagctgtt  15180
ttttgttttg tgttttggtt tttgagacag agtctcactc tgttcccag gctggagtgt  15240
gcagtggcgt gatcttggct cactggagcc tccatctccc aggttcaaat gatcctcatg  15300
cctcagcctc ctgagttgcc gggattacag gtgcacacca ccacgcctgg ctaattttg  15360
tgttttcagt agagacaggg tttcaccatg ttggccagge tggtcttgaa ctcctgacct  15420
caagtgatcc aacaacttca gcctcccaaa gtgctgggat gacaggcatg agccaccatg  15480
cccagcctga tgtagctgtt tctgtgcaca ttatttgctg tggggtatat tcagatttct  15540
taatacaaga tgattctttg cctcatgact tacacaccat tttctattta atttcagcta  15600
tgatattgga aatgacatg tcttttcaag gaaaataaaa gcaggctttc tggaatggcg  15660
acttccaaac atatttgtca atttaaagga gctgggagtg gggacccctat gctccgtaag  15720
cactctctta gctgttcttg gctgtgctcc ccgcttcagc ttcacactgc cctttgctgtg  15780
aagggagcag cctgggccgg gcgcggtggc ttacacctgt aatcctagca ctttgggagg  15840
ccgaggtggg tggatcacct gaggtcagga gttcaagacc agcctggcca acatggtgaa  15900
actccatctc tactaaaaat acaaaaaatt agctgggcat ggtggcaggt gcctgtaatc  15960
```

```
ccagctactt gggaggctga ggcagaagaa tcgcttgaac ccaggaggcg gaggttgcag    16020
tgagccgaga ttgcgccatt gcactccagc ctgggggcaa caagagcaaa actctgtctg    16080
gaaaaaaaag aaaggagcag cttggcaaac cccaccttgt cgcttttgtg agtgcctctg    16140
acccttrggc tgccaggacg ggcgtatttt atggaaatgc taagcaccaa cagagtaaag    16200
tggttrggtt tttcacagtg gtgggagata atagctccaa attgtctttt tcagcactga    16260
gtgaagaaat gaaagacaaa ggtggataca tgagcaagat ttgcaacttg ctacccatta    16320
ggataatgtc ttatgtaatg ctgccctgta ccctgcctgt ggaatctgcc attgcgattg    16380
tccagaggtg agcattttag gtggctccgt gtcttcctca cagggttgat atgaggatga    16440
aacaagatga tagatcatgg tggcatgtag tctgggacct ggattgtcgt gccacagatg    16500
acagctcaca gtctatgtgc aatgcccctg aatgttgccc acctgtcctc aagccacaca    16560
tgcacctgta actcagtgca agcccagaaa ctccccgtgg ggactcctag agctgtcagt    16620
ggcctcacat agcagctggt ccagtctctt gtgattgccc aaggaaactg aggcctggag    16680
agcttggggt cactgctctg aggccataga gatgcctagt agaagggcca ggcctagaag    16740
caggatcctt gctgcccctc tgagctgttt ccatttaaaa tcacatgaag gccggcgccg    16800
tggctcacgg ctgtaatccc agcattttgg gaggccaagg tgggtggatc atgtgaggtc    16860
aggagtttga gaccagcttg gccaacatgg tgaaatgcca tctgtactaa aaatacaaaa    16920
attagtggag catggtggca cgtgcctgta ctcccagcta cttggaaggc tggggcagaa    16980
gaatcgcttg agcctgggag gcagaggttg tagtgagcca agattgtacc actgcactcc    17040
agcctgggtg acaggagaga aaccctatct caaaataaaa tgaaaggtaa tgaaatgaat    17100
aaaataataa atcaagtcac ggccgggcac ggtggctcac acctgtaatc ccagcgcttt    17160
gggaggccga ggtgggtgga taatgaggtc aggagttcaa gaccagcctg gccaacatgg    17220
tgaaaccatg tctctactaa aaatacaaaa attagctgga catggtggtg catgcctgta    17280
atcccagcta ctccggaggc taaggcagga gaattgcttg aagcaggacc taggaggcgg    17340
aggttggttg cagtgagccg agatcatgcc actgcactct agcctgggct acagagcgaa    17400
actccgactc aaaaaaaaaa aaaaaaaaaa atcaaatcac atgaaagtag aacatagggg    17460
attccatctt tcgttctagg catagtttgt taatatgatt cagagccagc agttaggaga    17520
acacagtgtg actctcctag aacttcttga ttgggcttcc tctgattggg tttcctctga    17580
ttgggcttcc tctgaaagtg gggggatgg ggggtgggga gcagaatggt cagagcttgg    17640
ctcagcagtc agactgctct tcttcaaatc ctggctgcat tgcttactac agctgtgtga    17700
ctccagatga ctgaatccac ctctctgtgc tgcagcttcc cgtctagaga gatcacctgg    17760
agcagagggt ggtcaggaga ctcaatctgg ttactgactc acagtgcagg agtactcatc    17820
ccatagtaag catccagcta gagatgttga tttctatttt caggtaataa tgatgatcgt    17880
aaaattagag acagataaaa ggtatgggca ttaggccagg gcactgcaat ttctaagctg    17940
tgtgacctca ggcaagttac tcgacttctc tgagcctcag cggtttcatc cgcaatatat    18000
ggataggaaa accgacctca gtgggttgtc tgacagtgga gggcacttga ttaaaaaaaa    18060
aaaaattacc ctggtctgaa tattaccctg gactgaaaga aaaatattga gctaatacag    18120
gcatcaggaa tggggctgca gggagtccag ggaagggaga acgaagagcc tgaaggtgtg    18180
aggaggtgcg agtgctgatc tgtctgctac aaagaggctg ctgagcctcc tgtggatgtg    18240
gccctggact tggcagttta atacctgagc tgttaaaata acctcagatg ctgtgttctt    18300
taaggggtag gattcagatt cctgctgaaa tgcttctgaa agggagggaa tgagccagcc    18360
catcccccagt tgctttttaa gatcattggg aagttctggt cttgccatrtt gtccctggac    18420
cactcttagg tcctcctgcc ccacttccat ctgggtgtgt gccctgggct gtccaccaca    18480
cagctacatc ctgccatctt ccctcctgga gccactgtgc catgcatgga tctgtagctt    18540
cattttctct ggcttttccc tggttttrtct ggagcagagt ctctagtaaa ctcccaagga    18600
agaaaacgtt tgacttatg tgtgttggga aacgtgcttt ttttctatta catctcagtg    18660
ataggttggc catgtctaga attgcaggtt gaaaatcatt tcctctcagt atattggtta    18720
gtgagaagcc tgggactgag acagtcacat tctcacttct ttgcaggtga gtgctcttag    18780
gactgtctttt ttatcccctta tactctgaaa tgtcatatgt cttggtgtaa gtccttattt    18840
cagttattga gctggacaag tactggagac cccttcagtc aaagcttctg gtcattctcc    18900
agctctagga aattatcttc tattgttatt tctgttattc cttcccttcc attttctttt    18960
ttcttttttt tttttttttt ttgagacagg gtcttactct ggtgcccagg ctggaatgca    19020
gtgacctgat catggtacac tgcagcctga acctcccaga ctcaagtgat cctcccacct    19080
caacctccta gtagctggg actgcaagca cacatcacca cacccaacaa atatttttra    19140
aaaatttrgt aagatgggat cttactatgt tgcccagact ttttcttcct cttcctgggg    19200
ctcttattag gaagatgtrtt gacttcctgg gttggattcc tgtctccgtg tctgactttc    19260
tctctttrgtc atatttttca tcactcgttg tcttttrtgcg tctgctctga cagatttcct    19320
caaatttttgt cttctagtcc tatcctacag tttttacttt cagcaaatat aatttaatct    19380
ccaagagtac tctcttgttc tttttttctta gcattctgtt cttgttttat ggatgtaaca    19440
ttcttcttgga atatttgctg tcctctagat catcccttct ccatttcttc ttgggctagt    19500
ttttctgttt cttcatcttt ctctttatg ctacttattc tgggcgtgtt cttggtgggt    19560
tttttcccat atagcaacag aggacttgga gctcagggag aaaagggtag gtgcatcacc    19620
tggcagagct cccagacagt gacaggcagg ctgcgggaag gatgtctact tggcggtgct    19680
accgctttcc tagaaaccct ttccctggag ctggttgaac tgttgggttt tgccctggtg    19740
gtgaacgctg gctccccgtg ctctgcctgt ttcatcacca gcccctccc ctttctgactg    19800
gggtccagta atctgttgaa atatatatct tgctcattgg tgagctcctg ctccttcctc    19860
gttgctcttg cagatttatc acttctcgta aggctcgcct tgtacttcgg gattttrctct    19920
gtgccacact gggaaacata gggtggttgc atgctgcagt cctgagcact tatttcactc    19980
acatctttac acgaagattt ggtgggtgtt tactttgttt ttagtaagtt agtctgtcat    20040
gtcctttgat cctttttttt tgtttttrtga gatggagtct ctctgtgtcc tccaggctgg    20100
agtgcaatgt cgcgatctca gctcactgca acctccacct cctgggctca agagattctc    20160
ctgcttcagt ctcctgagta gctgggatta caggcatgtg ccaccacacc tggctaattt    20220
ttgtattttt agtagaggtg gggtttgca tgttggccag cctggtctca aactcctgac    20280
ctcctgacct gcctgcctgg cctcccaaa gtgctgggat tacaggtgtg agccaccaca    20340
cctgcccctg attaatcttt taatgcccag tctctcctta aaaagccagc tccttctct    20400
ccctcgcctt cctagattcc ttctccactc cccaggatca gcctcctcct ccccacccca    20460
ccactgccgg ggggatgtct gtggtcaggc atttatcaga gaccctgagg tgggggtcct    20520
ttatgtgtct ggggggatgga gagtctagag gaggtagcgt tcagacctct ccatggtgcc    20580
tctgctgggc tcacatgtga ccaagcacag caaaccatga ggcaggggat ggtcttgacc    20640
atgagagccc ttgcagcagc tgccatgggc ctcagctcct ctccaagctg ggaagagccc    20700
```

```
tgaaaagcca aggtgttttt ttttccctct ttatttcagt gtaagtccct tgagctttct   20760
tgaaccagaa gtgggctcat tttgctttag agatttcagg tgggcttgtc cttgtcctag   20820
catcccagat ccaccttctg ggaagtcatc agattggagg tgatgttggc agcttttgta   20880
aacaaagggt agtgttgtaa gctgttgtgt ctgcctatgt gtgtgtttgt gtacttggtc   20940
tcatctctgc agactggtga catggcttcc agatatgtcc gacgatgtcc tgtggttgca   21000
gtgggtgacc tcacaggtgt tcactcgagt gctgatgtgt ctgctccccg cctccaggta   21060
aatactttgg ctgtgggtgt gtgggccgga cgggcacctc tctcatctga tgaggcctca   21120
cacgacattc tagaaacagc tggctgaaca ccaagcaagg agcttgccct tgggtgtggg   21180
gaccctgtct catgggaggc agctgagtca gtcagaggtc ctggcacacc tgctgagagc   21240
tgccacccag gccaacctga accggagcct gggaagactt ccgtcggat gagtctcttt    21300
gagtgcagca ttgatggtgg aagagcgag aggcccaga taagcaggga aaggtgcttc     21360
agacagagtg gctgggatga ggactgggga gtgtcagata gcgctggcgt gtctgagcga   21420
aggagctctg gcacccatgg cacaggaagg aggtgggacc ctggagggc agggctagca    21480
gagctcctcg gagcgtgtgg ctaggtgcct ggtaatgcaa gccccctgtc ctccaccctc   21540
tgttgtactg agtcacagtc tccggggtga agcctagcag tctgcgttga caggccccag   21600
gggatgccgc tacttcctga attctgaatt ctggaaactg agccggagtt cagggcctgg   21660
ctcccattac caggggttggg cgttatcctg aaaatcatag gccttggttt cctcacttgg  21720
ctaacagggg tgatccccat cccctcaatg ggtttccgtg agctcctgag agcccgtagc   21780
atggtacttg gcacatgctg ggcatcagga ggtatggcct ctcttgctat tgttgttatt   21840
ggtagacaca gaaggattta aaagtagggg aatgcaaaga tccgatttgc tagggaagag   21900
ggcagtagtg gccaagtaga gggtggatcc tgggccctgg ctggcagcag gcagcaaggg   21960
gggctgccag ggcccaggca gggacgatct gtagaccgag aggcttccta aggctcttgg   22020
acaggaggag gtgtcggttc caagcctaag gagtgggggca gccctggtga ctggtggtca   22080
gtggtgccag gcggtgggtg gtaggacacc ctggcaggca agtaggtttg tgtggggaa    22140
actgataggc ccctccaggg attcgttggt ggacaacacc tgtgatgtcc agtgggaggt   22200
gtccaggtag ctgggagggc cacaggcttg aagacctag gtggtgacat cagcccagca    22260
ctgagggcta aagaagctg tgtctctggc tgtgacggca ccctagagtg tgtgtggtgc    22320
cctctactgg ccggcaatgt gggtccaccg tagctcagac tgcacactgc agcagcggga   22380
acggcctcta agccaacttc ctccatgtgt ttcaggtccc aaatgccagt gagcagccaa   22440
caggcctccc catgcacacc tgagcaggac tggccctgct ggactcctg ctcccccaag    22500
ggctgtccag cagagaccaa agcagaggcc accccgcggt ccatcctcag gtccagcctg   22560
aacttcttct tgggcaataa agtacctgct ggtgctgagg ggctctccac cttcccagt    22620
ttttcactag agaagagtct gtgagtcact tgaggaggcg agtctagcag attctttcag   22680
aggtgctaaa gtttcccatc tttgtgcagc tacctccgca ttgctgtgta gtgaccctgg   22740
cctgtgacgt ggaggatccc agcctctgag ctgagttggt tttatgaaaa gctaggaagc   22800
aacctttcgc ctgtgcagcg gtccagcact taactctaat acatcagcat gcgttaattc   22860
agctggttgg gaaatgacac caggaagccc agtgcagagg gtcccttact gactgtttcg   22920
tggccctatt aatggtcaga ctgttccagc atgaggttct tagaatgaca ggtgtttgga   22980
tgggtgggag ccttgtgatg gggggtaggc tggcccatgt gtgatcttgt gggtgggagg   23040
gaagagaata gcatgatccc acttcccat gctgtgggaa ggggtgcagt tcgtccccaa    23100
gaacgacact gcctgtcagg tggtctgcaa agatgataac cttgactact aaaaacgtct   23160
ccatggcggg ggtaacaaga tgataatcta cttaatttta gaacacctt ttcacctaac    23220
taaaataatg tttaaagagt tttgtataaa aatgtaaaga agcgttgtta cctgttgaat   23280
tttgtattat gtgaatcagt gagatgttag tagaataagc cttaaaaaaa aaaaatcg    23340
ttgggtgcag tggcacacgg ctgtaatccc agcactttgg gaggccaagg ttggcagatc   23400
acctgaggtc aggagttcaa gaccagtctg gccaacatag caaaaccctg tctctactaa   23460
aaatacaaaa attatctggg catggtggtg catgcctgta atcccagcta tcggaaggc    23520
tgaggcagga gaatcacttg aacccaggag gcggaggttg cggtgagctg agattgcacc   23580
atttcattcc agcctgggca acatgagtga aagtctgact caaaaaaaa aaatttaaaa    23640
aacaaaataa tctagtgtgc agggcattca cctcagcccc ccaggcagga gccaagcaca   23700
gcaggagctt ccgcctcctc tccactggag cacacaactt gaacctggct tattttctgc   23760
agggaccagc cccacatggt cagtgagttt ctccccatgt gtggcgatga gagagtgtag  23820
aaataaagac                                                          23830

SEQ ID NO: 32        moltype = RNA   length = 1443
FEATURE              Location/Qualifiers
source               1..1443
                     mol_type = mRNA
                     organism = Homo sapiens
SEQUENCE: 32
atgtacgacg cagagcgcgg ctggagcttg tccttcgcgg gctgcggctt cctgggcttc   60
taccacgtcg gggcgacccg ctgcctgagc gagcacgccc cgcacctcct ccgcgacgcg   120
cgcatgttgt tcggcgcttc ggccggggcg ttgcactgcg tcggcgtcct ctccggtatc   180
ccgctggagc agactctgca ggtcctctca gatcttgtgg ggaaggccag gagtcggaac   240
attggcatct tccatccatc cttcaactta agcaagttcc tccgacaggg tctctgcaaa   300
tgcctcccgg ccaatgtcca ccagctcatc tccggcaaaa taggcatctc tcttaccaga   360
gtgtctgatg gggaaaacgt tctggtgtct gactttcggt ccaaagacga agtcgtggat   420
gccttggtat gttcctgctt catcccccttc tacagtgctac ccttcattga tgccaaaaca  480
ggcgtgcgat atgtggatgg aggagtgagt gacaaacgtac ccttcattga tgccaaaaca   540
accatcaccg tgtcccccctt ctatgggggag tacgacatct gccctaaagt caagtccacg   600
aactttcttc atgtggacat caccaagctc agtctacgcc tctgcacagg gaacctctac   660
cttctctcga gagcttttgt cccccgggat ctcaaggtgc tgggagagat atgccttcga   720
ggatatttgg atgcattcag gttcttggaa gagaagggca tctgcaacag gccccagcca   780
ggcctgaagt catcctcaga agggatggat cctgaggtcg catgcccagc tgggcaaac    840
atgagtctgg attcttcccc ggagtcggct gccttggctg tgaggctgga gggagatgag   900
ctgctagacc acctgcgtct cagcatcctg ccctgggatg agagcatcct ggacaccctc   960
tcgcccaggc tcgctacagc actgagtgaa gaaatgaaag acaaaggtgg acacatgagc   1020
aagatttgca acttgctacc cattaggata atgtcttatg taatgctgcc ctgtaccctg   1080
cctgtggaat ctgccattgc gattgtccag agactggtga catggcttcc agatatgccc   1140
```

```
gacgatgtcc tgtggttgca gtgggtgacc tcacaggtgt tcactcgagt gctgatgtgt  1200
ctgctcccg  cctccaggtc ccaaatgcca gtgagcagcc aacaggcctc ccatgcaca   1260
cctgagcagg actggccctg ctggactccc tgctccccca agggctgtcc agcagagacc  1320
aaagcagagg ccaccccgcg gtccatcctc aggtccagcc tgaacttctt cttgggcaat  1380
aaagtacctg ctggtgctga ggggctctcc acctttccca gttttcact  agagaagagt  1440
ctg                                                                1443

SEQ ID NO: 33          moltype = RNA   length = 1431
FEATURE                Location/Qualifiers
source                 1..1431
                       mol_type = mRNA
                       organism = Homo sapiens
SEQUENCE: 33
atgtacgacg cagagcgcgg ctggagcttg tccttcgcgg gctgcggctt cctgggcttc   60
taccacgtcg gggcgacccg ctgcctgagc gagcacgccc gcacctcct  ccgcgacgcg  120
cgcatgttgt tcggcgcttc ggccggggcg ttgcactgcg tcggcgtcct ctccgagcag  180
actctgcagg tcctctcaga tcttgtgcgg aaggccagga gtcggaacat ggcatcttc   240
catccatcct tcaacttaag caagttcctc cgacagggtc tctgcaaatg cctcccggcc  300
aatgtccacc agctcatctc cggcaaaata ggcatctctc ttaccagagt gtctgatggg  360
gaaaacgttc tggtgtctga ctttcggtcc aaagacgaag tcgtggatgc cttggtatgt  420
tcctgcttca tccccttcta cagtggcctt atccctcctt ccttcagagg cgtgcgatat  480
gtggatggag gagtgagtga caacgtaccc ttcattgatg ccaaaacaac catcaccgtg  540
tcccccttct atggggagta cgacatctgc cctaaagtca agtccacgaa cttttcttcat 600
gtggacatca ccaagctcag tctacgcctc tgcacaggga acctctacct tctctcgaga  660
gcttttgtcc ccccggatct caaggtgctg gagagatat  gccttcgagg atatttggat  720
gcattcaggt tcttggaaga aagggcatc  tgcaacagca cccagccagg cctgaagtca  780
tcctcagaag ggatggatcc tgaggtcgcc atgcccagct gggcaaacat gagtctggat  840
tcttccccgg agtcggctgc cttggctgtg aggctggagg gagatgagct gctagaccac  900
ctgcgtctca gcatcctgcc ctgggatgag agcatcctgg acaccctctc gcccaggctc  960
gctacagcac tgagtgaaga aatgaaagac aaaggtggat acatgagcaa gatttgcaac 1020
ttgctaccca ttaggataat gtcttatgta atgctgccct gtaccctgcc tgtgaatctc 1080
gccattgcga ttgtccagag actggtgaca tggcttccag atatgcccga cgatgtcctg 1140
tggttgcagt gggtgacctc acaggtgttc actcgagtgc tgatgtgtct gctccccgcc 1200
tccaggtccc aaatgccagt gagcagccaa caggcctcc  catgcacact gaccaggac  1260
tggccctgct ggactccctg ctcccccaag ggctgtccag cagagaccaa agcagaggac 1320
accccgcggt ccatcctcag gtccagcctg aacttcttct tgggcaataa agtacctgct 1380
ggtgctgagg ggctctccac ctttcccagt tttcactag  agaagagtct g          1431

SEQ ID NO: 34          moltype = RNA   length = 1443
FEATURE                Location/Qualifiers
source                 1..1443
                       mol_type = mRNA
                       organism = Homo sapiens
SEQUENCE: 34
atgtacgacg cagagcgcgg ctggagcttg tccttcgcgg gctgcggctt cctgggcttc   60
taccacgtcg gggcgacccg ctgcctgagc gagcacgccc gcacctcct  ccgcgacgcg  120
cgcatgttgt tcggcgcttc ggccggggcg ttgcactgcg tcggcgtcct ctccggtatc  180
ccgctggagc agactctgca ggtcctctca gatcttgtgc ggaaggccag gagtcggaac  240
attggcatct tccatccatc cttcaactta agcaagttcc tccgacaggg tctctgcaaa  300
tgcctcccgg ccaatgtcca ccagctcatc tccggcaaaa taggcatctc tcttaccaga  360
gtgtctgatg gggaaaacgt tctggtgtct gactttcggt ccaaagacga agtcgtggat  420
gccttggtat gttcctgctt catgcccttc tacagtggcc ttatccctcc ttccttcaga  480
ggcgtgcgat atgtggatgg aggagtgagt gacaacgtac ccttcattga tgccaaaaca  540
accatcaccg tgtcccccct ctatggggag tacgacatct gccctaaagt caagtccacg  600
aacttttctt catgtggaca tcaccaagct cagtctacgc ctctgcacag gaacctctac  660
ctttctctcg agagcttttg tcccccggat ctcaaggtgc tgggagagat atgccttcga  720
ggatatttgg atgcattcag gttcttggaa gagaagggca tctgcaacag cccccagcca  780
ggcctgaagt catcctcaga agggatggat cctgaggtcg ccatgcccag ctgggcaaac  840
atgagtctgg attcttcccc ggagtcggct gccttggctg tgaggctgga gggagatgag  900
ctgctagacc acctgcgtct cagcatcctg ccctgggatg agagcatcct ggacaccctc  960
tcgcccaggc tcgctacagc actgagtgaa gaaatgaaag acaaaggtgg atacatgagc 1020
aagatttgca acttgctacc cattaggata atgtcttatg taatgctgcc ctgtaccctg 1080
cctgtggaat ctgccattgc gattgtccag actggtgaca tggcttccag atatgcccga 1140
cgatgtcctg tgtggttgca gtgggtgacc tcacaggtgt tcactcgagt gctgatgtgt 1200
ctgctcccg  cctccaggtc ccaaatgcca gtgagcagcc aacaggcctc ccatgcaca  1260
cctgagcagg actggccctg ctggactccc tgctccccca agggctgtcc agcagagacc 1320
aaagcagagg ccaccccgcg gtccatcctc aggtccagcc tgaacttctt cttgggcaat 1380
aaagtacctg ctggtgctga ggggctctcc acctttccca gttttcact  agagaagagt 1440
ctg                                                               1443

SEQ ID NO: 35          moltype = RNA   length = 1431
FEATURE                Location/Qualifiers
source                 1..1431
                       mol_type = mRNA
                       organism = Homo sapiens
SEQUENCE: 35
atgtacgacg cagagcgcgg ctggagcttg tccttcgcgg gctgcggctt cctgggcttc   60
taccacgtcg gggcgacccg ctgcctgagc gagcacgccc gcacctcct  ccgcgacgcg  120
cgcatgttgt tcggcgcttc ggccggggcg ttgcactgcg tcggcgtcct ctccgagcag  180
```

```
actctgcagg tcctctcaga tcttgtgcgg aaggccagga gtcggaacat tggcatcttc    240
catccatcct tcaacttaag caagttcctc cgacagggtc tctgcaaatg cctcccggcc    300
aatgtccacc agctcatctc cggcaaaata ggcatctctc ttaccagagt gtctgatggg    360
gaaaacgttc tggtgtctga ctttcggtcc aaagacgaag tcgtggatgc cttggtatgt    420
tcctgcttca tgcccttcta cagtggcctt atccctcctt ccttcagagg cgtgcgatat    480
gtggatggag gagtgagtga caacgtaccc ttcattgatg ccaaaacaac catcaccgtg    540
tccccttct atggggagta cgacatctgc cctaaagtca agtccacgaa ctttcttcat    600
gtggacatca ccaagctcag tctacgcctc tgcacaggga acctctacct tctctcgaga    660
gcttttgtcc ccccggatct caaggtgctg ggagagatat gccttcgagg atatttggat    720
gcattcaggt tcttggaaga aagggcatc tgcaacaggc cccagccagg cctgaagtca    780
tcctcagaag ggatggatcc tgaggtcgcc atgcccagct gggcaaacat gagtctggat    840
tcttcccgg agtcggctgc cttggctgtg aggctgaggg agatgagct gctagaccac    900
ctgcgtctca gcatcctgcc ctgggatgag agcatcctgg acaccctctc gcccaggctc    960
gctacagcac tgagtgaaga aatgaaagac aaaggtggat acatgagcaa gatttgcaac   1020
ttgctaccca ttaggataat gtcttatgta atgctgccct gtaccctgcc tgtggaatct   1080
gccattgcga ttgtccagag actggtgaca tggcttccag atatgcccga cgatgtcctg   1140
tggttgcagt gggtgacctc acaggtgttc actcgagtgc tgatgtgtct gctccccgcc   1200
tccaggtccc aaatgccagt gagcagccaa caggcctccc catgcacacc tgagcaggac   1260
tggccctgct ggactccctg ctcccccaag ggctgtccag cagagaccaa agcagaggcc   1320
accccgcggt ccatcctcag gtccagcctg aacttcttct tgggcaataa agtacctgct   1380
ggtgctgagg ggctctccac cttcccagt ttttcactag agaagagtct g             1431

SEQ ID NO: 36         moltype = DNA  length = 1443
FEATURE               Location/Qualifiers
source                1..1443
                      mol_type = other DNA
                      organism = Homo sapiens
SEQUENCE: 36
atgtacgacg cagagcgcgg ctggagcttg tccttcgcgg gctgcggctt cctgggcttc     60
taccacgtcg gggcgacccg ctgcctgagc gagcacgccc cgcacctcct ccgcgacgcg    120
cgcatgttgt tcggcgcttc ggccggggcg ttgcactgcg tcggcgtcct ctccggtatc    180
ccgctggagc agactctgca ggtcctctca gatcttgtgc ggaaggccag gagtcggaac    240
attggcatct ccatccatcc cttcaactta agcaagttcc tccgacaggg tctctgcaaa    300
tgcctcccgg ccaatgtcca ccagctcatc tccggcaaaa taggcatctc tcttaccaga    360
gtgtctgatg gggaaaaacgt tctggtgtct gactttcggt ccaaagacga agtcgtggat    420
gccttggtat gttcctgctt catcccctc tacagtggcc ttatccctcc ttccttcaga    480
ggcgtgcgat atgtggatgg aggagtgagt gacaacgtac ccttcattga tgccaaaaca    540
accatcaccg tgtccccctt ctatgggagt acgacatct gccctaaagt caagtccacg    600
aactttcttc atgtggacat caccaagctc agtctacgcc tctgcacagg gaacctctac    660
cttctctcga gagcttttgt cccccggat ctcaaggtgc tgggagagat atgccttcga    720
ggatatttgg atgcattcag gttcttggaa gagaagggca tctgcaacag gccccagcca    780
ggcctgaagt catcctcaga agggatggat cctgaggtcg ccatgcccag ctgggcaaac    840
atgagtctgg attcttcccc ggagtcggct gccttggctg tgaggctgga gggagatgag    900
ctgctagacc acctgcgtct cagcatcctg ccctgggatg agagcatcct ggacaccctc    960
tcgcccaggc tcgctacagc actgagtgaa gaaatgaaag acaaaggtgg atacatgagc   1020
aagatttgca acttgctacc cattaggata atgtcttatg taatgctgcc ctgtaccctg   1080
cctgtggaat ctgccattgc gattgtccag agactggtga catggcttcc agatatgccc   1140
gacgatgtcc tgtggttgca gtgggtgacc tcacaggtgt tcactcgagt gctgatgtgt   1200
ctgctccccg cctccaggtc ccaaatgcca gtgagcagcc aacaggcctc cccatgcaca   1260
cctgagcagg actggccctg ctggactccc tgctccccca agggctgtcc agcagagacc   1320
aaagcagagg ccaccccgcg cgtccatcct caggtccagc ctgaacttct tctgggcaat   1380
aaagtacctg ctggtgctga ggggctctcc acctttccca gttttcact agagaagagt   1440
ctg                                                                 1443

SEQ ID NO: 37         moltype = DNA  length = 1431
FEATURE               Location/Qualifiers
source                1..1431
                      mol_type = other DNA
                      organism = Homo sapiens
SEQUENCE: 37
atgtacgacg cagagcgcgg ctggagcttg tccttcgcgg gctgcggctt cctgggcttc     60
taccacgtcg gggcgacccg ctgcctgagc gagcacgccc cgcacctcct ccgcgacgcg    120
cgcatgttgt tcggcgcttc ggccggggcg ttgcactgcg tcggcgtcct ctccgagcag    180
actctgcagg tcctctcaga tcttgtgcgg aaggccagga gtcggaacat tggcatcttc    240
catccatcct tcaacttaag caagttcctc cgacagggtc tctgcaaatg cctcccggcc    300
aatgtccacc agctcatctc cggcaaaata ggcatctctc ttaccagagt gtctgatggg    360
gaaaacgttc tggtgtctga ctttcggtcc aaagacgaag tcgtggatgc cttggtatgt    420
tcctgcttca tgcccttcta cagtggcctt atccctcctt ccttcagagg cgtgcgatat    480
gtggatggag gagtgagtga caacgtaccc ttcattgatg ccaaaacaac catcaccgtg    540
tccccttct atggggagta cgacatctgc cctaaagtca agtccacgaa ctttcttcat    600
gtggacatca ccaagctcag tctacgcctc tgcacaggga acctctacct tctctcgaga    660
gcttttgtcc ccccggatct caaggtgctg ggagagatat gccttcgagg atatttggat    720
gcattcaggt tcttggaaga aagggcatc tgcaacaggc cccagccagg cctgaagtca    780
tcctcagaag ggatggatcc tgaggtcgcc atgcccagct gggcaaacat gagtctggat    840
tcttcccgg agtcggctgc cttggctgtg aggctgaggg agatgagct gctagaccac    900
ctgcgtctca gcatcctgcc ctgggatgag agcatcctgg acaccctctc gcccaggctc    960
gctacagcac tgagtgaaga aatgaaagac aaaggtggat acatgagcaa gatttgcaac   1020
ttgctaccca ttaggataat gtcttatgta atgctgccct gtaccctgcc tgtggaatct   1080
gccattgcga ttgtccagag actggtgaca tggcttccag atatgcccga cgatgtcctg   1140
```

```
tggttgcagt gggtgacctc acaggtgttc actcgagtgc tgatgtgtct gctccccgcc  1200
tccaggtccc aaatgccagt gagcagccaa caggcctccc catgcacacc tgagcaggac  1260
tggccctgct ggactccctg ctcccccaag ggctgtccag cagagaccaa agcagaggcc  1320
accccgcggt ccatcctcag gtccagcctg aacttcttct tgggcaataa agtacctgct  1380
ggtgctgagg ggctctccac ctttcccagt ttttcactag agaagagtct g            1431

SEQ ID NO: 38              moltype = DNA   length = 1443
FEATURE                    Location/Qualifiers
source                     1..1443
                           mol_type = other DNA
                           organism = Homo sapiens
SEQUENCE: 38
atgtacgacg cagagcgcgg ctggagcttg tccttcgcgg gctgcggctt cctgggcttc  60
taccacgtcg gggcgacccg ctgcctgagc gagcacgccc cgcacctcct ccgcgacgcg  120
cgcatgttgt tcggcgcttc ggccggggcg ttgcactgcg tcggcgtcct ctccggtatc  180
ccgctggagc agactctgca ggtcctctca gatcttgtgc ggaaggccag gagtcggaac  240
attggcatct tccatccatc cttcaactta agcaagttcc tccgacaggg tctctgcaaa  300
tgcctcccgg ccaatgtcca ccagctcatc tccggcaaaa taggcatctc tcttaccaga  360
gtgtctgatg gggaaaacgt tctggtgtct gactttcggt ccaaagacga agtcgtggat  420
gccttggtat gttcctgctt catgcccttc tacagtggcc ttatccctcc ttccttcaga  480
ggcgtgcgat atgtggatgg aggagtgagt gacaacgtac ccttcattga tgccaaaaca  540
accatcaccg tgtccccctt ctatggggag tacgacatct gccctaaagt caagtccacg  600
aactttcttc atgtggacat caccaagctc agtctacgcc tctgcacagg gaacctctac  660
cttctctcga gagcttttgt cccccccggat ctcaaggtgc tgggagagat atgccttcga  720
ggatatttgca atgcattcag gttcttggaa gagaagggca tctgcaacag gccccagcca  780
ggcctgaagt catcctcaga agggatggat cctgaggtcg ccatgcccag cggggcaaac  840
atgagtctgg attcttcccc ggagtcggct gccttggctg tgaggctgga gggagatgag  900
ctgctagacc acctcgtctc cagcatcctg ccctgggatg agagcatcct ggacaccctc  960
tcgcccaggc tcgctacagc actgagtgaa gaaatgaaag acaaaggtgg atacatgagc  1020
aagatttgca acttgctacc cattaggata atgtcttatg tgctgccct gtaccctgcc  1080
cctgtggaat ctgccattgc gattgtccag agactggtga catggcttcc agatatgccc  1140
gacgatgtcc tgtggttgca gtgggtgacc tcacaggtgt tcactcgagt gctgatgtgt  1200
ctgctccccg cctccaggtc ccaaatgcca gtgagcagcc aacaggcctc cccatgcaca  1260
cctgagcagg actggccctg ctggactccc tgctccccca agggctgtcc agcagagacc  1320
aaagcagagg ccaccccgcg cgtccatcctc aggtccagcc tgaacttctt cttgggcaat  1380
aaagtacctg ctggtgctga gggggctctcc acctttccca gttttcact agagaagagt  1440
ctg                                                                1443

SEQ ID NO: 39              moltype = DNA   length = 1431
FEATURE                    Location/Qualifiers
source                     1..1431
                           mol_type = other DNA
                           organism = Homo sapiens
SEQUENCE: 39
atgtacgacg cagagcgcgg ctggagcttg tccttcgcgg gctgcggctt cctgggcttc  60
taccacgtcg gggcgacccg ctgcctgagc gagcacgccc cgcacctcct ccgcgacgcg  120
cgcatgttgt tcggcgcttc ggccggggcg ttgcactgcg tcggcgtcct ctccgagcag  180
actctgcagg tcctctcaga tcttgtgcgc aaggccagga gtcggaacat tggcatcttc  240
catccatcct tcaacttaag caagttcctc cgacagggtc tctgcaaatg cctcccggcc  300
aatgtccacc agctcatctc cggcaaaata ggcatctctc ttaccagagt gtctgatggg  360
gaaaacgttc tggtgtctga ctttcggtcc aaagacgaag tcgtggatgc cttggtatgt  420
tcctgcttca tgcccttcta cagtggcctt atccctcctt ccttcagagg cgtgcgatat  480
gtggatggag gagtgagtga caacgtaccc ttcattgatg ccaaaacaac catcaccgtg  540
tccccccttct atggggagta cgacatctgc cctaaagtca agtccacgaa ctttcttcat  600
gtggacatca ccaagctcag tctacgcctc tgcacaggga acctctacct tctctctgaga  660
gcttttgtcc cccccgatct caaggtgctg ggagagatat gccttcgagg atatttggat  720
gcattcaggt tcttggaaga aagggcatc tgcaacaggc cccagccagg cctgaagtca  780
tcctcagaag gatggatcc tgaggtcgcc atgcccagct gggcaaacat gagtctggat  840
tcttccccgg agtcggctgc cttggctgtg aggctggagg gagatgagct gctagaccac  900
ctcgtctcca gcatcctgcc ctgggatgag agcatcctgg acaccctctc gcccaggctc  960
gctacagcac tgagtgaaga aatgaaagac aaaggtggat acatgagcaa gatttgcaac  1020
ttgctaccca ttaggataat gtcttatgta atgctgccct gtaccctgcc gtgtggaatct  1080
gccattgcga ttgtccagag actggtgaca tggcttccag atatgcccga cgatgtcctg  1140
tggttgcagt gggtgacctc acaggtgttc actcgagtgc tgatgtgtct gctccccgcc  1200
tccaggtccc aaatgccagt gagcagccaa caggcctccc catgcacacc tgagcaggac  1260
tggccctgct ggactccctg ctcccccaag ggctgtccag cagagaccaa agcagaggcc  1320
accccgcggt ccatcctcag gtccagcctg aacttcttct tgggcaataa agtacctgct  1380
ggtgctgagg ggctctccac ctttcccagt ttttcactag agaagagtct g            1431

SEQ ID NO: 40              moltype = AA    length = 481
FEATURE                    Location/Qualifiers
source                     1..481
                           mol_type = protein
                           organism = Homo sapiens
SEQUENCE: 40
MYDAERGWSL SFAGCGFLGF YHVGATRCLS EHAPHLLRDA RMLFGASAGA LHCVGVLSGI  60
PLEQTLQVLS DLVRKARSRN IGIFHPSFNL SKFLRQGLCK CLPANVHQLI SGKIGISLTR  120
VSDGENVLVS DFRSKDEVVD ALVCSCFIPF YSGLIPPSFR GVRYVDGGVS DNVPFIDAKT  180
TITVSPFYGE YDICPKVKST NFLHVDITKL SRLCTGNLY LLSRAFVPPD LKVLGEICLR  240
```

-continued

```
GYLDAFRFLE EKGICNRPQP GLKSSSEGMD PEVAMPSWAN MSLDSSPESA ALAVRLEGDE   300
LLDHLRLSIL PWDESILDTL SPRLATALSE EMKDKGGYMS KICNLLPIRI MSYVMLPCTL   360
PVESAIAIVQ RLVTWLPDMP DDVLWLQWVT SQVFTRVLMC LLPASRSQMP VSSQQASPCT   420
PEQDWPCWTP CSPKGCPAET KAEATPRSIL RSSLNFFLGN KVPAGAEGLS TFPSFSLEKS   480
L                                                                   481

SEQ ID NO: 41           moltype = AA  length = 477
FEATURE                 Location/Qualifiers
source                  1..477
                        mol_type = protein
                        organism = Homo sapiens
SEQUENCE: 41
MYDAERGWSL SFAGCGFLGF YHVGATRCLS EHAPHLLRDA RMLFGASAGA LHCVGVLSEQ    60
TLQVLSDLVR KARSRNIGIF HPSFNLSKFL RQGLCKCLPA NVHQLISGKI GISLTRVSDG   120
ENVLVSDFRS KDEVVDALVC SCFIPFYSGL IPPSFRGVRY VDGGVSDNVP FIDAKTTITV   180
SPFYGEYDIC PKVKSTNFLH VDITKLSLRL CTGNLYLLSR AFVPPDLKVL GEICLRGYLD   240
AFRFLEEKGI CNRPQPGLKS SSEGMDPEVA MPSWANMSLD SSPESAALAV RLEGDELLDH   300
LRLSILPWDE SILDTLSPRL ATALSEEMKD KGGYMSKICN LLPIRIMSYV MLPCTLPVES   360
AIAIVQRLVT WLPDMPDDVL WLQWVTSQVF TRVLMCLLPA SRSQMPVSSQ QASPCTPEQD   420
WPCWTPCSPK GCPAETKAEA TPRSILRSSL NFFLGNKVPA GAEGLSTFPS FSLEKSL     477

SEQ ID NO: 42           moltype = AA  length = 481
FEATURE                 Location/Qualifiers
source                  1..481
                        mol_type = protein
                        organism = Homo sapiens
SEQUENCE: 42
MYDAERGWSL SFAGCGFLGF YHVGATRCLS EHAPHLLRDA RMLFGASAGA LHCVGVLSGI    60
PLEQTLQVLS DLVRKARSRN IGIFHPSFNL SKFLRQGLCK CLPANVHQLI SGKIGISLTR   120
VSDGENVLVS DFRSKDEVVD ALVCSCFMPF YSGLIPPSFR GVRYVDGGVS DNVPFIDAKT   180
TITVSPFYGE YDICPKVKST NFLHVDITKL SLRLCTGNLY LLSRAFVPPD LKVLGEICLR   240
GYLDAFRFLE EKGICNRPQP GLKSSSEGMD PEVAMPSWAN MSLDSSPESA ALAVRLEGDE   300
LLDHLRLSIL PWDESILDTL SPRLATALSE EMKDKGGYMS KICNLLPIRI MSYVMLPCTL   360
PVESAIAIVQ RLVTWLPDMP DDVLWLQWVT SQVFTRVLMC LLPASRSQMP VSSQQASPCT   420
PEQDWPCWTP CSPKGCPAET KAEATPRSIL RSSLNFFLGN KVPAGAEGLS TFPSFSLEKS   480
L                                                                   481

SEQ ID NO: 43           moltype = AA  length = 477
FEATURE                 Location/Qualifiers
source                  1..477
                        mol_type = protein
                        organism = Homo sapiens
SEQUENCE: 43
MYDAERGWSL SFAGCGFLGF YHVGATRCLS EHAPHLLRDA RMLFGASAGA LHCVGVLSEQ    60
TLQVLSDLVR KARSRNIGIF HPSFNLSKFL RQGLCKCLPA NVHQLISGKI GISLTRVSDG   120
ENVLVSDFRS KDEVVDALVC SCFMPFYSGL IPPSFRGVRY VDGGVSDNVP FIDAKTTITV   180
SPFYGEYDIC PKVKSTNFLH VDITKLSLRL CTGNLYLLSR AFVPPDLKVL GEICLRGYLD   240
AFRFLEEKGI CNRPQPGLKS SSEGMDPEVA MPSWANMSLD SSPESAALAV RLEGDELLDH   300
LRLSILPWDE SILDTLSPRL ATALSEEMKD KGGYMSKICN LLPIRIMSYV MLPCTLPVES   360
AIAIVQRLVT WLPDMPDDVL WLQWVTSQVF TRVLMCLLPA SRSQMPVSSQ QASPCTPEQD   420
WPCWTPCSPK GCPAETKAEA TPRSILRSSL NFFLGNKVPA GAEGLSTFPS FSLEKSL     477

SEQ ID NO: 44           moltype = RNA  length = 2397
FEATURE                 Location/Qualifiers
source                  1..2397
                        mol_type = mRNA
                        organism = Homo sapiens
SEQUENCE: 44
agacagtacc tcctcccctag gactacacaa ggactgaacc agaaggaaga ggacagagca    60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catgaatag gcaggcagac tacttatgaa tttgcaaaac   240
gacagagcat attggttctg tgggatatta taagcgcgg tgtggaggaa actgcagctg   300
agtgccgaaa actaggcgtc actgcgcatg cgtatgtggt agactgcagc aacagagaag   360
agatctatcg ctctctaaat caggtgaaga aagaagtggg tgatgtaaca atcgtggtga   420
ataatgctgg gacagtatat ccagccgatc ttctcagcac caaggatgaa gagattacca   480
agacatttga ggtcaacatc ctaggacatt tttggatcac aaaagcactt cttccatcga   540
tgatggagag aaatcatggc cacatcgtca cagtggcttc agtgtgcggc cacgaaggga   600
ttccttacct catcccatat tgttccagca aatttgccgc tgttggcttt cacagaggtc   660
tgacatcaga acttcaggcc ttgggaaaaa ctggtatcaa aacctcatgt ctctgcccag   720
tttttgtgaa tactgggttc accaaaaatc caagcacaag attatggcct gtattggaga   780
cagatgaagt cgtaagaagt ctgatagatg gaatacttac caataagaaa atgattttg   840
ttccatcgta tatcaatatc tttctgagac tacagaagtt tcttcctgaa cgcgcctcag   900
cgattttaaa tcgtatgcag aatattcaat tgaagcagt ggttggccac aaaatcaaaa   960
tgaaatgaat aaataagctc cagccagaga tgtatgcatg ataatgatat gaatagtttc  1020
gaatcaatgc tgcaaagctt tatttcacat ttttcagtc ctgataatat taaaacactt  1080
ggtttggcac tagcagcagt caaacgaaca agattaatta cctgtcttcc tgtttctcaa  1140
gaatatttac gtagttttc ataggtctgt ttttcctttc atgcctctta aaaacttctg  1200
tgcttacata aacatactta aaaggttttc tttaagatat tttatttttc catttaaagg  1260
```

```
tggacaaaag ctacctccct aaaagtaaat acaaagagaa cttatttaca cagggaaggt   1320
ttaagactgt tcaagtagca ttccaatctg tagccatgcc acagaatatc aacaagaaca   1380
cagaatgagt gcacagctaa gagatcaagt ttcagcaggc agctttatct caacctggac   1440
atattttaag attcagcatt tgaaagattt ccctagcctc ttccttttc attagcccaa    1500
aacggtgcaa ctctattctg gactttatta cttgattctg tcttctgtat aactctgaag   1560
tccaccaaaa gtggaccctc tatatttcct ccctttttat agtcttataa gatacattat   1620
gaaaggtgac cgactctatt ttaaatctca gaattttaag ttctagcccc atgataacct   1680
ttttctttgt aatttatgct ttcatatatc cttggtccca gagatgttta gacaatttta   1740
ggctcaaaaa ttaaagctaa cacaggaaaa ggaactgtac tggctattac ataagaaaca   1800
atggacccaa gagaagaaaa ggaagaaaga aaggttttt ggtttttgtt ttgttttgt     1860
ttgtttttg tttttttgag atggagtctc actctttcgc ccaggctgga gtgcagtggt    1920
atgatctcag ctcactgcaa gctccacctc cggggttcac gccattctcc tgcctcagcc   1980
tcctgagtag ctgggactac aggcgccgc caccacaccc ggctaatttt ttgtattttt    2040
tgtagagacg gggttcacc atgttagcca agatggtctc gatctcctga cctcgtgatc    2100
cacctgcctc ggcctcccaa agtgctggga ttacgggtgt gagccaccgt gcccagcctt   2160
ttttttttta atagaaaaaa taatccgact cccactacat caagactaat cttgttttgt   2220
gtgttttca catgtattat agaatgcttt tgcatggact atcctcttgt tttattaaa     2280
aacaaatgat ttttttaaaa gtcacaaaaa caattcacta aaataaata tgtcattgtg    2340
ctttaaaaaa ataacctctt gtagttataa aataaaacgt ttgacttcta aactctg     2397

SEQ ID NO: 45         moltype = RNA   length = 2289
FEATURE               Location/Qualifiers
source                1..2289
                      mol_type = mRNA
                      organism = Homo sapiens
SEQUENCE: 45
agacagtacc tcctccctag gactacacaa ggactgaacc agaaggaaga ggacagagca   60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catgaatag cagggcagac tacttatgaa tttgcaaaac     240
gacagagcat attggttctg tgggatatta ataaggtgga gaaagaagtg ggtgatgtaa   300
caatcgtggt gaataatgct gggacagtat atccagccga tcttctcagc accaaggatg   360
aagagattac caagacattt gaggtcaaca tcctaggaca ttttttggatc acaaaagcac  420
ttcttccatc gatgatggag agaaatcatg gcccacatcgt cacagtggct tcagtgtgcg  480
gccacgaagg gattccttac ctcatcccat attgttccag caaatttgcc gctgttggct   540
ttcacagagg tctgacatca gaacttcagg ccttgggaaa aactggtatc aaaacctcat   600
gtctctgccc agttttttgtg aatactgggt tcaccaaaaa tccaagcaca agattatggc  660
ctgtattgga gacagatgaa gtcgtaagaa gtctgataga tggaatactt accaataaga   720
aaatgatttt tgttccatcg tatatcaata tctttctgaa actacagaag tttcttcctg   780
aacgcgcctc agcgattta aatcgtatgc agaatattca atttgaagca gtggttggcc    840
acaaaatcaa aatgaaatga ataaataagc tccagccaga gatgtatgca tgataatgat   900
atgaatagtt tcgaatcaat gctgcaaagc tttatttcac attttttcag tcctgataat   960
attaaaaaca ttggtttggc actagcagca gtcaaacgaa caagattaat tacctgtctt   1020
cctgtttctc aagaatattt acgtagtttt tcataggtct gtttttcctt tcatgcctct   1080
taaaaacttc tgtgcttaca taaacatact taaaaggttt tctttaagat atttttatttt  1140
tccatttaaa ggtggacaaa agctacctcc ctaaagtaaa atacaaagag aacttattta   1200
cacagggaag gtttaagact gttcaagtag cattccaatc tgtagccatg ccacagaata   1260
tcaacaagaa cacagaatga gtgcacagct aagagatcaa gtttcagcag gcagcttat    1320
ctcaacctgg acatatttta agattcagca tttgaaagat ttccctagcc tcttcctttt   1380
tcattagccc aaaacggtgc aactctattc tggactttat tacttgattc tgtcttctgt   1440
ataactctga agtccaccaa aagtggaccc tctatatttc ctccctttttt atagtcttat  1500
aagatacatt atgaaaggtg accgactcta ttttaaatct cagaattttta agttctagcc  1560
ccatgataac ctttttctt gtaatttatg ctttcatata tccttggtcc cagagatgtt    1620
tagacaattt taggctcaaa aattaaagct aacacaggaa aaggaactgt actggctatt   1680
acataagaaa caatggaccc aagagaagaa aaggaagaaa aaggaaagt ttggttttg    1740
ttttgttttg ttttgttttt tgtttttttg agatggagtc tcactctttc gccaggctg    1800
gagtgcagtg gtatgatctc agctcactgc aagctccacc tccgggttc acgccattct   1860
cctgcctcag cctcctgagt agctgggact acaggcgccc gccaccacac ccggctaatt   1920
ttttgtattt tttgtagaga cggggtttca ccatgttag caagatgtc tcgatctcct    1980
gacctcgtga tccacctgcc tcggcctccc aaagtgctgg gattacgggt gtgagccac    2040
gtgcccagcc ttttttttt taatagaaaa aataatccga ctcccactac atcaagacta   2100
atcttgtttt gtgtgttttt cacatgtatt atagaatgct tttgcatgga ctatcctctt   2160
gttttttatta aaaacaaatg attttttta agtcacaaa aacaattcac taaaataaa    2220
tatgtcattg tgctttaaaa aaataacctc ttgtagttat aaaataaaac gtttgacttc   2280
taaactctg                                                           2289

SEQ ID NO: 46         moltype = RNA   length = 2280
FEATURE               Location/Qualifiers
source                1..2280
                      mol_type = mRNA
                      organism = Homo sapiens
SEQUENCE: 46
agacagtacc tcctccctag gactacacaa ggactgaacc agaaggaaga ggacagagca   60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catgaatag cagggcagac tacttatgaa tttgcaaaac     240
gacagagcat attggttctg tgggatatta ataagcgcgg tgtggaggaa actgcagctg   300
agtgccgaaa actaggcgtc actgcgcatg cgtatgtggt agactgcagc aacagagaag   360
agatctatcg ctctctaaat caggtgaaga aagaagtggg tgatgtaaca atcgtggtga   420
```

-continued

```
ataatgctgg gacagtatat ccagccgatc ttctcagcac caaggatgaa gagattacca    480
agacatttga ggtcaacatc ctaggacatt tttggatcac aaaagcactt cttccatcga    540
tgatggagag aaatcatggc cacatcgtca cagtggcttc agtgtgcggc cacgaaggga    600
ttccttacct catcccatat tgttccagca aatttgccgc tgttggcttt cacagaggtc    660
tgacatcaga acttcaggcc ttgggaaaaa ctggtatcaa aacctcatgt ctctgcccag    720
tttttgtgaa tactgggttc accaaaaatc caagcacaag gtttcttcct gaacgcgcct    780
cagcgatttt aaatcgtatg cagaatattc aatttgaagc agtggttggc cacaaaatca    840
aaatgaaatg aataaataag ctccagccag agatgtatgc atgataatga tatgaatagt    900
ttcgaatcaa tgctgcaaag ctttatttca cattttttca gtcctgataa tattaaaaac    960
attggtttgg cactagcagc agtcaaacga caagattaa ttacctgtct tcctgtttct   1020
caagaatatt tacgtagttt ttcataggtc tgttttcct ttcatgcctc ttaaaaactt   1080
ctgtgcttac ataaacatac ttaaaaggtt ttctttaaga tattttatt ttccatttaa   1140
aggtggacaa aagctacctc cctaaaagta aatacaaaga gaacttattt acacagggaa   1200
ggtttaagac tgttcaagta gcattccaat ctgtagccat gccacagaat atcaacaaga   1260
acacagaatg agtgcacagc taagagatca agtttcagca ggcagcttta tctcaacctg   1320
gacatatttt aagattcagc atttgaaaga tttccctagc ctcttccttt ttcattagcc   1380
caaaacggtg caactctatt ctggacttta ttacttgatt ctgtcttctg tataactctg   1440
aagtccacca aaagtggacc ctctatattt cctcccttt tatagtctta taagatacat   1500
tatgaaaggt gaccgactct attttaaatc tcagaatttt aagttctagc cccatgataa   1560
cctttttctt tgtaatttat gctttcatat atccttggtc ccagagatgt ttagacaatt   1620
ttaggctcaa aaattaaagc taacacagga aaaggaactg tactggctat tacataagaa   1680
acaatggacc caagagaaga aaaggaagaa agaaaggttt tttggttttt gttttgtttt   1740
gttttgtttt ttgtttttt gagatggagt ctcactcttt cgcccaggct ggagtgcagt   1800
ggtatgatct cagctcactg caagctccac ctcccgggtt cacgccattc tcctgcctca   1860
gcctcctgag tagctgggac tacaggcgcc cgccaccaca cccggctaat ttttttgtatt   1920
ttttgtagag acggggtttc accatgttag ccaagatggt ctcgatcctg tgacctcgtg   1980
atccacctgc ctcggcctcc caaagtgctg ggattacggg tgtgagccac cgtgcccagc   2040
cttttttttt ttaatagaaa aaataatccg actcccacta catcaagact aatcttgttt   2100
tgtgtgtttt tcacatgtat tatagaatgc ttttgcatgg actatcctct tgttttatt   2160
aaaaacaaat gattttttta aaagtcacaa aaacaattca ctaaaaataa atatgtcatt   2220
gtgctttaaa aaaataacct cttgtagtta taaaataaaa cgtttgactt ctaaactctg   2280
```

SEQ ID NO: 47    moltype = RNA   length = 2398
FEATURE          Location/Qualifiers
source           1..2398
                 mol_type = mRNA
                 organism = Homo sapiens
SEQUENCE: 47

```
agacagtacc tcctccctag gactacacaa ggactgaacc agaaggaaga ggacagagca     60
aagccatgaa catcatccta gaaatccttc tgcttctgat caccatcatc tactcctact    120
tggagtcgtt ggtgaagttt ttcattcctc agaggagaaa atctgtggct ggggagattg    180
ttctcattac tggagctggg catggaatag gcaggcagac tacttatgaa tttgcaaaac    240
gacagagcat attggttctg tgggatatta ataagcgcag tgtggaggaa actgcagctg    300
agtgccgaaa actaggcgtc actgcgcatg cgtatgtggt agactgcagc aacagagaag    360
agatctatcg ctctctaaat caggtgaaga agaagtggg tgatgtaaca atcgtggtga    420
ataatgctgg gacagtatat ccagccgatc ttctcagcac caaggatgaa gagattacca    480
agacatttga ggtcaacatc ctaggacatt tttggatcac aaaagcactt cttccatcga    540
tgatggagag aaatcatggc cacatcgtca cagtggcttc agtgtgcggc cacgaaggga    600
ttccttacct catcccatat tgttccagca aatttgccgc tgttggcttt cacagaggtc    660
tgacatcaga acttcaggcc ttgggaaaaa ctggtatcaa aacctcatgt ctctgcccag    720
tttttgtgaa tactgggttc accaaaaatc caagcacaag attatggcct gtattggaga    780
cagatgaagt cgtaagaagt ctgatagatg gaatacttac caataagaaa atgatttttg    840
ttccatcgta tatcaatatc tttctgagac tacagaaggt ttcttcctga acgcgcctca    900
gcgatttaa atcgtatgca gaatattcaa tttgaagcag tggttggcca caaaatcaaa    960
atgaaatgaa taaataagct ccagccagag atgtatgcat gataatgata tgaatagtta   1020
cgaatcaatg ctgcaaagct ttatttcaca ttttttcagt cctgataata ttaaaaacat   1080
tggtttggca ctagcagcag tcaaacgaac aagattaatt acctgtcttc ctgtttctca   1140
agaatattta cgtagttttt cataggtctg ttttcctttt catgcctctt aaaaacttct   1200
gtgcttacat aaacatactt aaaaggtttt ctttaagata ttttatttt ccattaaag   1260
gtggacaaaa gctacctccc taaaagtaaa tacaaagaca acttatttac acagggaagg   1320
tttaagactg ttcaagtagc attccaatct gtagccatgc cacagaatat caacaagaac   1380
acagaatgag tgcacagcta agagatcaag tttcagcagg cagctttatc tcaacctgga   1440
catatttta gattcagcat ttgaaagatt tccctagcct cttccttttt cattagccca   1500
aaacggtgca actctattct ggactttatt acttgatttct gtcttctga taactctgaa   1560
gtccaccaaa agtggaccct ctatatttcc tccctttta tagtcttata agatacatta   1620
tgaaaggtga ccgactctat tttaaatctc agaattttaa gttctagccc catgataacc   1680
ttttttcttt taatttatgc tttcatatat ccttggtccc agagatgttt agacaatttt   1740
aggctcaaaa attaaagcta acacaggaaa aggaactgta ctggctatta cataagaac    1800
aatggaccca agagaagaaa aggaagaaag aaaggttttt tggttttttgt ttgtttttgt   1860
tttgttttt gttttttga gatggagtct cactctttcg cccaggctgg agtgcagtgg   1920
tatgatctca gctcactgca agctccacct cccgggttca cgccattctc ctgcctcagc   1980
ctcctgagta gctgggacta caggcgcccg ccaccacacc cggctaattt ttttgttattt   2040
ttgtagagac ggggtttcac catgttagcc aagatggtct cgatcctga cctcgtgat   2100
ccacctgcct cggcctccca aagtgctggg attacgggtg tgagccacc tgcccagcct   2160
ttttttttt aatagaaaaa ataatccgac tcccactatc aagactaa tcttgttttg   2220
tgtgtttttc acatgtatta tagaatgctt ttgcatggac tatcctctg tttttattaa   2280
aaacaaatga ttttttaaaa gtcacaaaaa caattcact aaaataaat atgtcattgt   2340
gctttaaaaa aataacctct tgtagttata aaataaaacg tttgacttct aaactctg     2398
```

| SEQ ID NO: 48 | moltype = RNA length = 2469 |
| --- | --- |
| FEATURE | Location/Qualifiers |
| source | 1..2469 |
| | mol_type = mRNA |
| | organism = Homo sapiens |

SEQUENCE: 48

```
agacagtacc tcctccctag gactacacaa ggactgaacc agaaggaaga ggacagagca    60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catggaatag gcaggcagac tacttatgaa tttgcaaaac   240
gacagagcat attggttctg tgggatatta ataagcgcgg tgtggaggaa actgcagctg   300
agtgccgaaa actaggcgtc actgcgcatg cgtatgtggt agactgcagc aacagagaag   360
agatctatcg ctctctaaat caggtgaaga agaagtggg tgatgtaaca atcgtggtga   420
ataatgctgg gacagtatat ccagccgatc ttctcagcac caaggatgaa gagattacca   480
agacatttga ggtcaacatc ctaggacatt tttggaatgg aaaggacatc agaagtaatt   540
acttggatgt atataggatc gaggacactt ttggacgaga ctctgagatc acaaaagcac   600
ttcttccatc gatgatggag agaaatcatg gccacatcgt cacagtggct tcagtgtgcg   660
gccacgaagg gattccttac ctcatcccat attgttccag caaatttgcc gctgttgget   720
ttcacagagg tctgacatca gaacttcagg ccttgggaaa aactggtatc aaaacctcat   780
gtctctgccc agtttttgtg aatactgggt tcaccaaaaa tccaagcaca agattatggc   840
ctgtattgga gacagatgaa gtcgtaagaa gtctgataga tggaatactt accaataaga   900
aaatgatttt tgttccatcg tatatcaata tctttctgaa actacagaag tttcttcctg   960
aacgcgcctc agcgatttta aatcgtatgc agaatattca atttgaagca gtggttggcc  1020
acaaaatcaa aatgaaatga ataataagc tccagccaga gatgtatgca tgataatgat  1080
atgaatagtt tcgaatcaat gctgcaaagc tttatttcac attttttcag tcctgataat  1140
attaaaaaca ttggtttggc actagcagca gtcaaacgaa caagattaat tacctgtctt  1200
cctgtttctc aagaatattt acgtagtttt tcataggtct gttttccctt tcatgcctct  1260
taaaaacttc tgtgcttaca taaacatact taaaaggttt tctttaagat attttatttt  1320
tccatttaaa ggtggacaaa agctacctcc ctaaaagtaa atacaaagag aacttattta  1380
cacagggaag gtttaagact gttcaagtag cattccaatc tgtagccatg ccacagaata  1440
tcaacaagaa cacagaatga gtgcacagct aagagatcaa gtttcagcag gcagctttat  1500
ctcaacctgg acatatttta agattcagca tttgaaagat ttccctagcc tcttccttt   1560
tcattagccc aaaacggtgc aactctattc tggactttat tacttgattc tgtcttctgt  1620
ataactctga agtccaccaa aagtggaccc tctatatttc ctcccttttt atagtcttat  1680
aagatacatt atgaaaggtg accgactcta ttttaaatct cagaatttta agttctagcc  1740
ccatgataac cttttttcttt gtaatttatg ctttcatata tccttggtcc cagagatgtt  1800
tagacaattt taggctcaaa aattaaagct aacacaggaa aaggaactgt actggctatt  1860
acataagaaa caatggaccc aagagaagaa aaggaagaa gaaaggtttt ttggttttg   1920
ttttgtttg ttttgttttt tgttttttg agatgagtc tcactcttc gcccaggctg  1980
gagtgcagtg gtatgatctc agctcactgc aagctccacc tcccgggttc acgccattct  2040
cctgcctcag cctcctgagt agctgggact acaggcgccc gccaccacac ccggctaatt  2100
ttttgtattt tttgtagaga cggggtttca ccatgttagc caagatggtc tcgatctcct  2160
gacctgctga tccacctgcc tcggcctccc aaagtgctgg gattacggt gtgagccacc  2220
gtcccagcc ttttttttt taatagaaaa aataatccga ctcccactac atcaagacta   2280
atcttgtttt gtgtgttttt cacatgtatt atagaatgct tttgcatgga ctatcctctt  2340
gttttattta aaaacaaatg atttttttaa aagtcacaaa acaattcac taaaaataaa  2400
tatgtcattg tgctttaaaa aaataaccct ttgtagttat aaaataaaac gtttgacttc  2460
taaactctg                                                         2469
```

| SEQ ID NO: 49 | moltype = RNA length = 1715 |
| --- | --- |
| FEATURE | Location/Qualifiers |
| source | 1..1715 |
| | mol_type = mRNA |
| | organism = Homo sapiens |

SEQUENCE: 49

```
agacagtacc tcctccctag gactacacaa ggactgaacc agaaggaaga ggacagagca    60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catggaatag gcaggcagac tacttatgaa tttgcaaaac   240
gacagagcat attggttctg tgggatatta ataagcgcgg tgtggaggaa actgcagctg   300
agtgccgaaa actaggcgtc actgcgcatg cgtatgtggt agactgcagc aacagagaag   360
agatctatcg ctctctaaat caggtgaaga agaagtggg tgatgtaaca atcgtggtga   420
ataatgctgg gacagtatat ccagccgatc ttctcagcac caaggatgaa gagattacca   480
agacatttga ggtcaacatc ctaggacatt tttggatcaa aaaagcactt cttccatcga   540
tgatggagag aaatcatggc cacatcgtca cagtggcttc agtgtgcggc cacgaaggga   600
ttccttacct catcccatat tgttccagca aatttgccgc tgttggcttt cacagaggtc   660
tgacatcaga acttcaggcc ttgggaaaaa ctggtatcaa aacctcatgt ctctgccag    720
ttttgtgaa tactgggttc accaaaaatc caagcacaag attatggcct gtattggaga   780
cagatgaagt cgtaagaagt ctgatagatg gaatacttac caataagaaa atgattttg   840
ttccatcgta tatcaatatc tttctgaac tacagaagtt aagtacagca cagaacaccc   900
aaatactaaa acaccaatag agcttttttt tttgctttt tttttttag acagagtctc   960
actctgtcac cctggctgga ttgcggtggt gcagtggca tgatcttggc tcactgcaac  1020
ctccgcctcc tgggttcaag caattctcat gcctcagacc cccaagtaac tgggattata  1080
ggtgtgtgct gccacactac acccagctaa tttttgtatt ttttgataga cagggtttc   1140
cccatgttgg ccaggctgga ctcgaactcc tgacctcaag ttatcctcct gtctcggcct  1200
cccaaagtgc tgggattaca gtcatgagcc accatgcctg gcccaataga gctattatta  1260
tggagcatct ttcagttgtg aaaattgca tggaaactct ccatccctgg ggagaacagt  1320
tatttcctct gttatttcc tacccagtct ataaaaagag agtgattcat tttctctacc  1380
aaatctactg tctctgccca aactttgctg aagactattc taactaaagg aaacacagtt  1440
```

```
taaaaagaat gcaatatagt gaagtagtta ataataaaga ctccattttt aaaagtctgc   1500
tggaagtttg gttgggattg cactgaatct atagagcaat tggggagtat tgacatatca   1560
acaatattga gttttctaat ccaagaacat aatatctatt tttaaaatct tcttcaaaat   1620
ctttaaatct ttaaattgta ttttgtagtt tttggtgttt aagtcttgca catattttgt   1680
cagatttatt ccaaagtatt tcacgggttc ttttt                              1715

SEQ ID NO: 50           moltype = RNA   length = 2290
FEATURE                 Location/Qualifiers
source                  1..2290
                        mol_type = mRNA
                        organism = Homo sapiens
SEQUENCE: 50
agacagtacc tcctccctag gactacacaa ggactgaacc agaaggaaga ggacagagca   60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catgaatag gcaggcagac tacttatgaa tttgcaaaac    240
gacagagcat attggttctg tgggatatta ataaggtgaa gaaagaagtg ggtgatgtaa   300
caatcgtggt gaataatgct gggacagtat atccagccga tcttctcagc accaaggatg   360
aagagattac caagacattt gaggtcaaca tcctaggaca ttttttggat caaaaagcac   420
ttcttccatc gatgatggag agaaatcatg gccacatcgt cacagtggct tcagtgtgcg   480
gccacgaagg gattccttac ctcatcccat attgttccag caaatttgcc gctgttggct   540
ttcacagagg tctgacatca gaacttcagg ccttgggaaa aactggtatc aaaacctcat   600
gtctctgccc agttttttgtg aatactgggt tcaccaaaaa tccaagcaca agattatggc   660
ctgtattgga gacagatgaa gtcgtaagaa gtctgataga tggaatactt accaataaga   720
aaatgatttt tgttccatcg tatatcaata tcttctgag actacagaag gtttcttcct    780
gaacgcgcct cagcgatttt aaatcgtatg cagaatattc aatttgaagc agtggttggc   840
cacaaaatca aaatgaaatg aataaataag ctccagccag agatgtatgc atgataatga   900
tatgaatagt ttcgaatcaa tgctgcaaag ctttatttca catttttca gtcctgataa    960
tattaaaaac attggtttgg cactagcagc agtcaaacga acaagattaa ttacctgtct  1020
tcctgttcct caagaatatt tacgtagttt ttcataggtc tgtttttcct ttcatgcctc  1080
ttaaaaactt ctgtgcttac ataaacatac ttaaaaggtt ttctttaaga tatttattt   1140
ttccatttaa aggtggacaa aagctacctc cctaaaagta aatacaaga gaacttattt   1200
acacagggaa ggtttaagac tgttcaagta gcattccaat ctgtagccat gccacagaat  1260
atcaacaaga acacagaatg agtgcacagc taagagatca agtttcagca ggcagcttta  1320
tctcaacctg gacatattt aagattcagc atttgaaata tttccctagc ctcttccttt   1380
ttcattagcc caaaacggtg caactctatt ctggactta ttacttgatt ctgtcttctg   1440
tataactctg aagtccacca aaagtggacc ctctatattt cctcccttt tatagtctta   1500
taagatacat tatgaaaggt gaccgactct atttttaaatc tcagaattt aagttctagc   1560
cccatgataa ccttttttctt tgtaatttat gctttcatat atccttggtc ccagagatg   1620
ttagacaatt ttaggctcaa aaattaaagc taacacagga aaaggaactg tactggctat  1680
tacataagaa acaatggacc caagagaaga aaaggaagaa agaaaggttt tttgttttt   1740
gttttgtttt gttttgtttt ttgttttttt gagatggagt ctcactcttt cgcccaggct   1800
ggagtgcagt ggtatgatct cagctcactg caagctccac ctcccgggtt cacgccattc   1860
tcctgcctca gcctcctgag tagctgggac tacaggcgcc cgccaccaca cccggctaat   1920
tttttgtatt ttttgtagag acggggtttc accatgttag ccaagatggt ctcgatctcc   1980
tgacctcgtg atccacctgc ctcggcctcc caaagtgctg ggattacggg tgtgagccac   2040
cgtgccagc ctttttttt ttaatagaaa aaataatccg actcccacta catcaagact   2100
aatcttgttc tgtgtgttt tcacatgtat tatagaatgc ttttgcatgg actatcctct   2160
tgttttatt aaaaacaaat gatttttta aaagtcacaa aaacaattca ctaaaaataa   2220
atatgtcatt gtgcttaaa aaaataacct cttgtagtta taaaataaaa cgtttgactt   2280
ctaaactctg                                                          2290

SEQ ID NO: 51           moltype = RNA   length = 2470
FEATURE                 Location/Qualifiers
source                  1..2470
                        mol_type = mRNA
                        organism = Homo sapiens
SEQUENCE: 51
agacagtacc tcctccctag gactacacaa ggactgaacc agaaggaaga ggacagagca   60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catgaatag gcaggcagac tacttatgaa tttgcaaaac    240
gacagagcat attggttctg tgggatatta ataagcgcgg tgtggaggaa actgcagctg   300
agtgccgaaa actaggcgtc actgcgcatg cgtatgtggt agactgcgac aacagagaag   360
agatctatcg ctctctaaat caggtgaaga aagaagtggg tgatgtaaca atcgtggtga   420
ataatgctgg gacagtatat ccagccgatc ttctcagcac caaggatgaa gagattacca   480
agacatttga ggtcaacatc ctaggacatt ttttggaatgg aaaggacatc agaagtaatt   540
acttggatgt ataiaggatc gaggacactt ttggacgaga ctctgagatc acaaaagcac   600
ttcttccatc gatgatggag agaaatcatg gccacatcgt cacagtggct tcagtgtgcg   660
gccacgaagg gattccttac ctcatcccat attgttccag caaatttgcc gctgttggct   720
ttcacagagg tctgacatca gaacttcagg ccttgggaaa aactggtatc aaaacctcat   780
gtctctgccc agttttttgtg aatactgggt tcaccaaaaa tccaagcaca agattatggc   840
ctgtattgga gacagatgaa gtcgtaagaa gtctgataga tggaatactt accaataaga   900
aaatgatttt tgttccatcg tatatcaata tcttctgag actacagaag gtttcttcct    960
gaacgcgcct cagcgatttt aaatcgtatg cagaatattc aatttgaagc agtggttggc  1020
cacaaaatca aaatgaaatg aataaataag ctccagccag agatgtatgc atgataatga  1080
tatgaatagt ttcgaatcaa tgctgcaaag ctttatttca catttttca gtcctgataa   1140
tattaaaaac attggtttgg cactagcagc agtcaaacga acaagattaa ttacctgtct  1200
tcctgttcct caagaatatt tacgtagttt ttcataggtc tgtttttcct ttcatgcctc  1260
```

-continued

```
ttaaaaactt ctgtgcttac ataaacatac ttaaaaggtt ttctttaaga tatttattt      1320
ttccatttaa aggtggacaa aagctaccct cctaaaagta aatacaaaga gaacttattt     1380
acacagggaa ggtttaagac tgttcaagta gcattccaat ctgtagccat gccacagaat    1440
atcaacaaga acacagaatg agtgcacagc taagagatca agtttcagca ggcagcttta    1500
tctcaacctg gacatatttt aagattcagc atttgaaaga tttccctagc ctcttccttt    1560
ttcattagcc caaaacggtg caactctatt ctggacttta ttacttgatt ctgtcttctg    1620
tataactctg aagtccacca aaagtggacc ctctatattt cctcccttt tatagtctta     1680
taagatacat tatgaaaggt gaccgactct attttaaatc tcagaatttt aagttctagc    1740
cccatgataa cctttttctt tgtaatttat gctttcatat atccttggtc ccagagatgt    1800
ttagacaatt ttaggctcaa aaattaaagc taacacagga aaaggaactg tactggctat    1860
tacataagaa acaatggacc caagagaaga aaaggaagaa agaaaggttt tttggttttt    1920
gttttgtttt gttttgtttt ttgttttttt gagatggagt ctcactcttt cgcccaggct    1980
ggagtgcagt ggtatgatct cagctcactg caagctccac ctcccgggtt cacgccattc    2040
tcctgcctca gcctcctgag tagctgggac tacaggcgcc cgccaccaca cccggctaat    2100
tttttgtatt ttttgtagag acggggtttc accatgttag ccaagatggt ctcgatctcc    2160
tgacctcgtg atccacctgc ctcggcctcc caaagtgctg ggattacggg tgtgagccac    2220
cgtgcccagc cttttttttt taatagaaa aaataatccg actcccacta catcaagact     2280
aatctctgtt tgtgtgtttt tcacatgtat tatagaatgc ttttgcatgg actatcctct    2340
tgttttatt aaaaacaaat gatttttta aaagtcacaa aaacaattca ctaaaaataa      2400
atatgtcatt gtgctttaaa aaaataacct cttgtagtta taaaatcaaaa cgtttgactt   2460
ctaaactctg                                                            2470

SEQ ID NO: 52           moltype = RNA   length = 1714
FEATURE                 Location/Qualifiers
source                  1..1714
                        mol_type = mRNA
                        organism = Homo sapiens
SEQUENCE: 52
agacagtacc tcctccctag gactacacaa ggactgaacc agaaggaaga ggacagagca      60
aagccatgaa catcatccta gaaatccttc tgcttctgat caccatcatc tactcctact     120
tggagtcgtt ggtgaagttt ttcattcctc agaggagaaa atctgtggct ggggagattg     180
ttctcattac tggagctggg catggaatag gcaggcagac tacttatgaa tttgcaaaac     240
gacagagcat attggttctg tgggatatta ataagcgcgg tgtggaggaa actgcagctg     300
agtgccgaaa actaggcgtc actgcgcatg cgtatgtggt agactgcagc aacagagaag     360
agatctatcg ctctctaaat caggtgaaga agaagtgggg tgatgtaaca atcgtggtca     420
ataatgctgg gacagtatat ccagccgatc ttctcagcac caaggatgaa gagattacca     480
agacatttga ggtcaacatc ctaggacatt tttggatcac aaaagcactt cttccatcga    540
tgatggagag aaatcatggc cacatcgtca cagtggcttc agtgtgcggc cacgaaggga   600
ttccttacct catcccatat tgttccagca aatttgccgc tgttggcttt cacagaggtc    660
tgacatcaga acttcaggcc ttgggaaaaa ctggtatcaa aacctcatgt ctctgcccag    720
tttttgtgaa tactgggttc accaaaaatc caagcacaag attatggcct gtattggaga    780
cagatgaagt cgtaagaagt ctgatagatg gaatacttac caataagaaa atgattttg     840
ttccatcgta tatcaatatc tttctgagac tacagaagta gtacagcac agaacaccca    900
aatactaaaa caccaataga gctttttttt ttgcttttt tttttttaga cagagtctca    960
ctctgtcacc ctggctggat gcggtggtt gcagtggcat gatcttggct cactgcaacc   1020
tccgcctcct gggttcaagc aattctcatg cctcagaccc caagtaact gggattatag    1080
gtgtgtgctg ccacactaca cccagctaat ttttgtattt tttgatagag acaggtttcc   1140
ccatgttggc caggctggac tcgaactcct gacctcaagt tatcctcctg tctcggcctc   1200
ccaaagtgct gggattacag tcatgagcca ccatgcctgg cccaatagag ctattattat    1260
ggagcatctt tcagttgtga aaattggcat ggaaactctc catccctggg gagaacagtt    1320
atttcctctg ttattttcct acccagtcta taaaaagaga gtgattcatt ttctctacca    1380
aatctactgt ctctgcccaa actttgctga agactattct aactaaagga aacacagttt    1440
aaaagaatg caatatagtg aagtagttaa taataaagac tccatttta aaagtctgct      1500
ggaagtttgg ttgggattgc actgaatcta tagagcaatt ggggagtatt gacatatcaa   1560
caatattgag ttttctaatc caagaacata atatcatttt ttaaaatctt cttcaaaatc    1620
tttaaatctt taaattgtat tttgtagttt ttggtgttta agtcttgcac atattttgtc    1680
agatttattc caaagtattt cacgggttct tttt                                  1714

SEQ ID NO: 53           moltype = DNA   length = 2397
FEATURE                 Location/Qualifiers
source                  1..2397
                        mol_type = other DNA
                        organism = Homo sapiens
SEQUENCE: 53
agacagtacc tcctccctag gactacacaa ggactgaacc agaaggaaga ggacagagca      60
aagccatgaa catcatccta gaaatccttc tgcttctgat caccatcatc tactcctact     120
tggagtcgtt ggtgaagttt ttcattcctc agaggagaaa atctgtggct ggggagattg     180
ttctcattac tggagctggg catggaatag gcaggcagac tacttatgaa tttgcaaaac     240
gacagagcat attggttctg tgggatatta ataagcgcgg tgtggaggaa actgcagctg     300
agtgccgaaa actaggcgtc actgcgcatg cgtatgtggt agactgcagc aacagagaag     360
agatctatcg ctctctaaat caggtgaaga agaagtgggg tgatgtaaca atcgtggtga     420
ataatgctgg gacagtatat ccagccgatc ttctcagcac caaggatgaa gagattacca     480
agacatttga ggtcaacatc ctaggacatt tttggatcac aaaagcactt cttccatcga    540
tgatggagag aaatcatggc cacatcgtca cagtggcttc agtgtgcggc cacgaaggga   600
ttccttacct catcccatat tgttccagca aatttgccgc tgttggcttt cacagaggtc    660
tgacatcaga acttcaggcc ttgggaaaaa ctggtatcaa aacctcatgt ctctgcccag    720
tttttgtgaa tactgggttc accaaaaatc caagcacaag attatggcct gtattggaga    780
cagatgaagt cgtaagaagt ctgatagatg gaatacttac caataagaaa atgattttg     840
ttccatcgta tatcaatatc tttctgagac tacagaagtt tcttcctgaa cgcgcctcag    900
```

```
cgatttttaaa tcgtatgcag aatattcaat ttgaagcagt ggttggccac aaaatcaaaa  960
tgaaatgaat aaataagctc cagccagaga tgtatgcatg ataatgatat gaatagtttc 1020
gaatcaatgc tgcaaagctt tatttcacat tttttcagtc ctgataatat taaaaacatt 1080
ggtttggcac tagcagcagt caaacgaaca agattaatta cctgtcttcc tgtttctcaa 1140
gaatatttac gtagttttc ataggtctgt ttttcctttc atgcctctta aaaacttctg 1200
tgcttacata aacatactta aaaggttttc tttaagatat tttatttttc catttaaagg 1260
tggacaaaag ctacctccct aaaagtaaat acaaagagaa cttatttaca cagggaaggt 1320
ttaagactgt tcaagtagca ttccaatctg tagccatgcc acagaatatc aacaagaaca 1380
cagaatgatg gcacagctaa gagatcaagt ttcagcaggc agctttatct caacctggac 1440
atattttaag attcagcatt tgaaagattt ccctagcctc ttcctttttc attagcccaa 1500
aacggtgcaa ctctattctg gactttatta cttgattctg tcttctgtat aactctgaag 1560
tccaccaaaa gtggaccctc tatatttcct ccctttttat agtcttataa gatacattat 1620
gaaaggtgac cgactctatt ttaaatctca gaattttaag ttctagcccc atgataacct 1680
tttctttgt aatttatgct ttcatatatc cttggtccca gagatgttta gacaatttta 1740
ggctcaaaaa ttaaagctaa cacaggaaaa ggaactgtac tggctattac ataagaaaca 1800
atggacccaa gagaagaaaa ggaagaaaga aaggtttttt ggtttttgtt ttgtttttgtt 1860
ttgtttttg tttttttgag atggagtctc actctttcgc ccaggctgga gtgcagtggt 1920
atgatctcag ctcactgcaa gctccacctc ccgggttcac gccattctcc tgcctcagcc 1980
tcctgagtag ctgggactac aggcgcccgc caccaccc ggctaatttt tgtatttttt 2040
tgtagagacg gggtttcacc atgttagcca gatggtctc gatctcctga cctcgtgatc 2100
cacctgcctc ggcctcccaa agtgctggga ttacgggtgt gagccaccgt gcccagcctt 2160
ttttttttta atagaaaaaa taatccgact cccactacat caagactaat cttgttttgt 2220
gtgttttca catgtattat agaatgcttt tgcatggact atcctcttgt ttttattaaa 2280
aacaaatgat ttttttaaaa gtcacaaaaa caattcacta aaaataaata tgtcattgtg 2340
ctttaaaaaa ataacctctt gtagttataa aataaaacgt tgacttcta aactctg    2397

SEQ ID NO: 54         moltype = DNA length = 2289
FEATURE               Location/Qualifiers
source                1..2289
                      mol_type = other DNA
                      organism = Homo sapiens SEQUENCE: 54
agacagtacc tcctccctag gactacacaa ggactgaacc agaaggaaga ggacagagca   60
aagccatgaa catcatccta gaaatccttc tgcttctgat caccatcatc tactcctact  120
tggagtcgtt ggtgaagttt ttcattcctc agaggagaaa atctgtggct ggggagattg  180
ttctcattac tggagctggg catgaatag gcaggcagac tacttatgaa tttgcaaaac  240
gacagagcat attggttctg tgggatatta ataaggtgaa gaaagaagtg ggtgatgtaa  300
caatcgtggt gaataatgct gggacagtat atccagccga tcttctcagc accaaggatg  360
aagagattac caagacattt gaggtcaaca tcctaggaca ttttttggatc acaaaagcac  420
ttcttccatc gatgatggag agaaatcatg gccacatcgt cacagtggct tcagtgtgcg  480
gccacgaagg gattccttac ctcatcccat attgttccag caaatttgcc gctgttggct  540
tcacagagg tctgacatca gaacttcagg ccttgggaaa aactggtatc aaaacctcat  600
gtctctgccc agtttttgtg aatactgggt tcaccaaaaa tccaagcaca agattatggc  660
ctgtattgga gacagatgaa gtcgtaagaa gtctgataga tggaatactt accaataaga  720
aaatgatttt tgttccatcg tatatcaata tctttctgag actacagaag tttcttcctg  780
aacgcgcctc agcgattta aatcgtatgc agaaattca atttgaagca gtggttggcc  840
acaaaatcaa aatgaaatga ataaaataagc tccagccaga gatgtatgca tgataatgat  900
atgaatagtt tcgaatcaat gctgcaaagc tttatttcac attttttcag tcctgataat  960
attaaaaaca ttggtttggc actagcagca gtcaaacgaa caagattaat tacctgtctt 1020
cctgtttctc aagaatattt acgtagtttt tcataggtct gttttttcctt tcatgcctct 1080
taaaaacttc tgtgcttaca taaacatact taaaaggttt ctttaagat attttatttt 1140
tccatttaaa ggtggacaaa agctacctcc ctaaaagtaa atacaaagag aacttatttta 1200
cacagggaag gtttaagact gttcaagtag cattccaatc tgtagccatg ccacagaata 1260
tcaacaagaa cacagaatga gtgcacagct aagagatcaa gtttcagcag gcagctttat 1320
ctcaacctgg acatatttta agattcagca tttgaaagat ttccctagcc tcttcctttt 1380
tcattagccc aaaacggtgc aactctattc tggactttat tacttgattc tgtcttctgt 1440
ataactctga gtccaccaa aagtggaccc tctatatttc ctccctttt atagtcttat 1500
aagatacatt atgaaaggtg accgactcta ttttaaatct cagaattta agttctagcc 1560
ccatgataac cttttttctt gtaatttatg ctttcatata tccttggtcc cagagatgtt 1620
tagacaattt taggctcaaa aattaaagct aacacaggaa aaggaactgt actggctatt 1680
acataagaaa caatggaccc aagagaagaa aaggaagaaa gaaaggtttt ttggtttttg 1740
ttttgttttg ttttgttttt tgttttttg agatggagtc tcactctttc gcccaggctg 1800
gagtgcagtg gtatgatctc agctcactgc aagctccacc tcccgggttc acgccattct 1860
cctgcctcag cctcctgagt agctgggact acaggcgccc gccaccaccc cggctaattt 1920
ttttgtattt tttgtagaga cggggtttca ccatgttagc caagatggtc tcgatctcct 1980
gacctcgtga tccacctgcc tcggcctccc aaagtgctgg gattacgggt gtgagccacc 2040
gtgcccagcc ttttttttt taatagaaaa aataatccga ctcccactac atcaagacta 2100
atcttgtttt gtgtgttttt cacatgtatt atagaatgct tttgcatgga ctatcctctt 2160
gttttattta aaacaaatg attttttaa agtcacaaa aacaattcac taaaaataaa 2220
tatgtcattg tgctttaaaa aaataacctc ttgtagttat aaaataaaac gtttgacttc 2280
taaactctg                                                          2289

SEQ ID NO: 55         moltype = DNA length = 2280
FEATURE               Location/Qualifiers
source                1..2280
                      mol_type = other DNA
                      organism = Homo sapiens SEQUENCE: 55
agacagtacc tcctccctag gactacacaa ggactgaacc agaaggaaga ggacagagca   60
```

```
aagccatgaa catcatccta gaaatccttc tgcttctgat caccatcatc tactcctact    120
tggagtcgtt ggtgaagttt ttcattcctc agaggagaaa atctgtggct ggggagattg    180
ttctcattac tggagctggg catgaatag  gcaggcagac tacttatgaa tttgcaaaac    240
gacagagcat attggttctg tgggatatta ataagcgcgg tgtggaggaa actgcagctg    300
agtgccgaaa actaggcgtc actgcgcatg cgtatgtggt agactgcagc aacagagaag    360
agatctatcg ctctctaaat caggtgaaga aagaagtggg tgatgtaaca atcgtggtga    420
ataatgctgg gacagtatat ccagccgatc ttctcagcac caaggatgaa gagattacca    480
agacatttga ggtcaacatc ctaggacatt tttggatcac aaaagcactt cttccatcga    540
tgatggagag aaatcatggc cacatcgtca cagtggcttc agtgtgcggc cacgaaggga    600
ttccttacct catcccatat tgttccagca aatttgccgc tgttggcttt cacagaggtc    660
tgacatcaga acttcaggcc ttgggaaaaa ctggtatcaa aacctcatgt ctctgcccag    720
tttttgtgaa tactgggttc accaaaaatc caagcacaag gtttcttcct gaacgcgcct    780
cagcgatttt aaatcgtatg cagaatattc aatttgaagc agtggttggc cacaaaatca    840
aaatgaaatg aataaataag ctccagccag agatgtatgc atgataatga tatgaatagt    900
ttcgaatcaa tgctgcaaag ctttatttca cattttttca gtcctgataa tattaaaaac    960
attggtttgg cactagcagc agtcaaacga acaagattaa ttacctgtct tcctgtttct   1020
caagaatatt tacgtagttt ttcataggtc tgttttttcct ttcatgcctc ttaaaaactt   1080
ctgtgcttac ataaacatac ttaaaaggtt ttcctttaaga tattttattt ttccatttaa   1140
aggtggacaa aagctacctc cctaaaagta aatacaaaga gaacttatttt acacagggaa   1200
ggtttaagac tgttcaagta gcattccaat ctgtagccat gccacagaat atcaacaaga   1260
acacagaatg agtgcacagc taagagatca agtttcagca ggcagctttta tctcaacctg   1320
gacataitttt aagattcagc atttgaaaga tttccctagc ctcttccttt ttcattagcc   1380
caaaacggtg caactctatt ctggacttta ttacttgatt ctgtcttctg tataactctg   1440
aagtccacca aaagtggacc ctctatattt cctccctttt tatagtctta taagatacat   1500
tatgaaaggt gaccgactct attttaaatc tcagaatttt aagttctagc cccatgataa   1560
cctttttctt tgtaatttat gctttcatat atccttggtc ccagagatgt ttagacaatt   1620
ttaggctcaa aaattaaagc taacacagga aaaggaactg tactggctat tacataagaa   1680
acaatggacc caagagaaga aaaggaagaa agaaaggttt tttggttttt gttttgtttt   1740
gttttgtttt ttgttttttt gagatggagt ctcactcttt cgcccaggct ggagtgcagt   1800
ggtatgatct cagctcactg caagctccac ctcccggttc cacgccattc tcctgcctca   1860
gcctcctgag tagctgggac tacaggcgcc cgccaccaca cccggctaat tttttgtatt   1920
ttttgtagag acggggtttc accatgttag ccaagatggt ctcgatctcc tgacctcgtg   1980
atccacctgc ctcggcctcc caaagtgctg ggattacggg tgtgagccac cgtgcccagc   2040
cttttttttt ttaatagaaa aaataatccg actcccacta catcaagact aatcttgttt   2100
tgtgtgtttt tcacatgtat tatagaatgc ttttgcatgg actatcctct tgtttttatt   2160
aaaaacaaat gatttttttta aaagtcacaa aaacaattca ctaaaaataa atatgtcatt   2220
gtgctttaaa aaaataaacct cttgtagtta aaaataaaaa cgtttgactt ctaaactctg   2280

SEQ ID NO: 56           moltype = DNA    length = 2398
FEATURE                 Location/Qualifiers
source                  1..2398
                        mol_type = other DNA
                        organism = Homo sapiens
SEQUENCE: 56
agacagtacc tcctccctag gactacacaa ggactgaacc agaaggaaga ggacagagca     60
aagccatgaa catcatccta gaaatccttc tgcttctgat caccatcatc tactcctact    120
tggagtcgtt ggtgaagttt ttcattcctc agaggagaaa atctgtggct ggggagattg    180
ttctcattac tggagctggg catgaatag  gcaggcagac tacttatgaa tttgcaaaac    240
gacagagcat attggttctg tgggatatta ataagcgcgg tgtggaggaa actgcagctg    300
agtgccgaaa actaggcgtc actgcgcatg cgtatgtggt agactgcagc aacagagaag    360
agatctatcg ctctctaaat caggtgaaga aagaagtggg tgatgtaaca atcgtggtga    420
ataatgctgg gacagtatat ccagccgatc ttctcagcac caaggatgaa gagattacca    480
agacatttga ggtcaacatc ctaggacatt tttggatcac aaaagcactt cttccatcga    540
tgatggagag aaatcatggc cacatcgtca cagtggcttc agtgtgcggc cacgaaggga    600
ttccttacct catcccatat tgttccagca aatttgccgc tgttggcttt cacagaggtc    660
tgacatcaga acttcaggcc ttgggaaaaa ctggtatcaa aacctcatgt ctctgcccag    720
tttttgtgaa tactgggttc accaaaaatc caagcacaag attatggcct gtattggaga    780
cagatgaagt cgtaagaagt ctgatagatg gaatacttac caataagaaa atgatttttg    840
ttccatcgta tatcaatatc tttctgagac tacagaaggt ttcttcctgca acgcgcctca    900
gcgattttaa atcgtatgca gaatattcaa tttgaagcag tggttggcca caaatcaaa    960
atgaaatgaa taaataagct ccagccagag atgtatgcat gataatgata tgaatagttt   1020
cgaatcaatg ctgcaaagct ttatttcaca ttttttcagt cctgataata ttaaaaacat   1080
tggtttggca ctagcagcag tcaaacgaac aagattaatt acctgtcttc ctgtttctca   1140
agaatattta cgtagttttt cataggtctg ttttttccttt catgcctctc aaaaacttct   1200
gtgcttacat aaacatactt aaaaggtttt ctttaagata tttatttttt ccatttaaag   1260
gtggacaaaa gctacctccc taaaagtaaa tacaaagaga acttatttac acagggaagg   1320
tttaagactt tcaagtagc attccaatct gtagccatgc cacagaatat caacaagaac   1380
acagaatgag tgcacagcta agagatcaag tttcagcagg cagctttatc tcaacctgga   1440
catattttaa gattcagcat ttgaaagatt tccctagcct cttccttttt cattagccca   1500
aaacggtgca actctattct ggactttatt acttgattct gtcttctgta taactctgaa   1560
gtccaccaaa agtggaccct ctatatttcc tccctttta tagtcttata agatacatta   1620
tgaaaggtga ccgactctat tttaaatctc agaattttaa gttctagccc catgataacc   1680
ttttttcttt taatttatgc tttcatatat ccttggtccc agagatgttt agacaatttt   1740
aggctcaaaa attaaagcta acacaggaaa aggaactgta ctggctatta cataagaaac   1800
aatggaccca agagaagaaa aggaagaaag aaaggttttt tggttttttgt tttgttttgt   1860
tttgttttt  gttttttga  gatggagtct cactctttcg cccaggctgg agtgcagtgg   1920
tatgatctca gctcactgca agctccacct cccgggttca cgccattctc tgcctcagc   1980
ctcctgagta gctgggacta caggcgcccg ccaccacacc cggctaattt tttgtatttt   2040
ttgtagagac ggggtttcac catgttagcc aagatggtct cgatctcctg acctcgtgat   2100
```

```
ccacctgcct cggcctccca aagtgctggg attacgggtg tgagccaccg tgcccagcct   2160
ttttttttt aatagaaaaa ataatccgac tcccactaca tcaagactaa tcttgttttg   2220
tgtgtttttc acatgtatta tagaatgctt ttgcatggac tatcctctg ttttattaa   2280
aaacaaatga tttttttaaa agtcacaaaa acaattcact aaaaataaat atgtcattgt   2340
gctttaaaaa aataacctct tgtagttata aaataaaacg tttgacttct aaactctg    2398

SEQ ID NO: 57           moltype = DNA   length = 2469
FEATURE                 Location/Qualifiers
source                  1..2469
                        mol_type = other DNA
                        organism = Homo sapiens
SEQUENCE: 57
agacagtacc tcctccctag gactacacaa ggactgaacc agaaggaaga ggacagagca     60
aagccatgaa catcatccta gaaatccttc tgcttctgat caccatcatc tactcctact    120
tggagtcgtt ggtgaagttt ttcattcctc agaggagaaa atctgtggct ggggagattg    180
ttctcattac tggagctggg catgaatag gcaggcagac tacttatgaa tttgcaaaac    240
gacagagcat attggttctg tgggatatta ataagcgcgg tgtggaggaa actgcagctg    300
agtgccgaaa actaggcgtc actgcgcatg cgtatgtggt agactgcagc aacagagaag    360
agatctatcg ctctctaaat caggtgaaga aagaagtggg tgatgtaaca atcgtggtga    420
ataatgctgg gacagtatat ccagccgatc ttctcagcac caaggatgaa gagattacca    480
agacatttga ggtcaacatc ctaggacatt tttggaatgg aaaggacatc agaagtaatt    540
acttggatgt atataggatc gaggacactt ttggacgaga ctctgagatc acaaaagcac    600
ttcttccatc gatgatggag agaaatcatg gccacatcgt cacagtggct tcagtgtgcg    660
gccacgaagg gattccttac ctcatcccat attgttccag caaatttgcc gctgttggct    720
ttcacagagg tctgacatca gaacttcagg ccttgggaaa aactggtatc aaaacctcat    780
gtctctgccc agtttttgtg aatactgggt tcaccaaaaa tccaagcaca agattatgc    840
ctgtattgga gacagatgaa gtcgtaagaa gtctgataga tggaatactt accaataaga    900
aaatgatttt tgttccatcg tatatcaata tctttctgag actacagaag tttcttcctg    960
aacgcgcctc agcgattta aatcgtatgc agaatattca atttgaagca gtggttggcc   1020
acaaaatcaa aatgaaatga ataaataagc tccagccaga gatgtatgca tgataatgat   1080
atgaatagtt tcgaatcaat gctgcaaagc tttatttcac attttttcag tcctgataat   1140
attaaaaaca ttggtttggc actagcagca gtcaaacgaa caagattaat tacctgtctt   1200
cctgtttctc aagaatattt acgtagtttt tcataggtct gtttttcctt tcatgcctct   1260
taaaaactte tgtgcttaca taaacatact taaaaggttt tctttaagat attttatttt   1320
tccatttaaa ggtggacaaa agctacctcc ctaaaagtaa atacaaagag aacttattta   1380
cacagggaag gtttaagact gttcaagtag cattccaatc tgtagccatg ccacagaata   1440
tcaacaagaa cacagaatga gtgcacagct aagagatcaa gttcagcag gcagctttat   1500
ctcaacctgg acatatttta agattcagca tttgaaagat ttccctagcc tcttcctttt   1560
tcattagccc aaaacggtgc aactctattc tggactttat tacttgattc tgtcttcttg   1620
ataactctga agtccaccaa aagtggaccc tctatatttc ctccctttt atagtctat    1680
aagatacatt atgaaaggtg accgactcta ttttaaatct cagaatttta agttctagcc   1740
ccatgataac cttttttcttt gtaatttatg ctttcatata tccttggtcc cagagatgtt   1800
tagacaattt taggctcaaa aattaaagct aacacaggaa aaggaactgt actggctatt   1860
acataagaaa caatgaccc aagagaagaa aaggaagaaa gaaaggtttt ttggtttttg   1920
ttttgttttg ttttgttttt tgttttttttg agatggagtc tcactctttc gcccaggctg   1980
gagtgcagtg gtatgatctc agctcactgc aagctccacc tcccgggttc acgccattct   2040
cctgcctcag cctcctgagt agctgggact acaggcgccc tgccaccacac ccggctaatt   2100
ttttgtattt tttgtagaga cggggtttca ccatgttagc caagatggtc tcgatctcct   2160
gacctcgtga tccacctgcc tcggcctccca aagtgctgg gattacgggt gtgagccacc   2220
gtgcccagcc tttttttttt taatagaaaa ataatccga ctcccactac atcaagacta   2280
atcttgtttt gtgtgttttt cacatgtatt atagaatgct tttgcatgga ctatcctctg   2340
ttttttatta aaaacaaatg attttttttaa aagtcacaaa acaattcac taaaaataaa   2400
tatgtcattg tgctttaaaa aaataacctc ttgtagttat aaaataaaac gtttgacttc   2460
taaactctg                                                           2469

SEQ ID NO: 58           moltype = DNA   length = 1715
FEATURE                 Location/Qualifiers
source                  1..1715
                        mol_type = other DNA
                        organism = Homo sapiens
SEQUENCE: 58
agacagtacc tcctccctag gactacacaa ggactgaacc agaaggaaga ggacagagca     60
aagccatgaa catcatccta gaaatccttc tgcttctgat caccatcatc tactcctact    120
tggagtcgtt ggtgaagttt ttcattcctc agaggagaaa atctgtggct ggggagattg    180
ttctcattac tggagctggg catgaatag gcaggcagac tacttatgaa tttgcaaaac    240
gacagagcat attggttctg tgggatatta ataagcgcgg tgtggaggaa actgcagctg    300
agtgccgaaa actaggcgtc actgcgcatg cgtatgtggt agactgcagc aacagagaag    360
agatctatcg ctctctaaat caggtgaaga aagaagtggg tgatgtaaca atcgtggtga    420
ataatgctgg gacagtatat ccagccgatc ttctcagcac caaggatgaa gagattacca    480
agacatttga ggtcaacatc ctaggacatt tttggatcac aaaagcactt cttccatcga    540
tgatggagag aaatcatggc cacatcgtca cagtggcttc agtgtgcggc cacgaaggga    600
ttccttacct catcccatat tgttccagca aatttgccgc tgttggcttt cacagaggtc    660
tgacatcaga acttcaggcc ttgggaaaaa ctggtatcaa aacctcatgt ctctgccag    720
tttttgtgaa tactgggttc accaaaaatc caagcacaag attatgcct gtattggaga    780
cagatgaagt cgtaagaagt ctgatagatg gaatacttac caataagaaa atgattttg    840
ttccatcgta tatcaatatc tttctgagac tacagaagtt aagtacagca cagaacaccc    900
aaatactaaa acaccaatag agctttttt ttgctttttt ttttttttag acagagtctc    960
actctgtcac cctggctgga ttgcggtggt tgcagtggca tgatcttggc tcactgcaac   1020
ctccgcctcc tgggttcaag caattctcat gcctcagacc cccaagtaac tgggattata   1080
```

```
ggtgtgtgct gccacactac acccagctaa ttttcgtatt ttttgataga gacaggtttc   1140
cccatgttgg ccaggctgga ctcgaactcc tgacctcaag ttatcctcct gtctcggcct   1200
cccaaagtgc tgggattaca gtcatgagcc accatgcctg gcccaataga gctattatta   1260
tggagcatct ttcagttgtg aaaattggca tggaaactct ccatccctgg ggagaacagt   1320
tatttcctct gttattttcc tacccagtct ataaaaagag agtgattcat tttctctacc   1380
aaatctactg tctctgccca aactttgctg aagactattc taactaaagg aaacacagtt   1440
taaaaagaat gcaatatagt gaagtagtta ataataaaga ctccattttt aaaagtctgc   1500
tggaagtttg gttgggattg cactgaatct atagagcaat ggggagtat tgacatatca    1560
acaatattga gttttctaat ccaagaacat aatatctatt tttaaaatct tcttcaaaat   1620
ctttaaatct ttaaattgta ttttgtagtt tttggtgttt aagtcttgca catattttgt   1680
cagatttatt ccaaagtatt tcacgggttc ttttt                              1715

SEQ ID NO: 59         moltype = DNA  length = 2290
FEATURE               Location/Qualifiers
source                1..2290
                      mol_type = other DNA
                      organism = Homo sapiens
SEQUENCE: 59
agacagtacc tcctccctag gactacacaa ggactgaacc agaaggaaga ggacagagca    60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catggaatag gcaggcagac tacttatgaa tttgcaaaac   240
gacagagcat attggttctg tgggatatta ataaggtgaa gaaagaagtg ggtgatgtaa   300
caatcgtggt gaataatgct gggacagtat atccagccga tcttctcagc accaaggatg   360
aagagattac caagacattt gaggtcaaca tcctaggaca ttttggatc acaaaagcac    420
ttcttccatc gatgatggag agaaatcatg gccacatcgt cacagtggct tcagtgtgcg   480
gccacgaagg gattccttac ctcatcccat attgttccag caatttgcc gctgttggct    540
ttcacagagg tctgacatca gaacttcagg ccttgggaaa aactggtatc aaaacctcat   600
gtctctgccc agttttgtg aatactgggt tcaccaaaaa tccaagcaca agattatggc    660
ctgtattgga gacagatgaa gtcgtaagaa gtctgataga tggaatactt accaataaga   720
aaatgatttt tgttccatcg tatatcaata tctttctgag actacagaag gtttcttcct   780
gaacgcgcct cagcgatttt aaatcgtatg cagaatattc aatttgaagc agtggttggc   840
cacaaaatca aaatgaaatg aataaataag ctccagccag atgtatgc atgataatga     900
tatgaatagt ttcgaatcaa tgctgcaaag ctttatttca cattttttca gtcctgataa    960
tattaaaaac attggtttgg cactagcagc agtcaaacga acaagattaa ttacctgtct   1020
tcctgtttct caagaatatt tacgtagttt tcataggtc tgttttttcct ttcatgcctc    1080
ttaaaaactt ctgtgcttac ataaacatac ttaaaaggtt ttctttaaga tattttattt   1140
ttccatttaa aggtggacaa aagctacctc cctaaaagta aatacaaaga gaacttattt   1200
acacagggaa ggtttaagac tgttcaagta gcattccaat ctgtagccat gccacagaat   1260
atcaacaaga acacagaatg agtgcacagc taagagatca agtttcagca ggcagcttta   1320
tctcaacctg gacatatttt aagattcagc atttgaaaga tttccctagc ctcttccttt   1380
ttcattagcc caaaacggtg caactctatt ctggacttta ttacttgatt ctgtcttctg   1440
tataactctg aagtccacca aaagtggacc ctctatattt cctccctttt tatagtctta   1500
taagatacat tatgaaaggt gaccgactct atttttaaatc tcagaatttt aagttctagc   1560
cccatgataa cctttttctt tgtaatttat gctttcatat atccttggtc ccagagatgt   1620
ttagacaatt ttaggctcaa aaattaaagc taacacagga aaaggaactg tactggctat   1680
tacataagaa acaatggacc caagagaaga aaaggaagaa agaaaggttt tttggttttt   1740
gttttgtttt gttttgtttt ttgttttttt gagatggagt ctcactcttt cgcccaggct   1800
ggagtgcagt ggtatgatct cagctcactg caagctccac ctcccgggtt cacgccattc   1860
tcctgcctca gcctcctgag tagctgggac tacaggcgcc cgccaccaca cccggctaat   1920
ttttttgtatt ttttgtagag acggggtttc accatgttga ccaagatggt ctcgatctcc   1980
tgacctcgtg atccacctgc ctcggcctcc caaagtgctg ggattacggg tgtgagccac   2040
cgtgcccagc ctttttttttt ttaatagaaa aaataatccg actcccacta catcaagact   2100
aatcttgttt tgtgtgtttt tcacatgtat tatagaatgc ttttgcatgg actatcctct   2160
tgttttttatt aaaaacaaat gatttttta aaagtcacaa aaacaattca ctaaaaataa   2220
atatgtcatt gtgctttaaa aaataaccct cttgtagtta taaaataaaa cgtttgactt   2280
ctaaactctg                                                          2290

SEQ ID NO: 60         moltype = DNA  length = 2470
FEATURE               Location/Qualifiers
source                1..2470
                      mol_type = other DNA
                      organism = Homo sapiens
SEQUENCE: 60
agacagtacc tcctccctag gactacacaa ggactgaacc agaaggaaga ggacagagca    60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catggaatag gcaggcagac tacttatgaa tttgcaaaac   240
gacagagcat attggttctg tgggatatta ataagcgcga tgtggaggaa actgcagctg   300
agtgccgaaa actaggcgtc actgcgcatg cgtatgtggt agactgcagc aacagagaag   360
agatctatcg ctctctaaat caggtgaaga aagaagtggg tgatgtaaca atcgtggtga   420
ataatgctgg gacagtatat ccagccgatc ttctcagcac caaggatgaa gagattacca   480
agacatttga ggtcaacatc ctaggacatt tttggaatgg aaaggacatc agaagtaatt   540
acttggatgt atataggatg gaggacactt tggacgagga tctgagatca aaaagcac     600
ttcttccatc gatgatggag agaaatcatg gccacatcgt cacagtggct tcagtgtgcg   660
gccacgaagg gattccttac ctcatcccat attgttccag caatttgcc gctgttggct    720
ttcacagagg tctgacatca gaacttcagg ccttgggaaa aactggtatc aaaacctcat   780
gtctctgccc agttttgtg aatactgggt tcaccaaaaa tccaagcaca agattatggc    840
ctgtattgga gacagatgaa gtcgtaagaa gtctgataga tggaatactt accaataaga   900
```

```
aaatgatttt tgttccatcg tatatcaata tctttctgag actacagaag gtttcttcct    960
gaacgcgcct cagcgatttt aaatcgtatg cagaatattc aatttgaagc agtggttggc   1020
cacaaaatca aaatgaaatg aataaataag ctccagccag agatgtatgc atgataatga   1080
tatgaatagt ttcgaatcaa tgctgcaaag ctttatttca cattttttca gtcctgataa   1140
tattaaaaac attggtttgg cactagcagc agtcaaacga acaagattaa ttacctgtct   1200
tcctgtttct caagaatatt tacgtagttt ttcataggtc tgttttttcct ttcatgcctc   1260
ttaaaaactt ctgtgcttac ataaacatac ttaaaaggtt ttcttaaga tattttattt    1320
ttccatttaa aggtggacaa aagctacctc cctaaaagta aatacaaaga gaacttattt   1380
acacagggaa ggtttaagac tgttcaagta gcattccaat ctgtagccat gccacagaat   1440
atcaacaaga acacagaatg agtgcacagc taagagatca agtttcagca ggcagcttta   1500
tctcaacctg gacatatttt aagattcagc atttgaaaga tttccctagc ctcttccttt   1560
ttcattagcc caaacggtg caactctatt ctggactttta ttacttgatt ctgtcttctg   1620
tataactctg aagtccacca aaagtggacc ctctatattt cctccctttt tatagtctta   1680
taagatacat tatgaaaggt gaccgactct attttaaatc tcagaattt aagttctagc    1740
cccatgataa cctttttctt tgtaatttat gctttcatat atccttggtc ccagagatgt   1800
ttagacaatt ttaggctcaa aaattaaagc taacacagga aaaggaactg tactggctat   1860
tacataagaa acaatggacc caagagaaga aaaggaagaa agaaaggttt tttggttttt   1920
gttttgtttt gttttgtttt ttgttttttt gagatggagt ctcactcttt cgcccaggct   1980
ggagtgcagt ggtatgatct cagctcactg caagctccac ctcccgggtt cacgccattc   2040
tcctgcctca gcctcctgag tagctgggac tacaggcgcc cgccaccaca cccggctaat   2100
ttttttgtatt ttttgtagag acggggtttc accatgttag ccaagatggt ctcgatctcc   2160
tgacctcgtg atccacctgc ctcggcctcc caaagtgctg ggattacggc tgtgagccac   2220
cgtgcccagc ctttttttt taatagaaa aaataatccg actcccacta catcaagact    2280
aatcttgttt tgtgtgtttt tcacatgtat tatagaatgc ttttgcatgg actatcctct   2340
tgttttatt aaaacaaat gatttttta aaagtcacaa aaacaattca ctaaaaataa     2400
atatgtcatt gtgctttaaa aaaataaacct cttgtagtta taaaataaaa cgtttgactt   2460
ctaaactctg                                                         2470

SEQ ID NO: 61           moltype = DNA  length = 1714
FEATURE                 Location/Qualifiers
source                  1..1714
                        mol_type = other DNA
                        organism = Homo sapiens
SEQUENCE: 61
agacagtacc tcctccctag gactacacaa ggactgaacc agaaggaaga ggacagagca    60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catggaatag gcaggcagac tacttatgaa tttgcaaaac   240
gacagagcat attggttctg tgggatatta ataagcgtga tgtggaggaa actgcagctg   300
agtgccgaaa actaggcgtc actgcgcatg cgtatgtggt agactgcagc aacagagaag   360
agatctatcg ctctctaaat caggtgaaga agaagtgggg tgatgtaaca atcgtggtga   420
ataatgctgg gacagtatat ccagccgatc ttctcagcac caaggatgaa gagattacca   480
agacatttga ggtcaacatc ctaggacatt tttggatcac aaaaagcactt cttccatcga   540
tgatggagag aaaatcatgg cacatcgtca cagtggcttc agtgtgcggc cacgaaggga   600
ttccttacct catcccatat tgttccagca aatttgccgc tgttggcttt cacagaggtc   660
tgacatcaga acttcaggcc ttgggaaaaa ctggtatcaa aacctcatgt ctctgcccag   720
tttttgtgaa tactgggttc accaaaaaatc caagcacaag attatggcct gtattggaga   780
cagatgaagt cgtaagaagt ctgatagatg gaatacttac caataagaaa atgatttttg   840
ttccatcgta tatcaatatc tttctgagac tacagaagta agtacagcac agaacaccca   900
aatactaaaa caccaataga gcttttttttt ttgcttttt tttttttaga cagagtctca   960
ctctgtcacc ctggctggat tgcggtggt gcagtggcat gatcttggct cactgcaacc   1020
tccgcctcct gggttcaagc aattctcatg cctcagaccc ccaagtaact gggattatag   1080
gtgtgtgctg ccacactaca cccagctaat ttttgtattt tttgatagag acaggtttcc   1140
ccatgttggc caggctggac tcgaactcct gacctcaagt tatcctcctg tctcggcctc   1200
ccaaagtgct gggattacag tcatgagcca ccatgcctgg cccaataagg ctattattat   1260
ggagcatctt tcagttgtga aaattggcat ggaactctc catccctggg gagaacagtt   1320
atttcctctg ttatttcct acccagtcta taaaagaga gtgattcatt ttctctacca    1380
aatctactgt ctctgcccaa actttgctga agactattct aactaaagga aacacagttt   1440
aaaaagaatg caatatagtg aagtagttaa taataaagac tccattttta aaagtctgct   1500
ggaagtttgg ttgggattgc actgaatcta tagagcaatt ggggagtatt gacatatcaa   1560
caatattgag ttttctaatc caagaacata atatctatttt ttaaaatctt cttcaaaatc  1620
tttaaatctt taaattgtat tttgtagttt tggtgtttta agtcttgcac atattttgtc   1680
agatttattc caaagtattt cacgggttct tttt                              1714

SEQ ID NO: 62           moltype = DNA  length = 25
FEATURE                 Location/Qualifiers
misc_feature            1..25
                        note = forward primer
source                  1..25
                        mol_type = other DNA
                        organism = synthetic construct
SEQUENCE: 62
atgaacatca tcctagaaat ccttc                                          25

SEQ ID NO: 63           moltype = DNA  length = 25
FEATURE                 Location/Qualifiers
misc_feature            1..25
                        note = reverse primer
source                  1..25
```

```
                        mol_type = other DNA
                        organism = synthetic construct
SEQUENCE: 63
atcatgcata catctctggc tggag                                        25

SEQ ID NO: 64           moltype = DNA  length = 20
FEATURE                 Location/Qualifiers
misc_feature            1..20
                        note = primer
source                  1..20
                        mol_type = other DNA
                        organism = synthetic construct
SEQUENCE: 64
atcagaactt caggccttgg                                              20

SEQ ID NO: 65           moltype = DNA  length = 21
FEATURE                 Location/Qualifiers
misc_feature            1..21
                        note = first exon
source                  1..21
                        mol_type = other DNA
                        organism = synthetic construct
SEQUENCE: 65
gcaaagccat gaacatcatc c                                            21

SEQ ID NO: 66           moltype = DNA  length = 24
FEATURE                 Location/Qualifiers
misc_feature            1..24
                        note = last exon
source                  1..24
                        mol_type = other DNA
                        organism = synthetic construct
SEQUENCE: 66
tcttgatgta gtgggagtcg gatt                                         24
```

INHIBITION OF HSD17B13 IN THE TREATMENT OF LIVER DISEASE IN PATIENTS EXPRESSING THE PNPLA3 I148M VARIATION

REFERENCE TO A SEQUENCE LISTING

This application includes a Sequence Listing submitted electronically as a text file named 18923801001SEQ, created on Oct. 9, 2018, with a size of 238 kilobytes. The Sequence Listing is incorporated by reference herein.

FIELD

The disclosure relates generally to the field of precision medicine. More particularly, the disclosure relates to methods of identifying subjects who are patatin like phospholipase domain containing 3 (PNPLA3) Ile148Met positive and have a liver disease or susceptibility to liver disease, and treating such subjects with an inhibitor of hydroxysteroid 17-beta dehydrogenase 13 (HSD17B13).

BACKGROUND

Various references, including patents, patent applications, accession numbers, technical articles, and scholarly articles are cited throughout the specification. Each reference is incorporated by reference herein, in its entirety and for all purposes.

Chronic liver disease and cirrhosis are leading causes of morbidity and mortality in the United States, accounting for 38,170 deaths (1.5% of total deaths) in 2014 (Kochanek et al., Nat'l. Vital Stat. Rep., 2016, 65, 1-122). The most common etiologies of cirrhosis in the U.S. are alcoholic liver disease, chronic hepatitis C, and nonalcoholic fatty liver disease (NAFLD), together accounting for about 80% of patients awaiting liver transplant between 2004 and 2013 (Wong et al., Gastroenterology, 2015, 148, 547-555). The estimated prevalence of NAFLD in the U.S. is between 19 and 46 percent (Browning et al., Hepatology, 2004, 40, 1387-1395; Lazo et al., Am. J. Epidemiol., 2013, 178, 38-45; and Williams et al., Gastroenterology, 2011, 140, 124-131) and is rising over time (Younossi et al., Clin. Gastroenterol. Hepatol., 2011, 9, 524-530), likely in conjunction with increased rates of obesity, its primary risk factor (Cohen et al., Science, 2011, 332, 1519-1523). While significant advances have been made in the treatment of hepatitis C, there are currently no evidence-based treatments for alcoholic or nonalcoholic liver disease and cirrhosis.

Previous genome wide association studies (GWAS) have identified sequence variations associated with increased risk of chronic liver disease. The most robustly validated association is with a common missense variant in patatin-like phospholipase domain-containing 3, encoded by the gene PNPLA3. This variant (rs738409, p.Ile148Met) was initially found to be associated with an increase in hepatic triglyceride levels (Romeo et al., Nat. Genet., 2008, 40, 1461-5), and subsequently associated with nonalcoholic steatohepatitis (NASH) (Rotman et al., Hepatology, 2010, 52, 894-903; Sookoian et al., J. Lipid Res., 2009, 50, 2111-2116) and cirrhosis (Shen et al., J. Lipid Res., 2015, 56, 167-175). A missense variant in TM6SF2, encoding transmembrane 6 superfamily member 2, also confers increased risk of nonalcoholic fatty liver disease (NAFLD)(Kozlitina et al., Nat. Genet., 2014, 46, 352-6; Liu et al., Nat. Commun., 2014, 5, 4309; and Sookoian et al., Hepatology, 2015, 61, 515-25). Exactly how the variants in PNPLA3 and TM6SF2 contribute to liver disease has yet to be fully elucidated (Smagris et al., J. Biol. Chem., 2016, 291, 10659-76; Mahdessian et al., Proc. Natl. Acad. Sci. USA, 2014, 111, 8913-8; Huang et al., J. Biol. Chem., 2011, 286, 37085-93; and Pirazzi et al., J. Hepatol., 2012, 57, 1276-82). To date, no genetic variants that protect from chronic liver disease have been identified.

SUMMARY

The present disclosure provides methods for identifying a human subject as a candidate for treating or inhibiting a liver disease, the method comprising: determining whether or not a sample from the subject comprises: i) a first nucleic acid encoding a patatin like phospholipase domain containing 3 (PNPLA3) protein comprising an I148M variation and a second nucleic acid encoding a functional HSD17B13 protein; and/or ii) a PNPLA3 protein comprising an I148M variation and a functional HSD17B13 protein; and identifying the subject as a candidate for treating or inhibiting a liver disease by inhibiting HSD17B13 when both the first and second nucleic acids as defined in i) and/or both of the proteins as defined in ii) are detected.

In some embodiments, the first nucleic acid molecule comprises genomic DNA, mRNA, or a cDNA obtained from mRNA.

In some embodiments, the genomic DNA comprises an ATG codon at the positions corresponding to positions 5107 to 5109 according to SEQ ID NO:31; the mRNA comprises an AUG codon at the positions corresponding to positions 442 to 444 according to SEQ ID NO:34; the mRNA comprises an AUG codon at the positions corresponding to positions 430 to 432 according to SEQ ID NO:35; the cDNA comprises an ATG codon at the positions corresponding to positions 442 to 444 according to SEQ ID NO:38; or the cDNA comprises an ATG codon at the positions corresponding to positions 430 to 432 according to SEQ ID NO:39.

In some embodiments, the genomic DNA comprises the nucleotide sequence according to SEQ ID NO:31, or a nucleotide sequence having at least 90% sequence identity to SEQ ID NO:31 and encoding a PNPLA3 protein which comprises the I148M variation; the mRNA comprises the nucleotide sequence according to SEQ ID NO:34, or a nucleotide sequence having at least 90% sequence identity to SEQ ID NO:34 and encoding a PNPLA3 protein which comprises the I148M variation; the mRNA comprises the nucleotide sequence according to SEQ ID NO:35, or a nucleotide sequence having at least 90% sequence identity to SEQ ID NO:35 and encoding a PNPLA3 protein which comprises the I148M variation; the cDNA comprises the nucleotide sequence according to SEQ ID NO:38, or a nucleotide sequence having at least 90% sequence identity to SEQ ID NO:38 and encoding a PNPLA3 protein which comprises the I148M variation; or the cDNA comprises the nucleotide sequence according to SEQ ID NO:39, or a nucleotide sequence having at least 90% sequence identity to SEQ ID NO:39 and encoding a PNPLA3 protein which comprises the I148M variation.

In some embodiments, detecting the first nucleic acid comprises: sequencing at least a portion of the first nucleic acid, wherein the portion comprises the codon which encodes the I148M variation; or hybridizing the first nucleic acid with a probe or primer that specifically hybridizes to a portion of the first nucleic acid, wherein the portion comprises the codon encoding the I148M variation.

In some embodiments, the probe or primer is an allele-specific probe or primer, and wherein the probe or primer optionally comprises a label.

In some embodiments, the methods further comprise determining whether the subject is homozygous or heterozygous for the I148M variation.

In some embodiments, the second nucleic acid comprises genomic DNA, mRNA, or a cDNA obtained from mRNA.

In some embodiments, the genomic DNA comprises an adenine at the position corresponding to position 12,667 according to SEQ ID NO:1; the genomic DNA comprises the nucleotide sequence according to SEQ ID NO:1, or a nucleotide sequence having at least 90% sequence identity to SEQ ID NO:1 and encoding a functional HSD17B13 protein; the mRNA comprises the nucleotide sequence according to SEQ ID NO:3, or a nucleotide sequence having at least 90% sequence identity to SEQ ID NO:3 and encoding a functional HSD17B13 protein; the mRNA comprises the nucleotide sequence according to SEQ ID NO:4 or a nucleotide sequence having at least 90% sequence identity to SEQ ID NO:4 and encoding a functional HSD17B13 protein; the mRNA comprises the nucleotide sequence according to SEQ ID NO:7 or a nucleotide sequence having at least 90% sequence identity to SEQ ID NO:7 and encoding a functional HSD17B13 protein; the mRNA comprises the nucleotide sequence according to SEQ ID NO:11 or a nucleotide sequence having at least 90% sequence identity to SEQ ID NO:11 and encoding a functional HSD17B13 protein; the cDNA comprises the nucleotide sequence according to SEQ ID NO:12 or a nucleotide sequence having at least 90% sequence identity to SEQ ID NO:12 and encoding a functional HSD17B13 protein; the cDNA comprises the nucleotide sequence according to SEQ ID NO:13 or a nucleotide sequence having at least 90% sequence identity to SEQ ID NO:13 and encoding a functional HSD17B13 protein; the cDNA comprises the nucleotide sequence according to SEQ ID NO:16 or a nucleotide sequence having at least 90% sequence identity to SEQ ID NO:16 and encoding a functional HSD17B13 protein; or the cDNA comprises the nucleotide sequence according to SEQ ID NO:20 or a nucleotide sequence having at least 90% sequence identity to SEQ ID NO:20 and encoding a functional HSD17B13 protein.

In some embodiments, detecting the second nucleic acid comprises: sequencing the second nucleic acid; or hybridizing the second nucleic acid with a probe or primer that specifically hybridizes to a portion of the second nucleic acid, wherein the portion comprises the adenine at the position corresponding to position 12,667 according to SEQ ID NO:1.

In some embodiments, the probe or primer is an allele-specific probe or primer, and wherein the probe or primer optionally comprises a label.

In some embodiments, the methods further comprise determining whether the subject is homozygous or heterozygous for the second nucleic acid encoding a functional HSD17B13 protein in the sample.

In some embodiments, the methods further comprise administering an inhibitor of HSD17B13 to the subject.

In some embodiments, the liver disease is an alcoholic liver disease. In some embodiments, the alcoholic liver disease comprises one or more of cirrhosis, steatosis, or hepatocellular carcinoma resulting from alcohol consumption.

In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

BRIEF DESCRIPTION OF THE FIGURES

The accompanying figures, which are incorporated in and constitute a part of this specification, illustrate several aspects and together with the description serve to explain the principles of the present disclosure.

FIG. 1 shows baseline characteristics of sequenced European-ancestry individuals from the discovery and replication cohorts.

FIG. 2 shows single nucleotide variants associated with serum transaminase levels at $P<1.0\times10^{-7}$ in the discovery cohort.

FIG. 3 shows replication and joint meta-analysis of 35 exome-wide significant single nucleotide variants from the discovery cohort in three separate European-ancestry cohorts.

FIG. 4 shows association of thirteen exome-wide significant and replicating single nucleotide variants with liver disease phenotypes in the discovery cohort.

FIG. 5 shows baseline characteristics of genotyped multi-ethnic cases and controls from the Dallas Liver and Pediatric Liver Studies.

FIG. 9 shows an analysis of the genetic interaction between PNPLA3 rs738409 (p.I148M) and HSD17B13 rs72613567.

Figure 6:
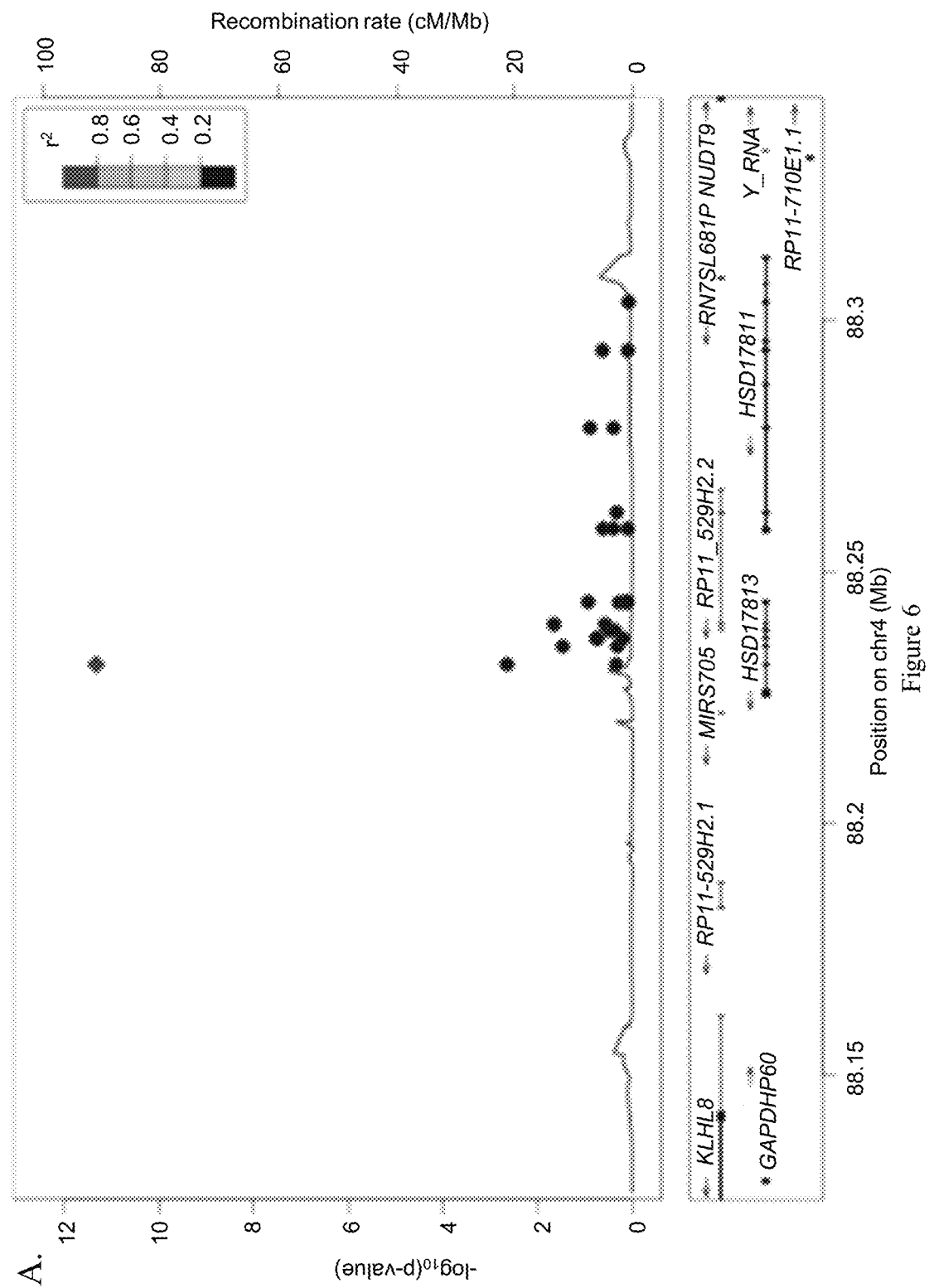
FIG. 6 (panels A and B) shows regional association plots for alanine aminotransferase (ALT; A) and aspartate aminotransferase (AST; B) levels in the GHS discovery cohort in the region around HSD17B13.
Figure 6:
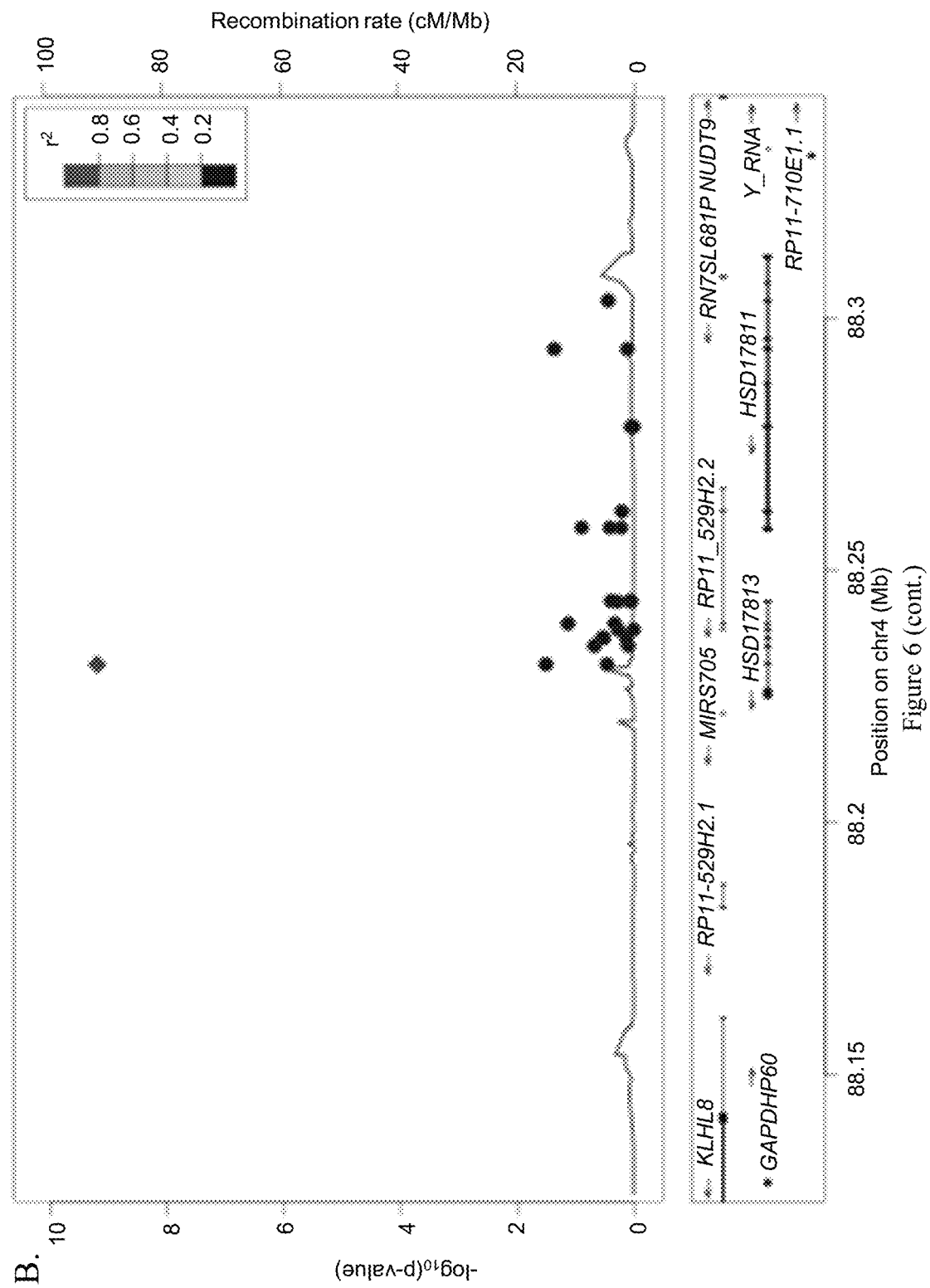

Additional advantages of the disclosure will be set forth in part in the description which follows, and in part will be apparent from the description, or can be learned by practice of the embodiments disclosed herein. The advantages of the disclosure will be realized and attained by means of the elements and combinations particularly pointed out in the appended claims. It is to be understood that both the foregoing general description and the following detailed description are exemplary and explanatory only and are not restrictive of the embodiments, as claimed.

DESCRIPTION

Various terms relating to aspects of disclosure are used throughout the specification and claims. Such terms are to be given their ordinary meaning in the art, unless otherwise indicated. Other specifically defined terms are to be construed in a manner consistent with the definition provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the terms "subject" and "patient" are used interchangeably. A subject may include any animal, including mammals. Mammals include, without limitation, farm animals (e.g., horse, cow, pig), companion animals (e.g., dog, cat), laboratory animals (e.g., mouse, rat, rabbits), and non-human primates. In some embodiments, the subject is a human being.

As used herein, a "nucleic acid," a "nucleic acid molecule," a "nucleic acid sequence," "polynucleotide," or "oligonucleotide" can comprise a polymeric form of nucleotides of any length, may comprise DNA and/or RNA, and can be single-stranded, double-stranded, or multiple stranded. One strand of a nucleic acid also refers to its complement.

As used herein, the phrase "corresponding to" or grammatical variations thereof when used in the context of the numbering of a given amino acid or nucleic acid sequence or position refers to the numbering of a specified reference sequence when the given amino acid or nucleic acid sequence is compared to the reference sequence (e.g., with the reference sequence herein being the nucleic acid molecule or polypeptide of (functional or transcript behaving as a functional) HSD17B13, for example). In other words, the residue (e.g., amino acid or nucleotide) number or residue (e.g., amino acid or nucleotide) position of a given polymer is designated with respect to the reference sequence rather than by the actual numerical position of the residue within the given amino acid or nucleic acid sequence. For example, a given amino acid sequence can be aligned to a reference sequence by introducing gaps to optimize residue matches between the two sequences. In these cases, although the gaps are present, the numbering of the residue in the given amino acid or nucleic acid sequence is made with respect to the reference sequence to which it has been aligned.

For example, the phrase "nucleic acid molecule encoding an HSD17B13 loss-of-function variant protein which comprises a thymine at the position corresponding to position 12,667 according to SEQ ID NO:2" (and similar phrases) means that, if the nucleic acid sequence of the HSD17B13 genomic DNA being examined is aligned to the nucleotide sequence according to SEQ ID NO:2, the HSD17B13 genomic DNA being examined comprises a thymine at the position that corresponds to position 12,667 of SEQ ID NO:2.

A nucleic acid molecule encoding an HSD17B13 loss-of-function variant protein which comprises a thymine at the position corresponding to position 12,667 according to SEQ ID NO:2, for example, can easily be identified by performing a sequence alignment between the given HSD17B13 protein and the nucleic acid sequence of SEQ ID NO:2. Likewise, a PNPLA3 Ile148Met protein having a methionine at a position corresponding to position 148 according to SEQ ID NO:42, or at a position corresponding to position 144 according to SEQ ID NO:43 can easily be identified by performing a sequence alignment between the given PNPLA3 protein and the amino acid sequence of SEQ ID NO:42 or SEQ ID NO:43. A variety of computational algorithms exist that can be used for performing a sequence alignment in order to identify particular nucleic acid molecules and proteins having particular nucleotides or amino acids at the particular position that corresponds to a position of a particular SEQ ID NOs. For example, programs for identifying percent sequence identity can be used to perform a sequence alignment. Percent identity (or percent complementarity) between particular stretches of nucleic acid sequences within nucleic acids or amino acid sequences within polypeptides can be determined using BLAST programs (basic local alignment search tools) and Power-BLAST programs (Altschul et al., J. Mol. Biol., 1990, 215, 403-410; Zhang and Madden, Genome Res., 1997, 7, 649-656) or CLUSTALW software (Sievers et al., 2014, Methods Mol. Biol., 1079, 105-116) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). However, sequences can also be aligned manually. Herein, if reference is made to percent sequence identity, the higher percentages of sequence identity are preferred over the lower ones.

The present disclosure provides methods of identifying a human subject as a candidate for treating or inhibiting a liver disease by inhibiting HSD17B13; methods of treating or inhibiting liver disease comprising administering an inhibitor of HSD17B13; methods of detecting PNPLA3 Ile148Met (also referred to herein as "I148M") and functional HSD17B13 in a subject; methods of identifying a subject having a protective effect against liver disease; and inhibitors of HSD17B13 for use in the treatment of a liver disease.

The present disclosure provides methods of classifying a human subject as a candidate for treating or inhibiting a liver disease by inhibiting HSD17B13; methods of treating or inhibiting liver disease comprising administering an inhibitor of HSD17B13; methods of detecting PNPLA3 Ile148Met (also referred to herein as "I148M") and functional HSD17B13 in a subject; methods of classifying a subject having a protective effect against liver disease; and inhibitors of HSD17B13 for use in the treatment of a liver disease.

It has been observed in accordance with the disclosure that a splice variant (rs72613567:TA) in HSD17B13, which encodes 17-beta hydroxysteroid dehydrogenase 13, a hepatic lipid droplet protein, was reproducibly associated with reduced ALT (P=4.2×10$^{-12}$) and AST (P=6.2×10$^{-10}$) levels. It was also observed that this variant was associated with reduced risk of alcoholic and nonalcoholic liver disease (by 38%, 95% confidence interval (CI) 19%-52%; and by 16%, 95% CI 9%-22%, respectively, for each rs72613567:TA allele) and cirrhosis (by 44%, 95% CI 22-59%; and by 26%, 95% CI 12%-38% for alcoholic and nonalcoholic cirrhosis, respectively, for each rs72613567:TA allele) in an allele dosage-dependent manner. The associations were confirmed in two independent cohorts. rs72613567:TA was associated with decreased severity of histological features of nonalcoholic steatohepatitis (NASH) (23% reduction, 95% CI 10%-34% in nonalcoholic steatohepatitis (NASH) for each rs72613567:TA allele among individuals with fatty liver disease), and mitigated liver injury associated with PNPLA3 p.I148M. rs72613567:TA results in a truncated isoform deficient in enzymatic activity against steroid substrates. Thus, a loss-of-function variant in HSD17B13 was associated with reduced risk of alcoholic and nonalcoholic liver disease, and progression from steatosis to NASH. U.S. Patent Application Publication No. US2018/0216084 (corresponding to PCT Publication No. WO 2018/136702) is incorporated herein by reference in its entirety.

The present disclosure provides methods for identifying a human subject as a candidate for treating or inhibiting a liver disease by inhibiting hydroxysteroid 17-beta dehydrogenase 13 (HSD17B13), the method comprising determining whether or not a sample from the subject comprises a first nucleic acid encoding a patatin like phospholipase domain containing 3 (PNPLA3) protein comprising an I148M variation and a second nucleic acid encoding a functional HSD17B13 protein, and/or a PNPLA3 protein comprising an I148M variation and a functional HSD17B13 protein, and identifying the subject as a candidate for treating or inhibiting a liver disease by inhibiting HSD17B13 when both the first and second nucleic acids are detected and/or both of the proteins are detected.

The present disclosure also provides methods of classifying a human subject as a candidate for treating or inhibiting a liver disease by inhibiting HSD17B13; methods of treating or inhibiting liver disease comprising administering an inhibitor of HSD17B13; methods of detecting PNPLA3 Ile148Met (also referred to herein as "I148M") and functional HSD17B13 in a subject; methods of classifying a subject having a protective effect against liver disease; and inhibitors of HSD17B13 for use in the treatment of a liver disease.

The present disclosure also provides methods of treating or inhibiting liver disease, comprising administering an inhibitor of hydroxysteroid 17-beta dehydrogenase 13 (HSD17B13) to a human liver disease patient expressing a patatin like phospholipase domain containing 3 (PNPLA3) protein comprising an I148M variation such that liver disease is treated or inhibited in the patient.

In the methods described herein, various PNPLA3 and HSD17B13 proteins, and nucleic acid molecules (e.g., genomic DNA, mRNA, and cDNA derived from the mRNA) encoding the same are detected, expressed, or employed. These PNPLA3 and HSD17B13 proteins and nucleic acid molecules encoding the same are described in more detail.

The amino acid sequences for two wild type PNPLA3 proteins are set forth in SEQ ID NO:40 and SEQ ID NO:41. The wild type PNPLA3 protein having SEQ ID NO:40 is 481 amino acids in length, whereas the wild type PNPLA3 protein having SEQ ID NO:41 is 477 amino acids in length. The wild type PNPLA3 protein having SEQ ID NO:40 has an isoleucine at position 148. The wild type PNPLA3 protein having SEQ ID NO:41 has an isoleucine at position 144.

In some embodiments, a variant PNPLA3 Ile148Met protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:42, and comprises a methionine at a position corresponding to position 148 according to SEQ ID NO:42. In some embodiments, the variant PNPLA3 Ile148Met protein comprises an amino acid sequence that has at least about 95%, at least about 96%, at least about 97%, at least about 98%, or at least about 99% sequence identity to the amino acid sequence according to SEQ ID NO:42, and comprises a methionine at a position corresponding to position 148 according to SEQ ID NO:42. In some embodiments, the variant PNPLA3 Ile148Met protein comprises or consists of the amino acid sequence according to SEQ ID NO:42.

In some embodiments, a variant PNPLA3 Ile144Met protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:43, and comprises a methionine at a position corresponding to position 144 according to SEQ ID NO:43. In some embodiments, the variant PNPLA3 Ile144Met protein comprises an amino acid sequence that has at least about 95%, at least about 96%, at least about 97%, at least about 98%, or at least about 99% sequence identity to the amino acid sequence according to SEQ ID NO:43, and comprises a methionine at a position corresponding to position 144 according to SEQ ID NO:43. In some embodiments, the variant PNPLA3 Ile144Met protein comprises or consists of the amino acid sequence according to SEQ ID NO:43.

In some embodiments, the variant PNPLA3 Ile148Met and variant PNPLA3 Ile144Met proteins are fragments of the proteins described above, wherein the fragments comprise a methionine at a position corresponding to position 148 according to SEQ ID NO:42, or comprise a methionine at a position corresponding to position 144 according to SEQ ID NO:43. In some embodiments, the fragments comprise at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 150, or at least about 200 contiguous amino acid residues of the encoded polypeptide (such as the polypeptide having the amino acid sequence of SEQ ID NO:42 or SEQ ID NO:43). In this regard, the longer fragments are preferred over the shorter ones. In some embodiments, the fragments comprise at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 contiguous amino acid residues of the encoded polypeptide. In this regard, the longer fragments are preferred over the shorter ones.

The nucleic acid sequence for a genomic DNA molecule encoding wild type PNPLA3 protein is set forth in SEQ ID NO:30. The wild type PNPLA3 genomic DNA molecule having SEQ ID NO:30 comprises a cytosine at position 5109. The wild type PNPLA3 genomic DNA molecule having SEQ ID NO:30 comprises the codon ATC at the positions 5107 to 5109.

In some embodiments, the variant PNPLA3 genomic DNA molecule comprises or consists of a nucleic acid sequence that encodes a PNPLA3 Ile148Met protein or a PNPLA3 Ile144Met protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 genomic DNA molecule comprises or consists of a nucleic acid sequence that encodes a PNPLA3 Ile148Met protein or a PNPLA3 Ile144Met protein that comprises an amino acid sequence that has at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 genomic DNA molecule comprises or consists a nucleic acid sequence that encodes a PNPLA3 Ile148Met protein or a PNPLA3 Ile144Met protein that comprises or consists of an amino acid sequence according to SEQ ID NO:42 or SEQ ID NO:43, respectively.

In some embodiments, the variant PNPLA3 genomic DNA molecule encoding the variant PNPLA3 Ile148Met protein or the variant PNPLA3 Ile144Met protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:31, and comprises a guanine at a position corresponding to position 5109 according to SEQ ID NO:31, or comprises the codon ATG at the positions corresponding to positions 5107 to 5109 according to SEQ ID NO:31. In some embodiments, the variant PNPLA3 genomic DNA molecule encoding the variant PNPLA3 Ile148Met protein or the variant PNPLA3 Ile144Met protein comprises or consists of a nucleic acid sequence that has at least about 95%, at least about 96%, at least about 97%, at least about 98%, or at least about 99% sequence identity to SEQ ID NO:31, and comprises a guanine at a position corresponding to position 5109 according to SEQ ID NO:31, or comprises the codon ATG at the positions corresponding to positions 5107 to 5109 according to SEQ ID NO:31. In some embodiments, the variant PNPLA3 genomic DNA molecule encoding the variant PNPLA3 Ile148Met protein or the variant PNPLA3 Ile144Met protein comprises or consists of the nucleotide sequence according to SEQ ID NO:31.

In some embodiments, the variant PNPLA3 genomic DNA molecules comprise less than the entire genomic DNA sequence. In some embodiments, the variant PNPLA3 genomic DNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, or at least about 11500 contiguous nucleotides of SEQ ID NO:31. In some embodiments, the variant PNPLA3 genomic DNA molecules comprise or consist of at least about 1000 to at least about 2000 contiguous nucleotides of SEQ ID NO:31.

In some embodiments, the variant PNPLA3 genomic DNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, or at least about 2500 contiguous nucleotides of SEQ ID NO:31.

The nucleic acid sequences of two wild type PNPLA3 mRNA molecules are set forth in SEQ ID NO:32 and SEQ ID NO:33. The wild type PNPLA3 mRNA molecule having SEQ ID NO:32 comprises a cytosine at position 444. The wild type PNPLA3 mRNA molecule having SEQ ID NO:32 comprises the codon AUC at the positions 442 to 444. The wild type PNPLA3 mRNA molecule having SEQ ID NO:33 comprises a cytosine at position 432. The wild type PNPLA3 mRNA molecule having SEQ ID NO:33 comprises the codon AUC at the positions 430 to 432.

In some embodiments, the variant PNPLA3 mRNA molecule comprises or consists of a nucleic acid sequence that encodes a PNPLA3 Ile148Met protein or a PNPLA3 Ile144Met protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 mRNA molecule comprises or consists of a nucleic acid sequence that encodes a PNPLA3 Ile148Met protein or a PNPLA3 Ile144Met protein that comprises an amino acid sequence that has at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 mRNA molecule comprises or consists a nucleic acid sequence that encodes a PNPLA3 Ile148Met protein or a PNPLA3 Ile144Met protein that comprises or consists of an amino acid sequence according to SEQ ID NO:42 or SEQ ID NO:43, respectively.

In some embodiments, the variant PNPLA3 mRNA molecule encoding the variant PNPLA3 Ile148Met protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:34, and comprises a guanine at a position corresponding to position 444 according to SEQ ID NO:34, or comprises the codon AUG at the positions corresponding to positions 442 to 444 according to SEQ ID NO:34. In some embodiments, the variant PNPLA3 mRNA molecule encoding the variant PNPLA3 Ile148Met protein comprises or consists of a nucleic acid sequence that has at least about 95%, at least about 96%, at least about 97%, at least about 98%, or at least about 99% sequence identity to SEQ ID NO:34, and comprises a guanine at a position corresponding to position 444 according to SEQ ID NO:34, or comprises the codon AUG at the positions corresponding to positions 442 to 444 according to SEQ ID NO:34. In some embodiments, the variant PNPLA3 mRNA molecule encoding the variant PNPLA3 Ile148Met protein comprises or consists of the nucleotide sequence according to SEQ ID NO:34.

In some embodiments, the variant PNPLA3 mRNA molecule encoding the variant PNPLA3 Ile144Met protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:35, and comprises a guanine at a position corresponding to position 432 according to SEQ ID NO:35, or comprises the codon AUG at the positions corresponding to positions 430 to 432 according to SEQ ID NO:35. In some embodiments, the variant PNPLA3 mRNA molecule encoding the variant PNPLA3 Ile144Met protein comprises or consists of a nucleic acid sequence that has at least about 95%, at least about 96%, at least about 97%, at least about 98%, or at least about 99% sequence identity to SEQ ID NO:35, and comprises a guanine at a position corresponding to position 432 according to SEQ ID NO:35, or comprises the codon AUG at the positions corresponding to positions 430 to 432 according to SEQ ID NO:35. In some embodiments, the variant PNPLA3 mRNA molecule encoding the variant PNPLA3 Ile144Met protein comprises or consists of the nucleotide sequence according to SEQ ID NO:35.

In some embodiments, the variant PNPLA3 mRNA molecule comprises less nucleotides than the entire variant PNPLA3 mRNA sequence. In some embodiments, the variant PNPLA3 mRNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, or at least about 600 contiguous nucleotides of SEQ ID NO:34 or SEQ ID NO:35. In some embodiments, the variant PNPLA3 mRNA molecules comprise or consist of at least about 200 to at least about 500 contiguous nucleotides of SEQ ID NO:34 or SEQ ID NO:35. In this regard, the longer mRNA molecules are preferred over the shorter ones. In some embodiments, the variant PNPLA3 mRNA molecules comprise or consist of at least about 50, at least about 60, at least about 70, at least about 80, at least about 90, at least about 100, at least about 200, at least about 300, at least about 400, or at least about 500 contiguous nucleotides of SEQ ID NO:34 or SEQ ID NO:35. In this regard, the longer mRNA molecules are preferred over the shorter ones. In some embodiments, such variant PNPLA3 mRNA molecules include the codon that encodes the methionine at the position that corresponds to position 148 according to SEQ ID NO:42 or the codon that encodes the methionine at the position that corresponds to position 144 according to SEQ ID NO:43. In some embodiments, such variant PNPLA3 mRNA molecules include the guanine at the position corresponding to position 444 according to SEQ ID NO:34 or the guanine at the position corresponding to position 432 according to SEQ ID NO:35. In some embodiments, such variant PNPLA3 mRNA molecules include the codon AUG at the positions corresponding to positions 442 to 444 according to SEQ ID NO:34, or the codon AUG at the positions corresponding to positions 430 to 432 according to SEQ ID NO:35.

The nucleic acid sequences of two wild type PNPLA3 cDNA molecules are set forth in SEQ ID NO:36 and SEQ ID NO:37. The wild type PNPLA3 cDNA molecule having SEQ ID NO:36 comprises a cytosine at position 444. The wild type PNPLA3 cDNA molecule having SEQ ID NO:36 comprises the codon ATC at positions 442 to 444. The wild type PNPLA3 cDNA molecule having SEQ ID NO:37 comprises a cytosine at position 432. The wild type PNPLA3 cDNA molecule having SEQ ID NO:37 comprises the codon ATC at positions 430 to 432.

In some embodiments, the variant PNPLA3 cDNA molecule comprises or consists of a nucleic acid sequence that encodes a PNPLA3 Ile148Met protein or a PNPLA3 Ile144Met protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 cDNA molecule comprises or consists of a nucleic acid sequence that encodes a PNPLA3 Ile148Met protein or a PNPLA3 Ile144Met protein that comprises an amino acid sequence that has at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 cDNA molecule comprises or consists a nucleic acid sequence that encodes a PNPLA3 Ile148Met protein or a PNPLA3 Ile144Met protein that comprises or consists of an amino acid sequence according to SEQ ID NO:42 or SEQ ID NO:43, respectively.

In some embodiments, the variant PNPLA3 cDNA molecule encoding the variant PNPLA3 Ile148Met protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:38, and comprises a guanine at a position corresponding to position 444 according to SEQ ID NO:38, or comprises the codon ATG at the positions corresponding to positions 442 to 444 according to SEQ ID NO:38. In some embodiments, the variant PNPLA3 cDNA molecule encoding the variant PNPLA3 Ile148Met protein comprises or consists of a nucleic acid sequence that has at least about 95%, at least about 96%, at least about 97%, at least about 98%, or at least about 99% sequence identity to SEQ ID NO:38, and comprises a guanine at a position corresponding to position 444 according to SEQ ID NO:38, or comprises the codon ATG at the positions corresponding to positions 442 to 444 according to SEQ ID NO:38. In some embodiments, the variant PNPLA3 cDNA molecule encoding the variant PNPLA3 Ile148Met protein comprises or consists of the nucleotide sequence according to SEQ ID NO:38.

In some embodiments, the variant PNPLA3 cDNA molecule encoding the variant PNPLA3 Ile144Met protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:39, and comprises a guanine at a position corresponding to position 432 according to SEQ ID NO:39, or comprises the codon ATG at the positions corresponding to positions 430 to 432 according to SEQ ID NO:39. In some embodiments, the variant PNPLA3 cDNA molecule encoding the variant PNPLA3 Ile144Met protein comprises or consists of a nucleic acid sequence that has at least about 95%, at least about 96%, at least about 97%, at least about 98%, or at least about 99% sequence identity to SEQ ID NO:39, and comprises a guanine at a position corresponding to position 432 according to SEQ ID NO:39, or comprises the codon ATG at the positions corresponding to positions 430 to 432 according to SEQ ID NO:39. In some embodiments, the variant PNPLA3 cDNA molecule encoding the variant PNPLA3 Ile144Met protein comprises or consists of the nucleotide sequence according to SEQ ID NO:39.

In some embodiments, the variant PNPLA3 cDNA molecule comprises less nucleotides than the entire variant PNPLA3 cDNA sequence. In some embodiments, the variant PNPLA3 cDNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, or at least about 600 contiguous nucleotides of SEQ ID NO:38 or SEQ ID NO:39. In some embodiments, the variant PNPLA3 cDNA molecules comprise or consist of at least about 200 to at least about 500 contiguous nucleotides of SEQ ID NO:38 or SEQ ID NO:39. In this regard, the longer cDNA molecules are preferred over the shorter ones. In some embodiments, the variant PNPLA3 cDNA molecules comprise or consist of at least about 50, at least about 60, at least about 70, at least about 80, at least about 90, at least about 100, at least about 200, at least about 300, at least about 400, or at least about 500 contiguous nucleotides of SEQ ID NO:38 or SEQ ID NO:39. In this regard, the longer cDNA molecules are preferred over the shorter ones. In some embodiments, such variant PNPLA3 cDNA molecules include the codon that encodes the methionine at the position that corresponds to position 148 according to SEQ ID NO:42 or the codon that encodes the methionine at the position that corresponds to position 144 according to SEQ ID NO:43. In some embodiments, such variant PNPLA3 cDNA molecules include the guanine at the position corresponding to position 444 according to SEQ ID NO:38 or the guanine at the position corresponding to position 432 according to SEQ ID NO:39. In some embodiments, such variant PNPLA3 cDNA molecules include the codon ATG at the positions corresponding to positions 442 to 444 according to SEQ ID NO:38, or the codon ATG at the positions corresponding to positions 430 to 432 according to SEQ ID NO:39.

The amino acid sequences for four HSD17B13 isoform proteins associated with the functional HSD17B13 protein are set forth in SEQ ID NO:21 (Isoform A), SEQ ID NO:22 (Isoform B), SEQ ID NO:25 (Isoform E), and SEQ ID NO:29 (Isoform I). The HSD17B13 protein having SEQ ID NO:21 (Isoform A) is 300 amino acids in length. The HSD17B13 protein having SEQ ID NO:22 (Isoform B) is 264 amino acids in length. The HSD17B13 protein having SEQ ID NO:25 (Isoform E) is 324 amino acids in length. The HSD17B13 protein having SEQ ID NO:29 (Isoform I) is 271 amino acids in length.

In some embodiments, an HSD17B13 isoform protein associated with the functional HSD17B13 protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:21 (Isoform A). In some embodiments, the HSD17B13 isoform protein associated with the functional HSD17B13 protein comprises an amino acid sequence that has at least about 95%, at least about 96%, at least about 97%, at least about 98%, or at least about 99% sequence identity to the amino acid sequence according to SEQ ID NO:21 (Isoform A). In some embodiments, the HSD17B13 isoform protein associated with the functional HSD17B13 protein comprises or consists of the amino acid sequence according to SEQ ID NO:21 (Isoform A).

In some embodiments, an HSD17B13 isoform protein associated with the functional HSD17B13 protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:22 (Isoform B). In some embodiments, the HSD17B13 isoform protein associated with the functional HSD17B13 protein comprises an amino acid sequence that has at least about 95%, at least about 96%, at least about 97%, at least about 98%, or at least about 99% sequence identity to the amino acid sequence according to SEQ ID NO:22 (Isoform B). In some embodiments, the HSD17B13 isoform protein associated with the functional HSD17B13 protein comprises or consists of the amino acid sequence according to SEQ ID NO:22 (Isoform B).

In some embodiments, an HSD17B13 isoform protein associated with the functional HSD17B13 protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:25 (Isoform E). In some embodiments, the HSD17B13 isoform protein associated with the functional HSD17B13 protein comprises an amino acid sequence that has at least about 95%, at least about 96%, at least about 97%, at least about 98%, or at least about 99% sequence identity to the amino acid sequence according to SEQ ID NO:25 (Isoform E). In some embodiments, the HSD17B13 isoform protein associated with the functional HSD17B13 protein comprises or consists of the amino acid sequence according to SEQ ID NO:25 (Isoform E).

In some embodiments, an HSD17B13 isoform protein associated with the functional HSD17B13 protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:29 (Isoform I). In some embodiments, the HSD17B13 isoform protein associated with the functional HSD17B13 protein comprises an amino acid sequence that has at least about 95%, at least about 96%, at least about 97%, at least about 98%, or at least about 99% sequence identity to the amino acid sequence according to SEQ ID NO:29 (Isoform I). In some embodiments, the HSD17B13 isoform protein associated with the functional HSD17B13 protein comprises or consists of the amino acid sequence according to SEQ ID NO:29 (Isoform I).

The amino acid sequences for five HSD17B13 isoform proteins associated with the loss-of-function rs72613567 HSD17B13 protein (SEQ ID NO:2) are set forth in SEQ ID NO:23 (Isoform C), SEQ ID NO:24 (Isoform D), SEQ ID NO:26 (Isoform F), SEQ ID NO:27 (Isoform G), and SEQ ID NO:28 (Isoform H). The HSD17B13 protein having SEQ ID NO:23 (Isoform C) is 261 amino acids in length. The HSD17B13 protein having SEQ ID NO:24 (Isoform D) is 274 amino acids in length. The HSD17B13 protein having SEQ ID NO:26 (Isoform F) is 284 amino acids in length. The HSD17B13 protein having SEQ ID NO:27 (Isoform G) is 238 amino acids in length. The HSD17B13 protein having SEQ ID NO:28 (Isoform H) is 298 amino acids in length.

In some embodiments, an HSD17B13 variant protein associated with a loss-of-function comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:23 (Isoform C). In some embodiments, the HSD17B13 variant protein associated with a loss-of-function comprises an amino acid sequence that has at least about 95%, at least about 96%, at least about 97%, at least about 98%, or at least about 99% sequence identity to the amino acid sequence according to SEQ ID NO:23 (Isoform C). In some embodiments, the HSD17B13 variant protein associated with a loss-of-function comprises or consists of the amino acid sequence according to SEQ ID NO:23 (Isoform C).

In some embodiments, an HSD17B13 variant protein associated with a loss-of-function comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:24 (Isoform D). In some embodiments, the HSD17B13 variant protein associated with a loss-of-function comprises an amino acid sequence that has at least about 95%, at least about 96%, at least about 97%, at least about 98%, or at least about 99% sequence identity to the amino acid sequence according to SEQ ID NO:24 (Isoform D). In some embodiments, the HSD17B13 variant protein associated with a loss-of-function comprises an amino acid sequence that comprises or consists of the amino acid sequence according to SEQ ID NO:24 (Isoform D).

In some embodiments, an HSD17B13 variant protein associated with a loss-of-function comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:26 (Isoform F). In some embodiments, the HSD17B13 variant protein associated with a loss-of-function comprises an amino acid sequence that has at least about 95%, at least about 96%, at least about 97%, at least about 98%, or at least about 99% sequence identity to the amino acid sequence according to SEQ ID NO:26 (Isoform F). In some embodiments, the HSD17B13 variant protein associated with a loss-of-function comprises or consists of the amino acid sequence according to SEQ ID NO:26 (Isoform F).

In some embodiments, an HSD17B13 variant protein associated with a loss-of-function comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:27 (Isoform G). In some embodiments, the HSD17B13 variant protein associated with a loss-of-function comprises an amino acid sequence that has at least about 95%, at least about 96%, at least about 97%, at least about 98%, or at least about 99% sequence identity to the amino acid sequence according to SEQ ID NO:27 (Isoform G). In some embodiments, the HSD17B13 variant protein associated with a loss-of-function comprises or consists of the amino acid sequence according to SEQ ID NO:27 (Isoform G).

In some embodiments, an HSD17B13 variant protein associated with a loss-of-function comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:28 (Isoform H). In some embodiments, the HSD17B13 variant protein associated with a loss-of-function comprises an amino acid sequence that has at least about 95%, at least about 96%, at least about 97%, at least about 98%, or at least about 99% sequence identity to the amino acid sequence according to SEQ ID NO:28 (Isoform H). In some embodiments, the HSD17B13 variant protein associated with a loss-of-function comprises or consists of the amino acid sequence according to SEQ ID NO:28 (Isoform H).

In some embodiments, the HSD17B13 isoform proteins associated with the functional HSD17B13 protein and the HSD17B13 variant proteins associated with a loss-of-function are fragments of the proteins described above. In some embodiments, the fragments comprise at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 150, or at least about 200 contiguous amino acid residues of the encoded polypeptide (such as the polypeptides having the amino acid sequence of SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:29). In this regard, the longer fragments are preferred over the shorter ones. In some embodiments, the fragments comprise at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 contiguous amino acid residues of the encoded polypeptide. In this regard, the longer fragments are preferred over the shorter ones.

A nucleic acid sequence for the functional HSD17B13 genomic DNA molecule is set forth in SEQ ID NO:1. The functional HSD17B13 genomic DNA molecule having SEQ ID NO:1 comprises an adenine at position 12,667.

In some embodiments, the functional HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21 (Isoform A). In some embodiments, the functional HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:21 (Isoform A). In some embodiments, the functional HSD17B13 genomic DNA molecule comprises or consists a nucleic acid sequence that encodes an HSD17B13 isoform protein that comprises or consists of an amino acid sequence according to SEQ ID NO:21 (Isoform A).

In some embodiments, the functional HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:22 (Isoform B). In some embodiments, the functional HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:22 (Isoform B). In some embodiments, the functional HSD17B13 genomic DNA molecule comprises or consists a nucleic acid sequence that encodes an HSD17B13 isoform protein that comprises or consists of an amino acid sequence according to SEQ ID NO:22 (Isoform B).

In some embodiments, the functional HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25 (Isoform E). In some embodiments, the functional HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:25 (Isoform E). In some embodiments, the functional HSD17B13 genomic DNA molecule comprises or consists a nucleic acid sequence that encodes an HSD17B13 isoform protein that comprises or consists of an amino acid sequence according to SEQ ID NO:25 (Isoform E).

In some embodiments, the functional HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29 (Isoform I). In some embodiments, the functional HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:29 (Isoform I). In some embodiments, the functional HSD17B13 genomic DNA molecule comprises or consists a nucleic acid sequence that encodes an HSD17B13 isoform protein that comprises or consists of an amino acid sequence according to SEQ ID NO:29 (Isoform I).

In some embodiments, the functional HSD17B13 genomic DNA molecule comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:1. In some embodiments, the functional HSD17B13 genomic DNA molecule comprises or consists of a nucleic acid sequence that has at least about 95%, at least about 96%, at least about 97%, at least about 98%, or at least about 99% sequence identity to SEQ ID NO:1. In some embodiments, the functional HSD17B13 genomic DNA molecule comprises or consists a nucleic acid sequence according to SEQ ID NO:21.

A nucleic acid sequence for the variant HSD17B13 genomic DNA molecule encoding an HSD17B13 variant protein associated with a loss-of-function is set forth in SEQ ID NO:2. The variant HSD17B13 genomic DNA molecule having SEQ ID NO:2 comprises a thymine at position 12,667.

In some embodiments, the variant HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:23 (Isoform C). In some embodiments, the variant HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:23 (Isoform C). In some embodiments, the variant HSD17B13 genomic DNA molecule comprises or consists a nucleic acid sequence that encodes an HSD17B13 isoform protein that comprises or consists of an amino acid sequence according to SEQ ID NO:23 (Isoform C).

In some embodiments, the variant HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24 (Isoform D). In some embodiments, the variant HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:24 (Isoform D). In some embodiments, the variant HSD17B13 genomic DNA molecule comprises or consists a nucleic acid sequence that encodes an HSD17B13 isoform protein that comprises or consists of an amino acid sequence according to SEQ ID NO:24 (Isoform D).

In some embodiments, the variant HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26 (Isoform F). In some embodiments, the variant HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:26 (Isoform F). In some embodiments, the variant HSD17B13 genomic DNA molecule comprises or consists a nucleic acid sequence that encodes an HSD17B13 isoform protein that comprises or consists of an amino acid sequence according to SEQ ID NO:26 (Isoform F).

In some embodiments, the variant HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:27 (Isoform G). In some embodiments, the variant HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:27 (Isoform G). In some embodiments, the variant HSD17B13 genomic DNA molecule comprises or consists a nucleic acid sequence that encodes an HSD17B13 isoform protein that comprises or consists of an amino acid sequence according to SEQ ID NO:27 (Isoform G).

In some embodiments, the variant HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:28 (Isoform H). In some embodiments, the variant HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:28 (Isoform H). In some embodiments, the variant HSD17B13 genomic DNA molecule comprises or consists a nucleic acid sequence that encodes an HSD17B13 isoform protein that comprises or consists of an amino acid sequence according to SEQ ID NO:28 (Isoform H).

In some embodiments, the variant HSD17B13 genomic DNA molecule comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2. In some embodiments, the variant HSD17B13 genomic DNA molecule comprises or consists of a nucleic acid sequence that has at least about 95%, at least about 96%, at least about 97%, at least about 98%, or at least about 99% sequence identity to SEQ ID NO:2. In some embodiments, the variant HSD17B13 genomic DNA molecule comprises or consists a nucleic acid sequence according to SEQ ID NO:2.

In some embodiments, the functional HSD17B13 genomic DNA and variant HSD17B13 genomic DNA molecules comprise less than the entire genomic DNA sequence. In some embodiments, the functional HSD17B13 genomic DNA and variant HSD17B13 genomic DNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, or at least about 11500 contiguous nucleotides of SEQ ID NO:1 (functional HSD17B13 genomic DNA) or SEQ ID NO:2 (variant HSD17B13 genomic DNA). In some embodiments, the functional HSD17B13 genomic DNA and variant HSD17B13 genomic DNA molecules comprise or consist of at least about 1000 to at least about 2000 contiguous nucleotides of SEQ ID NO:1 (functional HSD17B13 genomic DNA) or SEQ ID NO:2 (variant HSD17B13 genomic DNA).

In some embodiments, the functional HSD17B13 genomic DNA and variant HSD17B13 genomic DNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, or at least about 2500 contiguous nucleotides of SEQ ID NO:1 (functional HSD17B13 genomic DNA) or SEQ ID NO:2 (variant HSD17B13 genomic DNA).

The nucleic acid sequences for four HSD17B13 RNA transcripts encoding isoform proteins associated with the functional HSD17B13 protein are set forth in SEQ ID NO:44 (Transcript A), SEQ ID NO:45 (Transcript B), SEQ ID NO:48 (Transcript E), and SEQ ID NO:52 (Transcript I).

In some embodiments, an HSD17B13 RNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21 (Isoform A). In some embodiments, the HSD17B13 RNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:21 (Isoform A). In some embodiments, the HSD17B13 RNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:21 (Isoform A).

In some embodiments, an HSD17B13 RNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:22 (Isoform B). In some embodiments, the HSD17B13 RNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:22 (Isoform B). In some embodiments, the HSD17B13 RNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:22 (Isoform B).

In some embodiments, an HSD17B13 RNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25 (Isoform E). In some embodiments, the HSD17B13 RNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:25 (Isoform E). In some embodiments, the HSD17B13 RNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:25 (Isoform E).

In some embodiments, an HSD17B13 RNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29 (Isoform I). In some embodiments, the HSD17B13 RNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:29 (Isoform I). In some embodiments, the HSD17B13 RNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:29 (Isoform I).

In some embodiments, an HSD17B13 RNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:44 (Transcript A). In some embodiments, the HSD17B13 RNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:44 (Transcript A). In some embodiments, the HSD17B13 RNA transcript encoding the isoform protein associated with the functional HSD17B13 protein comprises or consists of a nucleic acid sequence according to SEQ ID NO:44 (Transcript A).

In some embodiments, an HSD17B13 RNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:45 (Transcript B). In some embodiments, the HSD17B13 RNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:45 (Transcript B). In some embodiments, the HSD17B13 RNA transcript encoding the isoform protein associated with the functional HSD17B13 protein comprises or consists of a nucleic acid sequence according to SEQ ID NO:45 (Transcript B).

In some embodiments, an HSD17B13 RNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:48 (Transcript E). In some embodiments, the HSD17B13 RNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:48 (Transcript E). In some embodiments, the HSD17B13 RNA transcript encoding the isoform protein associated with the functional HSD17B13 protein comprises or consists of a nucleic acid sequence according to SEQ ID NO:48 (Transcript E).

In some embodiments, an HSD17B13 RNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:52 (Transcript I). In some embodiments, the HSD17B13 RNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:52 (Transcript I). In some embodiments, the HSD17B13 RNA transcript encoding the isoform protein associated with the functional HSD17B13 protein comprises or consists of a nucleic acid sequence according to SEQ ID NO:52 (Transcript I).

The nucleic acid sequences for five HSD17B13 RNA transcripts encoding isoform proteins associated with a loss-of-function are set forth in SEQ ID NO:46 (Transcript C), SEQ ID NO:47 (Transcript D), SEQ ID NO:49 (Transcript F), SEQ ID NO:50 (Transcript G), and SEQ ID NO:51 (Transcript H).

In some embodiments, an HSD17B13 RNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:23 (Isoform C). In some embodiments, the HSD17B13 RNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:23 (Isoform C). In some embodiments, the HSD17B13 RNA transcript encoding the isoform protein associated with a loss-of-function comprises or consists of a nucleic acid sequence that encodes an HSD17B13 isoform protein that comprises or consists of an amino acid sequence according to SEQ ID NO:23 (Isoform C).

In some embodiments, an HSD17B13 RNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24 (Isoform D). In some embodiments, the HSD17B13 RNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:24 (Isoform D). In some embodiments, the HSD17B13 RNA transcript encoding the isoform protein associated with a loss-of-function comprises or consists of a nucleic acid sequence that encodes an HSD17B13 isoform protein that comprises or consists of an amino acid sequence according to SEQ ID NO:24 (Isoform D).

In some embodiments, an HSD17B13 RNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26 (Isoform F). In some embodiments, the HSD17B13 RNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:26 (Isoform F). In some embodiments, the HSD17B13 RNA transcript encoding the isoform protein associated with a loss-of-function comprises or consists of a nucleic acid sequence that encodes an HSD17B13 isoform protein that comprises or consists of an amino acid sequence according to SEQ ID NO:26 (Isoform F).

In some embodiments, an HSD17B13 RNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:27 (Isoform G). In some embodiments, the HSD17B13 RNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:27 (Isoform G). In some embodiments, the HSD17B13 RNA transcript encoding the isoform protein associated with a loss-of-function comprises or consists of a nucleic acid sequence that encodes an HSD17B13 isoform protein that comprises or consists of an amino acid sequence according to SEQ ID NO:27 (Isoform G).

In some embodiments, an HSD17B13 RNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:28 (Isoform H). In some embodiments, the HSD17B13 RNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:28 (Isoform H). In some embodiments, the HSD17B13 RNA transcript encoding the isoform protein associated with a loss-of-function comprises or consists of a nucleic acid sequence that encodes an HSD17B13 isoform protein that comprises or consists of an amino acid sequence according to SEQ ID NO:28 (Isoform H).

In some embodiments, an HSD17B13 RNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:46 (Transcript C). In some embodiments, the HSD17B13 RNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:46 (Transcript C). In some embodiments, the HSD17B13 RNA transcript encoding the isoform protein associated with a loss-of-function comprises or consists of a nucleic acid sequence according to SEQ ID NO:46 (Transcript C).

In some embodiments, an HSD17B13 RNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:47 (Transcript D). In some embodiments, the HSD17B13 RNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:47 (Transcript D). In some embodiments, the HSD17B13 RNA transcript encoding the isoform protein associated with a loss-of-function comprises or consists of a nucleic acid sequence according to SEQ ID NO:47 (Transcript D).

In some embodiments, an HSD17B13 RNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:49 (Transcript F). In some embodiments, the HSD17B13 RNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:49 (Transcript F). In some embodiments, the HSD17B13 RNA transcript encoding the isoform protein associated with a loss-of-function comprises or consists of a nucleic acid sequence according to SEQ ID NO:49 (Transcript F).

In some embodiments, an HSD17B13 RNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:50 (Transcript G). In some embodiments, the HSD17B13 RNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:50 (Transcript G). In some embodiments, the HSD17B13 RNA transcript encoding the isoform protein associated with a loss-of-function comprises or consists of a nucleic acid sequence according to SEQ ID NO:50 (Transcript G).

In some embodiments, an HSD17B13 RNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:51 (Transcript H). In some embodiments, the HSD17B13 RNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:51 (Transcript H). In some embodiments, the HSD17B13 RNA transcript encoding the isoform protein associated with a loss-of-function comprises or consists of a nucleic acid sequence according to SEQ ID NO:51 (Transcript H).

In some embodiments, the functional HSD17B13 RNA transcripts and variant HSD17B13 RNA transcripts comprise less than the RNA transcript sequence. In some embodiments, the functional HSD17B13 RNA transcripts and variant HSD17B13 RNA transcripts comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, or at least about 2500 contiguous nucleotides of SEQ ID NO:44, SEQ ID NO:45, SEQ ID NO:48, or SEQ ID NO:52 (functional HSD17B13 RNA transcripts) or SEQ ID NO:46, SEQ ID NO:47, SEQ ID NO:49, SEQ ID NO:50, or SEQ ID NO:51 (variant HSD17B13 RNA transcripts). In some embodiments, the functional HSD17B13 RNA transcripts and variant HSD17B13 RNA transcripts comprise less than the RNA transcript sequence. In some embodiments, the functional HSD17B13 RNA transcripts and variant HSD17B13 RNA transcripts comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, or at least about 500 contiguous nucleotides of SEQ ID NO:44, SEQ ID NO:45, SEQ ID NO:48, or SEQ ID NO:52 (functional HSD17B13 RNA transcripts) or SEQ ID NO:46, SEQ ID NO:47, SEQ ID NO:49, SEQ ID NO:50, or SEQ ID NO:51 (variant HSD17B13 RNA transcripts). In some embodiments, the functional HSD17B13 RNA transcripts and variant HSD17B13 RNA transcripts comprise or consist of at least about 1000 to at least about 2000 contiguous nucleotides of SEQ ID NO:44, SEQ ID NO:45, SEQ ID NO:48, or SEQ ID NO:52 (functional HSD17B13 RNA transcripts) or SEQ ID NO:46, SEQ ID NO:47, SEQ ID NO:49, SEQ ID NO:50, or SEQ ID NO:51 (variant HSD17B13 RNA transcripts).

The nucleic acid sequences for four HSD17B13 cDNA transcripts encoding isoform proteins associated with the functional HSD17B13 protein are set forth in SEQ ID NO:53 (Transcript A), SEQ ID NO:54 (Transcript B), SEQ ID NO:57 (Transcript E), and SEQ ID NO:61 (Transcript I).

In some embodiments, an HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21 (Isoform A). In some embodiments, the HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:21 (Isoform A). In some embodiments, the HSD17B13 cDNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:21 (Isoform A).

In some embodiments, an HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:22 (Isoform B). In some embodiments, the HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:22 (Isoform B). In some embodiments, the HSD17B13 cDNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:22 (Isoform B).

In some embodiments, an HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25 (Isoform E). In some embodiments, the HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:25 (Isoform E). In some embodiments, the HSD17B13 cDNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:25 (Isoform E).

In some embodiments, an HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29 (Isoform I). In some embodiments, the HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:29 (Isoform I). In some embodiments, the HSD17B13 cDNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:29 (Isoform I).

In some embodiments, an HSD17B13 cDNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:53 (Transcript A). In some embodiments, the HSD17B13 cDNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:53 (Transcript A). In some embodiments, the HSD17B13 cDNA transcript encoding the isoform protein associated with the functional HSD17B13 protein comprises or consists of a nucleic acid sequence according to SEQ ID NO:53 (Transcript A).

In some embodiments, an HSD17B13 cDNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:54 (Transcript B). In some embodiments, the HSD17B13 cDNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:54 (Transcript B). In some embodiments, the HSD17B13 cDNA transcript encoding the isoform protein associated with the functional HSD17B13 protein comprises or consists of a nucleic acid sequence according to SEQ ID NO:54 (Transcript B).

In some embodiments, an HSD17B13 cDNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:57 (Transcript E). In some embodiments, the HSD17B13 cDNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:57 (Transcript E). In some embodiments, the HSD17B13 cDNA transcript encoding the isoform protein associated with the functional HSD17B13 protein comprises or consists of a nucleic acid sequence according to SEQ ID NO:57 (Transcript E).

In some embodiments, an HSD17B13 cDNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:61 (Transcript I). In some embodiments, the HSD17B13 cDNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:61 (Transcript I). In some embodiments, the HSD17B13 cDNA transcript encoding the isoform protein associated with the functional HSD17B13 protein comprises or consists of a nucleic acid sequence according to SEQ ID NO:61 (Transcript I).

The nucleic acid sequences for five HSD17B13 cDNA transcripts encoding isoform proteins associated with a loss-of-function are set forth in SEQ ID NO:55 (Transcript C), SEQ ID NO:56 (Transcript D), SEQ ID NO:58 (Transcript F), SEQ ID NO:59 (Transcript G), and SEQ ID NO:60 (Transcript H).

In some embodiments, an HSD17B13 cDNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:23 (Isoform C). In some embodiments, the HSD17B13 cDNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:23 (Isoform C). In some embodiments, the HSD17B13 cDNA transcript encoding the isoform protein associated with a loss-of-function comprises or consists of a nucleic acid sequence that encodes an HSD17B13 isoform protein that comprises or consists of an amino acid sequence according to SEQ ID NO:23 (Isoform C).

In some embodiments, an HSD17B13 cDNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24 (Isoform D). In some embodiments, the HSD17B13 cDNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:24 (Isoform D). In some embodiments, the HSD17B13 cDNA transcript encoding the isoform protein associated with a loss-of-function comprises or consists of a nucleic acid sequence that encodes an HSD17B13 isoform protein that comprises or consists of an amino acid sequence according to SEQ ID NO:24 (Isoform D).

In some embodiments, an HSD17B13 cDNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26 (Isoform F). In some embodiments, the HSD17B13 cDNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:26 (Isoform F). In some embodiments, the HSD17B13 cDNA transcript encoding the isoform protein associated with a loss-of-function comprises or consists of a nucleic acid sequence that encodes an HSD17B13 isoform protein that comprises or consists of an amino acid sequence according to SEQ ID NO:26 (Isoform F).

In some embodiments, an HSD17B13 cDNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:27 (Isoform G). In some embodiments, the HSD17B13 cDNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:27 (Isoform G). In some embodiments, the HSD17B13 cDNA transcript encoding the isoform protein associated with a loss-of-function comprises or consists of a nucleic acid sequence that encodes an HSD17B13 isoform protein that comprises or consists of an amino acid sequence according to SEQ ID NO:27 (Isoform G).

In some embodiments, an HSD17B13 cDNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:28 (Isoform H). In some embodiments, the HSD17B13 cDNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:28 (Isoform H). In some embodiments, the HSD17B13 cDNA transcript encoding the isoform protein associated with a loss-of-function comprises or consists of a nucleic acid sequence that encodes an HSD17B13 isoform protein that comprises or consists of an amino acid sequence according to SEQ ID NO:28 (Isoform H).

In some embodiments, an HSD17B13 cDNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:55 (Transcript C). In some embodiments, the HSD17B13 cDNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:55 (Transcript C). In some embodiments, the HSD17B13 cDNA transcript encoding the isoform protein associated with a loss-of-function comprises or consists of a nucleic acid sequence according to SEQ ID NO:55 (Transcript C).

In some embodiments, an HSD17B13 cDNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:56 (Transcript D). In some embodiments, the HSD17B13 cDNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:56 (Transcript D). In some embodiments, the HSD17B13 cDNA transcript encoding the isoform protein associated with a loss-of-function comprises or consists of a nucleic acid sequence according to SEQ ID NO:56 (Transcript D).

In some embodiments, an HSD17B13 cDNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:58 (Transcript F). In some embodiments, the HSD17B13 cDNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:58 (Transcript F). In some embodiments, the HSD17B13 cDNA transcript encoding the isoform protein associated with a loss-of-function comprises or consists of a nucleic acid sequence according to SEQ ID NO:58 (Transcript F).

In some embodiments, an HSD17B13 cDNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:59 (Transcript G). In some embodiments, the HSD17B13 cDNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:59 (Transcript G). In some embodiments, the HSD17B13 cDNA transcript encoding the isoform protein associated with a loss-of-function comprises or consists of a nucleic acid sequence according to SEQ ID NO:59 (Transcript G).

In some embodiments, an HSD17B13 cDNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:60 (Transcript H). In some embodiments, the HSD17B13 cDNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:60 (Transcript H). In some embodiments, the HSD17B13 cDNA transcript encoding the isoform protein associated with a loss-of-function comprises or consists of a nucleic acid sequence according to SEQ ID NO:60 (Transcript H).

In some embodiments, the HSD17B13 cDNA transcripts comprise less than the cDNA transcript sequence. In some embodiments, the HSD17B13 cDNA transcripts comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, or at least about 2500 contiguous nucleotides of SEQ ID NO:53, SEQ ID NO:54, SEQ ID NO:57, or SEQ ID NO:61 or SEQ ID NO:55, SEQ ID NO:56, SEQ ID NO:58, SEQ ID NO:59, or SEQ ID NO:60. In some embodiments, the HSD17B13 cDNA transcripts comprise less than the cDNA transcript sequence. In some embodiments, the HSD17B13 cDNA transcripts comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, or at least about 500 contiguous nucleotides of SEQ ID NO:53, SEQ ID NO:54, SEQ ID NO:57, or SEQ ID NO:61 or SEQ ID NO:55, SEQ ID NO:56, SEQ ID NO:58, SEQ ID NO:59, or SEQ ID NO:60. In some embodiments, the HSD17B13 cDNA transcripts comprise or consist of at least about 1000 to at least about 2000 contiguous nucleotides of SEQ ID NO:53, SEQ ID NO:54, SEQ ID NO:57, or SEQ ID NO:61 or SEQ ID NO:55, SEQ ID NO:56, SEQ ID NO:58, SEQ ID NO:59, or SEQ ID NO:60.

The nucleic acid sequences for four HSD17B13 mRNA molecules encoding isoform proteins associated with the functional HSD17B13 protein are set forth in SEQ ID NO:3 (Transcript A), SEQ ID NO:4 (Transcript B), SEQ ID NO:7 (Transcript E), and SEQ ID NO:11 (Transcript I).

In some embodiments, an HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21 (Isoform A). In some embodiments, the HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:21 (Isoform A). In some embodiments, the HSD17B13 mRNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:21 (Isoform A).

In some embodiments, an HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:22 (Isoform B). In some embodiments, the HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:22 (Isoform B). In some embodiments, the HSD17B13 mRNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:22 (Isoform B).

In some embodiments, an HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25 (Isoform E). In some embodiments, the HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:25 (Isoform E). In some embodiments, the HSD17B13 mRNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:25 (Isoform E).

In some embodiments, an HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29 (Isoform I). In some embodiments, the HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:29 (Isoform I). In some embodiments, the HSD17B13 mRNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:29 (Isoform I).

In some embodiments, an HSD17B13 mRNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:3 (Transcript A). In some embodiments, the HSD17B13 mRNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:3 (Transcript A). In some embodiments, the HSD17B13 mRNA molecule encoding the isoform protein associated with the functional HSD17B13 protein comprises or consists of a nucleic acid sequence according to SEQ ID NO:3 (Transcript A).

In some embodiments, an HSD17B13 mRNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:4 (Transcript B). In some embodiments, the HSD17B13 mRNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:4 (Transcript B). In some embodiments, the HSD17B13 mRNA molecule encoding the isoform protein associated with the functional HSD17B13 protein comprises or consists of a nucleic acid sequence according to SEQ ID NO:4 (Transcript B).

In some embodiments, an HSD17B13 mRNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:7 (Transcript E). In some embodiments, the HSD17B13 mRNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:7 (Transcript E). In some embodiments, the HSD17B13 mRNA molecule encoding the isoform protein associated with the functional HSD17B13 protein comprises or consists of a nucleic acid sequence according to SEQ ID NO:7 (Transcript E).

In some embodiments, an HSD17B13 mRNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:11 (Transcript I). In some embodiments, the HSD17B13 mRNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:11 (Transcript I). In some embodiments, the HSD17B13 mRNA molecule encoding the isoform protein associated with the functional HSD17B13 protein comprises or consists of a nucleic acid sequence according to SEQ ID NO:11 (Transcript I).

The nucleic acid sequences for five HSD17B13 mRNA molecules encoding isoform proteins associated with a loss-of-function are set forth in SEQ ID NO:5 (Transcript C), SEQ ID NO:6 (Transcript D), SEQ ID NO:8 (Transcript F), SEQ ID NO:9 (Transcript G), and SEQ ID NO:10 (Transcript H).

In some embodiments, an HSD17B13 mRNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:23 (Isoform C). In some embodiments, the HSD17B13 mRNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:23 (Isoform C). In some embodiments, the HSD17B13 mRNA molecule encoding the isoform protein associated with a loss-of-function comprises or consists of a nucleic acid sequence that encodes an HSD17B13 isoform protein that comprises or consists of an amino acid sequence according to SEQ ID NO:23 (Isoform C).

In some embodiments, an HSD17B13 mRNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24 (Isoform D). In some embodiments, the HSD17B13 mRNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:24 (Isoform D). In some embodiments, the HSD17B13 mRNA molecule encoding the isoform protein associated with a loss-of-function comprises or consists of a nucleic acid sequence that encodes an HSD17B13 isoform protein that comprises or consists of an amino acid sequence according to SEQ ID NO:24 (Isoform D).

In some embodiments, an HSD17B13 mRNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26 (Isoform F). In some embodiments, the HSD17B13 mRNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:26 (Isoform F). In some embodiments, the HSD17B13 mRNA molecule encoding the isoform protein associated with a loss-of-function comprises or consists of a nucleic acid sequence that encodes an HSD17B13 isoform protein that comprises or consists of an amino acid sequence according to SEQ ID NO:26 (Isoform F).

In some embodiments, an HSD17B13 mRNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:27 (Isoform G). In some embodiments, the HSD17B13 mRNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:27 (Isoform G). In some embodiments, the HSD17B13 mRNA molecule encoding the isoform protein associated with a loss-of-function comprises or consists of a nucleic acid sequence that encodes an HSD17B13 isoform protein that comprises or consists of an amino acid sequence according to SEQ ID NO:27 (Isoform G).

In some embodiments, an HSD17B13 mRNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:28 (Isoform H). In some embodiments, the HSD17B13 mRNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:28 (Isoform H). In some embodiments, the HSD17B13 mRNA molecule encoding the isoform protein associated with a loss-of-function comprises or consists of a nucleic acid sequence that encodes an HSD17B13 isoform protein that comprises or consists of an amino acid sequence according to SEQ ID NO:28 (Isoform H).

In some embodiments, an HSD17B13 mRNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:5 (Transcript C). In some embodiments, the HSD17B13 mRNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:5 (Transcript C). In some embodiments, the HSD17B13 mRNA molecule encoding the isoform protein associated with a loss-of-function comprises or consists of a nucleic acid sequence according to SEQ ID NO:5 (Transcript C).

In some embodiments, an HSD17B13 mRNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:6 (Transcript D). In some embodiments, the HSD17B13 mRNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:6 (Transcript D). In some embodiments, the HSD17B13 mRNA molecule encoding the isoform protein associated with a loss-of-function comprises or consists of a nucleic acid sequence according to SEQ ID NO:6 (Transcript D).

In some embodiments, an HSD17B13 mRNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:8 (Transcript F). In some embodiments, the HSD17B13 mRNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:8 (Transcript F). In some embodiments, the HSD17B13 mRNA molecule encoding the isoform protein associated with a loss-of-function comprises or consists of a nucleic acid sequence according to SEQ ID NO:8 (Transcript F).

In some embodiments, an HSD17B13 mRNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:9 (Transcript G). In some embodiments, the HSD17B13 mRNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:9 (Transcript G). In some embodiments, the HSD17B13 mRNA molecule encoding the isoform protein associated with a loss-of-function comprises or consists of a nucleic acid sequence according to SEQ ID NO:9 (Transcript G).

In some embodiments, an HSD17B13 mRNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:10 (Transcript H). In some embodiments, the HSD17B13 mRNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:10 (Transcript H). In some embodiments, the HSD17B13 mRNA molecule encoding the isoform protein associated with a loss-of-function comprises or consists of a nucleic acid sequence according to SEQ ID NO:10 (Transcript H).

In some embodiments, the HSD17B13 mRNA molecules comprise less nucleotides than the entire mRNA sequence. In some embodiments, the HSD17B13 mRNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, or at least about 900 contiguous nucleotides of SEQ ID NO:3, SEQ ID NO:4, SEQ ID NO:7, or SEQ ID NO:11, or SEQ ID NO:5, SEQ ID NO:6, SEQ ID NO:8, SEQ ID NO:9, or SEQ ID NO:10. In some embodiments, the HSD17B13 mRNA molecules comprise or consist of at least about 200 to at least about 500 contiguous nucleotides of SEQ ID NO:3, SEQ ID NO:4, SEQ ID NO:7, or SEQ ID NO:11, or SEQ ID NO:5, SEQ ID NO:6, SEQ ID NO:8, SEQ ID NO:9, or SEQ ID NO:10. In this regard, the longer mRNA molecules are preferred over the shorter ones. In some embodiments, the HSD17B13 mRNA molecules comprise or consist of at least about 50, at least about 60, at least about 70, at least about 80, at least about 90, at least about 100, at least about 200, at least about 300, at least about 400, or at least about 500 contiguous nucleotides of SEQ ID NO:3, SEQ ID NO:4, SEQ ID NO:7, or SEQ ID NO:11, or SEQ ID NO:5, SEQ ID NO:6, SEQ ID NO:8, SEQ ID NO:9, or SEQ ID NO:10. In this regard, the longer mRNA molecules are preferred over the shorter ones.

The nucleic acid sequences for four HSD17B13 cDNA molecules encoding isoform proteins associated with the functional HSD17B13 protein are set forth in SEQ ID NO:12 (Transcript A), SEQ ID NO:13 (Transcript B), SEQ ID NO:16 (Transcript E), and SEQ ID NO:20 (Transcript I).

In some embodiments, an HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21 (Isoform A). In some embodiments, the HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:21 (Isoform A). In some embodiments, the HSD17B13 cDNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:21 (Isoform A).

In some embodiments, an HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:22 (Isoform B). In some embodiments, the HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:22 (Isoform B). In some embodiments, the HSD17B13 cDNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:22 (Isoform B).

In some embodiments, an HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25 (Isoform E). In some embodiments, the HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:25 (Isoform E). In some embodiments, the HSD17B13 cDNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:25 (Isoform E).

In some embodiments, an HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29 (Isoform I). In some embodiments, the HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:29 (Isoform I). In some embodiments, the HSD17B13 cDNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:29 (Isoform I).

In some embodiments, an HSD17B13 cDNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:12 (Transcript A). In some embodiments, the HSD17B13 cDNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:12 (Transcript A). In some embodiments, the HSD17B13 cDNA molecule encoding the isoform protein associated with the functional HSD17B13 protein comprises or consists of a nucleic acid sequence according to SEQ ID NO:12 (Transcript A).

In some embodiments, an HSD17B13 cDNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:13 (Transcript B). In some embodiments, the HSD17B13 cDNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:13 (Transcript B). In some embodiments, the HSD17B13 cDNA molecule encoding the isoform protein associated with the functional HSD17B13 protein comprises or consists of a nucleic acid sequence according to SEQ ID NO:13 (Transcript B).

In some embodiments, an HSD17B13 cDNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:16 (Transcript E). In some embodiments, the HSD17B13 cDNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:16 (Transcript E). In some embodiments, the HSD17B13 cDNA molecule encoding the isoform protein associated with the functional HSD17B13 protein comprises or consists of a nucleic acid sequence according to SEQ ID NO:16 (Transcript E).

In some embodiments, an HSD17B13 cDNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:20 (Transcript I). In some embodiments, the HSD17B13 cDNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:20 (Transcript I). In some embodiments, the HSD17B13 cDNA molecule encoding the isoform protein associated with the functional HSD17B13 protein comprises or consists of a nucleic acid sequence according to SEQ ID NO:20 (Transcript I).

The nucleic acid sequences for five HSD17B13 cDNA molecules encoding isoform proteins associated with a loss-of-function are set forth in SEQ ID NO:14 (Transcript C), SEQ ID NO:15 (Transcript D), SEQ ID NO:17 (Transcript F), SEQ ID NO:18 (Transcript G), and SEQ ID NO:19 (Transcript H).

In some embodiments, an HSD17B13 cDNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:23 (Isoform C). In some embodiments, the HSD17B13 cDNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:23 (Isoform C). In some embodiments, the HSD17B13 cDNA molecule encoding the isoform protein associated with a loss-of-function comprises or consists of a nucleic acid sequence that encodes an HSD17B13 isoform protein that comprises or consists of an amino acid sequence according to SEQ ID NO:23 (Isoform C).

In some embodiments, an HSD17B13 cDNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24 (Isoform D). In some embodiments, the HSD17B13 cDNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:24 (Isoform D). In some embodiments, the HSD17B13 cDNA molecule encoding the isoform protein associated with a loss-of-function comprises or consists of a nucleic acid sequence that encodes an HSD17B13 isoform protein that comprises or consists of an amino acid sequence according to SEQ ID NO:24 (Isoform D).

In some embodiments, an HSD17B13 cDNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26 (Isoform F). In some embodiments, the HSD17B13 cDNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:26 (Isoform F). In some embodiments, the HSD17B13 cDNA molecule encoding the isoform protein associated with a loss-of-function comprises or consists of a nucleic acid sequence that encodes an HSD17B13 isoform protein that comprises or consists of an amino acid sequence according to SEQ ID NO:26 (Isoform F).

In some embodiments, an HSD17B13 cDNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:27 (Isoform G). In some embodiments, the HSD17B13 cDNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:27 (Isoform G). In some embodiments, the HSD17B13 cDNA molecule encoding the isoform protein associated with a loss-of-function comprises or consists of a nucleic acid sequence that encodes an HSD17B13 isoform protein that comprises or consists of an amino acid sequence according to SEQ ID NO:27 (Isoform G).

In some embodiments, an HSD17B13 cDNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:28 (Isoform H). In some embodiments, the HSD17B13 cDNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:28 (Isoform H). In some embodiments, the HSD17B13 cDNA molecule encoding the isoform protein associated with a loss-of-function comprises or consists of a nucleic acid sequence that encodes an HSD17B13 isoform protein that comprises or consists of an amino acid sequence according to SEQ ID NO:28 (Isoform H).

In some embodiments, an HSD17B13 cDNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:14 (Transcript C). In some embodiments, the HSD17B13 cDNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:14 (Transcript C). In some embodiments, the HSD17B13 cDNA molecule encoding the isoform protein associated with a loss-of-function comprises or consists of a nucleic acid sequence according to SEQ ID NO:14 (Transcript C).

In some embodiments, an HSD17B13 cDNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:15 (Transcript D). In some embodiments, the HSD17B13 cDNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:15 (Transcript D). In some embodiments, the HSD17B13 cDNA molecule encoding the isoform protein associated with a loss-of-function comprises or consists of a nucleic acid sequence according to SEQ ID NO:15 (Transcript D).

In some embodiments, an HSD17B13 cDNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:17 (Transcript F). In some embodiments, the HSD17B13 cDNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:17 (Transcript F). In some embodiments, the HSD17B13 cDNA molecule encoding the isoform protein associated with a loss-of-function comprises or consists of a nucleic acid sequence according to SEQ ID NO:17 (Transcript F).

In some embodiments, an HSD17B13 cDNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:18 (Transcript G). In some embodiments, the HSD17B13 cDNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:18 (Transcript G). In some embodiments, the HSD17B13 cDNA molecule encoding the isoform protein associated with a loss-of-function comprises or consists of a nucleic acid sequence according to SEQ ID NO:18 (Transcript G).

In some embodiments, an HSD17B13 cDNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:19 (Transcript H). In some embodiments, the HSD17B13 cDNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:19 (Transcript H). In some embodiments, the HSD17B13 cDNA molecule encoding the isoform protein associated with a loss-of-function comprises or consists of a nucleic acid sequence according to SEQ ID NO:19 (Transcript H).

In some embodiments, the HSD17B13 cDNA molecules comprise less nucleotides than the entire cDNA sequence. In some embodiments, the HSD17B13 cDNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, or at least about 900 contiguous nucleotides of SEQ ID NO:12, SEQ ID NO:13, SEQ ID NO:16, or SEQ ID NO:20 or SEQ ID NO:14, SEQ ID NO:15, SEQ ID NO:17, SEQ ID NO:18, or SEQ ID NO:19. In some embodiments, the HSD17B13 cDNA molecules comprise or consist of at least about 200 to at least about 500 contiguous nucleotides of SEQ ID NO:12, SEQ ID NO:13, SEQ ID NO:16, or SEQ ID NO:20 or SEQ ID NO:14, SEQ ID NO:15, SEQ ID NO:17, SEQ ID NO:18, or SEQ ID NO:19. In this regard, the longer cDNA molecules are preferred over the shorter ones. In some embodiments, the HSD17B13 cDNA molecules comprise or consist of at least about 50, at least about 60, at least about 70, at least about 80, at least about 90, at least about 100, at least about 200, at least about 300, at least about 400, or at least about 500 contiguous nucleotides of SEQ ID NO:12, SEQ ID NO:13, SEQ ID NO:16, or SEQ ID NO:20 or SEQ ID NO:14, SEQ ID NO:15, SEQ ID NO:17, SEQ ID NO:18, or SEQ ID NO:19. In this regard, the longer cDNA molecules are preferred over the shorter ones.

The probes and primers described herein can be used to hybridize to any of the functional or variant PNPLA3 genomic DNA molecules, mRNA molecules, or cDNA molecules derived from mRNA molecules described herein. The primers can be used, for example, to amplify portions of any of the functional or variant PNPLA3 genomic DNA molecules, mRNA molecules, or cDNA molecules derived from mRNA molecules described herein, so that the amplifications products can be, for example, detected or sequenced.

For example, the probes and primers can be used to hybridize to any of the wild type PNPLA3 genomic DNA molecules described herein, including the wild type PNPLA3 genomic DNA molecule comprising SEQ ID NO:30. The probes and primers can also be used to hybridize to any of the wild type PNPLA3 mRNA molecules described herein, including the wild type PNPLA3 mRNA molecules comprising SEQ ID NO:32 or SEQ ID NO:33. The probes and primers can also be used to hybridize to any of the wild type PNPLA3 cDNA molecules described herein, including the wild type PNPLA3 cDNA molecules comprising SEQ ID NO:36 or SEQ ID NO:37.

The probes and primers can also be used to hybridize to any of the variant PNPLA3 genomic DNA molecules described herein, including the variant PNPLA3 genomic DNA molecule comprising SEQ ID NO:31. The probes and primers can also be used to hybridize to any of the variant PNPLA3 mRNA molecules described herein, including the variant PNPLA3 mRNA molecules comprising SEQ ID NO:34 or SEQ ID NO:35. The probes and primers can also be used to hybridize to any of the variant PNPLA3 cDNA molecules described herein, including the variant PNPLA3 cDNA molecules comprising SEQ ID NO:38 or SEQ ID NO:39.

The probes can be used, for example, to detect any of the functional or variant HSD17B13 genomic DNA molecules, mRNA molecules, or cDNA molecules derived from mRNA molecules described herein. The primers can be used, for example, to amplify portions of any of the functional or variant HSD17B13 genomic DNA molecules, mRNA molecules, or cDNA molecules derived from mRNA molecules described herein, so that the amplifications products can be, for example, detected or sequenced.

For example, the probes and primers can be used to hybridize to any of the functional HSD17B13 genomic DNA molecules described herein, including the functional HSD17B13 genomic DNA molecule comprising SEQ ID NO:1. The probes and primers can also be used to hybridize to any of the functional HSD17B13 RNA transcripts described herein, including the functional HSD17B13 RNA transcripts comprising SEQ ID NO:44, SEQ ID NO:45, SEQ ID NO:48, or SEQ ID NO:52. The probes and primers can also be used to hybridize to any of the functional HSD17B13 DNA transcripts described herein, including the functional HSD17B13 DNA transcripts comprising SEQ ID NO:53, SEQ ID NO:54, SEQ ID NO:57, or SEQ ID NO:61. The probes and primers can also be used to hybridize to any of the functional HSD17B13 mRNA molecules described herein, including the functional HSD17B13 mRNA molecules comprising SEQ ID NO:3, SEQ ID NO:4, SEQ ID NO:7, or SEQ ID NO:11. The probes and primers can also be used to hybridize to any of the functional HSD17B13 cDNA molecules described herein, including the functional HSD17B13 cDNA molecules comprising SEQ ID NO:12, SEQ ID NO:13, SEQ ID NO:16, or SEQ ID NO:20.

The probes and primers can also be used to hybridize to any of the variant HSD17B13 genomic DNA molecules described herein, including the variant HSD17B13 genomic DNA molecule comprising SEQ ID NO:2. The probes and primers can also be used to hybridize to any of the variant HSD17B13 RNA transcripts described herein, including the variant HSD17B13 RNA transcripts comprising SEQ ID NO:46, SEQ ID NO:47, SEQ ID NO:49, SEQ ID NO:50, or SEQ ID NO:51. The probes and primers can also be used to hybridize to any of the variant HSD17B13 DNA transcripts described herein, including the variant HSD17B13 DNA transcripts comprising SEQ ID NO:55, SEQ ID NO:56, SEQ ID NO:58, SEQ ID NO:59, or SEQ ID NO:60. The probes and primers can also be used to hybridize to any of the variant HSD17B13 mRNA molecules described herein, including the variant HSD17B13 mRNA molecules comprising SEQ ID NO:5, SEQ ID NO:6, SEQ ID NO:8, SEQ ID NO:9, or SEQ ID NO:10. The probes and primers can also be used to hybridize to any of the HSD17B13 cDNA molecules described herein, including the HSD17B13 cDNA molecules comprising SEQ ID NO:14, SEQ ID NO:15, SEQ ID NO:17, SEQ ID NO:18, or SEQ ID NO:19.

In some embodiments, the probes and/or primers described herein comprise a nucleic acid sequence that specifically hybridizes to any of the nucleic acid molecules disclosed herein, or the complement thereof. In some embodiments, the probe or primer specifically hybridizes to any of the nucleic acid molecules disclosed herein under stringent conditions. The present disclosure also provides nucleic acid molecules having nucleic acid sequences that hybridize under moderate conditions to any of the nucleic acid molecules disclosed herein, or the complement thereof.

Appropriate stringency conditions which promote DNA hybridization include, for example, 6× sodium chloride/sodium citrate (SSC) at about 45° C., followed by a wash of 2×SSC at 50° C. (see, also *Current Protocols in Molecular Biology*, John Wiley & Sons, N.Y. (1989), 6.3.1-6.3.6). Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In hybridization reactions, specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 1984, 138, 267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1° C., 2° C., 3° C., or 4° C. lower than the thermal melting point ($T_m$); moderately stringent conditions can utilize a hybridization and/or wash at 6° C., 7°

C., 8° C., 9° C., or 10° C. lower than the thermal melting point ($T_m$); low stringency conditions can utilize a hybridization and/or wash at 11° C., 12° C., 13° C., 14° C., 15° C., or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used.

The probes described herein can be linked or fused to a label to aid in detection. The label can be directly detectable (e.g., fluorophore) or indirectly detectable (e.g., hapten, enzyme, or fluorophore quencher). Such labels can be detectable by spectroscopic, photochemical, biochemical, immunochemical, or chemical means. Such labels include, for example, radiolabels that can be measured with radiation-counting devices; pigments, dyes or other chromogens that can be visually observed or measured with a spectrophotometer; spin labels that can be measured with a spin label analyzer; and fluorescent labels (e.g., fluorophores), where the output signal is generated by the excitation of a suitable molecular adduct and that can be visualized by excitation with light that is absorbed by the dye or can be measured with standard fluorometers or imaging systems. The label can also be, for example, a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term "label" can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidate (HRP) to bind to the tag, and then use a calorimetric substrate (e.g., tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The probe or primer can comprise any suitable length, non-limiting examples of which include at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides in length. In some embodiments, the probe or primer comprises at least about 18 nucleotides in length to about 25 nucleotides in length. The probe or primer can comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides in length. In some embodiments, the probe or primer is from about 18 to about 30 nucleotides in length. Alternately, in some embodiments, the probe comprises or consists of at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 nucleotides.

In some embodiments, the probes and/or primers can hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to any of the wild type PNPLA3 or HSD17B13 nucleic acid molecules or variant PNPLA3 or HSD17B13 nucleic acid molecules described herein.

In some embodiments, the probe or primer comprises DNA. In some embodiments, the probe or primer comprises RNA.

The probes and primers described herein can also be alteration-specific probes and alteration-specific primers. The alteration-specific probe or alteration-specific primer can comprise a nucleic acid sequence which is complementary to and/or hybridizes, or specifically hybridizes, to a nucleic acid sequence encoding a variant PNPLA3 protein but which is not complementary to and/or hybridizes, or specifically hybridizes, to a nucleic acid sequence encoding a wild type PNPLA3 protein. In this context, "specifically hybridizes" means that the probe or primer (e.g., the alteration-specific probe or alteration-specific primer) does not hybridize to a nucleic acid molecule encoding a wild type PNPLA3 protein. Herein, the term "specifically hybridizes" means that the probe or primer exclusively hybridizes to the indicated nucleic acid molecule and not to another nucleic acid molecule. Accordingly, a probe or primer which specifically hybridizes to a nucleic acid molecule encoding a PNPLA3 protein comprising the I148M variation does not hybridize to a nucleic acid molecule encoding a PNPLA3 protein which does not comprise the I148M variation. The alteration-specific probe or alteration-specific primer can also comprise a nucleic acid sequence which is complementary to and/or hybridizes, or specifically hybridizes, to a nucleic acid sequence encoding a wild type PNPLA3 protein but which is not complementary to and/or hybridizes, or specifically hybridizes, to a nucleic acid sequence encoding a variant PNPLA3 protein. In this context, "specifically hybridizes" means that the probe or primer (e.g., the alteration-specific probe or alteration-specific primer) does not hybridize to a nucleic acid molecule encoding a variant PNPLA3 protein.

The alteration-specific probe or alteration-specific primer can also comprise a nucleic acid sequence which is complementary to and/or hybridizes, or specifically hybridizes, to a nucleic acid sequence encoding a variant HSD17B13 protein but which is not complementary to and/or hybridizes, or specifically hybridizes, to a nucleic acid sequence encoding a functional HSD17B13 protein. In this context, "specifically hybridizes" means that the probe or primer (e.g., the alteration-specific probe or alteration-specific primer) does not hybridize to a nucleic acid molecule encoding a functional HSD17B13 protein. For example, in this context "specifically hybridizes" means that the probe or primer does not hybridize to a nucleic acid molecule encoding a non-active/loss of function HSD17B13 protein. The alteration-specific probe or alteration-specific primer can also comprise a nucleic acid sequence which is complementary to and/or hybridizes, or specifically hybridizes, to a nucleic acid sequence encoding a functional HSD17B13 protein but which is not complementary to and/or hybridizes, or specifically hybridizes, to a nucleic acid sequence encoding a variant HSD17B13 protein. In this context, "specifically hybridizes" means that the probe or primer (e.g., the alteration-specific probe or alteration-specific primer) does not hybridize to a nucleic acid molecule encoding a variant HSD17B13 protein.

In some embodiments, the alteration-specific probe or alteration-specific primer comprises a nucleic acid sequence which is complementary to and/or hybridizes, or specifically hybridizes, to a portion of a PNPLA3 nucleic acid sequence that comprises a methionine at a position corresponding to position 148 according to SEQ ID NO:42, or comprises a methionine at a position corresponding to position 144 according to SEQ ID NO:43. In some embodiments, the alteration-specific probe or alteration-specific primer comprises a nucleic acid sequence which is complementary to and/or hybridizes, or specifically hybridizes, to the portion of the variant PNPLA3 genomic DNA that comprises an ATG codon at the positions corresponding to positions 5107 to 5109 according to SEQ ID NO:31. In some embodiments, the alteration-specific probe or alteration-specific primer comprises a nucleic acid sequence which is complementary to and/or hybridizes, or specifically hybridizes, to the portion of the variant PNPLA3 mRNA that comprises an AUG codon at the positions corresponding to positions 442 to 444 according to SEQ ID NO:34. In some embodiments, the alteration-specific probe or alteration-specific primer comprises a nucleic acid sequence which is complementary to and/or hybridizes, or specifically hybridizes, to the portion of the variant PNPLA3 mRNA that comprises an AUG codon at the positions corresponding to positions 430 to 432 according to SEQ ID NO:35. In some embodiments, the alteration-specific probe or alteration-specific primer comprises a nucleic acid sequence which is complementary to and/or hybridizes, or specifically hybridizes, to the portion of the variant PNPLA3 cDNA that comprises an ATG codon at the positions corresponding to positions 442 to 444 according to SEQ ID NO:38. In some embodiments, the alteration-specific probe or alteration-specific primer comprises a nucleic acid sequence which is complementary to and/or hybridizes, or specifically hybridizes, to the portion of the variant PNPLA3 cDNA that comprises an ATG codon at the positions corresponding to positions 430 to 432 according to SEQ ID NO:39.

In some embodiments, the alteration-specific probe or alteration-specific primer comprises a nucleic acid sequence which is complementary to and/or hybridizes, or specifically hybridizes, to the portion of the HSD17B13 genomic DNA that comprises an adenine at a position corresponding to position 12,667 according to SEQ ID NO:1. In some embodiments, the alteration-specific probe or alteration-specific primer comprises a nucleic acid sequence which is complementary to and/or hybridizes, or specifically hybridizes, to the portion of the HSD17B13 genomic DNA that comprises a thymine at a position corresponding to position 12,667 according to SEQ ID NO:2.

In some embodiments, the portion of the nucleic acid molecule to which the probe or primer is hybridized comprises from about 10 to about 200, from about 10 to about 150, from about 10 to about 100, from about 10 to about 50, from about 10 to about 40, from about 10 to about 30, or from about 10 to about 20 nucleotides, and comprises the codon corresponding to the position containing codon encoding the particular variation (e.g., I148M of PNPLA3 or the portion of the variant HSD17B13 protein that is different from the corresponding wild type HSD17B13 protein). In some preferred embodiments, the portion of the nucleic acid molecule to which the probe or primer is hybridized comprises from about 10 to about 50, from about 10 to about 40, from about 10 to about 30, or from about 10 to about 20 nucleotides, and comprises the codon corresponding to the position containing codon encoding the particular variation (e.g., I148M of PNPLA3 or the portion of the variant HSD17B13 protein that is different from the corresponding wild type HSD17B13 protein).

The kits described herein can comprise detection and/or amplification assay reagents that can be used for detecting and/or amplifying any of the wild type PNPLA3 and/or HSD17B13 nucleic acid molecules described herein and/or any of the variant PNPLA3 and/or HSD17B13 nucleic acid molecules described herein. In some embodiments, the kits for such detection and/or amplification can contain any of the reagents (e.g., probes and primers) described herein. In some embodiments, a basic kit can comprise a container having at least one probe or primer or at least two probes or primers, such as alteration-specific probes or alteration-specific primers, for a locus in any of the nucleic acid molecules disclosed herein. A kit can also optionally comprise instructions for use. A kit can also comprise other optional kit components, such as, for example, one or more of an allelic ladder directed to each of the loci amplified, a sufficient quantity of enzyme for amplification, amplification buffer to facilitate the amplification, divalent cation solution to facilitate enzyme activity, dNTPs for strand extension during amplification, loading solution for preparation of the amplified material for electrophoresis, genomic DNA as a template control, a size marker to insure that materials migrate as anticipated in the separation medium, and a protocol and manual to educate the user and limit error in use. The amounts of the various reagents in the kits also can be varied depending upon a number of factors, such as the optimum sensitivity of the process. It is within the scope of these teachings to provide test kits for use in manual applications or test kits for use with automated sample preparation, reaction set-up, detectors or analyzers. In some embodiments, the kits comprise at least one labeled probe (e.g., alteration-specific probe) for detection. In some embodiments, any of the kits disclosed herein can further comprise products and reagents required to carry out an annealing reaction, and instructions.

The present disclosure provides methods for detecting the presence of any of the wild type PNPLA3 proteins described herein. The present disclosure also provides methods for detecting the presence of any of the variant PNPLA3 proteins described herein. The present disclosure also provides methods for detecting the presence of any of the wild type PNPLA3 nucleic acid molecules described herein (e.g., genomic DNA molecules, mRNA molecules, and cDNA molecules) described herein. The present disclosure also provides methods for detecting the presence of any of the variant PNPLA3 nucleic acid molecules described herein (e.g., genomic DNA molecules, mRNA molecules, and cDNA molecules) described herein.

The present disclosure also provides methods for detecting the presence of any of the functional HSD17B13 proteins described herein. The present disclosure also provides methods for detecting the presence of any of the variant HSD17B13 proteins described herein. The present disclosure also provides methods for detecting the presence of any of the functional HSD17B13 nucleic acid molecules described herein (e.g., genomic DNA molecules, RNA transcripts, cDNA transcripts, mRNA molecules, and cDNA molecules) described herein. The present disclosure also provides methods for detecting the presence of any of the variant HSD17B13 nucleic acid molecules described herein (e.g., genomic DNA molecules, RNA transcripts, cDNA transcripts, mRNA molecules, and cDNA molecules) described herein.

In some embodiments of any of the methods described herein, a functional HSD17B13 protein, or nucleic acid molecule encoding the same, is detected or sought to be detected in a subject or patient. In some embodiments, the subject or patient comprises a functional HSD17B13 protein. In some embodiments, the functional HSD17B13 protein is one of the functional HSD17B13 proteins described herein (which can be encoded by any of the nucleic acid molecules described herein encoding the same). In some embodiments, a functional HSD17B13 protein has at least 90%, at least 80%, at least 70%, at least 60%, at least 50%, at least 40%, at least 30%, at least 20%, at least 10%, at least 5%, or at least 1% of the biological activity of the HSD17B13 protein having the amino acid sequence according to SEQ ID NO:40. In some embodiments, a functional HSD17B13 protein has at least 90%, at least 80%, at least 70%, at least 60%, or at least 50% of the biological activity of the HSD17B13 protein having the amino acid sequence according to SEQ ID NO:40. In some embodiments, a functional HSD17B13 protein has at least 90%, at least 80%, at least 70%, at least 60%, at least 50%, at least 40%, at least 30%, at least 20%, at least 10%, at least 5%, or at least 1% of the biological activity of HSD17B13 protein having SEQ ID NO:40. In some embodiments, a functional HSD17B13 protein has at least 70%, at least 60%, at least 50%, at least 40%, at least 30%, at least 20%, at least 10%, at least 5%, or at least 1% of the biological activity of HSD17B13 protein having SEQ ID NO:40. In some embodiments, a functional HSD17B13 protein has at least 50%, at least 40%, at least 30%, at least 20%, at least 10%, at least 5%, or at least 1% of the biological activity of HSD17B13 protein having SEQ ID NO:40. In some embodiments, a functional HSD17B13 protein has at least 30%, at least 20%, at least 10%, at least 5%, or at least 1% of the biological activity of HSD17B13 protein having SEQ ID NO:40. In some embodiments, a functional HSD17B13 protein has at least 90% of the biological activity of HSD17B13 protein having SEQ ID NO:40. In some embodiments, a functional HSD17B13 protein has at least 80% of the biological activity of HSD17B13 protein having SEQ ID NO:40. In some embodiments, a functional HSD17B13 protein has at least 70% of the biological activity of HSD17B13 protein having SEQ ID NO:40. In some embodiments, a functional HSD17B13 protein has at least 60% of the biological activity of HSD17B13 protein having SEQ ID NO:40. In some embodiments, a functional HSD17B13 protein has at least 50% of the biological activity of HSD17B13 protein having SEQ ID NO:40. In some embodiments, a functional HSD17B13 protein has at least 40% of the biological activity of HSD17B13 protein having SEQ ID NO:40. In some embodiments, a functional HSD17B13 protein has at least 30% of the biological activity of HSD17B13 protein having SEQ ID NO:40. In some embodiments, a functional HSD17B13 protein has at least 20% of the biological activity of HSD17B13 protein having SEQ ID NO:40. In some embodiments, a functional HSD17B13 protein has at least 10% of the biological activity of HSD17B13 protein having SEQ ID NO:40. In some embodiments, a functional HSD17B13 protein has at least 5% of the biological activity of HSD17B13 protein having SEQ ID NO:40. In some embodiments, a functional HSD17B13 protein has at least 1% of the biological activity of HSD17B13 protein having SEQ ID NO:40. In some embodiments, the activity of an HSD17B13 protein (e.g., functionality) can be determined by, for example, performing an oxidoreductase activity assay.

It is understood that gene sequences within a population and mRNAs and proteins encoded by such genes can vary due to polymorphisms such as single-nucleotide polymorphisms. The sequences provided herein are only exemplary sequences. Other sequences for the variant PNPLA3 and HSD17B13 genomic DNA, mRNA, cDNA, and polypeptide are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some embodiments, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting a variant PNPLA3 nucleic acid molecule, preliminary processing designed to isolate or enrich the sample for the genomic DNA can be employed. A variety of techniques can be used for this purpose. When detecting the level of variant PNPLA3 mRNA, different techniques can be used enrich the biological sample with mRNA. Various methods to detect the presence or level of an mRNA or the presence of a particular variant genomic DNA locus can be used.

In some embodiments, the presence or absence of a particular PNPLA3 protein or HSD17B13 protein (e.g., functional or variant) is detected by sequencing at least a portion of the protein to determine whether the protein comprises an amino acid sequence encoding any of the variant PNPLA3 proteins or HSD17B13 proteins (e.g., functional or variant) described herein. In some embodiments, the presence or absence of a particular PNPLA3 protein or HSD17B13 protein (e.g., functional or variant) is detected by performing an immunoassay, such as an ELISA, to determine whether any of the variant PNPLA3 proteins or HSD17B13 proteins (e.g., functional or variant) described herein are present in the sample.

In some embodiments, the portion of the protein sequenced comprises from about 5 to about 100, from about 5 to about 50, from about 5 to about 40, from about 5 to about 30, from about 5 to about 20, or from about 5 to about 10 amino acids, and comprises the position corresponding to the position containing the variation (e.g., I148M of PNPLA3 or the portion of the variant HSD17B13 protein that is different from the corresponding wild type HSD17B13 protein). In some preferred embodiments, the portion of the protein sequenced comprises from about 5 to about 20, or from about 5 to about 10 amino acids, and comprises the position corresponding to the position containing the variation (e.g., I148M of PNPLA3 or the portion of the variant HSD17B13 protein that is different from the corresponding wild type HSD17B13 protein).

Illustrative non-limiting examples of protein sequencing techniques include, but are not limited to, mass spectrometry and Edman degradation. Illustrative examples of immunoassays include, but are not limited to, immunoprecipitation, Western blot, immunohistochemistry, ELISA, immunocytochemistry, flow cytometry, and immuno-PCR. Polyclonal or monoclonal antibodies detectably labeled using various techniques (e.g., calorimetric, fluorescent, chemiluminescent, or radioactive) are suitable for use in the immunoassays.

In some embodiments, the presence or absence of a particular PNPLA3 nucleic acid molecule or HSD17B13 nucleic acid molecule (e.g., functional or variant genomic DNA, mRNA, cDNA, RNA transcript, or cDNA transcript) is detected by sequencing at least a portion of the nucleic acid molecule to determine whether the nucleic acid molecule comprises a nucleic acid sequence according to any of the variant PNPLA3 nucleic acid molecules or HSD17B13 nucleic acid molecules (e.g., functional or variant) described herein.

In some embodiments, the portion of the nucleic acid molecule sequenced comprises from about 10 to about 200, from about 10 to about 150, from about 10 to about 100, from about 10 to about 50, from about 10 to about 40, from about 10 to about 30, or from about 10 to about 20 nucleotides, and comprises the codon corresponding to the position containing codon encoding the particular variation (e.g., I148M of PNPLA3 or the portion of the variant HSD17B13 protein that is different from the corresponding wild type HSD17B13 protein). In some preferred embodiments, the portion of the nucleic acid molecule sequenced comprises from about 10 to about 50, from about 10 to about 40, from about 10 to about 30, or from about 10 to about 20 nucleotides, and comprises the codon corresponding to the position containing codon encoding the particular variation (e.g., I148M of PNPLA3 or the portion of the variant HSD17B13 protein that is different from the corresponding wild type HSD17B13 protein).

In some embodiments, the methods of detecting the presence or absence of any of the particular PNPLA3 nucleic acid molecules or HSD17B13 nucleic acid molecules (e.g., any of the functional or variant genomic DNA molecules, mRNA molecules, cDNA molecules, RNA transcripts, or cDNA transcripts) described herein in a subject, comprise: performing an assay on a biological sample obtained from the subject, which assay determines whether a nucleic acid molecule in the biological sample comprises any of the particular PNPLA3 nucleic acid molecules or HSD17B13 nucleic acid molecules (e.g., any of the functional or variant genomic DNA molecules, mRNA molecules, cDNA molecules, RNA transcripts, or cDNA transcripts) described herein. In some embodiments, the biological sample comprises a cell or cell lysate. Such methods can further comprise, for example, obtaining a biological sample from the subject, optionally reverse transcribing the mRNA into cDNA, and performing the assay. Such assays can comprise, for example, determining the identity of particular positions of the particular nucleic acid molecules described herein.

For example, the assay can comprise the use of alteration-specific probes or alteration-specific primers that comprise a nucleic acid sequence which is complementary to and/or hybridizes, or specifically hybridizes, to a portion of a PNPLA3 nucleic acid sequence that comprises a methionine at a position corresponding to position 148 according to SEQ ID NO:42, or comprises a methionine at a position corresponding to position 144 according to SEQ ID NO:43, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the variant PNPLA3 genomic DNA that comprises an ATG codon at the positions corresponding to positions 5107 to 5109 according to SEQ ID NO:31, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the variant PNPLA3 mRNA that comprises an AUG codon at the positions corresponding to positions 442 to 444 according to SEQ ID NO:34, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the variant PNPLA3 mRNA that comprises an AUG codon at the positions corresponding to positions 430 to 432 according to SEQ ID NO:35, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the variant PNPLA3 cDNA that comprises an ATG codon at the positions corresponding to positions 442 to 444 according to SEQ ID NO:38, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the variant PNPLA3 cDNA that comprises an ATG codon at the positions corresponding to positions 430 to 432 according to SEQ ID NO:39, or a portion adjacent thereto.

In some embodiments, the assay can comprise the use of alteration-specific probes or alteration-specific primers that comprise a nucleic acid sequence which is complementary to and/or hybridizes, or specifically hybridizes, to the portion of the HSD17B13 genomic DNA that comprises an adenine at a position corresponding to position 12,667 according to SEQ ID NO:1, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the HSD17B13 genomic DNA that comprises a thymine at a position corresponding to position 12,667 according to SEQ ID NO:2, or a portion adjacent thereto.

In some embodiments, the assay comprises: sequencing at least a portion of the nucleic acid molecules described herein present in the biological sample from the subject, wherein the portion sequenced includes the positions disclosed herein. For example, the portion sequenced can be a portion of a PNPLA3 nucleic acid sequence that comprises a methionine at a position corresponding to position 148 according to SEQ ID NO:42, or comprises a methionine at a position corresponding to position 144 according to SEQ ID NO:43. In some embodiments, the portion sequenced can be portion of the variant PNPLA3 genomic DNA that comprises an ATG codon at the positions corresponding to positions 5107 to 5109 according to SEQ ID NO:31. In some embodiments, the portion sequenced can be a portion of the variant PNPLA3 mRNA that comprises an AUG codon at the positions corresponding to positions 442 to 444 according to SEQ ID NO:34. In some embodiments, the portion sequenced can be a portion of the variant PNPLA3 mRNA that comprises an AUG codon at the positions corresponding to positions 430 to 432 according to SEQ ID NO:35. In some embodiments, the portion sequenced can be a portion of the variant PNPLA3 cDNA that comprises an ATG codon at the positions corresponding to positions 442 to 444 according to SEQ ID NO:38. In some embodiments, the portion sequenced can be a portion of the variant PNPLA3 cDNA that comprises an ATG codon at the positions corresponding to positions 430 to 432 according to SEQ ID NO:39.

In some embodiments, the portion sequenced can be a portion of the HSD17B13 genomic DNA that comprises an adenine at a position corresponding to position 12,667 according to SEQ ID NO:1. In some embodiments, the portion sequenced can be a portion of the HSD17B13 genomic DNA that comprises a thymine at a position corresponding to position 12,667 according to SEQ ID NO:2.

In some embodiments, the assay comprises: a) contacting the biological sample with a primer (or alteration-specific primer) hybridizing to the regions adjacent to the portions of the nucleic acid molecules identified herein (e.g., adjacent to a portion of a PNPLA3 nucleic acid sequence that comprises a methionine at a position corresponding to position 148 according to SEQ ID NO:42, or comprises a methionine at a position corresponding to position 144 according to SEQ ID NO:43; adjacent to a portion of the variant PNPLA3 genomic DNA that comprises an ATG codon at the positions corresponding to positions 5107 to 5109 according to SEQ ID NO:31; adjacent to a portion of the variant PNPLA3 mRNA that comprises an AUG codon at the positions corresponding to positions 442 to 444 according to SEQ ID NO:34; adjacent to a portion of the variant PNPLA3 mRNA that comprises an AUG codon at the positions corresponding to positions 430 to 432 according to SEQ ID NO:35; adjacent to a portion of the variant PNPLA3 cDNA that comprises an ATG codon at the positions corresponding to positions 442 to 444 according to SEQ ID NO:38; adjacent to a portion of the variant PNPLA3 cDNA that comprises an ATG codon at the positions corresponding to positions 430 to 432 according to SEQ ID NO:39; adjacent to a portion of the HSD17B13 genomic DNA that comprises an adenine at a position corresponding to position 12,667 according to SEQ ID NO:1; or adjacent to a portion of the HSD17B13 genomic DNA that comprises a thymine at a position corresponding to position 12,667 according to SEQ ID NO:2); b) extending the primer at least through the position of the nucleic acid molecules corresponding to nucleotide positions beyond the altered site (e.g., the portion of a PNPLA3 nucleic acid sequence that comprises a methionine at a position corresponding to position 148 according to SEQ ID NO:42, or comprises a methionine at a position corresponding to position 144 according to SEQ ID NO:43; the portion of the variant PNPLA3 genomic DNA that comprises an ATG codon at the positions corresponding to positions 5107 to 5109 according to SEQ ID NO:31; the portion of the variant PNPLA3 mRNA that comprises an AUG codon at the positions corresponding to positions 442 to 444 according to SEQ ID NO:34; the portion of the variant PNPLA3 mRNA that comprises an AUG codon at the positions corresponding to positions 430 to 432 according to SEQ ID NO:35; the portion of the variant PNPLA3 cDNA that comprises an ATG codon at the positions corresponding to positions 442 to 444 according to SEQ ID NO:38; the portion of the variant PNPLA3 cDNA that comprises an ATG codon at the positions corresponding to positions 430 to 432 according to SEQ ID NO:39; the portion of the HSD17B13 genomic DNA that comprises an adenine at a position corresponding to position 12,667 according to SEQ ID NO:1; or the portion of the HSD17B13 genomic DNA that comprises a thymine at a position corresponding to position 12,667 according to SEQ ID NO:2); and c) determining whether the extension product of the primer comprises the nucleic acid sequence of any of the variant or wild type PNPLA3 or HSD17B13 nucleic acid molecules described herein.

In some embodiments, only PNPLA3 genomic DNA is analyzed. In some embodiments, only PNPLA3 mRNA is analyzed. In some embodiments, only PNPLA3 cDNA obtained from PNPLA3 mRNA is analyzed. In some embodiments, only HSD17B13 genomic DNA is analyzed. In some embodiments, only HSD17B13 mRNA is analyzed. In some embodiments, only HSD17B13 cDNA obtained from HSD17B13 mRNA is analyzed. In some embodiments, only HSD17B13 RNA transcripts is analyzed. In some embodiments, only HSD17B13 cDNA obtained from HSD17B13 RNA transcripts is analyzed.

In some embodiments, the assay comprises contacting the biological sample with a primer or probe that specifically hybridizes to any of the particular variant PNPLA3 nucleic acid molecules or variant HSD17B13 nucleic acid molecules (e.g., any of the variant genomic DNA molecules, mRNA molecules, cDNA molecules, RNA transcripts, or cDNA transcripts) described herein and not the corresponding functional nucleic acid molecules under stringent conditions, and determining whether hybridization has occurred.

In some embodiments, the assay comprises contacting the biological sample with a primer or probe that specifically hybridizes to any of the particular variant PNPLA3 nucleic acid molecules (e.g., any of the variant genomic DNA molecules, mRNA molecules, cDNA molecules, RNA transcripts, or cDNA transcripts) or nucleic acid molecules encoding a functional HSD17B13 protein (e.g., any of the genomic DNA molecules, mRNA molecules, cDNA molecules, RNA transcripts, or cDNA transcripts encoding a functional HSD17B13 protein) described herein and not to the corresponding nucleic acid molecules encoding wild type PNPLA3 or variant HSD17B13, respectively, under stringent conditions, and determining whether hybridization has occurred.

In some embodiments, the assay comprises RNA sequencing (RNA-Seq). In some embodiments, the assays also comprise reverse transcribing mRNA into cDNA via the reverse transcriptase polymerase chain reaction (RT-PCR).

Such probes and primers can hybridize specifically to a target sequence under high stringency hybridization conditions. Probes and primers may have complete nucleic acid sequence identity of contiguous nucleotides with the target sequence, although probes differing from the target nucleic acid sequence and that retain the ability to specifically detect and/or identify a target nucleic acid sequence may be designed by conventional methods. Accordingly, probes and primers can share at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity or complementarity to the target nucleic acid molecule.

When a probe is hybridized with a nucleic acid molecule in a biological sample under conditions that allow for the binding of the probe to the nucleic acid molecule, this binding can be detected and allow for an indication of the presence of the particular variant or wild type PNPLA3 or variant or functional HSD17B13 locus or the presence or the level of the particular variant or wild type PNPLA3 or variant or functional HSD17B13 mRNA or cDNA in the biological sample. Such identification of a bound probe has been described. The specific probe may comprise a sequence of at least about 80%, from about 80% to about 85%, from about 85% to about 90%, from about 90% to about 95%, and from about 95% to about 100% identical (or complementary) to a specific region of a variant or wild type PNPLA3 or variant or functional HSD17B13 gene. The specific probe may comprise a sequence of at least about 80%, from about 80% to about 85%, from about 85% to about 90%, from about 90% to about 95%, and from about 95% to about 100% identical (or complementary) to a specific region of a variant or wild type PNPLA3 or variant or functional HSD17B13 mRNA. The specific probe may comprise a sequence of at least about 80%, from about 80% to about 85%, from about 85% to about 90%, from about 90% to about 95%, and from about 95% to about 100% identical (or complementary) to a specific region of a variant or wild type PNPLA3 or variant or functional HSD17B13 cDNA.

In some embodiments, to determine whether a particular nucleic acid complement of a biological sample comprises a nucleic acid sequence encoding a particular functional or variant PNPLA3 protein or HSD17B13 protein, the biological sample may be subjected to a nucleic acid amplification method using a primer pair that includes a first primer derived from the 5' flanking sequence adjacent to positions encoding a site of interest (e.g., any of the positions described herein), and a second primer derived from the 3' flanking sequence adjacent to positions encoding the same site of interest, to produce an amplicon that is diagnostic for the presence of the particular functional or variant PNPLA3 protein or HSD17B13 protein. For example, with regard to PNPLA3 the amplicon may comprise a nucleotide sequence encoding the position which corresponds to position 148 according to SEQ ID NO: 42. With regard to HSD17B13 the amplicon may comprise a nucleotide sequence which corresponds to positions 5107 to 5109 according to SEQ ID NO: 31. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions encoding the site of interest and at least 1, 2, 3, 4, 5, 6, 7, 8, 9, 10, or more nucleotides on each side of positions encoding the site of interest. Similar amplicons can be generated from the mRNA and/or cDNA sequences.

Representative methods for preparing and using probes and primers are described, for example, in *Molecular Cloning: A Laboratory Manual,* 2nd Ed., Vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990). PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using guidelines.

Any nucleic acid hybridization or amplification or sequencing method can be used to specifically detect the presence of the functional or variant PNPLA3 or HSD17B13 gene locus and/or the level of functional or variant PNPLA3 or HSD17B13 mRNA or cDNA produced from mRNA. In some embodiments, the nucleic acid molecule can be used either as a primer to amplify a region of the functional or variant PNPLA3 or HSD17B13 nucleic acid or the nucleic acid molecule can be used as a probe that specifically hybridizes, for example, under stringent conditions, to a nucleic acid molecule comprising the functional or variant PNPLA3 or HSD17B13 gene locus or a nucleic acid molecule comprising a functional or variant PNPLA3 or HSD17B13 mRNA or cDNA produced from mRNA.

A variety of techniques are available in the art including, for example, nucleic acid sequencing, nucleic acid hybridization, and nucleic acid amplification. Illustrative examples of nucleic acid sequencing techniques include, but are not limited to, chain terminator (Sanger) sequencing and dye terminator sequencing.

Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

Any method can be used for detecting either the non-amplified or amplified polynucleotides including, for example, Hybridization Protection Assay (HPA), quantitative evaluation of the amplification process in real-time, and determining the quantity of target sequence initially present in a sample, but which is not based on a real-time amplification.

Also provided are methods for identifying nucleic acids which do not necessarily require sequence amplification and are based on, for example, the methods of Southern (DNA:DNA) blot hybridizations, in situ hybridization (ISH), and fluorescence in situ hybridization (FISH) of chromosomal material. Southern blotting can be used to detect specific nucleic acid sequences. In such methods, nucleic acid that is extracted from a sample is fragmented, electrophoretically separated on a matrix gel, and transferred to a membrane filter. The filter bound nucleic acid is subject to hybridization with a labeled probe complementary to the sequence of interest. Hybridized probe bound to the filter is detected. In any such methods, the process can include hybridization using any of the probes described or exemplified herein.

In hybridization techniques, stringent conditions can be employed such that a probe or primer will specifically hybridize to its target. In some embodiments, a polynucleotide primer or probe under stringent conditions will hybridize to its target sequence (e.g., the functional or variant PNPLA3 or HSD17B13 locus, functional or variant PNPLA3 or HSD17B13 mRNA, or functional or variant PNPLA3 or HSD17B13 cDNA) to a detectably greater degree than to other sequences (e.g., the corresponding functional or variant PNPLA3 or HSD17B13 locus, functional or variant PNPLA3 or HSD17B13 mRNA, or functional or variant PNPLA3 or HSD17B13 cDNA), such as, at least 2-fold, at least 3-fold, at least 4-fold, or more over background, including over 10-fold over background. In some embodiments, a polynucleotide primer or probe under stringent conditions will hybridize to its target sequence to a detectably greater degree than to other sequences by at least 2-fold. In some embodiments, a polynucleotide primer or probe under stringent conditions will hybridize to its target sequence to a detectably greater degree than to other sequences by at least 3-fold. In some embodiments, a polynucleotide primer or probe under stringent conditions will hybridize to its target sequence to a detectably greater degree than to other sequences by at least 4-fold. In some embodiments, a polynucleotide primer or probe under stringent conditions will hybridize to its target sequence to a detectably greater degree than to other sequences by over 10-fold over background. Stringent conditions are sequence-dependent and will be different in different circumstances. By controlling the stringency of the hybridization and/or washing conditions, target sequences that are 100% complementary to the probe can be identified (homologous probing). Alternately, stringency conditions can be adjusted to allow some mismatching in sequences so that lower degrees of identity are detected (heterologous probing).

In some embodiments, the detecting step comprises: amplifying at least a portion of the nucleic acid molecule that encodes a site of interest (e.g., any of the positions described herein); labeling the nucleic acid molecule with a detectable label; contacting the labeled nucleic acid with a support comprising a probe, wherein the probe comprises a nucleic acid sequence which hybridizes under stringent conditions to a nucleic acid sequence encoding the a site of interest (e.g., any of the positions described herein); and detecting the detectable label.

In some embodiments, the detecting step comprises: amplifying at least a portion of the nucleic acid molecule that encodes a PNPLA3 or HSD17B13 protein, wherein the amplified nucleic acid molecule encodes an amino acid sequence which comprises a site of interest (e.g., any of the positions described herein); labeling the nucleic acid molecule with a detectable label; contacting the labeled nucleic acid with a support comprising a probe, wherein the probe comprises a nucleic acid sequence which hybridizes under stringent conditions to a nucleic acid sequence encoding a site of interest (e.g., any of the positions described herein); and detecting the detectable label. Any of the nucleic acid molecules disclosed herein can be amplified. For example, any of the genomic DNA, cDNA, or mRNA molecules disclosed herein can be amplified. In some embodiments, the nucleic acid molecule is mRNA and the method further comprises reverse-transcribing the mRNA into a cDNA prior to the amplifying step.

In some embodiments, the detecting step comprises: contacting the nucleic acid molecule that encodes a PNPLA3 or HSD17B13 protein with a probe comprising a detectable label, wherein the probe comprises a nucleic acid sequence which hybridizes under stringent conditions to a nucleic acid sequence encoding the variant PNPLA3 or HSD17B13 protein, and detecting the detectable label. In some embodiments, the detecting step comprises: contacting the nucleic acid molecule that encodes a PNPLA3 or HSD17B13 protein with a probe comprising a detectable label, wherein the probe comprises a nucleic acid sequence which hybridizes under stringent conditions to a nucleic acid sequence encoding a site of interest (e.g., any of the positions described herein), and detecting the detectable label. In some embodiments, the nucleic acid molecule is present within a cell obtained from the human subject, such that the detection is according to an in situ hybridization technique.

Other assays that can be used in the methods disclosed herein include, for example, reverse transcription polymerase chain reaction (RT-PCR) or quantitative RT-PCR (qRT-PCR). Yet other assays that can be used in the methods disclosed herein include, for example, RNA sequencing (RNA-Seq) followed by detection of the presence and quantity of variant mRNA or cDNA in the biological sample.

In some embodiments, the detecting step comprises amplifying at least a portion of the nucleic acid molecule that encodes a particular PNPLA3 or HSD17B13 protein, labeling the amplified nucleic acid molecule with a detectable label, contacting the labeled nucleic acid molecule with a support comprising a probe, wherein the probe comprises a nucleic acid sequence which specifically hybridizes, including, for example, under stringent conditions, to a nucleic acid sequence encoding the particular PNPLA3 or HSD17B13 protein, and detecting the detectable label. In some embodiments, the detecting step comprises amplifying at least a portion of the nucleic acid molecule that encodes a particular PNPLA3 or HSD17B13 protein, labeling the amplified nucleic acid molecule with a detectable label, contacting the labeled nucleic acid molecule with a support comprising a probe, wherein the probe comprises a nucleic acid sequence which specifically hybridizes, including, for example, under stringent conditions, to a nucleic acid sequence encoding a site of interest (e.g., the portion of a PNPLA3 nucleic acid sequence that encodes a methionine at a position corresponding to position 148 according to SEQ ID NO:42, or encodes a methionine at a position corresponding to position 144 according to SEQ ID NO:43; the portion of the variant PNPLA3 genomic DNA that comprises an ATG codon at the positions corresponding to positions 5107 to 5109 according to SEQ ID NO:31; the portion of the variant PNPLA3 mRNA that comprises an AUG codon at the positions corresponding to positions 442 to 444 according to SEQ ID NO:34; the portion of the variant PNPLA3 mRNA that comprises an AUG codon at the positions corresponding to positions 430 to 432 according to SEQ ID NO:35; the portion of the variant PNPLA3 cDNA that comprises an ATG codon at the positions corresponding to positions 442 to 444 according to SEQ ID NO:38; the portion of the variant PNPLA3 cDNA that comprises an ATG codon at the positions corresponding to positions 430 to 432 according to SEQ ID NO:39; the portion of the HSD17B13 genomic DNA that comprises an adenine at a position corresponding to position 12,667 according to SEQ ID NO:1; or the portion of the HSD17B13 genomic DNA that comprises a thymine at a position corresponding to position 12,667 according to SEQ ID NO:2), and detecting the detectable label. If the nucleic acid includes mRNA, the method may further comprise reverse-transcribing the mRNA into a cDNA prior to the amplifying step. In some embodiments, the determining step comprises contacting the nucleic acid molecule that encodes a particular PNPLA3 or HSD17B13 protein with a probe comprising a detectable label and detecting the detectable label.

The disclosure provides methods for identifying a human subject as a candidate for treating or inhibiting a liver disease by inhibiting hydroxysteroid 17-beta dehydrogenase 13 (HSD17B13), the method comprising determining whether or not a sample from the subject comprises a first nucleic acid encoding a patatin like phospholipase domain containing 3 (PNPLA3) protein comprising an I148M variation and a second nucleic acid encoding a functional HSD17B13 protein, and/or a PNPLA3 protein comprising an I148M variation and a functional HSD17B13 protein, and identifying the subject as a candidate for treating or inhibiting a liver disease by inhibiting HSD17B13 when both the first and second nucleic acids are detected and/or both of the proteins are detected. In some embodiments, the subject is obese. In some embodiments, the subject has a fatty liver. In some embodiments, the first nucleic acid molecule comprises genomic DNA. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31. In some embodiments, the first nucleic acid molecule comprises mRNA. In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35. In some embodiments, the first nucleic acid molecule comprises a cDNA obtained from mRNA. In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39. In some embodiments, detecting the first nucleic acid comprises sequencing at least a portion of the first nucleic acid and the portion comprises the codon which encodes the I148M variation. In some embodiments, detecting the first nucleic acid comprises hybridizing the first nucleic acid with a probe or primer that specifically hybridizes to a portion of the first nucleic acid, wherein the portion comprises the codon encoding the I148M variation. In some embodiments, the probe or primer is an allele-specific probe or primer. In some embodiments, the probe or primer comprises a label. In some embodiments, the methods further comprise determining whether the subject is homozygous or heterozygous for the I148M variation.

In some embodiments, the second nucleic acid comprises genomic DNA. In some embodiments, the genomic DNA comprises an adenine at a position corresponding to position 12,667 according to SEQ ID NO:1. In some embodiments, the genomic DNA comprises SEQ ID NO:1. In some embodiments, the second nucleic acid molecule comprises mRNA. In some embodiments, the mRNA comprises SEQ ID NO:3. In some embodiments, the mRNA comprises SEQ ID NO:4. In some embodiments, the mRNA comprises SEQ ID NO:7. In some embodiments, the mRNA comprises SEQ ID NO:11. In some embodiments, the second nucleic acid molecule comprises cDNA obtained from mRNA. In some embodiments, the cDNA comprises SEQ ID NO:12. In some embodiments, the cDNA comprises SEQ ID NO:13. In some embodiments, the cDNA comprises SEQ ID NO:16. In some embodiments, the cDNA comprises SEQ ID NO:20. In some embodiments, detecting the second nucleic acid comprises sequencing the second nucleic acid. In some embodiments, detecting the second nucleic acid comprises hybridizing the second nucleic acid with a probe or primer that specifically hybridizes to the second nucleic acid. In some embodiments, the probe or primer is an allele-specific probe or primer. In some embodiments, the probe or primer comprises a label. In some embodiments, the methods further comprise determining whether the subject is homozygous or heterozygous for the second nucleic acid encoding a functional HSD17B13 protein in the sample.

The present disclosure provides methods of identifying a subject who is a candidate for HSD17B13 inhibition, the method comprising determining whether or not a sample from the subject comprises a nucleic acid encoding a PNPLA3 Ile148Met variant or PNPLA3 Ile144Met variant. The present disclosure also provides methods for identifying a human subject as a candidate for treating or inhibiting a liver disease by inhibiting HSD17B13, the method comprising determining whether or not a sample from the subject comprises a first nucleic acid encoding a PNPLA3 protein comprising an I148M variation and a second nucleic acid encoding a functional HSD17B13 protein, and/or a PNPLA3 protein comprising an I148M variation and a functional HSD17B13 protein, and identifying the subject as a candidate for treating or inhibiting a liver disease by inhibiting HSD17B13 when both the first and second nucleic acids are detected and/or when both proteins are detected.

The present disclosure also provides methods of classifying a subject who is a candidate for HSD17B13 inhibition, the method comprising determining whether or not a sample from the subject comprises a nucleic acid encoding a PNPLA3 Ile148Met variant or PNPLA3 Ile144Met variant. The present disclosure also provides methods for classifying a human subject as a candidate for treating or inhibiting a liver disease by inhibiting HSD17B13, the method comprising determining whether or not a sample from the subject comprises a first nucleic acid encoding a PNPLA3 protein comprising an I148M variation and a second nucleic acid encoding a functional HSD17B13 protein, and/or a PNPLA3 protein comprising an I148M variation and a functional HSD17B13 protein, and classifying the subject as a candidate for treating or inhibiting a liver disease by inhibiting HSD17B13 when both the first and second nucleic acids are detected and/or when both proteins are detected.

The variant PNPLA3 Ile148Met variant or PNPLA3 Ile144Met variant can be any of the variant PNPLA3 Ile148Met variants and PNPLA3 Ile144Met variants described herein. The variant PNPLA3 Ile148Met variant or PNPLA3 Ile144Met variant can be detected by any of the methods described herein. In some embodiments, the methods further comprise determining whether the subject is homozygous or heterozygous for the variant PNPLA3 Ile148Met variant or PNPLA3 Ile144Met variant. In some embodiments, the subject is homozygous for the variant PNPLA3 Ile148Met variant or PNPLA3 Ile144Met variant. In some embodiments, the subject is heterozygous for the variant PNPLA3 Ile148Met variant or PNPLA3 Ile144Met variant. In some embodiments, the subject is homozygous for the variant PNPLA3 Ile148Met variant. In some embodiments, the subject is heterozygous for the variant PNPLA3 Ile148Met variant. In some embodiments, the subject is homozygous for the variant PNPLA3 Ile144Met variant. In some embodiments, the subject is heterozygous for the variant PNPLA3 Ile144Met variant.

In preferred embodiments, the subject does not comprise any genes encoding loss of function variations in the HSD17B13 protein. It is believed that loss of function variations in the HSD17B13 protein, including those described or exemplified herein, confer a liver disease-protective effect and it is further believed that this protective effect is enhanced in the presence of the variant PNPLA3 Ile148M variation. Thus, it is believed that subjects (e.g., subjects comprising the I148M variation in PNPLA3) in whom both copies of the genes (from each chromosome) encoding the HSD17B13 protein encode a loss of function variation are unlikely to benefit from HSD17B13 inhibition therapy. Nevertheless, it is believed that subjects who express at least a partially functional HSD17B13 protein will benefit from HSD17B13 inhibition therapy. Thus, the methods may comprise classifying the status of the gene (in one or both chromosomes) encoding HSD17B13, including whether the gene encodes a loss of function variation in the HSD17B13 protein, as well as whether the subject is homozygous or heterozygous.

In some embodiments, the methods further comprise detecting the presence of a nucleic acid molecule or gene encoding a functional HSD17B13 protein in a sample from the subject. The nucleic acid molecule can encode any of the functional HSD17B13 proteins described herein. The HSD17B13 nucleic acid molecule can be detected by any of the methods described herein. In some embodiments, the methods further comprise determining whether the subject is homozygous or heterozygous for a gene encoding a functional HSD17B13 protein. In some embodiments, the subject is homozygous for a gene encoding a functional HSD17B13 protein. In some embodiments, the subject is heterozygous for a gene encoding a functional HSD17B13.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern.

Solid-state substrates for use in solid supports can include any solid material to which molecules can be coupled. This includes materials such as acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A form for a solid-state substrate is a microtiter dish, such as a standard 96-well type. In some embodiments, a multi-well glass slide can be employed that normally contain one array per well. This feature allows for greater control of assay reproducibility, increased throughput and sample handling, and ease of automation. In some embodiments, the support is a microarray.

In some embodiments, the methods further comprises determining whether the subject is obese. In some embodiments, a subject is obese if their body mass index (BMI) is over 30 kg/m$^2$. Obesity is can be a characteristic of a subject having or at risk of developing a liver disease. In some embodiments, the methods further comprises determining whether the subject has a fatty liver. A fatty liver can be a characteristic of a subject having or at risk of developing a liver disease. In some embodiments, the methods further comprises determining whether the subject is obese and has a fatty liver.

In some embodiments, the methods further comprise administering an inhibitor of HSD17B13 to the subject. Methods of administering an inhibitor of HSD17B13 to the subject are described herein.

In some embodiments, the nucleic acid molecule encoding the variant PNPLA3 Ile148Met protein or PNPLA3 Ile144Met protein is any of the nucleic acid molecules described herein. In some embodiments, the nucleic acid molecule encoding the variant PNPLA3 Ile148Met protein or PNPLA3 Ile144Met protein is genomic DNA. In some embodiments, the genomic DNA encoding the variant PNPLA3 Ile148Met protein or PNPLA3 Ile144Met protein is any of the genomic DNA molecules described herein. In some embodiments, the nucleic acid molecule encoding the variant PNPLA3 Ile148Met protein is genomic DNA. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31. In some embodiments, the genomic DNA encoding the variant PNPLA3 protein is detected by nucleic acid sequencing or hybridization of a probe, as described herein. In some embodiments, the genomic DNA encoding the variant PNPLA3 protein that comprises the ATG codon is detected by nucleic acid sequencing or hybridization of a probe, as described herein.

In some embodiments, the nucleic acid molecule encoding the variant PNPLA3 Ile148Met protein or PNPLA3 Ile144Met protein is mRNA. In some embodiments, the mRNA encoding the variant PNPLA3 Ile148Met protein or PNPLA3 Ile144Met protein is any of the mRNA molecules described herein. In some embodiments, the nucleic acid molecule encoding the variant PNPLA3 Ile148Met protein is mRNA. In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35. In some embodiments, the mRNA encoding the variant PNPLA3 protein is detected by nucleic acid sequencing or hybridization of a probe, as described herein. In some embodiments, the mRNA encoding the variant PNPLA3 protein that comprises the AUG codon is identified by nucleic acid sequencing or hybridization of a probe, as described herein.

In some embodiments, the nucleic acid molecule encoding the variant PNPLA3 Ile148Met protein or PNPLA3 Ile144Met protein is cDNA. In some embodiments, the cDNA encoding the variant PNPLA3 Ile148Met protein or PNPLA3 Ile144Met protein is any of the cDNA molecules described herein. In some embodiments, the nucleic acid molecule encoding a PNPLA3 Ile148Met protein is cDNA. In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39. In some embodiments, the cDNA encoding the variant PNPLA3 protein is identified by nucleic acid sequencing or hybridization of a probe. In some embodiments, the cDNA encoding the variant PNPLA3 protein that comprises the ATG codon is identified by nucleic acid sequencing or hybridization of a probe, as described herein.

In some embodiments, the nucleic acid molecule encoding the functional HSD17B13 protein is any of the nucleic acid molecules described herein. In some embodiments, the nucleic acid molecule encoding the functional HSD17B13 protein is genomic DNA. In some embodiments, the genomic DNA encoding the functional HSD17B13 protein is any of the genomic DNA molecules described herein. In some embodiments, the genomic DNA comprises an adenine at a position corresponding to position 12,667 according to SEQ ID NO:1. In some embodiments, the genomic DNA comprises SEQ ID NO:1. In some embodiments, the presence of the functional HSD17B13 genomic DNA is determined by nucleic acid sequencing or hybridization of a probe, as described herein.

In some embodiments, the nucleic acid molecule encoding the functional HSD17B13 protein is mRNA. In some embodiments, the mRNA encoding the functional HSD17B13 protein is any of the mRNA molecules described herein. In some embodiments, the functional HSD17B13 nucleic acid molecule is mRNA. In some embodiments, the mRNA comprises SEQ ID NO:3. In some embodiments, the mRNA comprises SEQ ID NO:4. In some embodiments, the mRNA comprises SEQ ID NO:7. In some embodiments, the mRNA comprises SEQ ID NO:11. In some embodiments, the presence of the functional HSD17B13 mRNA is determined by nucleic acid sequencing or hybridization of a probe, as described herein.

In some embodiments, the nucleic acid molecule encoding the functional HSD17B13 protein is cDNA. In some embodiments, the cDNA encoding the functional HSD17B13 protein is any of the cDNA molecules described herein. In some embodiments, the cDNA comprises SEQ ID NO:12. In some embodiments, the cDNA comprises SEQ ID NO:13. In some embodiments, the cDNA comprises SEQ ID NO:16. In some embodiments, the cDNA comprises SEQ ID NO:20. In some embodiments, the presence of the functional HSD17B13 cDNA is determined by nucleic acid sequencing or hybridization of a probe, as described herein.

In some embodiments, the methods further comprising obtaining the sample from the subject. In some embodiments, the subject who is a candidate for HSD17B13 inhibition has a liver disease or is susceptible to developing a liver disease. In some embodiments, the liver disease is a chronic liver disease. In some preferred embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some preferred embodiments, the chronic liver disease is nonalcoholic fatty liver disease (NAFLD), alcoholic liver disease (ALD), non-alcoholic steatohepatitis (NASH), cirrhosis, or steatosis. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

The present disclosure also provides methods of detecting a PNPLA3 Ile148Met variant, or a PNPLA3 Ile144Met variant, and functional HSD17B13 in a subject comprising: detecting the presence of a PNPLA3 Ile148Met protein, or a nucleic acid molecule encoding a PNPLA3 Ile148Met protein, in a sample from the subject, or detecting the presence of a PNPLA3 Ile144Met protein, or a nucleic acid molecule encoding a PNPLA3 Ile144Met protein, in a sample from the subject; and detecting the presence of a functional HSD17B13 protein, or a nucleic acid molecule encoding a functional HSD17B13 protein, in a sample from the subject. The variant PNPLA3 Ile148Met variant protein or nucleic acid molecule can be any of the variant PNPLA3 Ile148Met variant proteins or nucleic acid molecules described herein. The variant PNPLA3 Ile144Met variant protein or nucleic acid molecule can be any of the variant PNPLA3 Ile144Met variant proteins or nucleic acid molecules described herein. The functional HSD17B13 protein or nucleic acid molecule can be any of the functional HSD17B13 proteins or nucleic acid molecules described herein.

In some embodiments, the methods further comprise determining whether the subject is homozygous or heterozygous for the variant PNPLA3 Ile148Met variant or PNPLA3 Ile144Met variant. In some embodiments, the subject is homozygous for the variant PNPLA3 Ile148Met variant or PNPLA3 Ile144Met variant. In some embodiments, the subject is heterozygous for the variant PNPLA3 Ile148Met variant or PNPLA3 Ile144Met variant. In some embodiments, the subject is homozygous for the variant PNPLA3 Ile148Met variant. In some embodiments, the subject is heterozygous for the variant PNPLA3 Ile148Met variant. In some embodiments, the subject is homozygous for the variant PNPLA3 Ile144Met variant. In some embodiments, the subject is heterozygous for the variant PNPLA3 Ile144Met variant.

In some embodiments, the methods further comprise determining whether the subject is homozygous or heterozygous for functional HSD17B13. In some embodiments, the subject is homozygous for functional HSD17B13. In some embodiments, the subject is heterozygous for functional HSD17B13.

In some embodiments, the presence of a functional HSD17B13 protein is detected in the sample. The functional HSD17B13 protein can be any of the functional HSD17B13 proteins described herein. In some embodiments, the functional HSD17B13 protein comprises an amino acid sequence according to SEQ ID NO:21, SEQ ID NO:22, SEQ ID NO:25, or SEQ ID NO:29. In some embodiments, the functional HSD17B13 protein is detected by amino acid sequencing or immunoassay, as described herein.

In some embodiments, the presence of a functional HSD17B13 nucleic acid molecule is detected in the sample. The functional HSD17B13 nucleic acid molecule can be any of the functional HSD17B13 nucleic acid molecules described herein. In some embodiments, the functional HSD17B13 nucleic acid molecule is genomic DNA. The functional HSD17B13 genomic DNA molecule can be any of the functional HSD17B13 genomic DNA molecules described herein. In some embodiments, the genomic DNA comprises an adenine at a position corresponding to position 12,667 according to SEQ ID NO:1. In some embodiments, the genomic DNA comprises SEQ ID NO:1. In some embodiments, the genomic DNA is detected by nucleic acid sequencing or hybridization of a probe, as described herein.

In some embodiments, the functional HSD17B13 nucleic acid molecule is mRNA. The functional HSD17B13 mRNA molecule can be any of the functional HSD17B13 mRNA molecules described herein. In some embodiments, the mRNA comprises SEQ ID NO:3. In some embodiments, the mRNA comprises SEQ ID NO:4. In some embodiments, the mRNA comprises SEQ ID NO:7. In some embodiments, the mRNA comprises SEQ ID NO:11. In some embodiments, the mRNA is detected by nucleic acid sequencing or hybridization of a probe, as described herein.

In some embodiments, the functional HSD17B13 nucleic acid molecule is cDNA. The functional HSD17B13 cDNA molecule can be any of the functional HSD17B13 cDNA molecules described herein. In some embodiments, the cDNA comprises SEQ ID NO:12. In some embodiments, the cDNA comprises SEQ ID NO:13. In some embodiments, the cDNA comprises SEQ ID NO:16. In some embodiments, the cDNA comprises SEQ ID NO:20. In some embodiments, the cDNA is detected by nucleic acid sequencing or hybridization of a probe, as described herein.

In some embodiments, the presence of a PNPLA3 Ile148Met protein or PNPLA3 Ile144Met protein is detected in the sample. The variant PNPLA3 Ile148Met protein or PNPLA3 Ile144Met protein can be any of the variant PNPLA3 Ile148Met proteins or PNPLA3 Ile144Met proteins described herein. In some embodiments, the variant PNPLA3 Ile148Met protein comprises a methionine at a position corresponding to position 148 according to SEQ ID NO:42, or comprises a methionine at a position corresponding to position 144 according to SEQ ID NO:43. In some embodiments, the variant PNPLA3 Ile148Met protein comprises a methionine at a position corresponding to position 148 according to SEQ ID NO:42. In some embodiments, the variant PNPLA3 protein in the sample comprises the amino acid sequence according to SEQ ID NO:42. In some embodiments, the variant PNPLA3 Ile148Met protein comprises a methionine at a position corresponding to position 144 according to SEQ ID NO:43. In some embodiments, the variant PNPLA3 protein in the sample comprises the amino acid sequence according to SEQ ID NO:43. In some embodiments, the variant PNPLA3 Ile148Met protein or PNPLA3 Ile144Met protein is detected by amino acid sequencing or immunoassay, as described herein.

In some embodiments, the presence of a nucleic acid molecule encoding a PNPLA3 Ile148Met protein or PNPLA3 Ile148Met protein is detected in the sample. The nucleic acid molecule encoding a PNPLA3 Ile148Met protein or PNPLA3 Ile148Met protein can be any of the nucleic acid molecules encoding a PNPLA3 Ile148Met protein or PNPLA3 Ile148Met protein described herein.

In some embodiments, the nucleic acid molecule encoding a PNPLA3 Ile148Met protein or PNPLA3 Ile144Met protein is genomic DNA. The genomic DNA encoding a PNPLA3 Ile148Met protein or PNPLA3 Ile144Met protein can be any of the genomic DNA molecules described herein. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31. In some embodiments, the genomic DNA encoding the variant PNPLA3 protein that comprises the ATG codon is detected by nucleic acid sequencing or hybridization of a probe, as described herein.

In some embodiments, the nucleic acid molecule encoding a PNPLA3 Ile148Met protein or PNPLA3 Ile148Met protein is mRNA. The mRNA molecule encoding a PNPLA3 Ile148Met protein or PNPLA3 Ile148Met protein can be any of the mRNA molecules described herein. In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35. In some embodiments, the mRNA encoding the variant PNPLA3 protein that comprises the AUG codon is identified by nucleic acid sequencing or hybridization of a probe, as described herein.

In some embodiments, nucleic acid molecule encoding a PNPLA3 Ile148Met protein or PNPLA3 Ile144Met protein is cDNA. The cDNA encoding a PNPLA3 Ile148Met protein or PNPLA3 Ile144Met protein can be any of the cDNA molecules described herein. In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39. In some embodiments, the cDNA encoding the variant PNPLA3 protein that comprises the ATG codon is identified by nucleic acid sequencing or hybridization of a probe, as described herein.

In some embodiments, the method further comprises obtaining the sample from the subject.

The present disclosure also provides methods of identifying a subject having a protective effect against liver disease, comprising: detecting the presence of a PNPLA3 Ile148Met variant or PNPLA3 Ile144Met variant in a sample from the subject; and detecting the presence of an HSD17B13 loss-of-function variant in a sample from the subject. The present disclosure also provides methods of classifying a subject having a protective effect against liver disease, comprising: detecting the presence of a PNPLA3 Ile148Met variant or PNPLA3 Ile144Met variant in a sample from the subject; and detecting the presence of an HSD17B13 loss-of-function variant in a sample from the subject. The variant PNPLA3 Ile148Met variant and PNPLA3 Ile144Met variant can be any of the variant PNPLA3 Ile148Met variants and PNPLA3 Ile144Met variants described herein. The HSD17B13 loss-of-function variant can be any of the HSD17B13 loss-of-function variants described herein.

In some embodiments, the methods further comprise determining whether the subject is homozygous or heterozygous for the variant PNPLA3 Ile148Met variant or PNPLA3 Ile144Met variant. In some embodiments, the subject is homozygous for the variant PNPLA3 Ile148Met variant or PNPLA3 Ile144Met variant. In some embodiments, the subject is heterozygous for the variant PNPLA3 Ile148Met variant or PNPLA3 Ile144Met variant. In some embodiments, the subject is homozygous for the variant PNPLA3 Ile148Met variant. In some embodiments, the subject is heterozygous for the variant PNPLA3 Ile148Met variant. In some embodiments, the subject is homozygous for the variant PNPLA3 Ile144Met variant. In some embodiments, the subject is heterozygous for the variant PNPLA3 Ile144Met variant.

In some embodiments, the methods further comprise determining whether the subject is homozygous or heterozygous for functional HSD17B13. In some embodiments, the subject is homozygous for functional HSD17B13. In some embodiments, the subject is heterozygous for functional HSD17B13.

In some embodiments, the variant PNPLA3 Ile148Met variant or PNPLA3 Ile144Met variant is detected in the subject by detecting a PNPLA3 Ile148Met protein, or a nucleic acid molecule encoding a PNPLA3 Ile148Met protein, in a sample from the subject, or detecting a PNPLA3 Ile144Met protein, or a nucleic acid molecule encoding a PNPLA3 Ile144Met protein, in a sample from the subject; and the HSD17B13 loss-of-function is detected in the subject by detecting an HSD17B13 loss-of-function variant protein, or a nucleic acid molecule encoding an HSD17B13 loss-of-function variant protein, in a sample from the subject. In some embodiments, the variant PNPLA3 Ile148Met variant or PNPLA3 Ile144Met variant is detected in the subject by detecting a PNPLA3 Ile148Met protein, or a nucleic acid molecule encoding a PNPLA3 Ile148Met protein, in a sample from the subject; and the HSD17B13 loss-of-function is detected in the subject by detecting an HSD17B13 loss-of-function variant protein, or a nucleic acid molecule encoding an HSD17B13 loss-of-function variant protein, in a sample from the subject.

In some embodiments, the presence of a PNPLA3 Ile148Met protein or PNPLA3 Ile144Met protein is detected in the sample. The variant PNPLA3 Ile148Met protein and PNPLA3 Ile144Met protein can be any of the variant PNPLA3 Ile148Met proteins and PNPLA3 Ile144Met proteins described herein. In some embodiments, the variant PNPLA3 Ile148Met protein comprises a methionine at a position corresponding to position 148 according to SEQ ID NO:42, or comprises a methionine at a position corresponding to position 144 according to SEQ ID NO:43. In some embodiments, the variant PNPLA3 Ile148Met protein comprises a methionine at a position corresponding to position 148 according to SEQ ID NO:42. In some embodiments, the variant PNPLA3 protein in the sample comprises the amino acid sequence according to SEQ ID NO:42. In some embodiments, the variant PNPLA3 Ile148Met protein comprises a methionine at a position corresponding to position 144 according to SEQ ID NO:43. In some embodiments, the variant PNPLA3 protein in the sample comprises the amino acid sequence according to SEQ ID NO:43. In some embodiments, the variant PNPLA3 Ile148Met protein is detected by amino acid sequencing or immunoassay, as described herein.

In some embodiments, the presence of a nucleic acid molecule encoding a PNPLA3 Ile148Met protein or PNPLA3 Ile144Met protein is detected in the sample. The nucleic acid molecule encoding the variant PNPLA3 Ile148Met protein or PNPLA3 Ile144Met protein can be any of the nucleic acid molecules encoding the variant PNPLA3 Ile148Met proteins and PNPLA3 Ile144Met proteins described herein.

In some embodiments, wherein the nucleic acid molecule encoding a PNPLA3 Ile148Met protein or PNPLA3 Ile144Met protein is genomic DNA. The genomic DNA encoding the variant PNPLA3 Ile148Met protein or PNPLA3 Ile144Met protein can be any of the variant PNPLA3 Ile148Met proteins and PNPLA3 Ile144Met proteins described herein. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31. In some embodiments, the genomic DNA encoding the variant PNPLA3 protein that comprises the ATG codon is detected by nucleic acid sequencing or hybridization of a probe.

In some embodiments, the nucleic acid molecule encoding the variant PNPLA3 Ile148Met protein or PNPLA3 Ile144Met protein is mRNA. The mRNA molecule encoding the variant PNPLA3 Ile148Met proteins and PNPLA3 Ile144Met proteins can be any of the variant PNPLA3 Ile148Met proteins and PNPLA3 Ile144Met proteins described herein. In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35. In some embodiments, the mRNA encoding the variant PNPLA3 protein that comprises the AUG codon is identified by nucleic acid sequencing or hybridization of a probe, as described herein.

In some embodiments, the nucleic acid molecule encoding a PNPLA3 Ile148Met protein or PNPLA3 Ile148Met protein is cDNA. The cDNA encoding the variant PNPLA3 Ile148Met protein and PNPLA3 Ile148Met protein can be any of the variant PNPLA3 Ile148Met proteins and PNPLA3 Ile148Met proteins described herein. In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39. In some embodiments, the cDNA encoding the variant PNPLA3 protein that comprises the ATG codon is identified by nucleic acid sequencing or hybridization of a probe, as described herein.

In some embodiments, the presence of an HSD17B13 loss-of-function variant protein is detected in the sample. The HSD17B13 loss-of-function variant can be any of the HSD17B13 loss-of-function variant proteins described herein. In some embodiments, the HSD17B13 loss-of-function variant protein comprises an amino acid sequence according to SEQ ID NO:23. In some embodiments, the HSD17B13 loss-of-function variant protein comprises an amino acid sequence according to SEQ ID NO:24. In some embodiments, the HSD17B13 loss-of-function variant protein comprises an amino acid sequence according to SEQ ID NO:26. In some embodiments, the HSD17B13 loss-of-function variant protein comprises an amino acid sequence according to SEQ ID NO:27. In some embodiments, the HSD17B13 loss-of-function variant protein comprises an amino acid sequence according to SEQ ID NO:28. In some embodiments, the HSD17B13 loss-of-function variant protein is detected by amino acid sequencing or immunoassay, as described herein.

In some embodiments, the presence of a nucleic acid molecule encoding an HSD17B13 loss-of-function variant protein is detected in the sample. The nucleic acid molecule encoding an HSD17B13 loss-of-function variant protein can be any of the nucleic acid molecules encoding the HSD17B13 loss-of-function variant protein described herein.

In some embodiments, the nucleic acid molecule encoding the HSD17B13 loss-of-function variant protein is genomic DNA. The genomic DNA molecule encoding the HSD17B13 loss-of-function variant protein can be any of the HSD17B13 loss-of-function variant proteins described herein. In some embodiments, the genomic DNA encoding an HSD17B13 loss-of-function variant protein which comprises a thymine at a position corresponding to position 12,667 according to SEQ ID NO:2. In some embodiments, the genomic DNA encoding an HSD17B13 loss-of-function variant protein comprises SEQ ID NO:2. In some embodiments, the genomic DNA encoding the HSD17B13 loss-of-function variant protein is detected by nucleic acid sequencing or hybridization of a probe, as described herein.

In some embodiments, the nucleic acid molecule encoding the HSD17B13 loss-of-function variant protein is mRNA. The mRNA molecule encoding the HSD17B13 loss-of-function variant protein can be any of the mRNA molecules encoding the HSD17B13 loss-of-function variant proteins described herein. In some embodiments, the mRNA encoding an HSD17B13 loss-of-function variant protein comprises SEQ ID NO:5. In some embodiments, the mRNA encoding an HSD17B13 loss-of-function variant protein comprises SEQ ID NO:6. In some embodiments, the mRNA encoding an HSD17B13 loss-of-function variant protein comprises SEQ ID NO:8. In some embodiments, the mRNA encoding an HSD17B13 loss-of-function variant protein comprises SEQ ID NO:9. In some embodiments, the mRNA encoding an HSD17B13 loss-of-function variant protein comprises SEQ ID NO:10. In some embodiments, the mRNA encoding the HSD17B13 loss-of-function variant protein is detected by nucleic acid sequencing or hybridization of a probe, as described herein.

In some embodiments, the nucleic acid molecule encoding the HSD17B13 loss-of-function variant protein is cDNA. The cDNA molecules encoding the HSD17B13 loss-of-function variant protein can be any of the cDNA molecules encoding the HSD17B13 loss-of-function variant protein described herein. In some embodiments, the cDNA encoding an HSD17B13 loss-of-function variant protein comprises SEQ ID NO:5. In some embodiments, the cDNA encoding an HSD17B13 loss-of-function variant protein comprises SEQ ID NO:6. In some embodiments, the cDNA encoding an HSD17B13 loss-of-function variant protein comprises SEQ ID NO:8. In some embodiments, the cDNA encoding an HSD17B13 loss-of-function variant protein comprises SEQ ID NO:9. In some embodiments, the cDNA encoding an HSD17B13 loss-of-function variant protein comprises SEQ ID NO:10. In some embodiments, the cDNA encoding the HSD17B13 loss-of-function variant protein is detected by nucleic acid sequencing or hybridization of a probe, as described herein.

In some embodiments, the methods further comprises obtaining the sample from the subject. In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

The present disclosure also provides any of the methods described herein further comprising administering to the subject an inhibitor of HSD17B13. In some embodiments, the inhibitor of HSD17B13 comprises a functional polypeptide, an antisense DNA, RNA, an siRNA, or an shRNA that hybridizes to the endogenous HSD17B13 genomic DNA or mRNA and decreases expression of HSD17B13 polypeptide in a cell in the subject. In some embodiments, the HSD17B13 inhibitor can also inhibit one or more additional members of the short-chain dehydrogenases/reductases (SDR) family, of which HSD17B13 is a member. Such other members include, but are not limited to, HSD17B1, HSD17B2, HSD17B3, HSD17B4, HSD17B6, HSD17B7, HSD17B8, HSD17B10, HSD17B11, HSD17B12, HSD17B13, HSD17B14, HSD11B1, HSD11B2, HSD3B1, HSD3B2, and HSD3B7, as well as close homologs dehydrogenase/reductase 3 (DHRS3) and retinol dehydrogenase 10 (RDH10). In some embodiments, the inhibitor of HSD17B13 is administered to inhibit liver disease in the subject. In some embodiments, the inhibitor of HSD17B13 is administered to treat liver disease in the subject. In some embodiments, the liver disease is a chronic liver disease. In some embodiments, the chronic liver disease is one or more of nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption. In some embodiments, the subject is homozygous for the gene encoding the I148M variation. In some embodiments, the subject is heterozygous for the gene encoding the I148M variation. In some embodiments, the subject further is homozygous for the gene encoding the functional HSD17B13 protein. In some embodiments, the subject further is heterozygous for the gene encoding the functional HSD17B13 protein and a gene encoding a loss of function variant of HSD17B13.

The disclosure also provides methods of treating or inhibiting liver disease, comprising administering an inhibitor of hydroxysteroid 17-beta dehydrogenase 13 (HSD17B13) to a human liver disease patient expressing a patatin like phospholipase domain containing 3 (PNPLA3) protein comprising an I148M variation such that liver disease is treated or inhibited in the patient. In some embodiments, the liver disease is a chronic liver disease. In some embodiments, the liver disease is one or more of nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption. In some embodiments, the patient is obese. In some embodiments, the patient has a fatty liver. In some embodiments, the patient has been determined to express the variant PNPLA3 protein (e.g., a PNPLA3 protein comprising the I148M or I144M variation) by detection of the variant PNPLA3 protein in a sample from the subject. In some embodiments, the variant PNPLA3 protein comprises a methionine at a position corresponding to position 148 according to SEQ ID NO:42. In some embodiments, the variant PNPLA3 protein in the sample comprises the amino acid sequence according to SEQ ID NO:42. In some embodiments, the variant PNPLA3 protein is detected by amino acid sequencing or by an immunoassay. In some embodiments, the subject has been determined to express the variant PNPLA3 protein by detection of a nucleic acid molecule encoding the variant PNPLA3 protein (e.g., a variant PNPLA3 nucleic acid molecule encoding a PNPLA3 protein comprising the I148M or 1144M variation) in a sample from the subject. In some embodiments, the variant PNPLA3 protein comprises a methionine at a position corresponding to position 148 according to SEQ ID NO:42. In some embodiments, the variant PNPLA3 protein comprises the amino acid sequence according to SEQ ID NO:42. In some embodiments, the nucleic acid molecule encoding the variant PNPLA3 protein comprises genomic DNA, mRNA, or cDNA obtained from mRNA. In some embodiments, the nucleic acid molecule comprises genomic DNA comprising an ATG codon at the positions corresponding to positions 5107 to 5109 according to SEQ ID NO:31. In some embodiments, the genomic DNA comprises the nucleotide sequence according to SEQ ID NO:31. In some embodiments, the nucleic acid molecule comprises mRNA comprising an AUG codon at the positions corresponding to positions 442 to 444 according to SEQ ID NO:34. In some embodiments, the mRNA comprises the nucleotide sequence according to SEQ ID NO:34. In some embodiments, the nucleic acid molecule comprises mRNA comprising an AUG codon at the positions corresponding to positions 430 to 432 according to SEQ ID NO:35. In some embodiments, the mRNA comprises the nucleotide sequence according to SEQ ID NO:35. In some embodiments, the nucleic acid molecule comprises cDNA obtained from mRNA, the cDNA comprising an ATG codon at the positions corresponding to positions 442 to 444 according to SEQ ID NO:38. In some embodiments, the cDNA comprises the nucleotide sequence according to SEQ ID NO:38. In some embodiments, the nucleic acid molecule comprises cDNA obtained from mRNA, the cDNA comprising an ATG codon at the positions corresponding to positions 430 to 432 according to SEQ ID NO:39. In some embodiments, the cDNA comprises the nucleotide sequence according to SEQ ID NO:39. In some embodiments, the nucleic acid is detected by sequencing at least a portion of the nucleic acid, the portion encoding the I148M variation. In some embodiments, the nucleic acid is detected by hybridization of a probe or primer that specifically hybridizes to a portion of the nucleic acid, wherein the portion comprises the codon encoding the I148M variation. In some embodiments, the probe or primer is an allele-specific probe or primer. In some embodiments, the probe or primer comprises a label. In some embodiments, the patient is homozygous for a gene encoding the variant PNPLA3 protein. In some embodiments, the patient is heterozygous for a gene encoding the variant PNPLA3 protein. In some embodiments, patient is homozygous for a gene encoding a functional HSD17B13 protein. In some embodiments, the patient is heterozygous for a gene encoding a functional HSD17B13 protein. In some embodiments, the patient is heterozygous for the gene encoding the functional HSD17B13 protein and a gene encoding a loss of function variant of HSD17B13.

Inhibitors of HSD17B13 can be used as described herein for treatment of a liver disease in a human subject having a PNPLA3 protein comprising an I148M variation and having a functional HSD17B13 protein. In some embodiments, the human subject has been tested positive for a PNPLA3 protein comprising an I148M variation and for a functional HSD17B13 protein. In some embodiments, the treatment comprises determining whether or not the human subject has a PNPLA3 protein comprising an I148M variation and a functional HSD17B13 protein. In some embodiments, the human subject has been identified as being a candidate for treating or inhibiting a liver disease by inhibiting HSD17B13 by using any of the method as defined herein. In some embodiments, the variant PNPLA3 protein comprises a methionine at the position corresponding to position 148 according to SEQ ID NO:42. In some embodiments, the variant PNPLA3 protein comprises the amino acid sequence according to SEQ ID NO:42, or an amino acid sequence having at least 90% sequence identity to SEQ ID NO:42 and comprising the I148M variation. In some embodiments, the variant PNPLA3 protein comprises a methionine at the position corresponding to position 144 according to SEQ ID NO:43. In some embodiments, the variant PNPLA3 protein comprises the amino acid sequence according to SEQ ID NO:43, or an amino acid sequence having at least 90% sequence identity to SEQ ID NO:43 and comprising the 1144M variation. In some embodiments, the nucleic acid molecule encoding the variant PNPLA3 protein is genomic DNA. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31, or a nucleotide sequence having at least 90% sequence identity to SEQ ID NO:31 and encoding a PNPLA3 protein which comprises the I148M variation. In some embodiments, the nucleic acid molecule encoding the variant PNPLA3 protein is mRNA. In some embodiments, the mRNA comprises an AUG codon at the positions corresponding to positions 442 to 444 according to SEQ ID NO:34. In some embodiments, the mRNA comprises the nucleotide sequence according to SEQ ID NO:34, or a nucleotide sequence having at least 90% sequence identity to SEQ ID NO:34 and encoding a PNPLA3 protein which comprises the I148M variation. In some embodiments, the mRNA comprises an AUG codon at the positions corresponding to positions 430 to 432 according to SEQ ID NO:35. In some embodiments, the mRNA comprises the nucleotide sequence according to SEQ ID NO:35, or a nucleotide sequence having at least 90% sequence identity to SEQ ID NO:35 and encoding a PNPLA3 protein which comprises the 1144M variation. In some embodiments, the nucleic acid molecule encoding the variant PNPLA3 protein is cDNA. In some embodiments, the cDNA comprises an ATG codon at the positions corresponding to positions 442 to 444 according to SEQ ID NO:38. In some embodiments, the cDNA comprises the nucleotide sequence according to SEQ ID NO:38, or a nucleotide sequence having at least 90% sequence identity to SEQ ID NO:38 and encoding a PNPLA3 protein which comprises the I148M variation. In some embodiments, the cDNA comprises an ATG codon at the positions corresponding to positions 430 to 432 according to SEQ ID NO:39. In some embodiments, the cDNA comprises the nucleotide sequence according to SEQ ID NO:39, or a nucleotide sequence having at least 90% sequence identity to SEQ ID NO:39 and encoding a PNPLA3 protein which comprises the 1144M variation. In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or nonalcoholic steatohepatitis (NASH). In some embodiments, the non-alcoholic liver disease comprises one or more of cirrhosis, steatosis, or hepatocellular carcinoma not caused by alcohol consumption. In some embodiments, the human subject is homozygous or heterozygous for functional HSD17B13.

In some embodiments, inhibitors of HSD17B13 reduce or inhibit HSD17B13 gene expression or the function of HSD17B13 protein. Inhibitors of HSD17B13 include, but are not limited to, naturally occurring and synthetic ligands, antagonists, agonists, antibodies, peptides, cyclic peptides, nucleic acids, functional polynucleotides, small organic molecules, and the like. Functional polynucleotides are nucleic acid molecules that have a specific function, such as binding a target molecule or catalyzing a specific reaction. Examples of functional polynucleotides include, but are not limited to, antisense molecules, aptamers, ribozymes, and triplex forming molecules. The functional polynucleotides can act as inhibitors of a specific activity possessed by a target molecule. Antisense molecules are designed to interact with a target nucleic acid molecule through either canonical or non-canonical base pairing. The interaction of the antisense molecule and the target molecule is designed to promote the destruction of the target molecule through, for example, RNase-H-mediated RNA-DNA hybrid degradation. Alternately, the antisense molecule is designed to interrupt a processing function that normally would take place on the target molecule, such as transcription or replication. Antisense molecules can be designed based on the sequence of the target molecule. Numerous methods for optimization of antisense efficiency by identifying the most accessible regions of the target molecule exist. Exemplary methods include, but are not limited to, in vitro selection experiments and DNA modification studies using DMS and DEPC. Antisense molecules generally bind the target molecule with a dissociation constant (kd) less than or equal to about 10-6, less than or equal to about 10-8, less than or equal to about 10-10, or less than or equal to about 10-12. A representative sample of methods and techniques which aid in the design and use of antisense molecules, and antisense molecules, can be found in the following non-limiting list of U.S. patents and applications: U.S. Pat. Nos. 5,135,917; 5,294,533; 5,627,158; 5,641,754; 5,691,317; 5,780,607; 5,786,138; 5,849,903; 5,856,103; 5,919,772; 5,955,590; 5,990,088; 5,994,320; 5,998,602; 6,005,095; 6,007,995; 6,013,522; 6,017,898; 6,018,042; 6,025,198; 6,033,910; 6,040,296; 6,046,004; 6,046,319; 6,057,437; and U.S. Ser. No. 62/645,941 filed Mar. 21, 2018, each of which is incorporated herein by reference in its entirety. Examples of antisense molecules include, but are not limited to, antisense RNAs, small interfering RNAs (siRNAs), and short hairpin RNAs (shRNAs). For example, the antisense RNAs, siRNAs, or shRNAs can be designed to target a region unique of the HSD17B13 genomic DNA or mRNA. In some embodiments, the inhibitor of HSD17B13 is an antisense molecule. In some embodiments, the inhibitor of HSD17B13 is an shRNA molecule. In some embodiments, the inhibitor of HSD17B13 is an siRNA molecule.

In any of the methods described herein, administration of an inhibitor of HSD17B13 can result in the reduction or elimination of particular characteristics of liver disease. In some embodiments, the characteristics of liver disease include, but are not limited to inflammation and fibrosis.

The present disclosure also provides methods of treating a subject who is PNPLA3 Ile148Met positive (i.e., "PNPLA3 Ile148Met+") or PNPLA3 Ile144Met positive (i.e., "PNPLA3 Ile144Met+"), comprising administering an inhibitor of HSD17B13 to the subject. The present disclosure also provides methods of treating or inhibiting liver disease comprising administering an inhibitor of HSD17B13 to a human liver disease patient expressing a PNPLA3 protein comprising an I148M variation such that liver disease is treated or inhibited in the patient.

The variant PNPLA3 Ile148Met positive or PNPLA3 Ile144Met positive subject can have any of the variant PNPLA3 proteins described herein. In some embodiments, the subject is also homozygous or heterozygous for functional HSD17B13. In some embodiments, the subject is homozygous for functional HSD17B13. In some embodiments, the subject is heterozygous for functional HSD17B13. In some embodiments, the subject is homozygous for the HSD17B13 loss-of-function variant. The subject can have any of the functional HSD17B13 proteins described herein.

In some embodiments, the subject who is PNPLA3 Ile148Met+ or PNPLA3 Ile144Met+ has been determined to be PNPLA3 Ile148Met+ or PNPLA3 Ile144Met+ by detection of a PNPLA3 protein in a sample from the subject, wherein the variant PNPLA3 protein comprises a methionine at a position corresponding to position 148 according to SEQ ID NO:42, or comprises a methionine at a position corresponding to position 144 according to SEQ ID NO:43. The variant PNPLA3 Ile148Met positive or PNPLA3 Ile144Met positive subject can have any of the variant PNPLA3 proteins described herein.

In some embodiments, the subject who is PNPLA3 Ile148Met+ has been determined to be PNPLA3 Ile148Met+ by detection of a PNPLA3 protein in a sample from the subject, wherein the variant PNPLA3 protein comprises a methionine at a position corresponding to position 148 according to SEQ ID NO:42. In some embodiments, the variant PNPLA3 protein in the sample comprises the amino acid sequence according to SEQ ID NO:42.

In some embodiments, the subject who is PNPLA3 Ile144Met+ has been determined to be PNPLA3 Ile144Met+ by detection of a PNPLA3 protein in a sample from the subject, wherein the variant PNPLA3 protein comprises a methionine at a position corresponding to position 144 according to SEQ ID NO:43. In some embodiments, the variant PNPLA3 protein in the sample comprises the amino acid sequence according to SEQ ID NO:43.

In some embodiments, the variant PNPLA3 protein that comprises the methionine at the position corresponding to position 148 according to SEQ ID NO:42, or that comprises the methionine at the position corresponding to position 144 according to SEQ ID NO:43 is identified by amino acid sequencing or immunoassay as described herein.

In some embodiments, the subject who is PNPLA3 Ile148Met+ or PNPLA3 Ile144Met+ has been determined to be PNPLA3 Ile148Met+ or PNPLA3 Ile144Met+ by detection of a nucleic acid molecule encoding a PNPLA3 protein in a sample from the subject, wherein the variant PNPLA3 protein comprises a methionine at a position corresponding to position 148 according to SEQ ID NO:42, or comprises a methionine at a position corresponding to position 144 according to SEQ ID NO:43. The variant PNPLA3 Ile148Met positive or PNPLA3 Ile144Met positive subject can have any of the variant PNPLA3 nucleic acid molecules described herein.

In some embodiments, the subject who is PNPLA3 Ile148Met+ has been determined to be PNPLA3 Ile148Met+ by detection of a nucleic acid molecule encoding a PNPLA3 protein in a sample from the subject, wherein the variant PNPLA3 protein comprises a methionine at a position corresponding to position 148 according to SEQ ID NO:42. In some embodiments, the variant PNPLA3 protein in the sample comprises the amino acid sequence according to SEQ ID NO:42.

In some embodiments, the subject who is PNPLA3 Ile144Met+ has been determined to be PNPLA3 Ile144Met+ by detection of a nucleic acid molecule encoding PNPLA3 protein in a sample from the subject, wherein the variant PNPLA3 protein comprises a methionine at a position corresponding to position 144 according to SEQ ID NO:43. In some embodiments, the variant PNPLA3 protein in the sample comprises the amino acid sequence according to SEQ ID NO:43.

In some embodiments, the nucleic acid molecule encoding the variant PNPLA3 protein is genomic DNA, mRNA, or cDNA derived from mRNA.

In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31. In some embodiments, the genomic DNA encoding the variant PNPLA3 protein that comprises the ATG codon is identified by nucleic acid sequencing or hybridization of a probe, as described herein.

In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35. In some embodiments, the mRNA encoding the variant PNPLA3 protein that comprises the AUG codon is identified by nucleic acid sequencing or hybridization of a probe, as described herein.

In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39. In some embodiments, the cDNA encoding the variant PNPLA3 protein that comprises the ATG codon is identified by nucleic acid sequencing or hybridization of a probe, as described herein.

Administration of the inhibitor of HSD17B13 can be by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

In some embodiments, the subject has a liver disease or is susceptible to developing a liver disease. In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

The present disclosure also provides methods for treating a patient with a liver disease therapeutic agent, wherein the patient is suffering from a liver disease. The methods comprise determining whether or not a sample from the subject comprises: i) a first nucleic acid encoding a PNPLA3 protein comprising an I148M variation and a second nucleic acid encoding a functional HSD17B13 protein, and/or ii) a PNPLA3 protein comprising an I148M variation and a functional HSD17B13 protein. In some embodiments, the methods comprise determining whether or not a sample from the subject comprises a first nucleic acid encoding a PNPLA3 protein comprising an I148M variation and a second nucleic acid encoding a functional HSD17B13 protein. In some embodiments, the methods comprise determining whether or not a sample from the subject comprises a PNPLA3 protein comprising an I148M variation and a functional HSD17B13 protein.

In some embodiments, this determination is carried out by obtaining or having obtained a biological sample from the patient. In some embodiments, the methods further comprise performing or having performed a genotyping assay on the biological sample to determine if the patient has a first nucleic acid encoding a PNPLA3 protein comprising an I148M variation and a second nucleic acid encoding a functional HSD17B13 protein. In some embodiments, the methods further comprise performing or having performed an assay on the biological sample to determine if the patient has a PNPLA3 protein comprising an I148M variation and a functional HSD17B13 protein.

In some embodiments, when the patient has a nucleic acid encoding a PNPLA3 protein comprising an I148M variation and/or has a PNPLA3 protein comprising an I148M variation, and has a nucleic acid encoding a functional HSD17B13 protein and/or has a functional HSD17B13 protein, then the method further comprises administering an inhibitor of HSD17B13 to the patient. In some embodiments, when the patient has a nucleic acid encoding a PNPLA3 protein comprising an I148M variation and/or has a PNPLA3 protein comprising an I148M variation, and has a nucleic acid encoding a functional HSD17B13 protein and/or has a functional HSD17B13 protein, then the method further comprises administering an inhibitor of HSD17B13 to the patient and administering a liver disease therapeutic agent to the patient. In some embodiments, when the patient has a nucleic acid encoding a PNPLA3 protein comprising an I148M variation and/or has a PNPLA3 protein comprising an I148M variation, but does not have a nucleic acid encoding a functional HSD17B13 protein and/or has a functional HSD17B13 protein, then the method further comprises administering a liver disease therapeutic agent to the patient.

Examples of liver disease therapeutic agents include, but are not limited to, Disulfiram, Naltrexone, Acamprosate, Prednisone, Prednisone, Azathioprine, Penicillamine, Trientine, Deferoxamine, Ciprofloxacin, Norofloxacin, Ceftriaxone, Ofloxacin, Amoxicillin-clavulanate, Phytonadione, Bumetanide, Furosemide, Hydrochlorothiazide, Chlorothiazide, Amiloride, Triamterene, Spironolactone, Octreotide, Atenolol, Metoprolol, Nadolol, Propranolol, Timolol, and Carvedilol.

Additional examples of liver disease therapeutic agents (e.g., for use in chronic hepatitis C treatment) include, but are not limited to, ribavirin, paritaprevir, simeprevir (Olysio), grazoprevir, ledipasvir, ombitasvir, elbasvir, daclatasvir (Daklinza), dasabuvir, ritonavir, sofosbuvir, velpatasvir, voxilaprevir, glecaprevir, pibrentasvir, peginterferon alfa-2a, peginterferon alfa-2b, and interferon alfa-2b.

Additional examples of liver disease therapeutic agents (e.g., for use in nonalcoholic fatty liver disease) include, but are not limited to, weight loss inducing agents such as orlistat or sibutramine; insulin sensitizing agents such as thiazolidinediones (TZDs), metformin, and meglitinides; lipid lowering agents such as statins, fibrates, and omega-3 fatty acids; atioxidants such as, vitamin E, betaine, N-Acetyl-cysteine, lecithin, silymarin, and beta-carotene; anti TNF agents such as pentoxifylline; probiotics, such as VSL #3; and cytoprotective agents such as ursodeoxycholic acid (UDCA). Other suitable treatments include ACE inhibitors/ARBs, oligofructose, and Incretin analogs.

Additional examples of liver disease therapeutic agents (e.g., for use in NASH) include, but are not limited to, obeticholic acid (Ocaliva®), Selonsertib, Elafibranor, Cenicriviroc, GR_MD_02, MGL_3196, IMM124E, arachidyl amido cholanoic acid (Aramchol™), GS0976, Emricasan, Volixibat, NGM282, GS9674, Tropifexor, MN_001, LMB763, BI_1467335, MSDC_0602, PF_05221304, DF102, Saroglitazar, BMS986036, Lanifibranor, Semaglutide, Nitazoxanide, GRI_0621, EYP001, VK2809, Nalmefene, LIK066, MT_3995, Elobixibat, Namodenoson, Foralumab, SAR425899, Sotagliflozin, EDP_305, Isosabutate, Gemcabene, TERN_101, KBP_042, PF_06865571, DUR928, PF_06835919, NGM313, BMS_986171, Namacizumab, CER_209, ND_L02_s0201, RTU_1096, DRX_065, IONIS_DGAT2Rx, INT_767, NC_001, Seladepar, PXL770, TERN_201, NV556, AZD2693, SP_1373, VK0214, Hepastem, TGFTX4, RLBN1127, GKT_137831, RYI_018, CB4209-CB4211, and JH_0920.

The present disclosure also provides inhibitors of HSD17B13 for use in the manufacture of a medicament for the treatment of liver disease in a human subject who is PNPLA3 Ile148Met positive or PNPLA3 Ile144Met positive and who is also homozygous or heterozygous for functional HSD17B13. In some embodiments, the subject is homozygous for PNPLA3 Ile148Met variant or PNPLA3 Ile144Met variant. In some embodiments, the subject is heterozygous for PNPLA3 Ile148Met variant or PNPLA3 Ile144Met variant. In some embodiments, the subject is homozygous for functional HSD17B13. In some embodiments, the subject is heterozygous for functional HSD17B13.

In some embodiments, the inhibitor of HSD17B13 is for use in the treatment of a liver disease in a human subject having a PNPLA3 protein comprising a methionine at a position corresponding to position 148 according to SEQ ID NO:42, or a nucleic acid molecule encoding a PNPLA3 protein comprising a methionine at a position corresponding to position 148 according to SEQ ID NO:42, or comprising a methionine at a position corresponding to position 144 according to SEQ ID NO:43, or a nucleic acid molecule encoding a PNPLA3 protein comprising a methionine at a position corresponding to position 148 according to SEQ ID NO:43. In some embodiments, the variant PNPLA3 protein comprises a methionine at a position corresponding to position 148 according to SEQ ID NO:42. In some embodiments, the variant PNPLA3 protein comprises the amino acid sequence according to SEQ ID NO:42. In some embodiments, the variant PNPLA3 protein comprises a methionine at a position corresponding to position 144 according to SEQ ID NO:43. In some embodiments, the variant PNPLA3 protein comprises the amino acid sequence according to SEQ ID NO:43.

In some embodiments, the nucleic acid molecule encoding the variant PNPLA3 protein is genomic DNA. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31.

In some embodiments, the nucleic acid molecule encoding the variant PNPLA3 protein is mRNA. In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35.

In some embodiments, nucleic acid molecule encoding the variant PNPLA3 protein is cDNA. In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39.

In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

In some embodiments, the human subject is homozygous or heterozygous for functional HSD17B13. In some embodiments, the subject is homozygous for functional HSD17B13. In some embodiments, the subject is heterozygous for functional HSD17B13.

In any of the methods described herein, a probe or primer or an alteration-specific probe or an alteration-specific primer can be specifically complementary to or specifically hybridize with a single nucleic acid species. For example, a probe or primer or an alteration-specific probe or an alteration-specific primer specifically complementary to or specifically hybridizing with a nucleic acid molecule for HSD17B13 transcript A, transcript B, transcript E, or transcript I (e.g., any of the mRNA, cDNA, RNA transcript, or cDNA transcript for functional HSD17B13 described herein) is not complementary to or does not hybridize with any of the nucleic acid molecules for a variant HSD17B13 (e.g., any of the mRNA, cDNA, RNA transcripts, or cDNA transcripts for variants C, D, F, G, H of HSD17B13).

The present disclosure also provides an inhibitor of HSD17B13 for use in the treatment of a liver disease in a human subject having a PNPLA3 protein comprising an I148M variation and having a functional HSD17B13 protein. In some embodiments, the human subject has been tested positive for a PNPLA3 protein comprising an I148M variation and for a functional HSD17B13 protein. In some embodiments, the treatment comprises determining whether or not the human subject has a PNPLA3 protein comprising an I148M variation and a functional HSD17B13 protein. In some embodiments, the human subject has been identified as being a candidate for treating or inhibiting a liver disease by inhibiting HSD17B13 by using any of the methods as defined herein.

In some embodiments, the variant PNPLA3 protein comprises a methionine at the position corresponding to position 148 according to SEQ ID NO:42. In some embodiments, the variant PNPLA3 protein comprises the amino acid sequence according to SEQ ID NO:42, or an amino acid sequence having at least 90% sequence identity to SEQ ID NO:42 and comprising the I148M variation. In some embodiments, the nucleic acid molecule encoding the variant PNPLA3 protein is genomic DNA. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31, or a nucleotide sequence having at least 90% sequence identity to SEQ ID NO:31 and encoding a PNPLA3 protein which comprises the I148M variation. In some embodiments, the nucleic acid molecule encoding the variant PNPLA3 protein is mRNA. In some embodiments, the mRNA comprises an AUG codon at the positions corresponding to positions 442 to 444 according to SEQ ID NO:34. In some embodiments, the mRNA comprises the nucleotide sequence according to SEQ ID NO:34, or a nucleotide sequence having at least 90% sequence identity to SEQ ID NO:34 and encoding a PNPLA3 protein which comprises the I148M variation. In some embodiments, the mRNA comprises an AUG codon at the positions corresponding to positions 430 to 432 according to SEQ ID NO:35. In some embodiments, the mRNA comprises the nucleotide sequence according to SEQ ID NO:35, or a nucleotide sequence having at least 90% sequence identity to SEQ ID NO:35 and encoding a PNPLA3 protein which comprises the I148M variation. In some embodiments, the nucleic acid molecule encoding the variant PNPLA3 protein is cDNA. In some embodiments, the cDNA comprises an ATG codon at the positions corresponding to positions 442 to 444 according to SEQ ID NO:38. In some embodiments, the cDNA comprises the nucleotide sequence according to SEQ ID NO:38, or a nucleotide sequence having at least 90% sequence identity to SEQ ID NO:38 and encoding a PNPLA3 protein which comprises the I148M variation. In some embodiments, the cDNA comprises an ATG codon at the positions corresponding to positions 430 to 432 according to SEQ ID NO:39. In some embodiments, the cDNA comprises the nucleotide sequence according to SEQ ID NO:39, or a nucleotide sequence having at least 90% sequence identity to SEQ ID NO:39 and encoding a PNPLA3 protein which comprises the I148M variation.

In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

In some embodiments, the human subject is homozygous or heterozygous for functional HSD17B13.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The nucleotide and amino acid sequences recited herein are shown using standard letter abbreviations for nucleotide bases, and one-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

The following examples are provided to describe the embodiments in greater detail. They are intended to illustrate, not to limit, the claimed embodiments.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of what the inventors regard as their subject matter. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Genetic Interaction Between PNPLA3 rs738409 (p.I148M) And HSD17B13 rs72613567—Study Design In this study, exome sequencing was used to identify variants associated with serum alanine aminotransferase (ALT) and aspartate aminotransferase (AST) levels, which are markers of hepatocyte injury, in the DiscovEHR human genetics study, a cohort that links exome sequence data to electronic health records (EHR), and in three additional studies. The associations between implicated genetic variants and clinical diagnoses of chronic liver disease in DiscovEHR and two independent cohorts was also studied. The association between one of these variants and the histopathological severity of liver disease in an independent cohort of bariatric surgery patients who underwent liver biopsy was also studied.

Study Design and Participants

Human genetics studies were conducted using genomic DNA samples and data from six cohorts. These studies included two Regeneron Genetics Center and the Geisinger Health System (GHS) DiscovEHR study populations originating from the first 50,726 adult consented participants from the MyCode® Community Health Initiative of GHS20. The GHS discovery cohort consisted of 46,544 European individuals recruited from outpatient primary care and specialty clinics between 2007 and 2016, excluding all those recruited to the bariatric surgery cohort. The GHS bariatric surgery cohort consisted of 2,644 European individuals who had been referred for bariatric surgery. Replication studies of associations with liver transaminases were performed in the Dallas Heart Study and the Penn Medicine Biobank, which included 1,357 and 8,527 individuals of European ancestry, respectively. Replication studies of the associations with chronic liver disease included 517 individuals from the Dallas Liver Study (DLS) and 439 individuals from the Dallas Pediatric Liver Study (DPLS). Full study descriptions and clinical phenotype and disease definitions are described the Methods section in the Supplementary Appendix.

Baseline characteristics of genotyped multi-ethnic cases and controls from the Dallas Liver and Pediatric Liver Studies are shown in FIG. 5.

Sample Preparation, Sequencing, and Genotyping

DNA sample preparation and whole exome sequencing for the participants in the DiscovEHR study, the Dallas Heart Study, and the Penn Medicine Biobank were performed at the Regeneron Genetics as previously described (Dewey et al., Science, 2016, In Press). HSD17B13 rs72613567 was genotyped by Taqman assay (and verified by Sanger sequencing in 5 individuals of each genotype) in the Dallas Liver Study and Dallas Pediatric Liver Study.

Clinical Measurements and Chronic Liver Disease Definitions in the Discovery Cohort Clinical laboratory measurements for alanine aminotransferase (ALT) and aspartate aminotransferase (AST) were extracted from EHRs of participants from the GHS discovery cohort and bariatric surgery cohort. Median ALT and AST values were calculated for all participants with two or more measurements, and were $\log_{10}$-transformed to normalize the distribution prior to association analyses.

International Classification of Diseases, Ninth Revision (ICD-9) disease diagnosis codes were extracted from EHRs and collapsed into clinical disease categories for non-viral, nonalcoholic (ICD-9 571.40, 571.41, 571.49, 571.5, 571.8, 571.9) or alcoholic (ICD-9 571.0, 571.1, 571.2, 571.3) liver disease case definitions. Additional case definitions based on single diagnosis codes included: alcoholic cirrhosis (ICD-9 571.2), nonalcoholic cirrhosis (ICD-9 571.5), and HCC (ICD-9 155.0). For these case definitions, a common control group without liver disease ("no liver disease") was defined as participants with no case criteria or single-encounter or problem-list diagnosis code indicating any type of liver disease.

Regional association plots for alanine aminotransferase (ALT; A) and aspartate aminotransferase (AST; B) levels in the GHS discovery cohort in the region around HSD17B13 are shown in FIG. 6 (panels A and B). Purple diamonds indicate the splice variant rs72613567. Each circle indicates a single nucleotide variant with the color of the circle indicating the linkage disequilibrium (r2 calculated in the DiscovEHR cohort) between that variant and rs72613567. Blue lines indicate estimated recombination rates in Hap-Map. The bottom portion of the panels show the relative position and the transcribed strand of each gene in the locus. There were no significant associations between AST or ALT and coding or splice region variants in the neighboring gene HSD17B11 (most significant P-values $1.4 \times 10^{-1}$ and $4.3 \times 10^{-2}$ for ALT and AST, respectively).

Liver Histopathologic Phenotype Definitions in the Bariatric Surgery Cohort

The GHS bariatric surgery cohort consisted of 2,644 individuals of European descent, with intra-operative liver biopsy specimens available from 2,391 of these individuals. Liver biopsy specimens were formalin-fixed and stained with hematoxylin and eosin for histology, and Masson's trichrome stain for assessment of fibrosis, as previously described (Gerhard et al., Patient Saf. Surg., 2011, 5, 1). Histologic diagnoses were determined by hepatopathologists using previously established criteria (Brunt et al., Am. J. Gastroenterol., 1999, 94, 2467-74). Histologic diagnoses were used to defined the following phenotypes: 1) Normal: no evidence of steatosis, NASH, or fibrosis; 2) Simple steatosis: Steatosis (regardless of grade) with no evidence of NASH or fibrosis; 3) NASH: Any presence of lobular inflammation or hepatocyte ballooning (regardless of grade), or any presence of fibrosis (regardless of stage).

Baseline characteristics of sequenced European-ancestry individuals from the discovery and replication cohorts are shown in FIG. 1. Single nucleotide variants associated with serum transaminase levels at $P<1.0\times10^{-7}$ in the discovery cohort are shown in FIG. 2.

DNA Sample Preparation and Sequencing

In brief, exome capture was performed using NimbleGen probes according to the manufacturer's recommended protocol (Roche NimbleGen). The captured DNA was PCR amplified and quantified by qRT-PCR (Kapa Biosystems). The multiplexed samples were sequenced using 75 bp paired-end sequencing on an Illumina v4 HiSeq 2500 to a coverage depth sufficient to provide greater than 20×haploid read depth of over 85% of targeted bases in 96% of samples (approximately 80×mean haploid read depth of targeted bases). Raw sequence data from each Illumina Hiseq 2500 run were uploaded to the DNAnexus platform (Reid et al., BMC Bioinformatics, 2014, 15, 30) for sequence read alignment and variant identification. In brief, raw sequence data were converted from BCL files to sample-specific FASTQ-files, which were aligned to the human reference build GRCh37.p13 with BWA-mem (Li et al., Bioinformatics, 2009, 25, 1754-60). Single nucleotide variants (SNV) and insertion/deletion (indel) sequence variants were identified using the Genome Analysis Toolkit (McKenna et al., Genome Res., 2010, 20, 1297-303).

Exome-wide Association Analysis of Liver Enzymes and Chronic Liver Disease Phenotypes 502,219 biallelic variants with missing data rate <1%, Hardy-Weinberg equilibrium P-value >$1.0 \times 10^{-6}$, and minor allele frequency >0.1%, were examined for association with transaminase levels. $Log_{10}$-transformed median ALT and AST were adjusted for age, $age^2$, sex, BMI, and the first four principal components of ancestry. To account for relatedness among study participants, a genetic relatedness matrix was fit as a random-effects covariate. Both principal components and the genetic relatedness matrix were constructed from 39,858 non-MHC markers in approximate linkage equilibrium and with minor allele frequency >0.1%. A linear mixed models was used as implemented in the GCTA package (Yang et al., Am. J. Hum. Genet., 2011, 88, 76-82) to test for association between trait residuals and single nucleotide variants. All P-values reported in the text correspond to the allelic model.

Replication of associations in the GHS discovery cohort was attempted in three separate European-ancestry cohorts: the GHS bariatric surgery cohort, the Dallas Heart Study, and the Penn Medicine Biobank (described above). ALT and AST measures from the GHS bariatric surgery cohort and from Penn Medicine Biobank were $log_{10}$-transformed and adjusted for age, $age^2$, sex, BMI, and the first four principal components of ancestry. Genetic relatedness matrices were included as random-effects covariates, and analysis was performed using linear mixed models in GCTA. In the Dallas Heart study, $log_{10}$-transformed ALT and AST measures were adjusted for age, $age^2$, sex, BMI, and the first ten principal components of ancestry, and analysis was performed using linear regression implemented in PLINK. Summary statistics for the three replication cohorts were meta-analyzed using METAL (Willer et al., Bioinformatics, 2010, 26, 2190-1) (replication meta-analysis). Summary statistics for the discovery cohort and the three replication cohorts were meta-analyzed similarly (joint meta-analysis).

Replication and joint meta-analysis of 35 exome-wide significant single nucleotide variants from the discovery cohort in three separate European-ancestry cohorts is shown in FIG. 3.

For variants with exome wide significant associations with transaminases ($p<1 \times 10^{-7}$) in the GHS discovery cohort, association analyses and meta-analysis were performed, as described herein, in the European-ancestry replication studies described herein. A Bonferroni significance threshold determined by the number of variants tested was used to define replicated associations. Meta-analysis of discovery and replication studies was also performed. All P-values reported in the text correspond to the allelic model.

Transaminase-associated single nucleotide variants was also examined for associations with chronic liver disease phenotypes (defined and analyzed as described herein). A Bonferroni significance threshold determined by the number of variants and broad chronic liver disease categories tested was used to determine significance of associations. Replicated novel variants were also examined for association with histopathologically defined liver phenotypes from the GHS bariatric surgery cohort.

Association Analysis with Chronic Liver Disease Phenotypes

Thirteen significant and replicated single nucleotide variants from the liver enzyme ExWAS were analyzed for associations with chronic liver disease phenotypes defined from the GHS discovery cohort, as described above. A Bonferroni significance threshold of P<0.05/26 ($P<1.92 \times 10^{-3}$) was used to account for the thirteen variants and two broad chronic liver disease categories (alcoholic and non-alcoholic) tested. The HSD17B13 rs72613567 variant was further tested for association with histopathologically defined liver phenotypes from the GHS bariatric surgery cohort, as described above. Odds ratios were estimated with the use of Firth's penalized likelihood method of logistic regression after adjustment for age, $age^2$, sex, BMI, and the first four principal components of ancestry. Genotypic odds ratios were estimated for HSD17B13 rs72613567 using the same covariates.

Odds ratios for liver disease in the DLS were estimated by logistic regression, adjusted for age, $age^2$, sex, BMI, and self-reported ethnicity. Participants from the Dallas Heart Study with available rs72613567 genotypes were used as normal controls (n=4,279). Odds ratios in the DPLS were estimated by logistic regression.

Association of thirteen exome-wide significant and replicating single nucleotide variants with liver disease phenotypes in the discovery cohort is shown in FIG. 4.

Genetic Interaction Between PNPLA3 rs738409 (p.I148M) And HSD17B13 rs72613567—Analysis To evaluate the combined effect of PNPLA3 rs738409 and HSD17B13 rs72613567, association analyses for quantitative (ALT and AST) and binary (nonalcoholic liver disease and alcoholic liver disease) traits were conducted using linear and logistic regression, respectively, modeling main effects for both genetic variants as well as an interaction term, assuming an additive genetic model. All models were adjusted for age, $age^2$, sex, BMI, and the first four principal components of ancestry. Statistical analyses were performed using the glm function in base R.

Software

Genetic association analyses were performed using GCTA software, version 1.25.0 (Yang et al., Am. J. Hum. Genet., 2011, 88, 76-82) and PLINK, version 1.9.0. Quantile-quantile and Manhattan plots were generated using R software, version 3.2.1 (R Project for Statistical Computing). Regional association plots were generated using LocusZoom (Pruim et al., Bioinformatics, 2010, 26, 2336-7).

RNA Sequencing Studies

RNA quality and concentration was evaluated by running total RNA on an Agilent RNA Nano Bioanalyzer chip; all samples had an RNA integrity number (RIN) greater than 8. Polyadenylated RNA transcripts were isolated using two rounds of enrichment with oligo(dT)25 beads (Thermo Fisher Scientific). Samples were purified and concentrated with RNAclean XP beads (Beckman Coulter) and heat-fragmented to approximately 140 base pairs. First-strand synthesis was completed with SuperScript III reverse transcriptase (Thermo Fisher Scientific) using random hexamers; dTTP was replaced with dUTP during second-strand synthesis. Samples were processed according to the standard DNA library preparation method referenced above for exomes with the addition of a uracil DNA-glycosylase step to generate strand-specific sequencing libraries. Samples were pooled and sequenced using 75 bp paired-end sequencing on an Illumina v4 HiSeq 2500.

Identification and Validation of Novel HSD17B13 Transcripts

Reads were mapped to the Human.B38 using ArrayStudio® software (OmicSoft®, Cary, NC) allowing two mismatches. Two approaches were employed to identify novel HSD17B13 transcripts. Novel exon junctions were discovered based on Gencode v24 using ArrayStudio. De novo transcript assembly was performed using Trinity (v2.2.0) in default setting. Custom gene models were built to incorporate novel transcripts of HSD17B13, and transcript quantification was estimated by read alignment to the custom gene model. Protein sequence alignment of all identified HSD17B13 isoforms was determined. RT-PCR was performed on total RNA from human liver samples using the SuperScript™ One-Step RT-PCR System with Platinum™ Taq DNA Polymerase (Thermofisher). Each 50 µL RT-PCR reaction contained 1×Reaction Mix, 500 nM each forward and reverse primers (PST516: ATGAACATCATCCTAGAAATCCTTC; SEQ ID NO:62) and PST517: ATCATGCATACATCTCTGGCT GGAG; SEQ ID NO:63), 1 µL of RT/Platinum Taq, and 75 ng RNA. Cycling conditions were: one cycle of 45° C. for 30 minutes; one cycle of 94° C. for 2 minutes; 40 cycles of 94° C. for 20 seconds, 53° C. for 30 seconds, and 72° C. for 90 seconds; one cycle of 72° C. for 5 minutes; then a 10° C. hold. Products were purified using the QIAquick PCR Purification Kit (Qiagen) and submitted for direct Sanger sequencing using the primer DE002 (ATCAGAACTTC AGGCCTTGG; SEQ ID NO:64). To identify the B and C transcripts, the RT-PCR products were run out on a 2% agarose gel stained with SYBR GoldSYBR® Gold Nucleic Acid Gel Stain (Thermofisher), and bands of the expected molecular weight were excised and purified using the QIAquick Gel Extraction Kit (Qiagen), then subjected to cloning with the TOPO® TA Cloning Kit (Thermofisher). Sequencing of the TOPO clones was performed using, M13F and M13R sequencing primers. Sequence analysis was performed using the Sequencher DNA analysis software (Gene Codes Corporation).

Full-length HSD17B13 transcripts were amplified directly from 50 ng of total RNA with the SuperScript III One-step RT-PCR System with Platinum Taq High Fidelity (Thermo Fisher Scientific) using gene-specific primers in the first (GCAAAGCCATGAACATCATCC; SEQ ID NO:65) and last exons (TCTTGATGTAGTGGGAGTCGGATT; SEQ ID NO:66) to generate an amplicon of about 2.2 kb (maximum predicted size transcript). Amplicons were verified on an Agilent Bioanalyzer. PacBio-compatible barcoded adapters were ligated to the amplicons and cleaned with PacBio PB beads (Pacific Biosciences). Libraries were pooled in equal amounts and sequenced on one SMRT cell for 180 minutes on the PacBio RSII platform. The data was demultiplexed using PacBio software smrtanalysis v2.3 tool labelzmw and then analyzed with ConsensusTools AmpliconAnalysis. Resulting amplicons were compared to HSD17B13 RefSeq genes to determine isoform and genotype status.

Subcellular Localization of HSD17B13 Isoforms

HepG2 cells were infected with lentivirus carrying the HSD17B13 A and D transcripts, stable cell lines were selected, and HSD17B13 isoforms, lipid droplets, and endoplasmic reticulum were visualized using immunofluorescence. Briefly, HepG2 cells were cultured in Eagle's Minimum Essential Medium supplemented with 10% fetal bovine serum. HSD17B13 transcripts A and D were subcloned into Myc-DDK backbone lentivirus constructs, and lentivirus were generated. HepG2 cells were infected with lentivirus carrying the HSD17B13 transcripts. Stable cell lines expressing each HSD17B13 transcript were selected with 1-3 mg/ml Geneticin G-418 sulfate in complete culture medium for two weeks. Following fixation, HSD17B13 isoforms were detected with mouse anti-Myc antibody. Lipid droplets were labeled with BODIPY FL dye (Sigma). Lipid coat protein and endoplasmic reticulum were labeled with rabbit anti-PLIN antibody (Sigma) and rabbit anti-calnexin antibody (Cell Signaling Technology). Secondary antibodies for immunofluorescence were Alexa Fluor 488 donkey anti-rabbit IgG and Alexa Fluor 594 donkey anti-mouse IgG (Jackson ImmunoResearch).

Quantification of HSD171B3 Protein Expression in Human Liver Biopsy Tissue

Human liver and cell pellet samples were homogenized in ice-cold 1×RIPA lysis buffer (EMD Millipore) in the presence of protease and phosphatase inhibitor mixtures (Thermo-Fisher). Supernatant was collected and used for protein concentration using BCA protein assay (Thermo-Fisher). Human tissue lysates were loaded at 30 µg/well and stable cell lines were loaded 9 ag/well and separated on SDS/PAGE gels (Bio-Rad) and transferred to PVDF membranes (Bio-Rad). The membranes were blocked for 1 hour with 5% (wt/vol) milk in 1×TBS supplemented with 0.1% Tween20 (Bio-Rad). Membranes were incubated with antibody at 4° C. overnight against HSD17B13 (1:200, Thermo-Fisher) and B-Actin (1:500, Cell Signaling Technology). Bound antibody was detected using HRP-conjugated anti-rabbit antibody (1:10,000, Jackson ImmunoResearch) and enhanced using chemiluminescence reagent (Thermo-Fisher). Band intensities were quantified using Image J software.

In Vitro and Cellular Characterization of HSD17B13 Enzymatic Activity

Recombinant human HSD17B13 protein was purified from E. coli (Genscript) transformed with plasmid DNA harboring HSD17B13 transcript A or transcript D. The HSD17B13 variants contained a 10×His tag at the C terminus and were purified from soluble fraction using a $Ni^{2+}$ affinity purification. Enzymatic activity was determined through measurement of NADH production using the NAD (P)H-Glo Detection System (Promega). Reactions were performed for 3 hours at 25° C. in 0.2 M tris-HCl, pH 7.5, 0.5 mM $NAD^+$, 75 µM of substrate (Sigma) and 500 ng purified enzyme in a final volume of 100 µL. After incubation, 20 µL of the reaction was combined with 20 µL luciferase reagent (Promega), incubated at room temperature for 1 hour and read on an Envision Plate Reader (Perkin Elmer).

HEK293 cells overexpressing HSD17B13 transcript A, transcript D or green fluorescent protein (GFP, control) were used to investigate the activity of HSD17B13 against estradiol in a cell-based assay. Estradiol was fed to each cell type. After 48 hours, the media was collected and the concentration of estradiol and its converted product estrone were identified and quantified by LC-MS. Hydroxyestradiol (metabolite from estradiol) and hydroxyestrone (metablolite from estrone) were identified by LC-MS.

Example 2: Gene Expression Analysis of HSD17B13 and PNPLA3 in 66 Human Liver Samples Gene expression of HSD17B13 and PNPLA3 were analyzed with 66 human liver samples. All the samples were from control donors without steatosis, lobular inflammation, or fibrosis. The distribution of HSD17B13 rs72613567 (T/T, T/TA, and TA/TA) and PNPLA3 rs738409 (C/C, C/G, and G/G) genotypes is shown in Table 1.

| Genotype | C/C | C/G | G/G | ND |
|---|---|---|---|---|
| T/T | 12 | 8 | 1 | 0 |
| T/TA | 15 | 12 | 0 | 2 |
| TA/TA | 12 | 4 | 0 | 0 |

Figure 7:
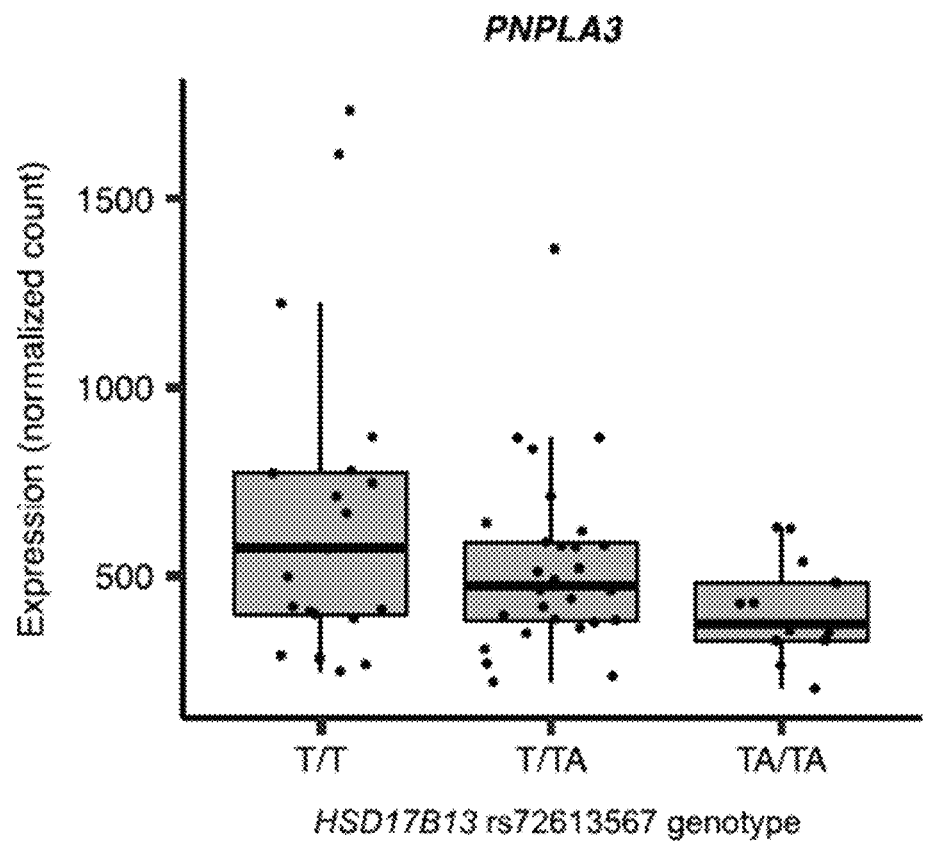
FIG. 7 shows the expression of PNPLA3 in homozygous reference (T/T), heterozygous (T/TA), and homozygous alternate (TA/TA) carriers of the HSD17B13 rs72613567 splice variant.
Figure 8:
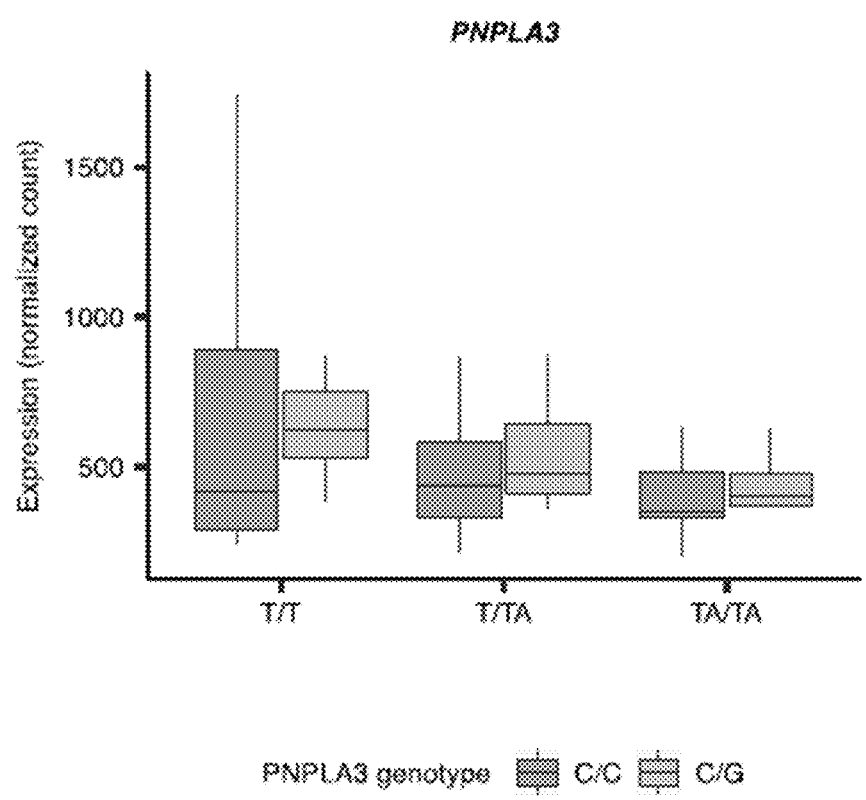
FIG. 8 shows the expression difference of the 63 PNPLA3 rs738409 carriers (C/C and C/G) in the three HSD17B13 rs72613567 genotypes (T/T, T/TA, TA/TA).

The expression of PNPLA3 was significantly reduced in homozygous alternate carriers of the HSD17B13 rs72613567 splice variant (see, FIG. 7). mRNA expression is displayed in FPKM units. A 1.6-fold decrease compared to T/T with FDR 0.0071 was observed. The variant PNPLA3 C/C carries with the HSD17B13 TA/TA genotype had significantly decreased expression when compared with HSD17B13 T/T carries: 1.7-fold (FDR 0.017) decrease. The variant PNPLA3 C/G carriers with TA/TA genotype showed decrease in expression but not statistically significant (1.4-fold, FDR 1). FIG. 8 shows the expression difference of the 63 PNPLA3 rs738409 carriers (C/C and C/G, see Table 1) in the three HSD17B13 rs72613567 genotypes (T/T, T/TA, TA/TA).

Figure 10:
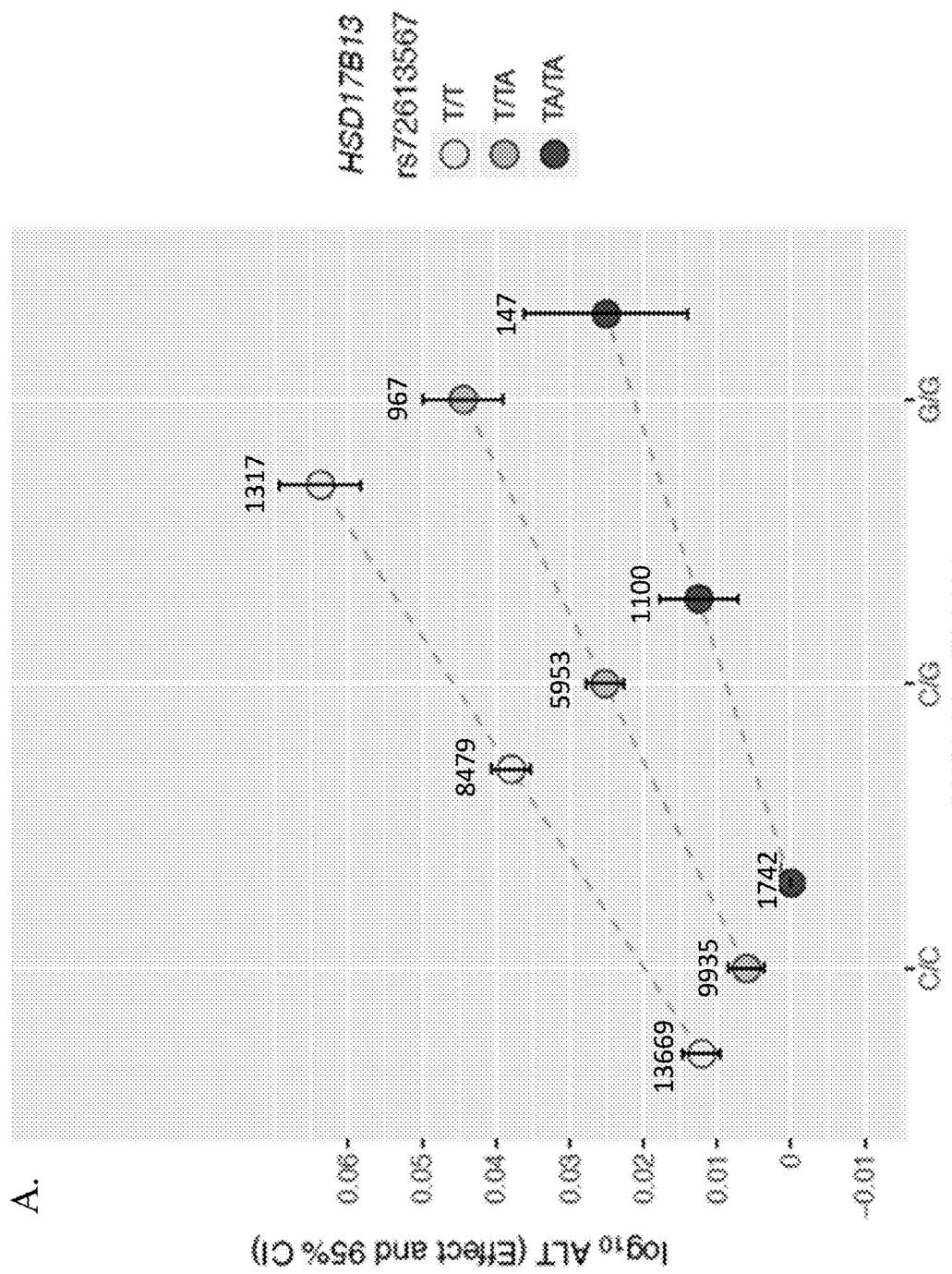
FIG. 10 (panels A and B) shows HSD17B13 rs72613567:TA mitigates the risk of liver injury associated with PNPLA3 p.I148M.
Figure 10:
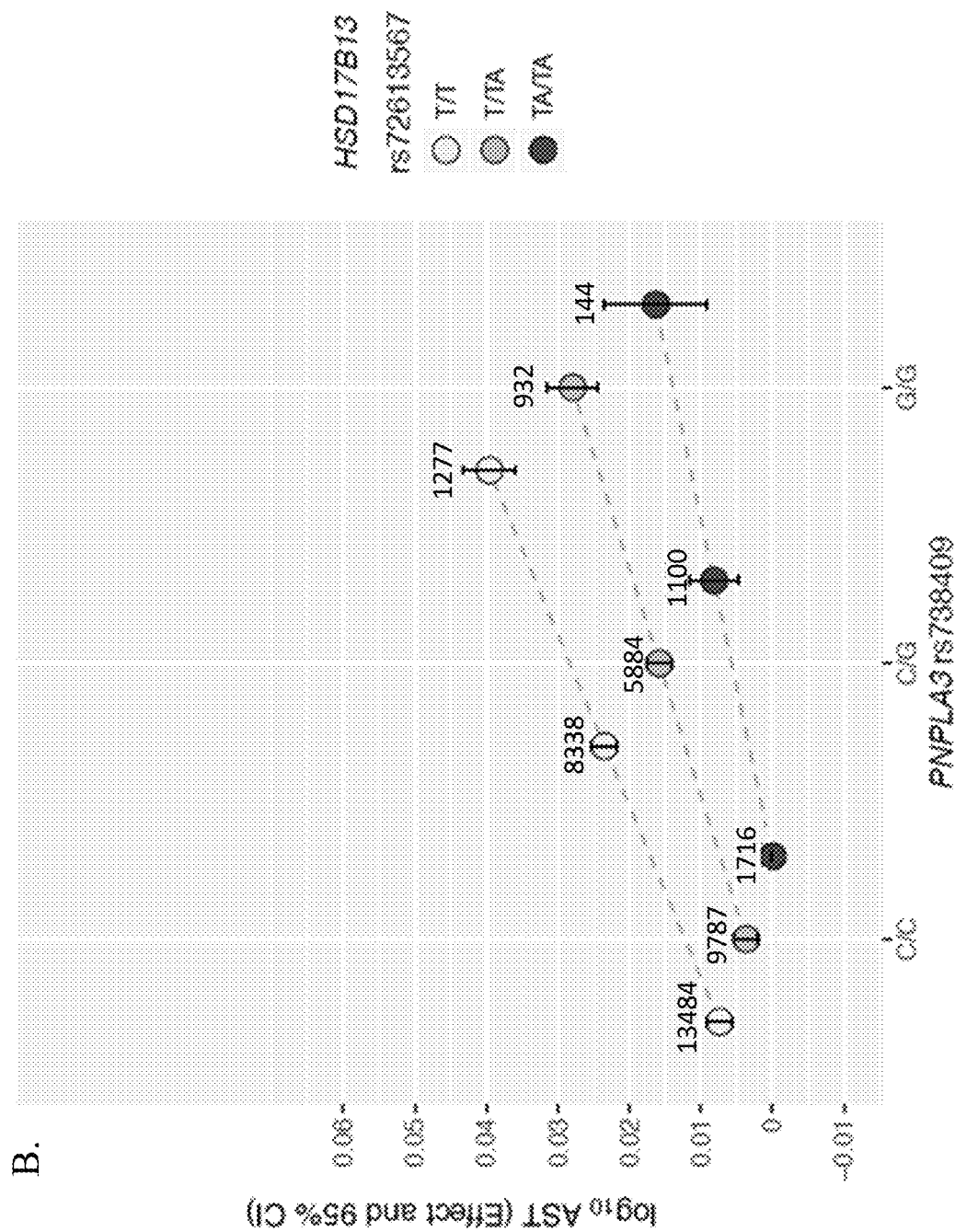
Figure 11:
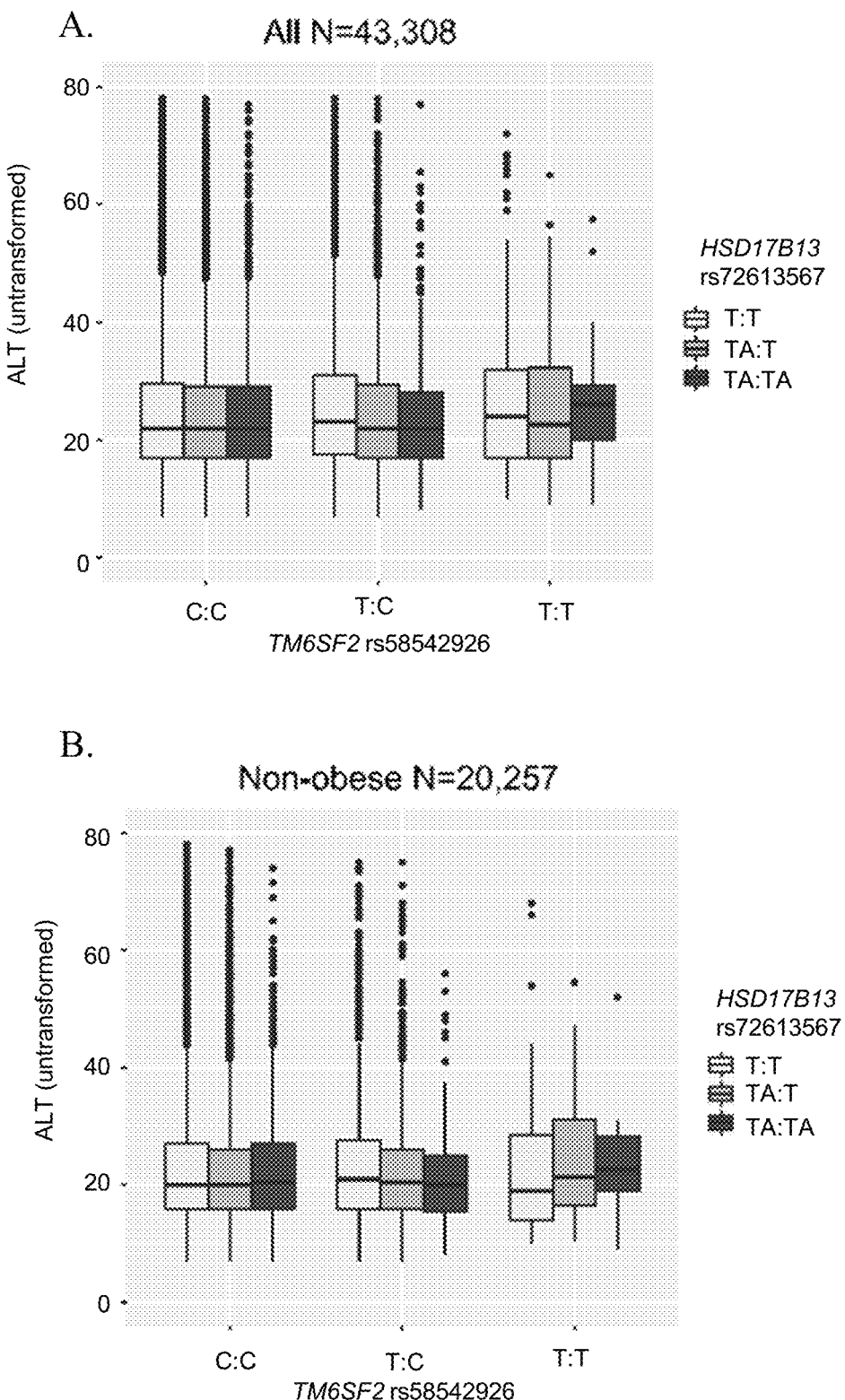
FIG. 11 (panels A through F) shows raw and residualized ALT levels by PNPLA3 rs738409 (p.I148M) and HSD17B13 rs72613567 genotype.
Figure 11:
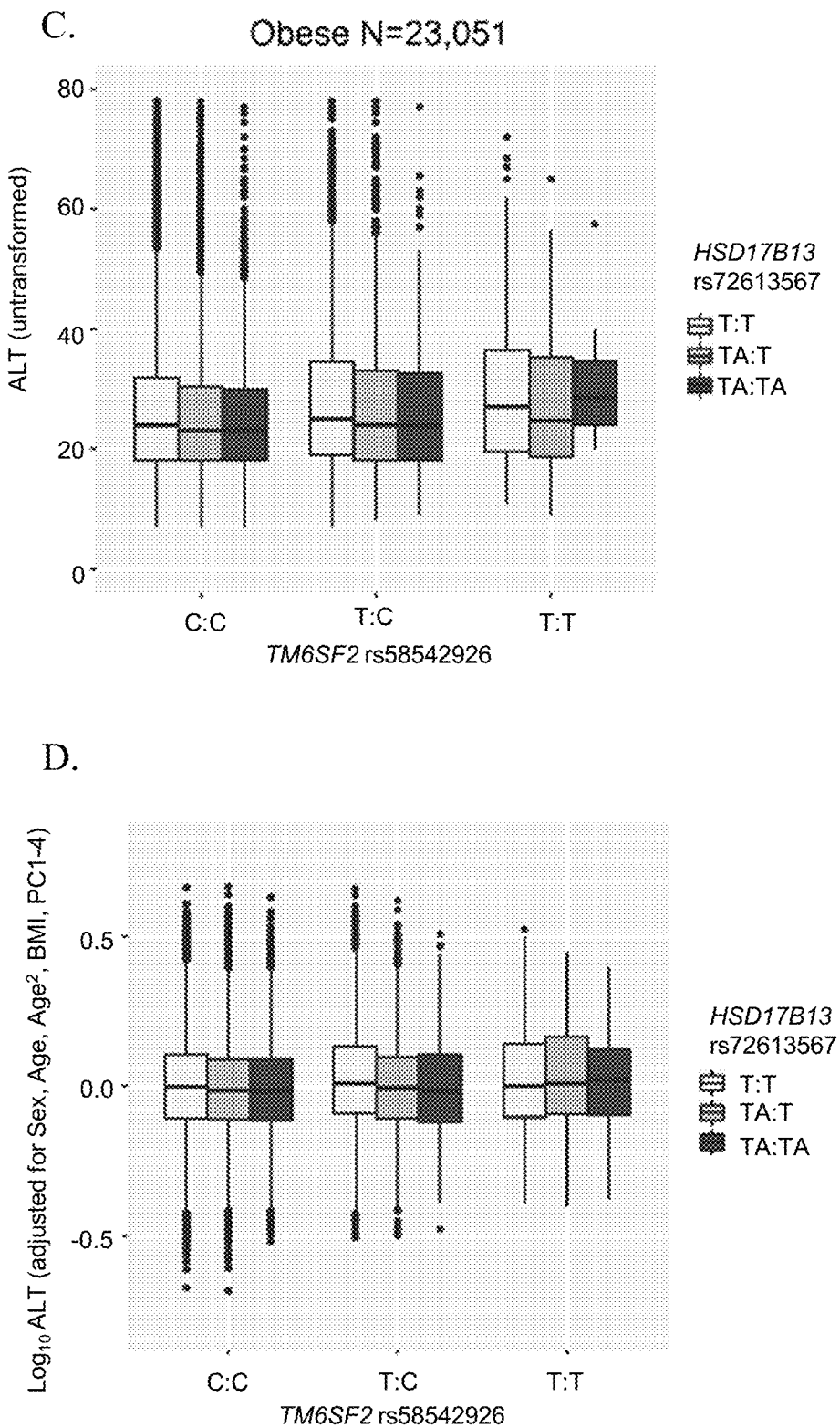
Figure 12:
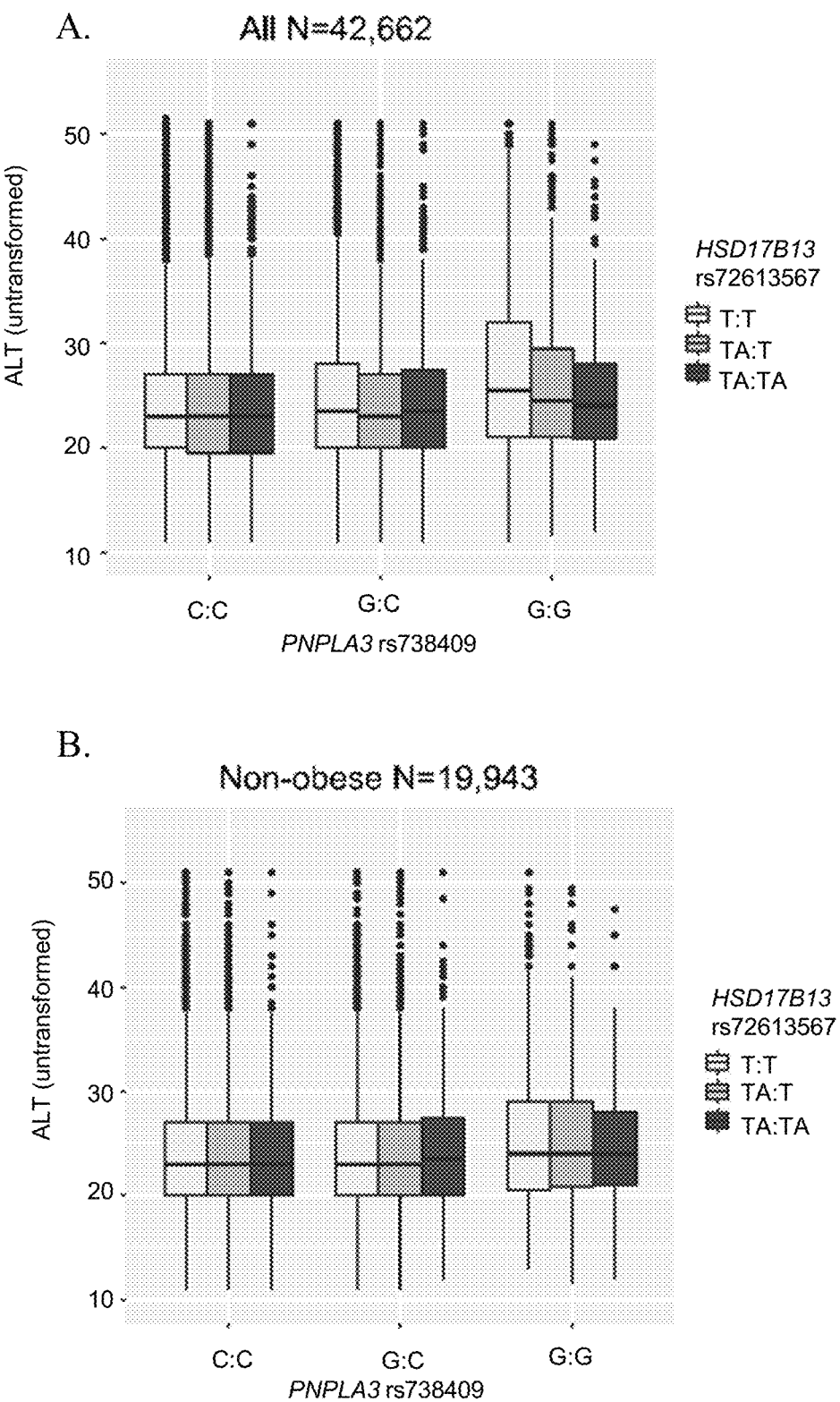
FIG. 12 (panels A through F) shows raw and residualized AST levels by PNPLA3 rs738409 (p.I148M) and HSD17B13 rs72613567 genotype.
Figure 13:
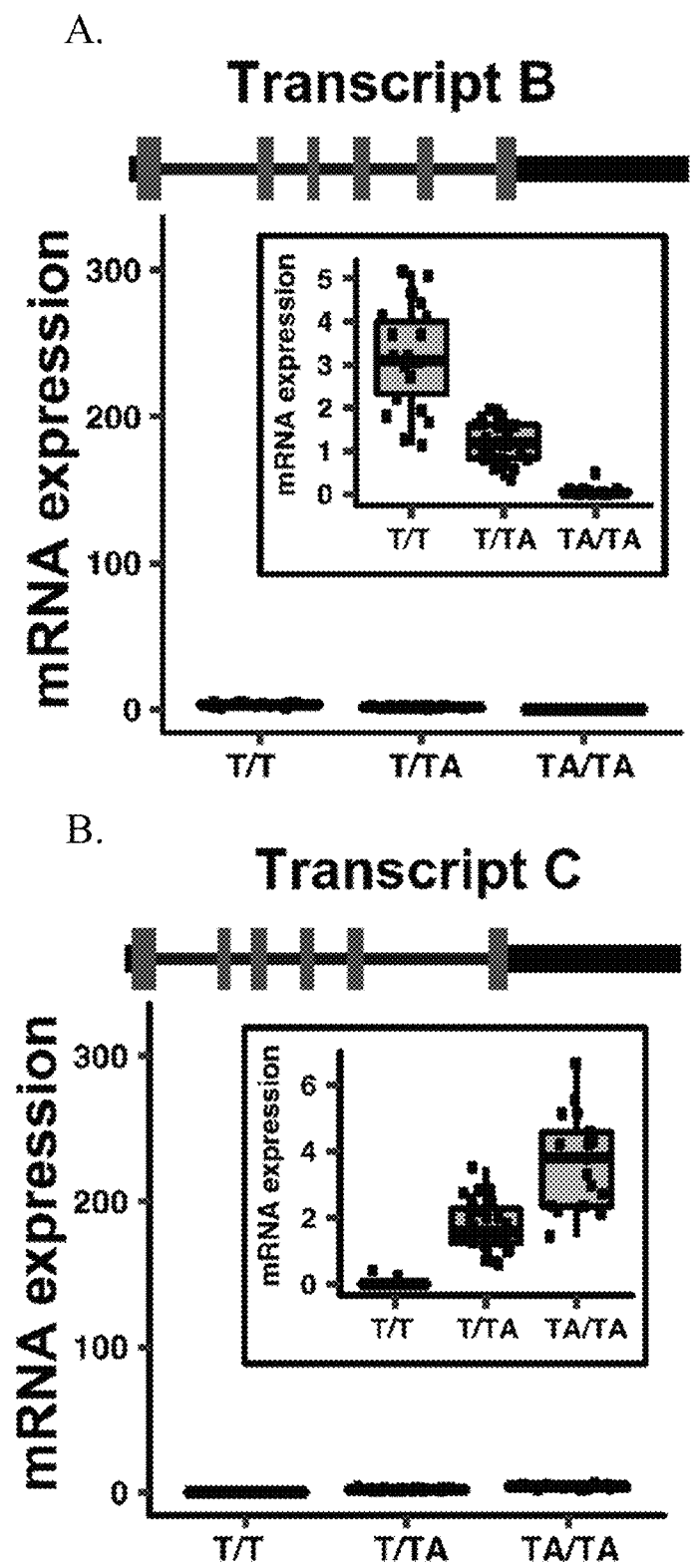
FIG. 13 (panels A through F) show mRNA expression of four additional novel HSD17B13 transcripts (E-H) in homozygous reference (T/T), heterozygous (T/TA), and homozygous alternate (TA/TA) carriers of the HSD17B13 splice variant.

The variant PNPLA3 p.I148M variant is the most well validated genetic risk factor for NAFLD, and the 148M allele exists in homozygous state in 5-25% of individuals, depending on ancestry. To understand whether the HSD17B13 rs72613567:TA modifies the risk of liver injury associated with PNPLA3 p.I148M, analyses of interaction between the two variants in association with ALT, AST, and chronic liver disease phenotypes in DiscovEHR was performed. These analyses were performed in all participants, as well as in obese (body mass index (BMI)>30 kg/m$^2$) and non-obese (BMI 30 kg/m$^2$) subpopulations. There was nominally significant interaction between HSD17B13 rs72613567:TA and PNPLA3 p.I148M in association analyses of ALT ($P=1.8\times10^{-3}$ for interaction) and AST ($P=4.5\times10^{-3}$ for interaction) levels; these associations were primarily driven by associations in obese individuals (see, FIG. 9). In these analyses, the rs72613567:TA allele mitigated the allele dosage-dependent associations of PNPLA3 148M allele with increased ALT and AST (see, FIG. 10). Referring to FIG. 10, panel A shows the association of HSD17B13 rs72613567 with ALT in individuals with each PNPLA3 p.I148M genotype, and panel B shows the association of HSD17B13 rs72613567 with AST in individuals with each PNPLA3 p.I148M genotype. Effect estimates (beta and 95% CI) were calculated using linear regression, with adjustment for age, age$^2$, sex, BMI, and four principal components of ancestry. FIG. 11 (panels A through F) show raw and residualized ALT levels by PNPLA3 rs738409 (p.I148M) and HSD17B13 rs72613567 genotype. Residuals were calculated by linear regression adjusted for age, age$^2$, sex, BMI, and four principal components 1-4. FIG. 12 (panels A through F) show raw and residualized AST levels by PNPLA3 rs738409 (p.I148M) and HSD17B13 rs72613567 genotype. Residuals were calculated by linear regression adjusted for age, age$^2$, sex, BMI, and four principal components 1-4. FIG. 13 (panels A through F) show mRNA expression of four additional novel HSD17B13 transcripts (E-H) in homozygous reference (T/T), heterozygous (T/TA), and homozygous alternate (TA/TA) carriers of the HSD17B13 splice variant. Coding regions in gene models are indicated in red and untranslated regions in black. Transcripts E and H contain an additional exon between exons 3 and 4. Transcript F involves read-through from exon 6 to intron 6. The blue arrow indicates the A insertion from rs72613567. Transcript G lacks exon 2. The asterisk in transcripts G and H illustrates insertion of G at the 3'-end of exon 6, which leads to premature truncation of the protein (similar to transcript D). Transcripts are differentially expressed according to HSD17B13 genotype, as shown in the box plots. mRNA expression is displayed in FPKM units.

These data suggest the HSD17B13 rs72613567:TA variant mitigates the risk of liver injury in individuals genetically predisposed to steatotic liver disease by the variant PNPLA3 p.I148M variant. This finding may suggest an important subpopulation for therapeutic modulation of HSD17B13—individuals heterozygous or homozygous for the variant PNPLA3 148M allele.

Figure 14:
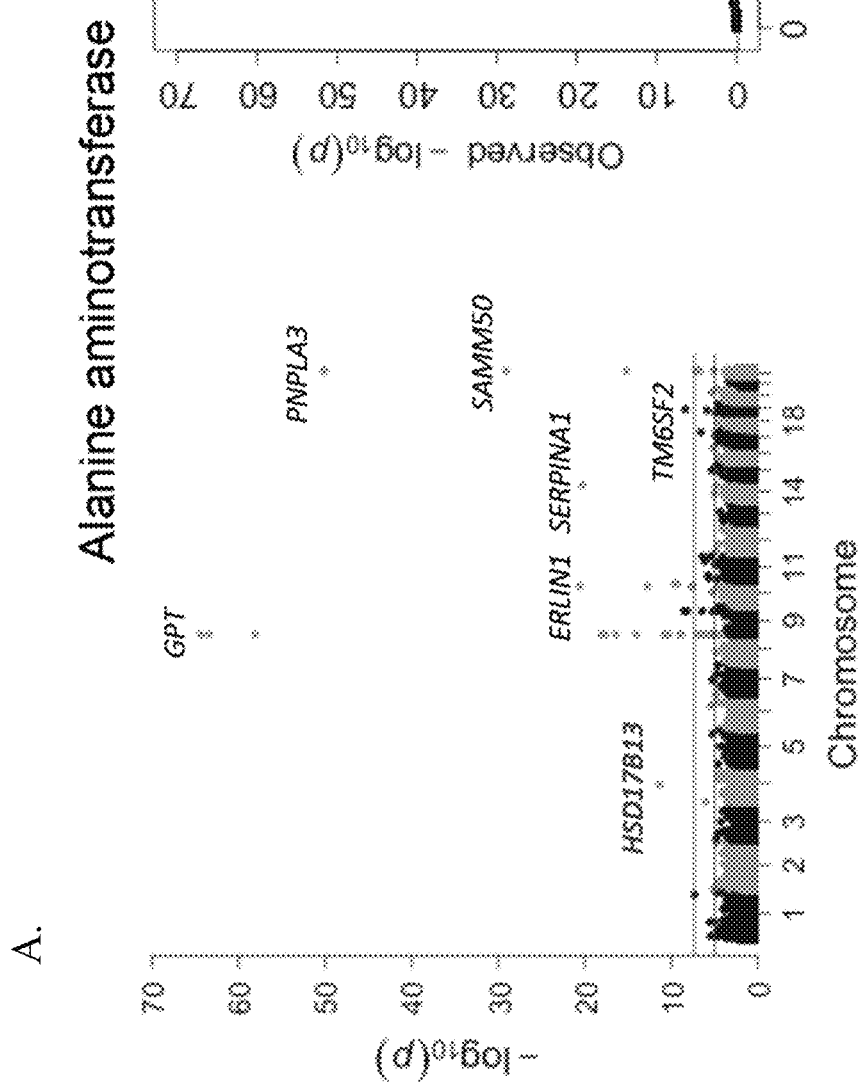
FIG. 14 (panels A and B) shows Manhattan plots (left) and quantile-quantile plots (right) of single nucleotide variant associations with serum transaminase levels in the GHS discovery cohort.
Figure 14:
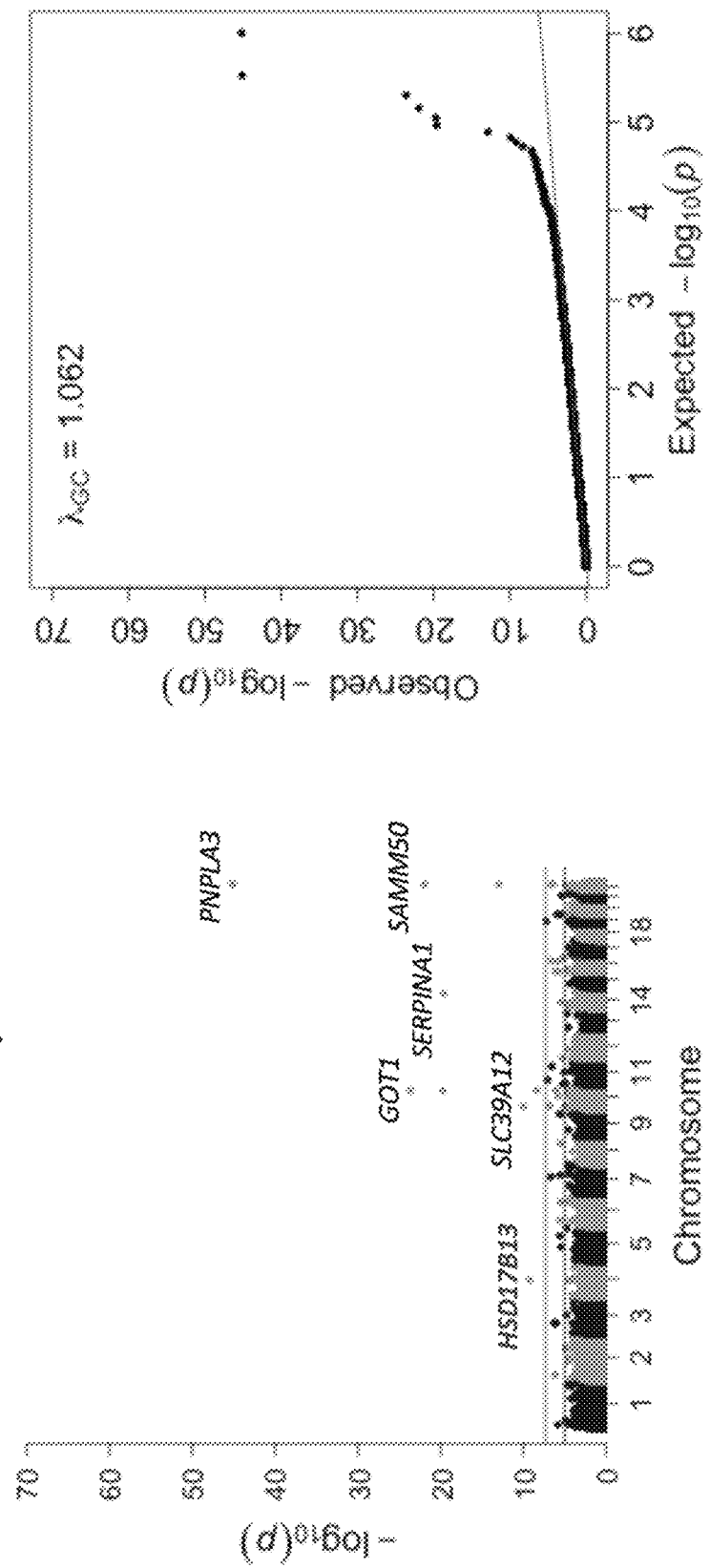

Example 3: Gene Expression Analysis of HSD17B13 and PNPLA3 in 66 Human Liver Samples Association of Exonic Variants with Aspartate and Alanine Aminotransferases 502,219 biallelic single genetic variants were examined for association with serum ALT or AST levels in 46,544 individuals of European descent from the DiscovEHR study ("GHS discovery cohort"; basic demographics in FIG. 1). A total of 35 variants in 19 genes were found to be associated with ALT or AST at $P<1.0\times10^{-7}$ (see, FIG. 14 and FIG. 2). Referring to FIG. 14, Manhattan plots (left) and quantile-quantile plots (right) of single nucleotide variant associations with serum transaminase levels in the GHS discovery cohort are shown. There were 31 variants in 16 genes significantly associated with alanine aminotransferase (ALT) levels at $P<1.0\times10^{-7}$ (see, Panel A). There were 12 variants in 10 genes significantly associated with aspartate aminotransferase (AST) levels at $P<1.0\times10^{-7}$ (see, Panel B). All significant associations are shown in FIG. 2. There were thirteen variants in nine genes (indicated here by their gene name), including HSD17B13, that remained significantly associated with ALT or AST in a replication meta-analysis of three separate European-ancestry cohorts (see, FIG. 3). The association tests were well calibrated, as shown by exome-wide quantile-quantile plots and genomic control lambda values.

Replication studies were performed in three cohorts of European-ancestry individuals: 1) bariatric surgery patients (n=2,644) from DiscovEHR ("GHS bariatric surgery cohort"); 2) 1,357 individuals from the Dallas Heart Study; and 3) 8,526 individuals from the Penn Medicine Biobank. In meta-analysis of the replication cohorts, thirteen variants in nine genes were significantly associated with serum levels of ALT or AST (Bonferroni significance threshold of $P<1.43\times10^{-3}$ for 35 variants tested; see, FIG. 3). These included variants that were previously reported to be associated with elevated transaminase levels, such as PNPLA3 (Romeo et al., Nat. Genet., 2008, 40, 1461-5), TM6SF2 (Kozlitina et al., Nat. Genet. 2014, 46, 352-6), SERPINA1 (Brantly et al., Am. J. Med., 1988, 84, 13-31), SAMM50 (Kitamoto et al., Hum. Genet., 2013, 132, 783-92), and ERLIN1 (Feitosa et al., Atherosclerosis, 2013, 228, 175-80). SERPINA1 encodes alpha-1-antitrypsin, whose functional deficiency causes liver disease; the association with SAMM50 is mediated via linkage disequilibrium with variation in PNPLA3, and ERLIN1 has been implicated in liver fat deposition. Variants that were not previously reported to be associated with liver disease were also identified. These included several variants in GPT and GOT1, the genes encoding ALT and AST, respectively, and SLC39A12, which encodes solute carrier family 39 member 12.

A reproducible association between a variant in HSD17B13, the gene encoding hydroxysteroid 17-beta dehydrogenase 13, an uncharacterized member of the 17-beta hydroxysteroid dehydrogenase family, and decreased levels of ALT (discovery P=4.2×10$^{-12}$, replication P=1.7×10$^{-4}$) and AST (discovery P=6.2×10$^{-10}$, replication P=1.7×10$^{-4}$, see, FIG. 3) was also identified. The associated variant, rs72613567, is an insertion of an adenine adjacent to the donor splice site of exon six (TA allele), and had an allele frequency of 26.0% in the GHS discovery cohort. Previously, Chambers, et al identified a nearby locus at 4q22 (rs6834314) associated with ALT levels (Chambers et al., Nat. Genet., 2011, 43, 1131-8); rs72613567 has not heretofore been reported to be associated with transaminase levels. HSD17B13 is 30 kb upstream of HSD17B11, another member of the same gene family. No exome-wide significant associations were observed between coding or splice variants in HSD17B11 and transaminase levels in the discovery cohort (see, FIG. 6) or in the joint meta-analysis of the discovery cohort and three replication cohorts. Furthermore, linkage disequilibrium of rs72613567 with variants in HSD17B11 was modest across all ancestry groups ($r^2<0.4$ with all ascertained variants in HSD17B11 in all ancestry groups; data not shown). Collectively, these findings suggest HSD17B13 as the gene in the genomic region that is most likely to be functionally related to transaminase levels.

Association of Exonic Variants with Clinical Diagnoses of Chronic Liver Disease

The relationship between the thirteen transaminase-associated variants in the nine genes found in the discovery and replication cohorts and chronic liver disease, including alcoholic and nonalcoholic (non-viral) liver disease, as well as the most advanced forms of chronic liver disease: alcoholic cirrhosis, nonalcoholic cirrhosis, and hepatocellular carcinoma (HCC), was also analyzed. Using a Bonferroni significance threshold of $P<1.92\times10^{-3}$ for the thirteen variants tested, significant associations were found between six variants in five genes (HSD17B13, SERPINA1, TM6SF2, PNPLA3, and SAMM50) and chronic liver disease phenotypes (see, FIG. 4). The SERPINA1, TM6SF2, PNPLA3, and SAMM50 associations confirm previously reported associations. In the discovery cohort, HSD17B13 rs72613567:TA was associated with lower odds of all EHR-derived categories of both alcoholic and nonalcoholic liver disease in an allele dosage-dependent manner (see, FIG. 15, panel A): all categories of alcoholic liver disease, heterozygous odds ratio (OR$_{het}$) (95% confidence interval) 0.58 (0.42-0.80), homozygous OR (OR$_{hom}$) 0.47 (0.23-0.97), allelic OR (OR$_{allelic}$) 0.62 (0.48-0.81), P=1.8×10$^{-4}$; all categories of nonalcoholic liver disease, OR$_{het}$ 0.83 (0.75-0.92), OR$_{hom}$ 0.70 (0.57-0.87), OR$_{allelic}$ 0.84 (0.78-0.91), P=1.3×10$^{-5}$. HSD17B13 rs72613567:TA was also associated with lower odds alcoholic and nonalcoholic cirrhosis, with 42% and 73% lower odds of alcoholic cirrhosis for heterozygotes and homozygotes, respectively, (OR$_{het}$ 0.58 (0.39-0.86), OR$_{hom}$ 0.27 (0.09-0.85), OR$_{allelic}$ 0.56 (0.41-0.78), P=3.4×10$^{-4}$) and 26% and 49% lower odds of nonalcoholic cirrhosis for heterozygotes and homozygotes, respectively (OR$_{het}$ 0.74 (0.60-0.93), OR$_{hom}$ 0.51 (0.31-0.85), OR$_{allelic}$ 0.74 (0.62-0.88), P=4.5×10$^{-4}$). HSD17B13 rs72613567:TA was also nominally associated with lower odds of HCC.

These findings were confirmed and extended in the multi-ethnic Dallas Liver Study (DLS) and the Dallas Pediatric Liver Study (DPLS) (see, FIG. 5). In the DLS, the TA allele was associated with lower odds of any liver disease in an allele-dosage dependent manner (OR$_{het}$ 0.74 (0.57-0.97), OR$_{hom}$ 0.41 (0.21-0.83), OR$_{allelic}$ 0.70 (0.5-0.88), P=1.8×10$^{-3}$, see FIG. 15, panel B). Similar effects were observed across EHR-derived liver disease subtypes, including protective associations with advanced, cirrhotic forms of alcoholic (OR$_{allelic}$ 0.72 (0.53-0.99), P=4.4×10$^{-2}$) and nonalcoholic (OR$_{allelic}$ 0.65 (0.40-1.07), P=9.0×10$^{-2}$) liver disease. In subset analyses of individuals grouped by self-reported ethnicity, the association with liver disease was significant in Hispanic Americans (n=326 cases and 722 controls, OR$_{allelic}$ 0.51 (0.35-0.74), P=4.0×10$^{-4}$); similar numerical trends, which did not achieve statistical significance, were also noted in the African American (n=33 cases and 2,291 controls, OR$_{allelic}$ 0.74 (0.25-2.47), P=0.67) and European American (n=158 cases and 1,266 controls, OR$_{allelic}$ 0.87 (0.65-1.15), P=0.32) subsets of the DLS. In the DPLS, a separate study of Hispanic American pediatric liver disease patients and obese controls, the TA allele was also associated with lower odds of liver disease (OR$_{allelic}$ 0.61 (0.37-0.99), P=4.6×10$^{-2}$). Thus, HSD17B13 rs72613567:TA was associated with reduced odds of multiple forms of chronic liver disease, including cirrhosis, in adults and children in three independent populations.

Figure 15:
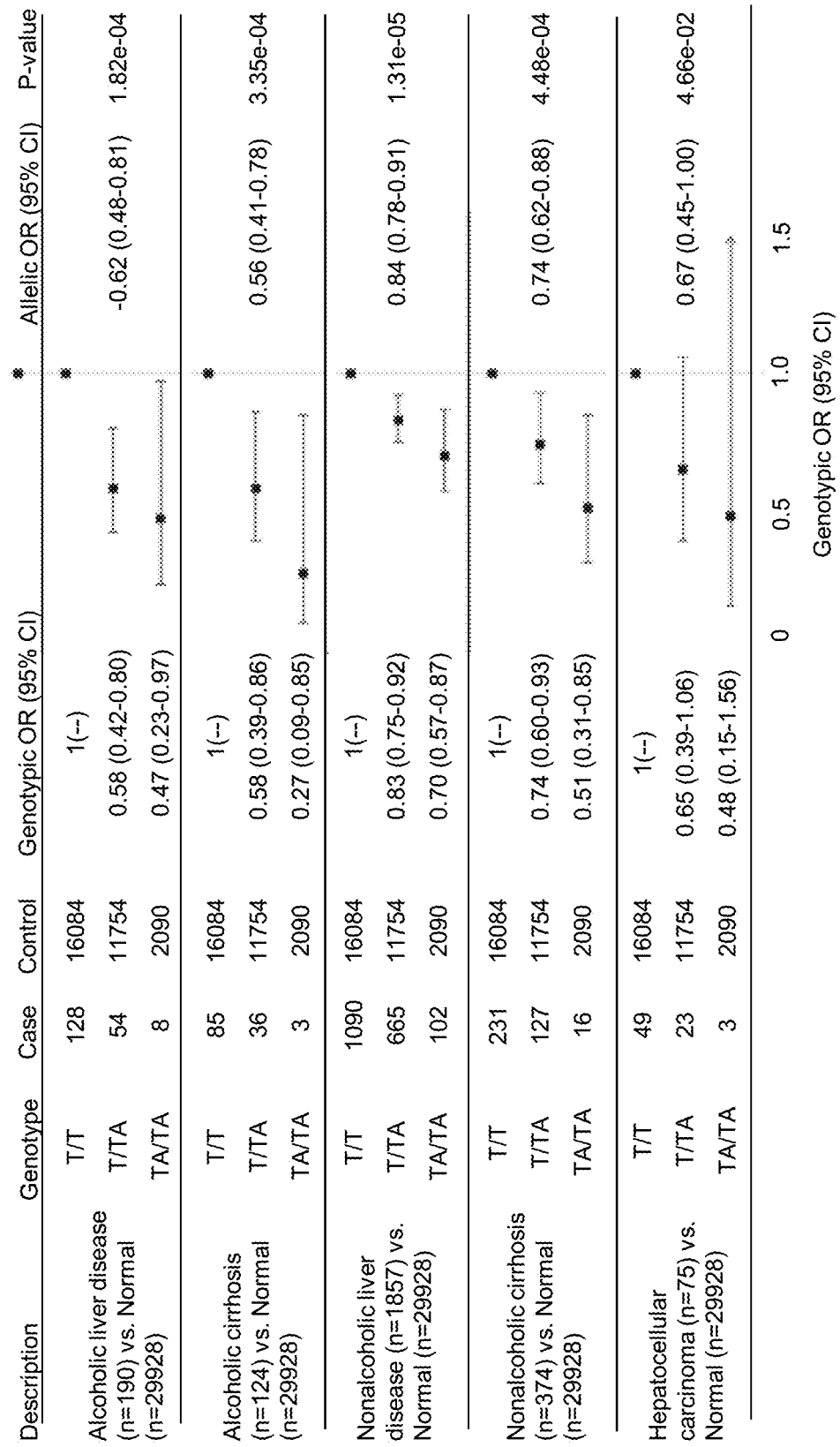
FIG. 15 (panels A and B) shows HSD17B13 rs72613567:TA is associated with reduced risk of alcoholic and nonalcoholic liver disease phenotypes.
Figure 15:
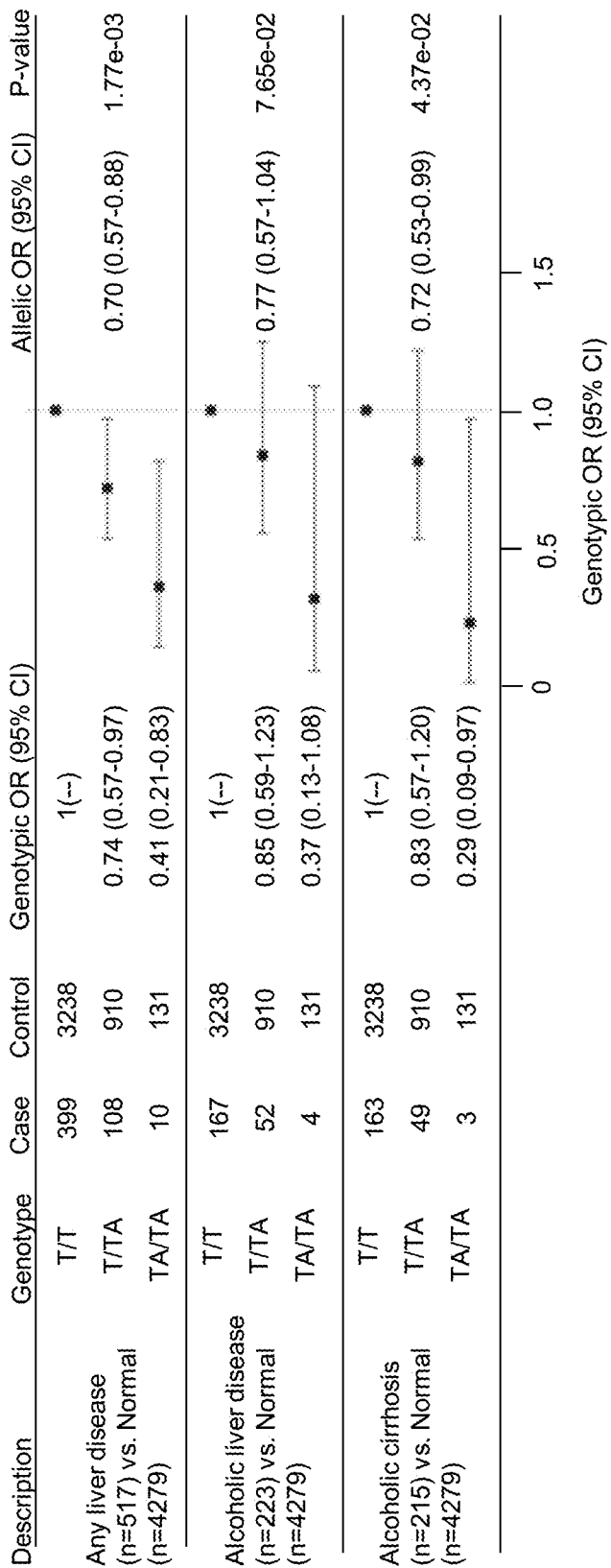
Figure 15:
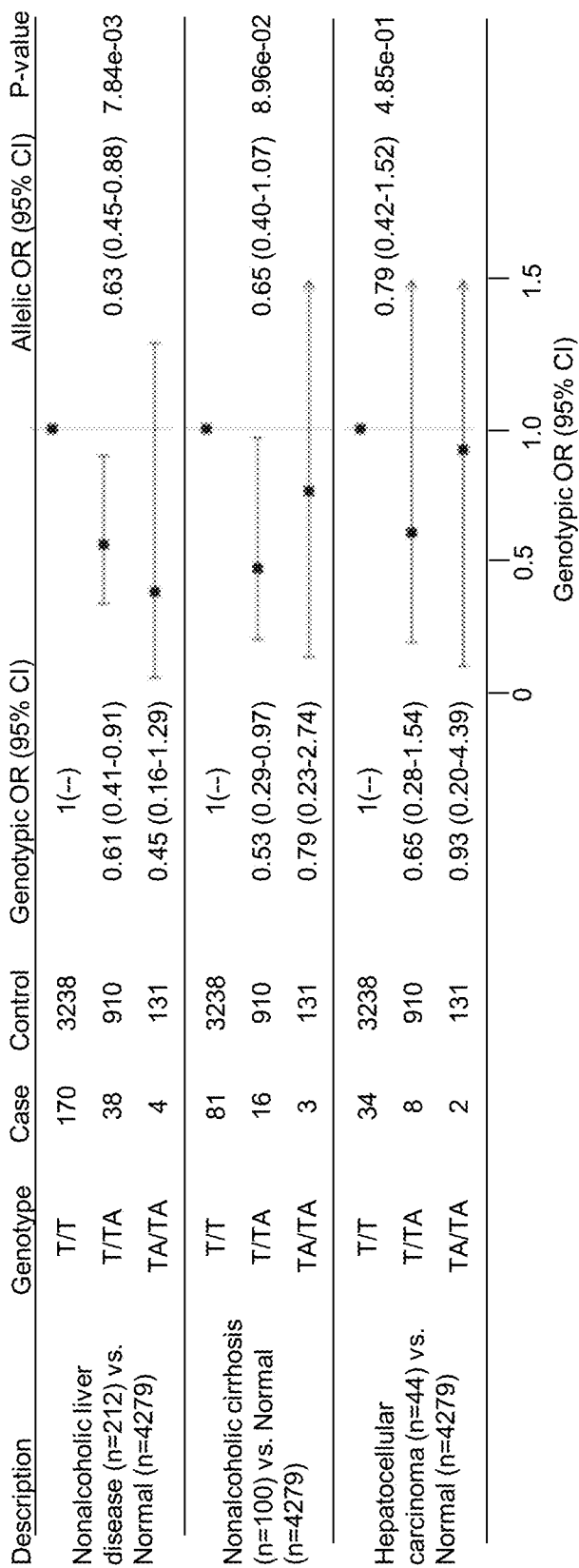

Referring to FIG. 15, HSD17B13 rs72613567:TA is associated with reduced risk of alcoholic and nonalcoholic liver disease phenotypes is shown. In the GHS discovery cohort, HSD17B13 rs72613567 was associated with lower odds of nonalcoholic and alcoholic liver disease, cirrhosis, and hepatocellular carcinoma in an allele dosage-dependent manner (see, Panel A). Odds ratios were calculated using logistic regression, with adjustment for age, age$^2$, sex, BMI, and principal components of ancestry. Genotypic odds ratios for heterozygous (Het OR) and homozygous (Hom OR) carriers are also shown. In the Dallas Liver Study, HSD17B13 rs72613567 was associated with lower odds of any liver disease in an allele dosage-dependent manner (see, Panel B). Similar allele dosage-dependent effects were observed across liver disease subtypes. Odds ratios were calculated using logistic regression, with adjustment for age, age$^2$, sex, BMI, and self-reported ethnicity.

Genetic Interaction Between PNPLA3 rs738409 (p.I148M) and HSD17B13 rs72613567

The variant PNPLA3 p.I148M variant is the most well validated genetic risk factor for NAFLD, and the 148M allele exists in homozygous state in 5-25% of individuals, depending on ancestry. To understand whether the HSD17B13 rs72613567:TA modifies the risk of liver injury associated with PNPLA3 p.I148M, analyses of interaction between the two variants in association with ALT, AST, and chronic liver disease phenotypes in DiscovEHR was performed. These analyses were performed in all participants, as well as in obese (body mass index [BMI]≥30 kg/m$^2$) and non-obese (BMI<30 kg/m$^2$) subpopulations. There was nominally significant interaction between HSD17B13 rs72613567:TA and PNPLA3 p.I148M in association analyses of ALT (P=1.8×10$^{-3}$ for interaction) and AST (P=4.5×10$^{-3}$ for interaction) levels; these associations were primarily driven by associations in obese individuals (see, FIG. 9). In these analyses, the rs72613567:TA allele mitigated the allele dosage-dependent associations of PNPLA3 148M allele with increased ALT and AST (see, FIG. 16, FIG. 11, and FIG. 12). RNA sequencing-based expression analysis revealed that HSD17B13 rs72613567:TA was associated with decreased PNPLA3 mRNA expression in an allele dosage-dependent manner (see, FIG. 7). These data suggest the HSD17B13 rs72613567:TA variant mitigates the risk of liver injury in individuals genetically predisposed to steatotic liver disease by the variant PNPLA3 p.I148M variant.

Figure 16:
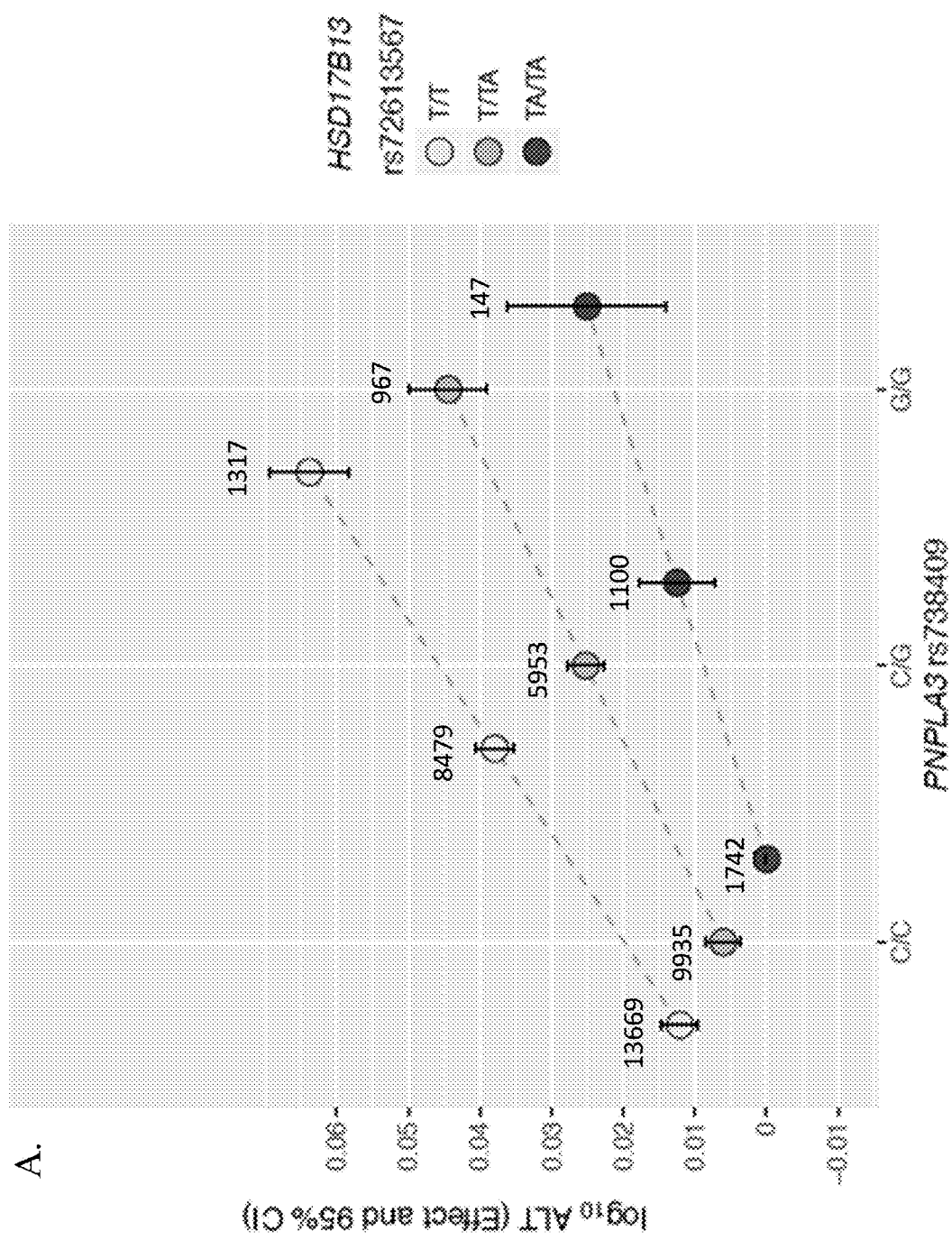
FIG. 16 (panels A and B) shows HSD17B13 rs72613567:TA mitigates the risk of liver injury associated with PNPLA3 p.I148M.
Figure 16:
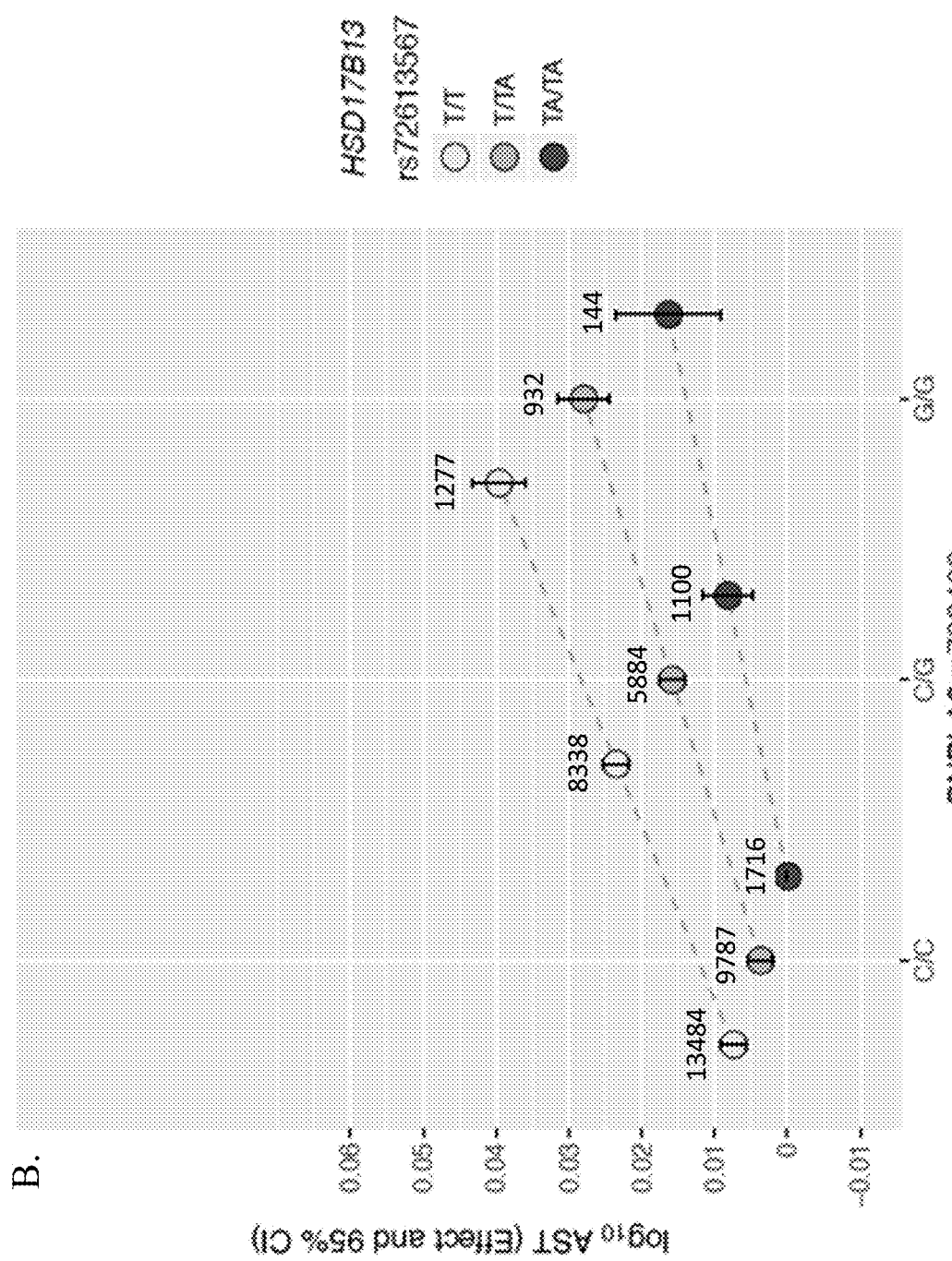

Referring to FIG. 16, HSD17B13 rs72613567:TA mitigates the risk of liver injury associated with PNPLA3 p.I148M is shown. Association of HSD17B13 rs72613567 with ALT in individuals with each PNPLA3 p.I148M genotype (see, Panel A). Association of HSD17B13 rs72613567 with AST in individuals with each PNPLA3 p.I148M genotype (see, Panel B). Effect estimates (beta and 95% CI) were calculated using linear regression, with adjustment for age, age$^2$, sex, BMI, and four principal components of ancestry. The P values for interaction between HSD17B13 rs72613567:TA and PNPLA3 p.I148M in association analyses of ALT and AST levels were P=$1.8 \times 10^{-3}$ and P=$4.5 \times 10^{-3}$, respectively.

Association of HSD17B13 rs72613567:TA with Liver Pathology

NAFLD describes a disease spectrum ranging from liver fat accumulation without evidence of significant inflammation (simple steatosis), to more clinically impactful NASH. To confirm the association between the HSD17B13 rs72613567:TA and EHR-derived liver disease diagnoses codes, and to further understand its association with histopathological progression of steatosis to NASH, tests of association in the GHS bariatric surgery cohort were performed. In this cohort of 2,391 of the whole exome sequenced individuals assessed by liver biopsy at the time of bariatric surgery, a total of 555 (23%) individuals had no evidence of steatosis, steatohepatitis, or fibrosis ("normal"), 830 (35%) had simple steatosis, and 1006 (42%) had NASH. When comparing prevalence of normal liver, simple steatosis, and NASH by genotype, it was observed that the prevalence of normal liver did not appear to differ by genotype (23%, 24%, and 23% for T/T, T/TA, and TA/TA carriers, respectively, P=0.5 by Chi-squared test for trend in proportions), but that the prevalence of NASH decreased (45%, 40%, and 31% for T/T, T/TA, and TA/TA carriers, respectively, P=$1.6 \times 10^{-4}$) and that of simple steatosis increased (33%, 35%, and 47% for T/T, T/TA, and TA/TA carriers, respectively, P=$1.1 \times 10^{-3}$) with each TA allele (see, FIG. 17, Panel A). Among individuals with steatosis, the TA allele was associated with statistically significantly lower odds of NASH, as compared to simple steatosis, in an allele dosage-dependent manner (OR$_{het}$ 0.87 (0.71-1.06), OR$_{hom}$ 0.48 (0.33-0.70), OR$_{allelic}$ 0.77 (0.66-0.90), P=$6.5 \times 10^{-4}$) (see, FIG. 17, Panel B). Altogether, these data suggest a role for HSD17B13 in mediating NAFLD progression from simple steatosis to more advanced stages of NASH and fibrosis.

Figure 17:
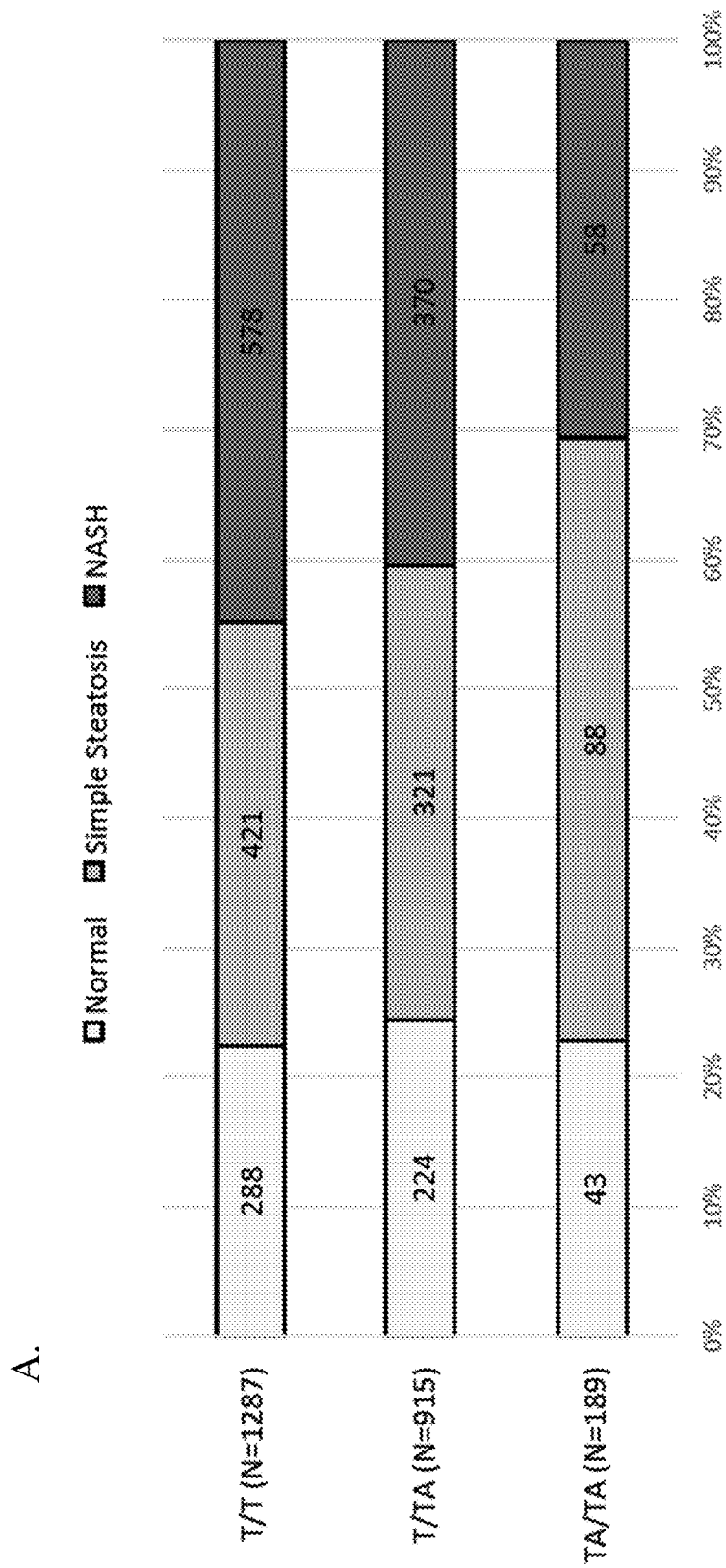
FIG. 17 (panels A and B) shows HSD17B13 rs72613567:TA is associated with reduced risk of progression from simple steatosis to steatohepatitis and fibrosis.
Figure 17:
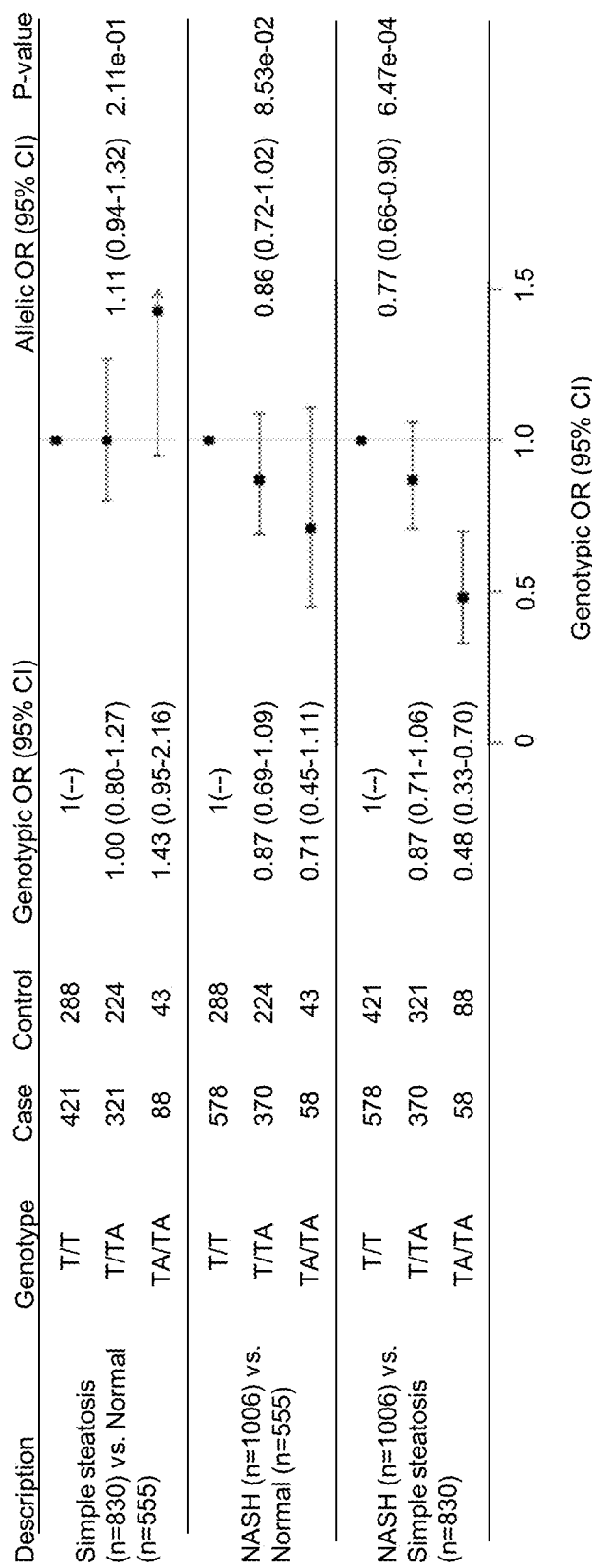

Referring to FIG. 17, HSD17B13 rs72613567:TA is associated with reduced risk of progression from simple steatosis to steatohepatitis and fibrosis is shown. Prevalence of histopathologically-characterized liver disease according to HSD17B13 rs72613567 genotype in 2,391 individuals with liver biopsies from the GHS bariatric surgery cohort (see, Panel A). The prevalence of normal liver did not appear to differ by genotype (P=0.5 by Chi-squared test for trend in proportions), but the prevalence of NASH decreased (P=$1.6 \times 10^{-4}$) and that of simple steatosis increased (P=$1.1 \times 10^{-3}$) with each TA allele. In the GHS bariatric surgery cohort, HSD17B13 rs72613567 was associated with 13% and 52% lower odds of NASH in heterozygous and homozygous TA carriers, respectively (see, Panel B). Odds ratios were calculated using logistic regression, with adjustment for age, age$^2$, sex, BMI, and principal components of ancestry. Genotypic odds ratios for heterozygous (Het OR) and homozygous (Hom OR) carriers are also shown.

Effect of rs72613567:TA on HSD17B13 mRNA and HSD17B13 Protein Expression

The effect of the HSD17B13 rs72613567:TA allele on expression of known and novel transcripts of the gene was examined. RNA sequencing was used to assess HSD17B13 mRNA expression in histologically normal liver samples from 22 T/T homozygous, 30 T/TA heterozygous, and 17 TA/TA homozygous carriers of the HSD17B13 rs72613567 splice variant. In addition to the two HSD17B13 transcripts, A and B, two novel transcripts were identified: transcript C, which lacked exon 6, and transcript D which contained an insertion of a guanine nucleotide at the 3' end of exon 6, which would be predicted to result in premature truncation of the protein. Four additional transcripts (E-H) were expressed at very low levels (see, FIG. 13). The transcripts were validated by RT-PCR and Sanger sequencing (data not shown). The D transcript was also validated using long read cDNA sequencing. The expression levels of these transcripts varied according to HSD17B13 rs72613567 genotype; levels of transcripts A and B decreased, while those of transcripts C and D increased in an allele dosage-dependent manner with each TA allele (see, FIG. 18, Panels A and B). Transcript A, which encodes the full-length 300 amino acid protein, was the predominant transcript in T/T homozygotes, while transcript D, which encodes the prematurely truncated protein, was the predominant transcript in TA/TA homozygotes. In human liver biopsy tissue, the truncated isoform D protein was minimally present in heterozygotes and TA/TA homozygotes, and isoform A protein abundance was reduced in an allele dosage-dependent manner (see, FIG. 18, Panels C and D). These data are consistent with HSD17B13 rs72613567 altering mRNA splicing, resulting in the synthesis of a truncated form of the protein with substantially reduced expression in human liver.

Figure 18:
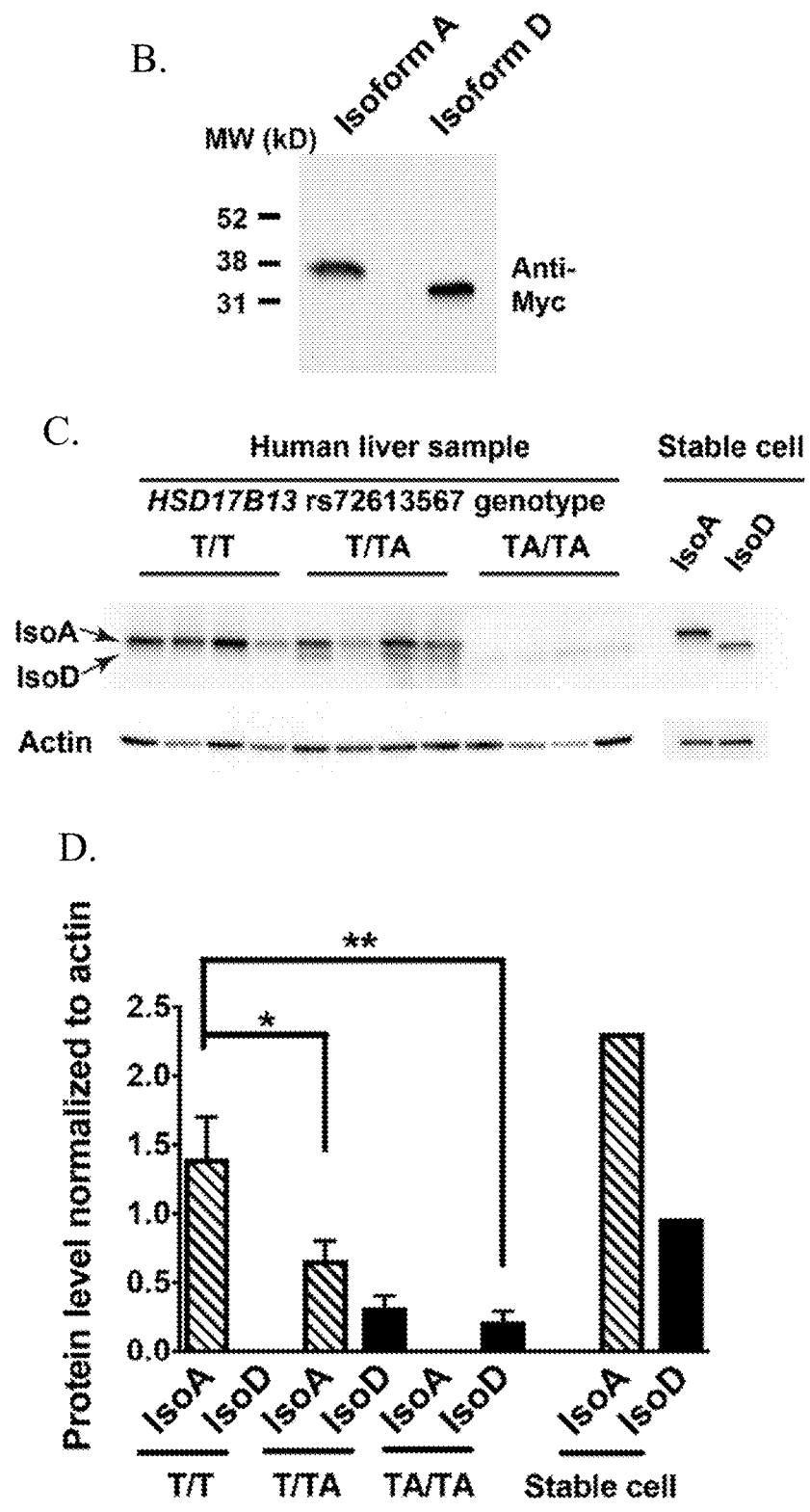
FIG. 18 (panels A through G) shows Expression, subcellular localization, and enzymatic activity of a novel HSD17B13 transcript.
Figure 18:
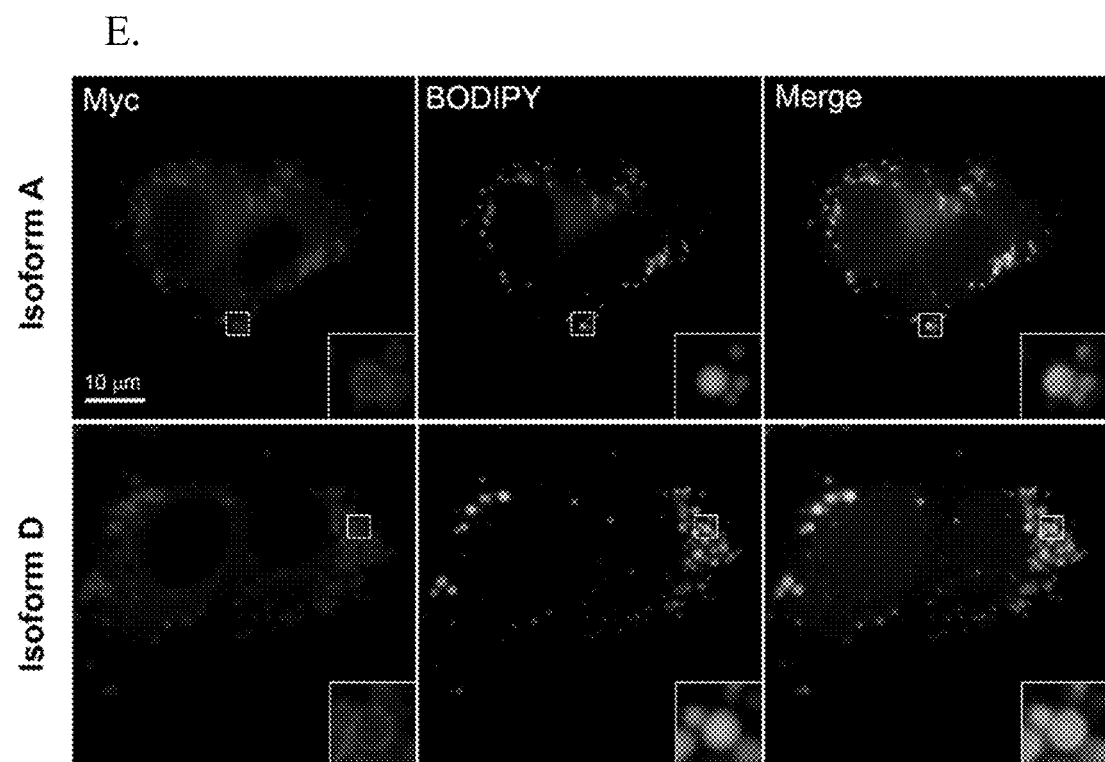

Referring to FIG. 18, expression, subcellular localization, and enzymatic activity of a novel HSD17B13 transcript is shown. Expression of HSD17B13 transcripts A and D in homozygous reference (T/T), heterozygous (T/TA), and homozygous alternate (TA/TA) carriers of the HSD17B13 rs72613567 splice variant (see, Panel A). Coding regions in HSD17B13 gene are indicated in red, untranslated regions as thick black lines, and introns as thin black lines. The asterisk in transcript D indicates the A insertion from rs72613567. mRNA expression is displayed in FPKM units (Fragments Per Kilobase of transcript per Million mapped reads). Western blot from HepG2 cells overexpressing HSD17B13 transcripts A and D. HSD17B13 transcript D was translated to a truncated protein with lower molecular weight compared to HSD17B13 transcript A (see, Panel B). HSD17B13 western blot from fresh frozen human liver and HEK293 cell samples (see, Panel C). Human liver samples are from homozygous reference (T/T), heterozygous (T/TA), and homozygous alternate (TA/TA) carriers of the HSD17B13 rs72613567 splice variant. Cell samples are from HEK293 cells overexpressing non-tagged HSD17B13 transcripts A and D. HSD17B13 transcript D was translated to a truncated protein IsoD with lower molecular weight than HSD17B13 IsoA. HSD17B13 IsoD protein levels were lower than IsoA protein levels from both human liver (left) and cell (right) samples (see, Panel D). Protein level normalized to Actin was shown in the bar columns; ** P<0.001, *P<0.05. Both HSD17B13 isoforms A and D were localized on lipid droplet membrane (see, Panel E). HepG2 stably overexpressing HSD17B13 transcripts A or D were labelled with BODIPY to show lipid droplets and anti-Myc to show HSD17B13 localization. All figures are magnified to the same extent. Scale bar indicates 10 µm. Insets represent 4×amplification of the original images. Enzymatic activity of HSD17B13 isoforms A and D to 17-beta estradiol (estradiol), leukotriene B4 (LTB4), and 13-Hydroxyoctadecadienoic acid (13(S)-HODE (see, Panel F). HSD17B13 isoform D show <10% enzymatic activity of the corresponding values for isoform A. G, HSD17B13 isoform D when overexpressed in HEK293 cells did not show much conversion of estradiol (substrate) to estrone (product) when measured in the culture media, while overexpressed HSD17B13 isoform A showed robust conversion.

Expression of HSD17B13 in Human Liver Cells

HSD17B13 is expressed primarily in the liver (Liu et al., Acta Biochim. Pol., 2007, 54, 213-8), where it localizes to lipid droplets (Su et al., Proc. Natl. Acad. Sci. USA, 2014, 111, 11437-42), consistent with a role in the pathogenesis of fatty liver disease. The expression of HSD171B3 and its localization was evaluated in an immortalized human liver cell line stably transduced with lentivirus expressing HSD17B13 transcripts A and D. HSD17B13 isoform A was mainly detected on membranes surrounding BODIPY-labeled lipid droplets (see, FIG. 18, Panel E). Similar subcellular localization was observed for HSD17B13 isoform D at the lipid droplet surface (see, FIG. 18, Panel F).

Effect of Rs72613567:TA on HSD17B13 Activity In Vitro and in Cellular Models

To understand the functional consequences of premature truncation of HSD17B13 protein due to rs72613567:TA, the enzymatic activity of isoforms A and D was evaluated in vitro using recombinant protein. Greater than 300 putative substrates were examined, of which estradiol, leukotriene B4, and 13-Hydroxyoctadecadienoic acid were enzymatically converted by HSD17B13, resulting in oxidation of a hydroxyl to a ketone group. HSD17B13 isoform D showed greatly reduced activity towards the 3 substrates (see, FIG. 18, Panel F).

Compared to GFP control, HSD17B13 transcript A overexpressing cells had lower concentration of estradiol as well as higher concentration of estrone in the cell culture medium, suggesting enzyme activity against estradiol (see, FIG. 18, Panel G). HSD17B13 transcript D overexpressing cells had similar ratio of estrone/estadiol to GFP control cells, suggesting that HSD17B13 transcript D has significant loss of function. The mass spec analysis revealed rapid conversion of estrone into hydroxyestrone and other products accounting for the low accumulation of estrone compared to consumed estradiol.

Through large-scale exome sequencing, a novel association was identified between a splice variant in HSD17B13 and decreased serum transaminase levels, as well as reduced risk of nonalcoholic and alcoholic forms of liver disease, including advanced cirrhotic forms of liver disease and HCC. To our knowledge, this is the first report of a protein-altering variant that has a protective association with liver disease. The HSD17B13 rs72613567:TA allele was not associated with simple steatosis, but reduced the risk of progression to NASH. The consistency of the dosage-dependent protective associations in four independent cohorts (DiscovEHR, an independent bariatric surgery cohort in DiscovEHR, DLS, and DPLS) across several different liver disease categories and ethnicities support the notion that the reported HSD17B13 variant protects from progression to more clinically advanced stages of chronic liver disease. The observed allele dosage-dependence also argues that more profound regulation of HSD17B13 function may result in more profound effects on disease risk and progression. The HSD17B13 rs72613567:TA allele also mitigated the risk of liver injury in individuals genetically predisposed to steatotic liver disease by the variant PNPLA3 p.I148M variant. This finding may suggest an important subpopulation for therapeutic modulation of HSD17B13—individuals heterozygous or homozygous for the variant PNPLA3 148M allele.

The association findings described herein were primarily based on observations in European and Hispanic Americans who have elevated BMI. HSD17B13 is in close proximity with HSD17B11, a member of the same gene family with high sequence similarity to HSD17B13 but broader tissue distribution. Overall, the data presented herein support the position that HSD17B13 is a potential therapeutic target for prevention and treatment of fatty liver disease in humans. The data presented herein indicate that targeting of HSD17B13 could reduce progression of liver disease from steatosis to later stages of NASH, fibrosis, and cirrhosis, which are associated with significant morbidity and mortality, and for which there are currently no effective treatments.

Figure 19:
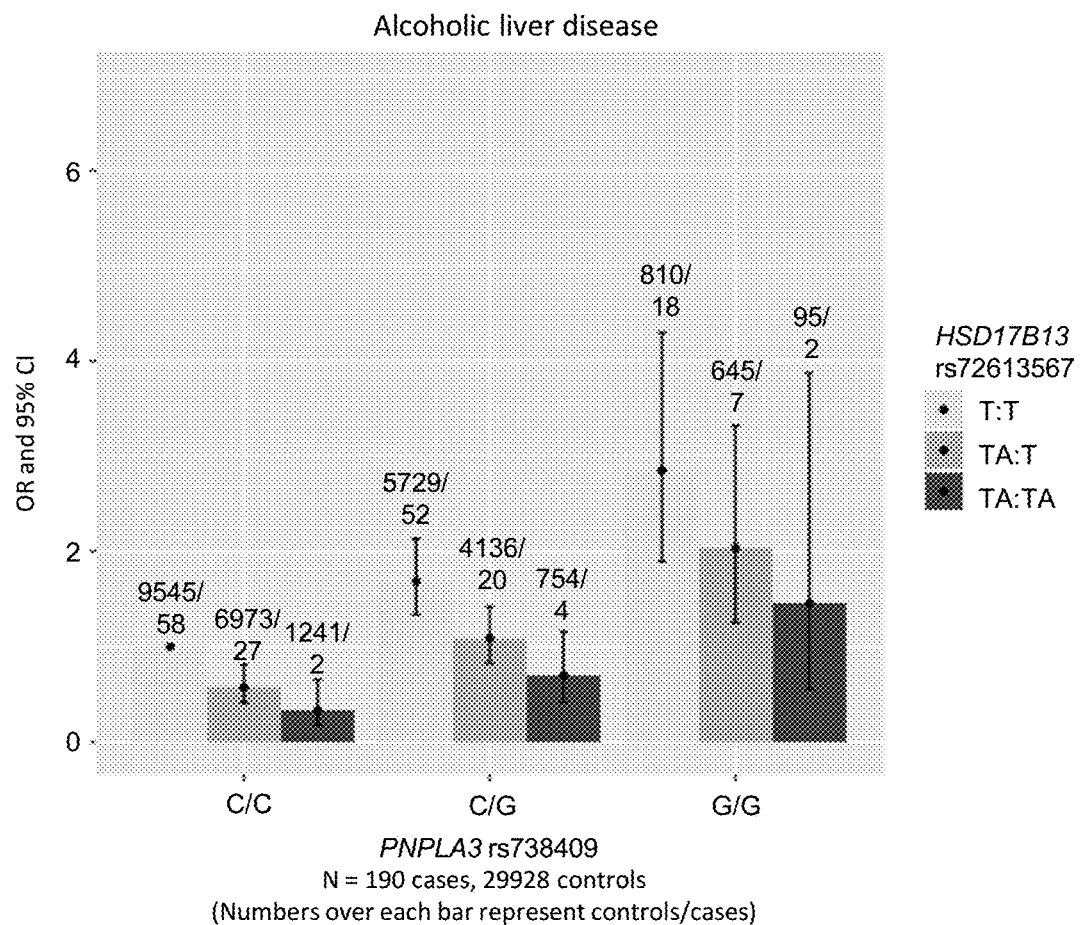
FIG. 19 (panels A and B) shows HSD17B13 rs72613567:TA mitigates the risk of alcoholic and nonalcoholic liver disease associated with PNPLA3 I148M. The numbers over each bar represent controls/cases.
Figure 19:
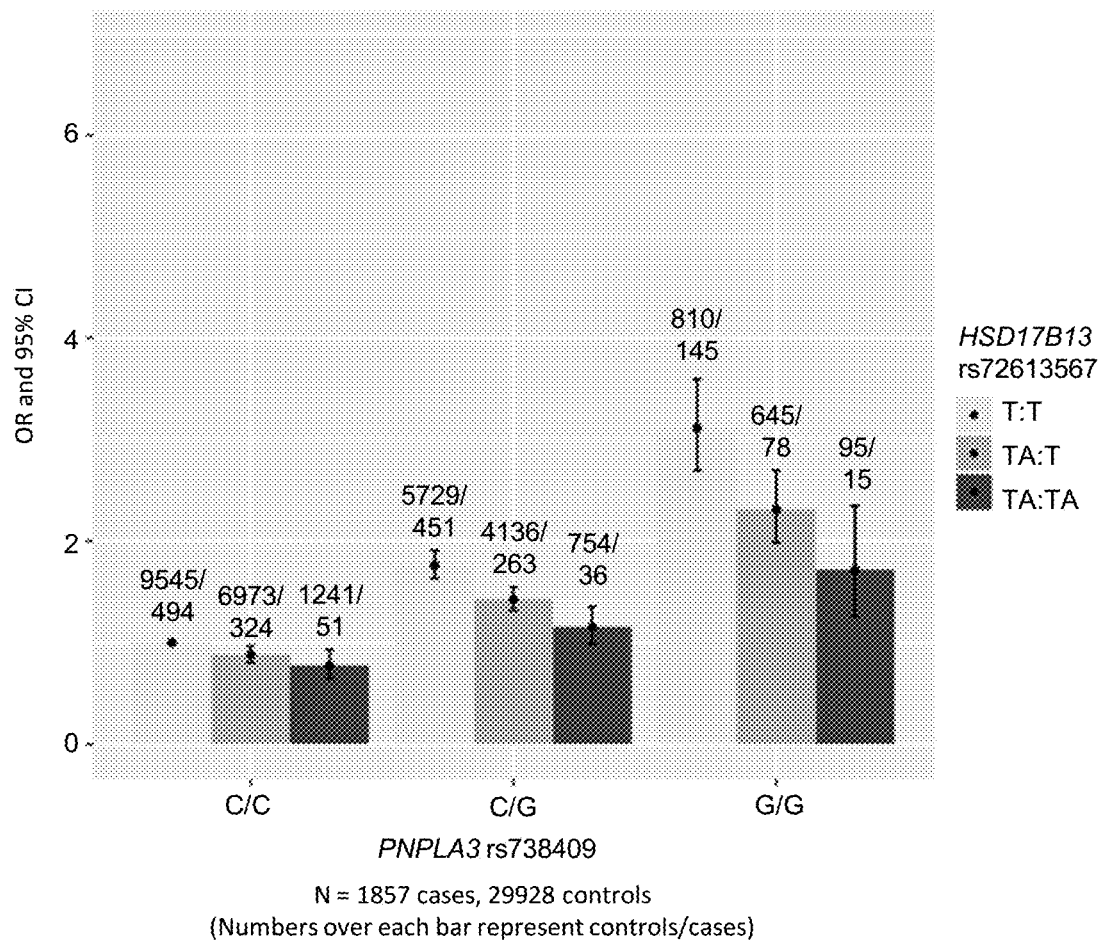

Example 4: HSD17B13 rs72613567:TA Mitigates the Risk of Alcoholic and Nonalcoholic Liver Disease Associated with PNPLA3 I148M Association of HSD17B13 and PNPLA3 genotypes with liver disease was analyzed by comparing HSD17B13 and PNPLA3 genotypes of 29,928 human liver samples from control donors without steatosis, lobular inflammation, or fibrosis with either 190 samples from patients having alcoholic liver disease, or with 1857 patients having nonalcoholic liver disease. The odds ratio was calculated by the equation of (incidence rate of a group having disease)/(incidence rate of the control group) for each combination of HSD17B13 and PNPLA3 genotype with 95% confidence intervals. Referring to FIG. 19, panel A shows the association of HSD17B13 rs72613567 with alcoholic liver disease in individuals with each PNPLA3 p.I148M genotype, and panel B shows the association of HSD17B13 rs72613567 with nonalcoholic liver disease in individuals with each PNPLA3 p.I148M genotype. The data demonstrate that PNPLA3 p.I148M is associated with higher incidence of both alcoholic and nonalcoholic liver disease in a dosage-dependent manner. The HSD17B13 rs72613567:TA genotype was associated with a reduced risk for both alcoholic and nonalcoholic liver disease in an allele dosage-dependent manner.

What is claimed:

1. A method for treating a subject having a nonalcoholic liver disease, the method comprising administering an inhibitor of hydroxysteroid 17-beta dehydrogenase 13 (HSD17B13) to the subject;
    wherein the subject has been determined to have a first nucleic acid molecule encoding a patatin like phospholipase domain containing 3 (PNPLA3) protein comprising an I148M variation and a second nucleic acid molecule encoding an HSD17B13 Isoform A, Isoform B, Isoform E, or Isoform I protein,
    wherein the inhibitor of HSD17B13 is an inhibitory nucleic acid molecule.

2. The method according to claim 1, wherein the inhibitory nucleic acid molecule comprises an antisense RNA.

3. The method according to claim 1, wherein the inhibitory nucleic acid molecule comprises a small interfering RNA (siRNA).

4. The method according to claim 1, wherein the inhibitory nucleic acid molecule comprises a short hairpin RNA (shRNA).

5. The method according to claim 1, wherein the first nucleic acid molecule is:
    genomic DNA that comprises an ATG codon at the positions corresponding to positions 5107 to 5109 according to SEQ ID NO:31;
    mRNA that comprises an AUG codon at the positions corresponding to positions 442 to 444 according to SEQ ID NO:34; or
    mRNA that comprises an AUG codon at the positions corresponding to positions 430 to 432 according to SEQ ID NO:35.

6. The method according to claim 1, wherein the first nucleic acid molecule is:
    genomic DNA that comprises the nucleotide sequence according to SEQ ID NO:31, or a nucleotide sequence having at least 90% sequence identity to SEQ ID NO:31 and encoding a PNPLA3 protein which comprises the I148M variation;
    mRNA that comprises the nucleotide sequence according to SEQ ID NO:34, or a nucleotide sequence having at least 90% sequence identity to SEQ ID NO:34 and encoding a PNPLA3 protein which comprises the I148M variation; or
    mRNA that comprises the nucleotide sequence according to SEQ ID NO:35, or a nucleotide sequence having at least 90% sequence identity to SEQ ID NO:35 and encoding a PNPLA3 protein which comprises the I148M variation.

7. The method according to claim 1, wherein the subject is heterozygous for the first nucleic acid molecule.

8. The method according to claim 1, wherein the second nucleic acid molecule is:
    genomic DNA that comprises an adenine at the position corresponding to position 12,667 according to SEQ ID NO:1;
    genomic DNA that comprises the nucleotide sequence according to SEQ ID NO:1, or a nucleotide sequence having at least 90% sequence identity to SEQ ID NO:1 and encoding a functional HSD17B13 protein
    mRNA that comprises the nucleotide sequence according to SEQ ID NO:3, or a nucleotide sequence having at least 90% sequence identity to SEQ ID NO:3 and encoding a functional HSD17B13 protein;
    mRNA that comprises the nucleotide sequence according to SEQ ID NO:4 or a nucleotide sequence having at least 90% sequence identity to SEQ ID NO:4 and encoding a functional HSD17B13 protein;

mRNA that comprises the nucleotide sequence according to SEQ ID NO:7 or a nucleotide sequence having at least 90% sequence identity to SEQ ID NO:7 and encoding a functional HSD17B13 protein; or mRNA that comprises the nucleotide sequence according to SEQ ID NO:11 or a nucleotide sequence having at least 90% sequence identity to SEQ ID NO:11 and encoding a functional HSD17B13 protein.

9. The method according to claim 1, wherein the subject is heterozygous for the second nucleic acid molecule.

10. The method according to claim 1, wherein the nonalcoholic liver disease is cirrhosis, steatosis, or hepatocarcinoma not caused by alcohol consumption.

11. The method according to claim 10, wherein the nonalcoholic liver disease comprises cirrhosis.

12. The method according to claim 10, wherein the nonalcoholic liver disease comprises steatosis.

13. The method according to claim 10, wherein the nonalcoholic liver disease comprises hepatocellular carcinoma not caused by alcohol consumption.

14. The method according to claim 1, wherein the nonalcoholic liver disease does not comprise liver fibrosis.

* * * * *